US012708247B2

(12) United States Patent
Horiuchi et al.

(10) Patent No.: US 12,708,247 B2
(45) Date of Patent: Aug. 18, 2026

(54) MEDICAL MANIPULATOR SYSTEM, CONTROLLER, AND CONTROLLING METHOD

(71) Applicant: OLYMPUS MEDICAL SYSTEMS CORP., Tokyo (JP)

(72) Inventors: Tatsuya Horiuchi, Sagamihara (JP); Kosuke Kishi, Mitaka (JP); Takahiro Komuro, Hachioji (JP); Yuji Sakaki, Tachikawa (JP); Michito Matsuoka, Hachioji (JP); Masao Nichogi, Kouza-gun (JP); Shu Kambe, Hachioji (JP); Toshihiro Yoshii, Hachioji (JP); Shota Sawada, Kokubunji (JP); Noriaki Yamanaka, Hachioji (JP); Hiroshi Ashiba, Tokorozawa (JP); Hiroki Jinnai, Musashino (JP); Soichiro Koshika, Koganei (JP); Ryota Yanagawa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 18/809,672

(22) Filed: Aug. 20, 2024

(65) Prior Publication Data

US 2024/0407628 A1 Dec. 12, 2024

Related U.S. Application Data

(63) Continuation of application No. PCT/JP2023/007304, filed on Feb. 28, 2023.
(Continued)

(51) Int. Cl.
*A61B 1/00* (2006.01)
*A61B 1/005* (2006.01)
(Continued)

(52) U.S. Cl.
CPC ...... *A61B 1/00006* (2013.01); *A61B 1/00039* (2013.01); *A61B 1/00133* (2013.01);
(Continued)

(58) Field of Classification Search
CPC ............. A61B 1/0004; A61B 1/00039; A61B 1/00133; A61B 1/0016; A61B 2034/301
(Continued)

(56) References Cited

U.S. PATENT DOCUMENTS

| | | | | |
|---|---|---|---|---|
| 5,938,588 | A | 8/1999 | Grabover et al. | |
| 9,214,139 | B2 * | 12/2015 | Nakayama | G09G 5/397 |

(Continued)

FOREIGN PATENT DOCUMENTS

| | | | |
|---|---|---|---|
| JP | H04176430 | A | 6/1992 |
| JP | H0622904 | A | 2/1994 |

(Continued)

OTHER PUBLICATIONS

International Search Report dated Dec. 20, 2022 received in PCT/JP2022/038580.

(Continued)

*Primary Examiner* — Justin W Rider
(74) *Attorney, Agent, or Firm* — Scully, Scott, Murphy & Presser, P.C.

(57) ABSTRACT

A medical manipulator system includes: a medical manipulator having a bending portion; a drive device connected to the medical manipulator and bending the bending portion; and a controller into which a manipulation input for bending the bending portion is input. The drive device is configured to determine a bending direction in which the bending portion is bent based on a first part of the manipulation input, and determine an amount of bending drive based on an entire input from a start to an end of the manipulation input.

20 Claims, 98 Drawing Sheets

Related U.S. Application Data

(60) Provisional application No. 63/314,579, filed on Feb. 28, 2022.

(51) Int. Cl.

| | |
|---|---|
| ***A61B 34/00*** | (2016.01) |
| ***A61B 34/37*** | (2016.01) |
| ***A61B 90/00*** | (2016.01) |
| ***G16H 40/63*** | (2018.01) |
| *A61B 34/30* | (2016.01) |
| *A61M 25/01* | (2006.01) |

(52) U.S. Cl.
CPC .......... *A61B 1/0016* (2013.01); *A61B 1/0051* (2013.01); *A61B 1/0057* (2013.01); *A61B 34/37* (2016.02); *A61B 34/71* (2016.02); *G16H 40/63* (2018.01); *A61B 2034/301* (2016.02); *A61B 2090/066* (2016.02); *A61M 25/0147* (2013.01)

(58) Field of Classification Search
USPC ............................................................ 348/65
See application file for complete search history.

(56) References Cited

U.S. PATENT DOCUMENTS

| | | | | |
|---|---|---|---|---|
| 10,666,854 | B2 | 5/2020 | Furuhata | |
| 2002/0062063 | A1 | 5/2002 | Ogura et al. | |
| 2002/0103418 | A1 | 8/2002 | Maeda et al. | |
| 2004/0138530 | A1 | 7/2004 | Kawai et al. | |
| 2007/0100201 | A1 | 5/2007 | Komiya et al. | |
| 2016/0128773 | A1 | 5/2016 | Ogawa et al. | |
| 2017/0080581 | A1 | 3/2017 | Iida et al. | |
| 2017/0143438 | A1 | 5/2017 | Komuro | |
| 2017/0209227 | A1 | 7/2017 | Yoshimura | |
| 2018/0095580 | A1 | 4/2018 | Yi et al. | |
| 2019/0303000 | A1 | 10/2019 | Furuhata | |
| 2020/0093353 | A1 | 3/2020 | Tezuka et al. | |
| 2020/0100857 | A1 | 4/2020 | Nakashima | |
| 2021/0000329 | A1 | 1/2021 | Tezuka et al. | |
| 2021/0146539 | A1 | 5/2021 | Tanaka et al. | |
| 2021/0259790 | A1 | 8/2021 | Kaiser | |
| 2021/0307591 | A1 | 10/2021 | OuYang | |
| 2022/0197487 | A1 | 6/2022 | Koo | |
| 2022/0409013 | A1 | 12/2022 | Kambe et al. | |
| 2024/0179394 | A1 * | 5/2024 | Oslie | H04N 23/74 |

FOREIGN PATENT DOCUMENTS

| | | | | |
|---|---|---|---|---|
| JP | H06269398 | A | 9/1994 | |
| JP | H06269401 | A | 9/1994 | |
| JP | 2000300511 | A | 10/2000 | |
| JP | 3233373 | B2 | 11/2001 | |
| JP | 2002224016 | A | 8/2002 | |
| JP | 2003235790 | A | 8/2003 | |
| JP | 2004041538 | A | 2/2004 | |
| JP | 3549434 | B2 | 8/2004 | |
| JP | 2007125180 | A | 5/2007 | |
| JP | 2010158566 | A | 7/2010 | |
| JP | 2012020028 | A | 2/2012 | |
| JP | 2013027466 | A | 2/2013 | |
| JP | 2015024038 | A | 2/2015 | |
| JP | 2019000351 | A | 1/2019 | |
| JP | 2019170853 | A | 10/2019 | |
| JP | 2019180488 | A | 10/2019 | |
| JP | 2021151468 | A | 9/2021 | |
| WO | 2004086957 | A2 | 10/2004 | |
| WO | 2018225121 | A1 | 12/2018 | |
| WO | 2019107226 | A1 | 6/2019 | |
| WO | 2021145411 | A1 | 7/2021 | |
| WO | 2021145424 | A1 | 7/2021 | |
| WO | WO-2021145410 | A1 * | 7/2021 | A61B 1/045 |
| WO | WO-2023163215 | A1 * | 8/2023 | A61B 1/0016 |

OTHER PUBLICATIONS

International Search Report dated Dec. 27, 2022 received in PCT/JP2022/039138.
International Search Report dated May 16, 2023 received in PCT/JP2023/007294.
International Search Report dated Apr. 18, 2023 received in PCT/JP2023/007332.
International Search Report dated May 9, 2023 received in PCT/JP2023/007334.
International Search Report dated Apr. 25, 2023 received in PCT/JP2023/007304.
US Office Action dated Nov. 6, 2025 received in U.S. Appl. No. 18/440,050.
US Office Action dated Nov. 17, 2025 received in U.S. Appl. No. 18/584,645.
US Office Action dated Mar. 9, 2026 received in U.S. Appl. No. 18/809,730.
US Office Action dated May 7, 2026 received in U.S. Appl. No. 18/809,780.

* cited by examiner

MEDICAL MANIPULATOR SYSTEM, CONTROLLER, AND CONTROLLING METHOD

CROSS-REFERENCE TO RELATED APPLICATIONS

The present application is a continuation application based on PCT Patent Application No. PCT/JP2023/007304, filed on Feb. 28, 2023, of which priority is claimed on U.S. Provisional Application No. 63/314,579, filed Feb. 28, 2022, the entire contents of which are hereby incorporated by reference.

TECHNICAL FIELD

The present disclosure relates to a medical manipulator system.

BACKGROUND

Conventionally, medical manipulator systems are used for observation and treatment within a luminal organ such as an alimentary canal. In a medical manipulator system, an insertion portion or the like inserted into the luminal organ can be electrically driven. A user can control an operation of the insertion portion and the like from an extracorporeally arranged manipulation portion.

PCT International Publication No. WO/2021/145411 (Patent Document 1) describes a medical system including an endoscope configured to be electrically driven. In the medical system described in Patent Document 1, the fatigue of a scopist can be reduced because the endoscope is electrically driven.

SUMMARY

However, the conventional medical manipulator system shown in Patent Document 1 and the like is not necessarily easy to use and is not a system that can perform treatment using a manipulator (endoscope) more efficiently.

The present disclosure provides a medical manipulator system and a controller that can more efficiently perform observation and treatment using a manipulator (endoscope).

According to a first aspect of the present disclosure, a medical manipulator system includes: a medical manipulator having a bending portion; a drive device connected to the medical manipulator and bending the bending portion; and a controller into which a manipulation input for bending the bending portion is input. The drive device is configured to determine a bending direction in which the bending portion is bent based on a first part of the manipulation input, and determine the amount of bending drive based on an entire input from a start to an end of the manipulation input.

The medical manipulator system and controller of the present disclosure can more efficiently perform observation and treatment using a manipulator.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

First Embodiment

Figure 1:
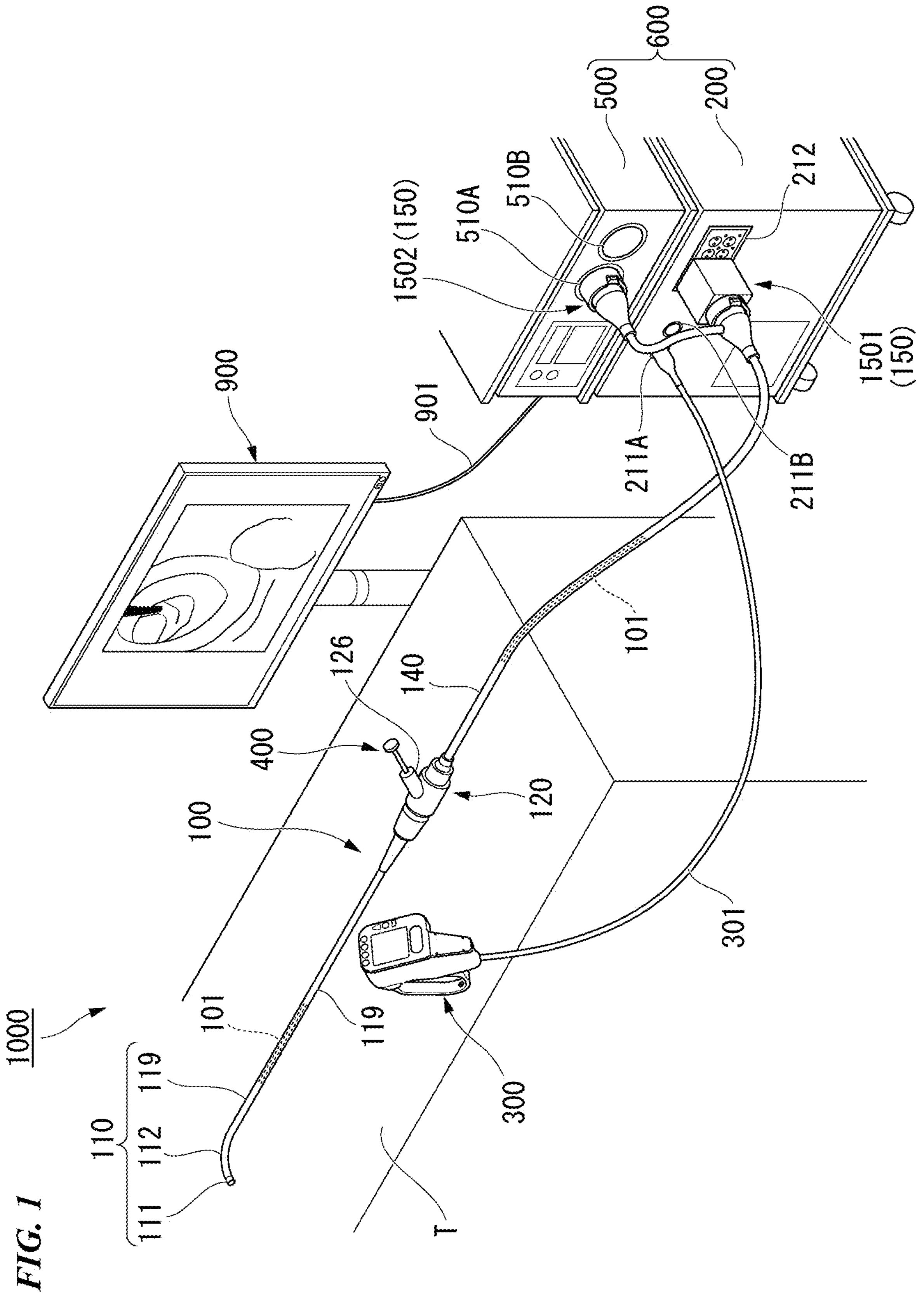
FIG. 1 illustrates an example of an overall view of an electric endoscope system according to a first embodiment.

An electric endoscope system 1000 according to a first embodiment of the present disclosure will be described with reference to FIGS. 1 to 22. FIG. 1 is an overall view of the electric endoscope system 1000 according to the present embodiment. The electric endoscope system 1000 is an example of a medical manipulator system. A medical manipulator includes an electrically driven endoscope, a catheter, a treatment tool, an endoluminal device, and the like to be intracorporeally inserted.

[Electric Endoscope System 1000]

The electric endoscope system 1000 is a medical system for observing and treating the inside of the body of a patient P lying on an operating table T, as shown in FIG. 1. The electric endoscope system 1000 includes an endoscope 100, a drive device 200, a manipulation device (controller) 300, a treatment tool 400, a video control device 500, and a display device 900.

The endoscope 100 is a device that is inserted into the lumen of the patient P to observe and treat an affected part. The endoscope 100 is detachable from the drive device 200. An internal path 101 is formed inside the endoscope 100. In the following description, a side of the endoscope 100 inserted into the lumen of the patient P is referred to as a "distal side A1" and a side of the endoscope 100 attached to the drive device 200 is referred to as a "proximal side A2."

The drive device 200 is detachably connected to the endoscope 100 and the manipulation device 300. The drive device 200 electrically drives the endoscope 100 by driving a built-in motor on the basis of a manipulation input to the manipulation device 300. Moreover, the drive device 200 drives a built-in pump or the like on the basis of the manipulation input to the manipulation device 300 to cause the endoscope 100 to perform supplied air suction. In the following description, "air supply" may include not only air supply but also water supply.

The manipulation device 300 is detachably connected to the drive device 200 via a manipulation cable 301. The manipulation device 300 may be able to communicate with the drive device 200 through wireless communication instead of wired communication. The scopist S can electrically drive the endoscope 100 by manipulating the manipulation device 300.

The treatment tool 400 is a device that is inserted into the internal path 101 of the endoscope 100 and then inserted into the lumen of the patient P to treat the affected part. In FIG. 1, the treatment tool 400 is inserted into the internal path 101 of the endoscope 100 from an instruments port 126.

The video control device 500 is detachably connected to the endoscope 100 and acquires a captured image from the endoscope 100. The video control device 500 causes the display device 900 to display the captured image acquired from the endoscope 100 and a GUI image or a CG image for the purpose of providing information to a manipulator.

The drive device 200 and the video control device 500 constitute a control device 600 that controls the electric endoscope system 1000. The control device 600 may further include a peripheral device such as a video printer. The drive device 200 and the video control device 500 may be an integrated device.

The display device 900 is a device capable of displaying an image such as an LCD. The display device 900 is connected to the video control device 500 via a display cable 901.

Figure 2:
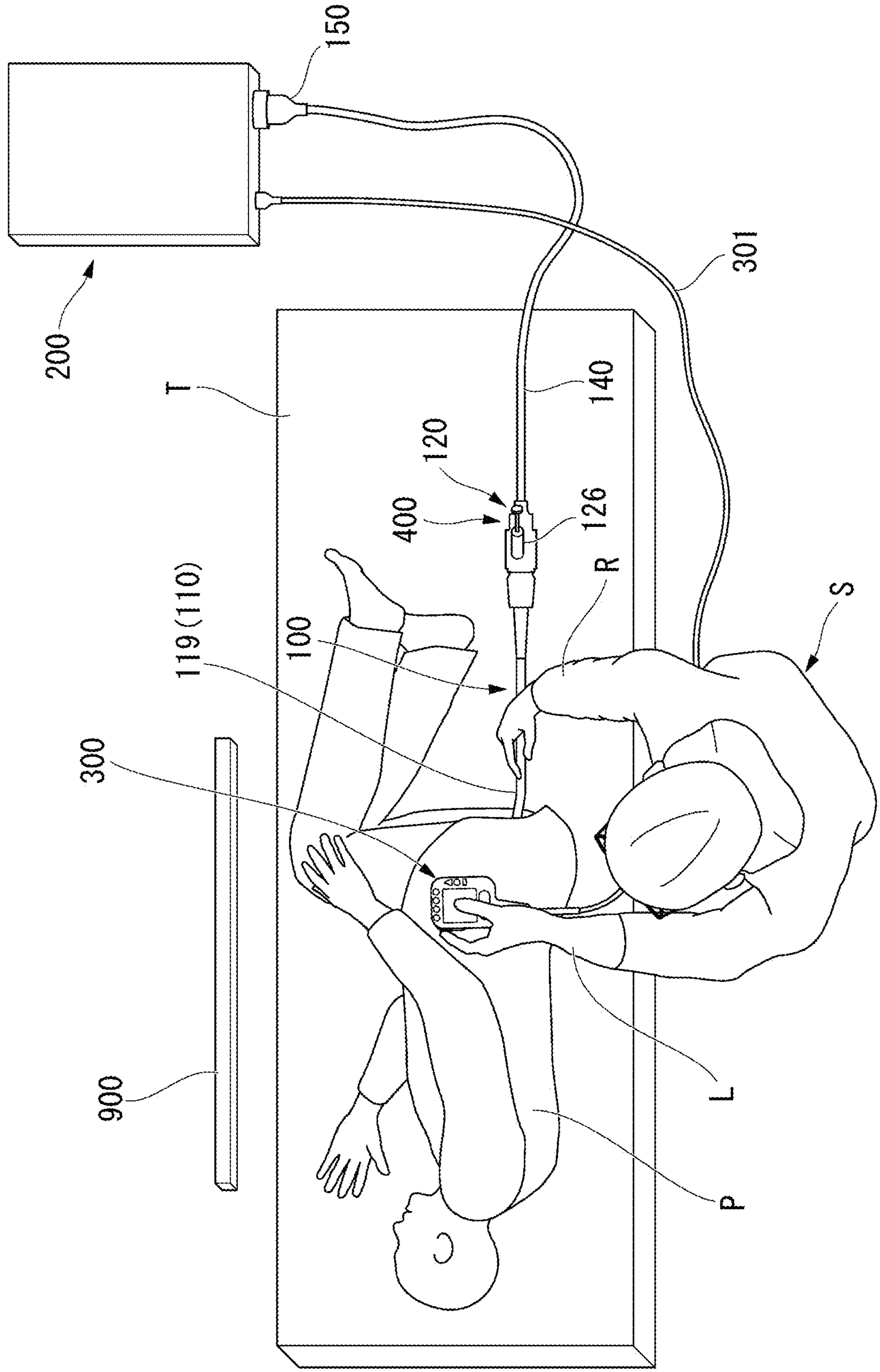
FIG. 2 illustrates an example of a view showing an endoscope and a manipulation device of the electric endoscope system used by a scopist.

FIG. 2 is a view showing the endoscope 100 and the manipulation device 300 used by the scopist S.

For example, the scopist S manipulates the endoscope 100 inserted into the lumen from the anus of the patient P with a right hand R and manipulates the manipulation device 300 with a left hand L while observing the imaging image displayed on the display device 900. Because the endoscope 100 and the manipulation device 300 are separated, the scopist S can manipulate the endoscope 100 and the manipulation device 300 independently in a state in which the endoscope 100 and the manipulation device 300 do not affect each other.

[Endoscope 100]

Figure 6:
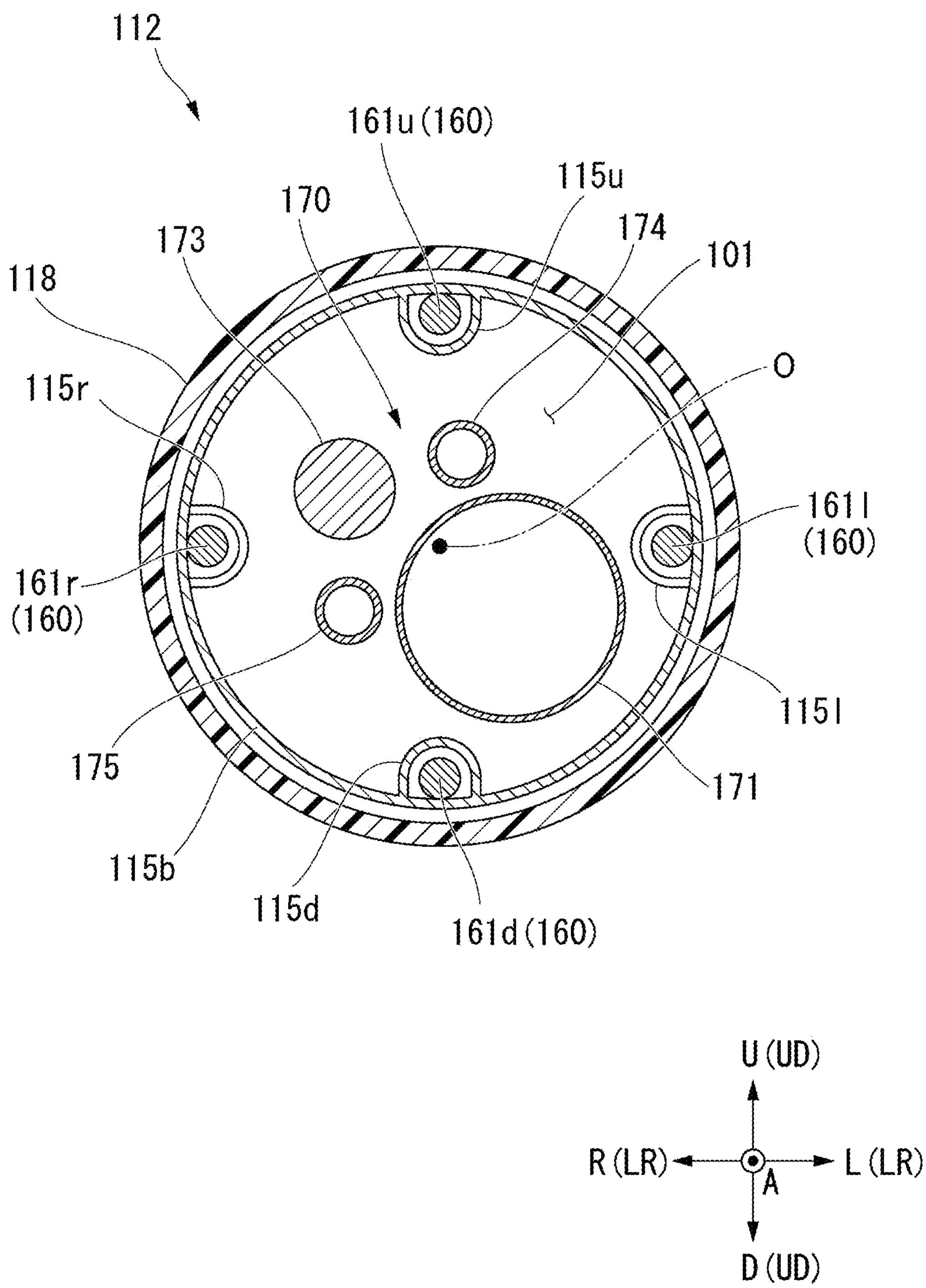
FIG. 6 illustrates an example of a cross-sectional view of the bending portion along line C1-C1 of FIGS. 4 and 5.

As shown in FIG. 1, the endoscope 100 includes an insertion portion 110, a connection portion 120, an extracorporeal flexible portion 140, a detachable portion 150, a bending wire 160 (see FIG. 6), and a built-in object 170 (see FIG. 6). The insertion portion 110, the connection portion 120, the extracorporeal flexible portion 140, and the detachable portion 150 are connected in order from the distal side.

Figure 3:
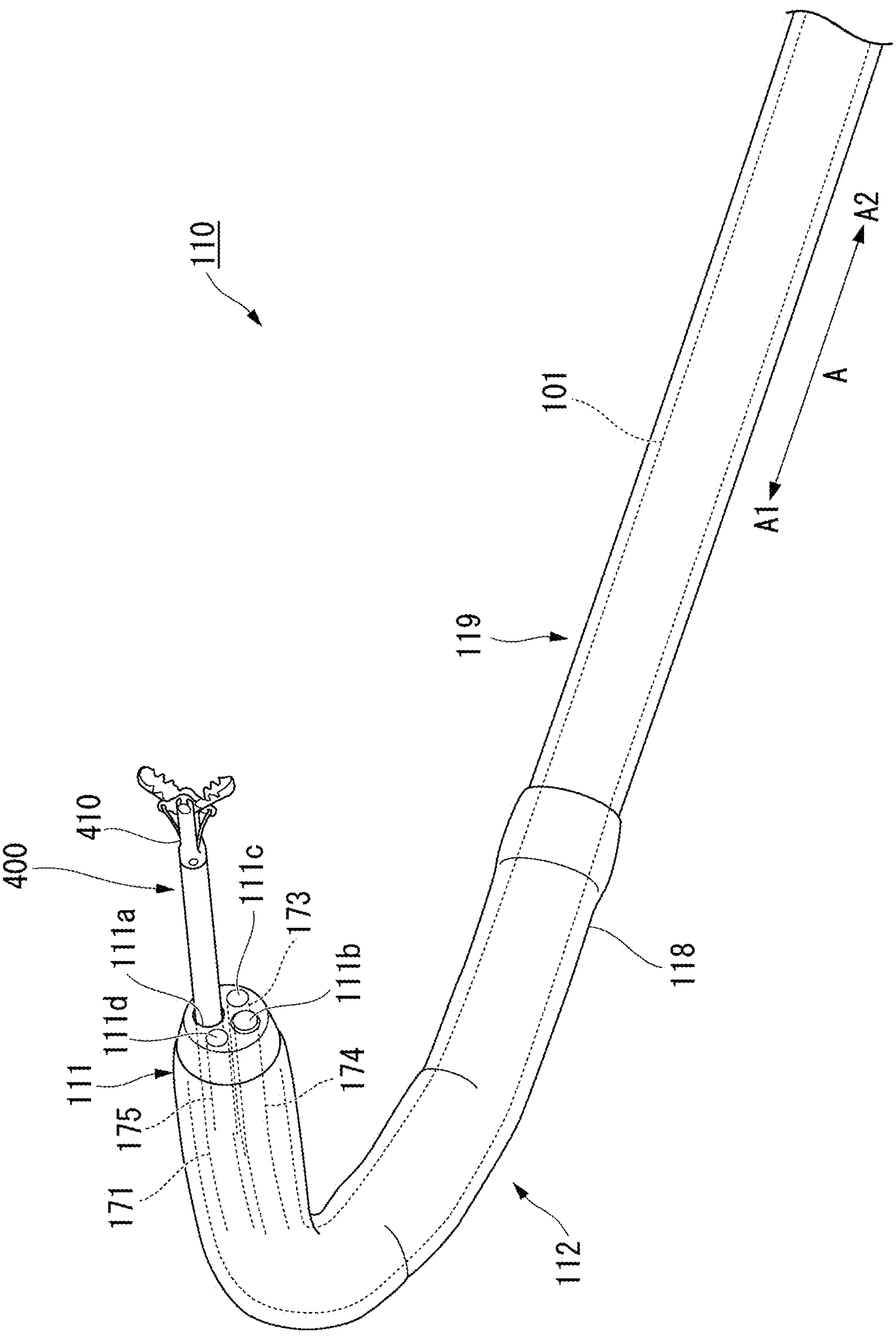
FIG. 3 illustrates an example of a view showing an insertion portion of the endoscope.

FIG. 3 is a view showing the insertion portion 110 of the endoscope 100.

Within the endoscope 100, the internal path 101 extending in a longitudinal direction A of the endoscope 100 is formed from the distal end of the insertion portion 110 to the proximal end of the detachable portion 150. The bending wire 160 and the built-in object 170 are inserted into the internal path 101.

The built-in object 170 includes a channel tube 171, a suction tube 172 (see FIG. 9), an imaging cable 173, a light guide 174, and an air/water supply tube 175.

[Insertion Portion 110]

The insertion portion 110 is an elongated long member that can be inserted into the lumen. The insertion portion 110 includes a distal end portion 111, a bending portion 112, and an intracorporeal flexible portion 119. The distal end portion 111, the bending portion 112, and the intracorporeal flexible portion 119 are connected in order from the distal side.

As shown in FIG. 3, the distal end portion 111 includes an opening 111*a*, an illumination portion 111*b*, an imaging portion 111*c*, and an air/water supply nozzle 111*d*. The opening 111*a* is an opening that communicates with the channel tube 171. As shown in FIG. 3, a treatment portion 410 such as a gripping forceps provided at the distal end of the treatment tool 400 into which the channel tube 171 is inserted protrudes from the opening 111*a*. The air/water supply nozzle 111*d* is an opening that communicates with the air/water supply tube 175. Water or air in a tank installed in the vicinity of the control device 600 is sent from the air/water supply nozzle 111*d* via the air/water supply tube 175.

The illumination portion 111*b* is connected to the light guide 174 that guides the illumination light, and emits illumination light that illuminates an imaging target. The imaging portion 111*c* includes an image sensor such as a CMOS and captures an imaging target. An imaging signal is sent to the video control device 500 via the imaging cable 173.

Figure 4:
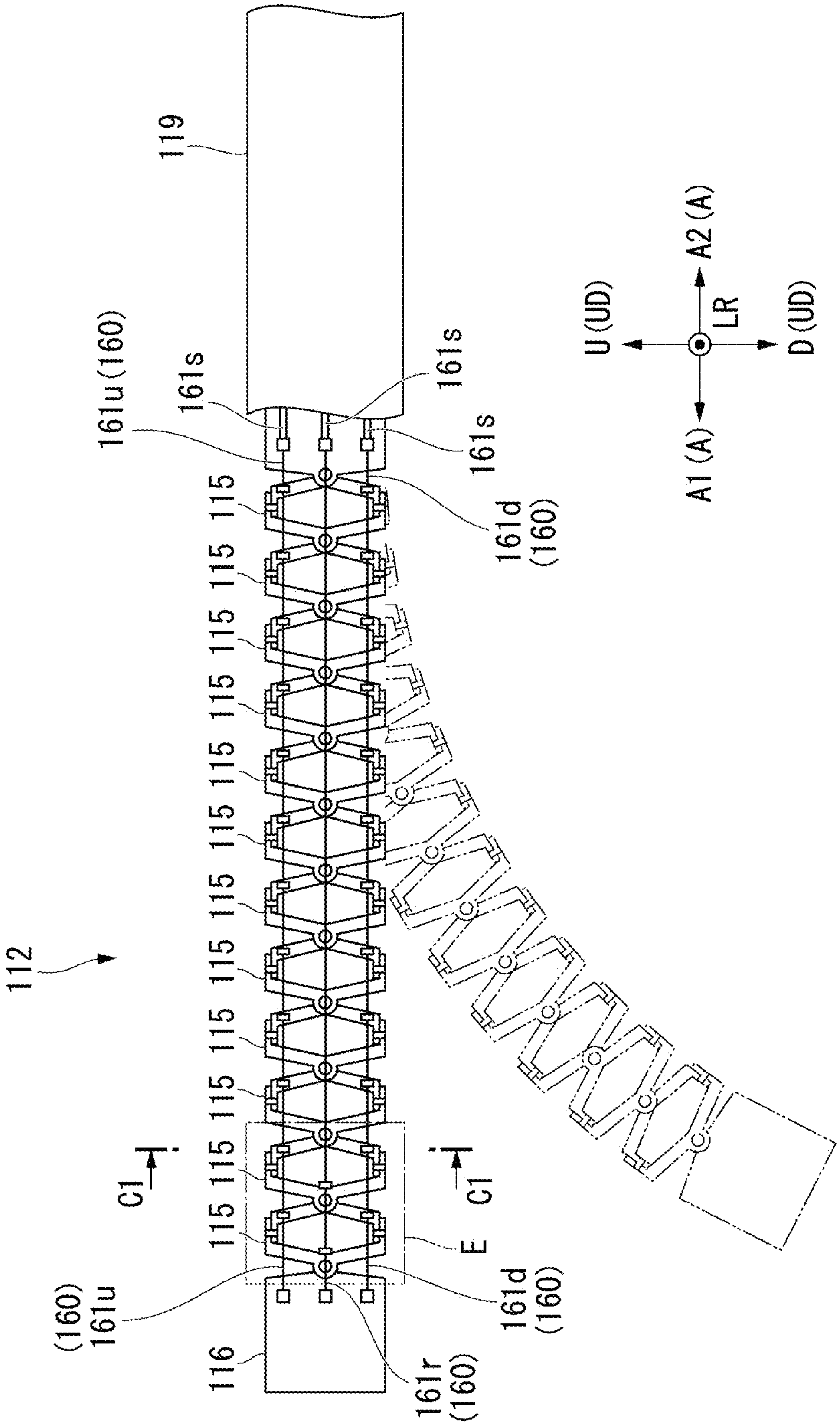
FIG. 4 illustrates an example of a view showing a part of a bending portion of the insertion portion in a cross-sectional view.

FIG. 4 is a view showing a part of the bending portion 112 in a cross-sectional view.

The bending portion 112 includes a plurality of joint rings (also referred to as bending pieces) 115, a distal end portion 116 connected to the distal ends of the plurality of joint rings 115, and an outer sheath 118 (see FIG. 3). The plurality of joint rings 115 and the distal end portion 116 are connected in a longitudinal direction A inside the outer sheath 118. The shapes and number of joint rings 115 provided in the bending portion 112 are not limited to those shown in FIG. 4.

Figure 5:
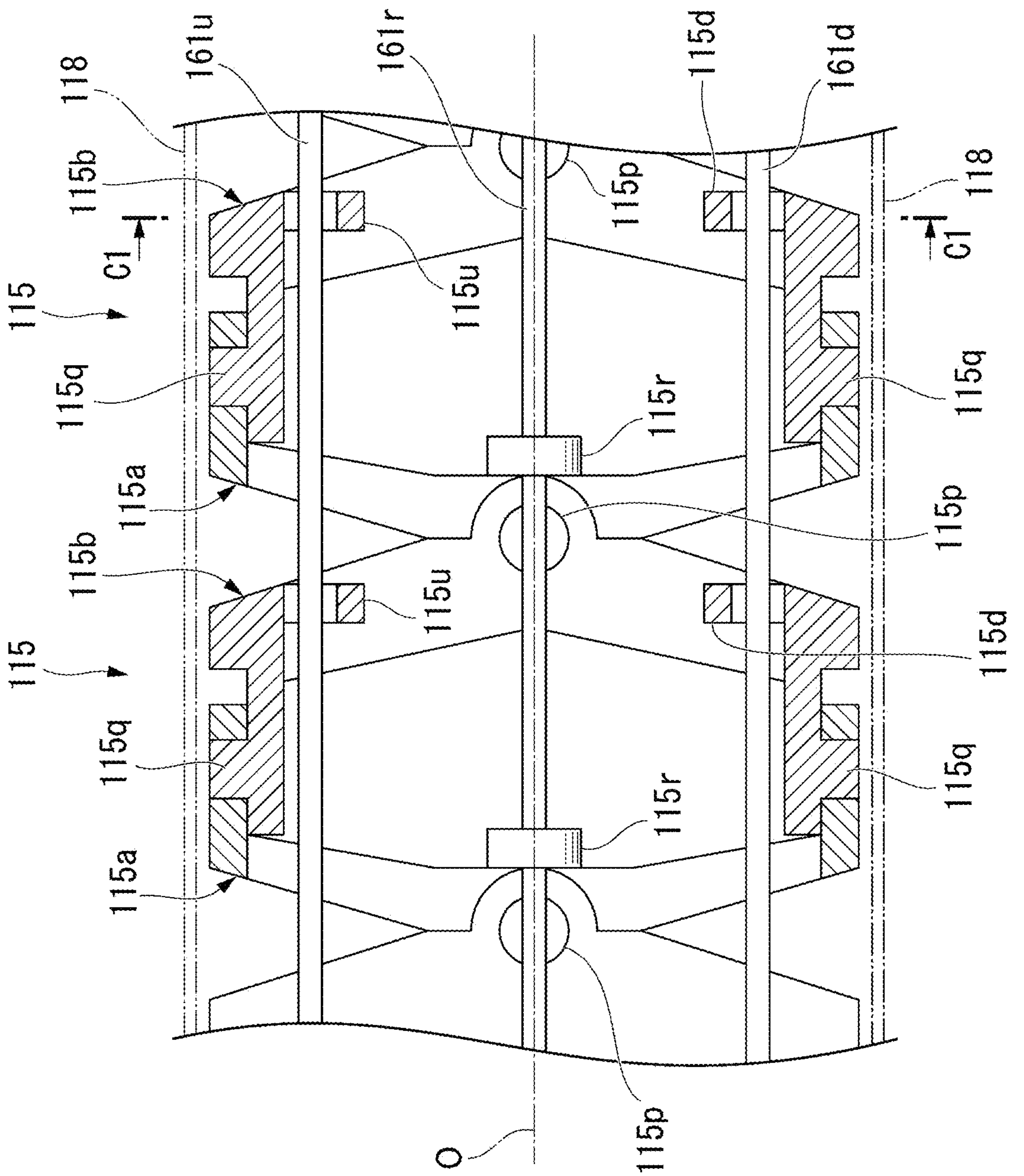
FIG. 5 illustrates an example of an enlarged view of a joint ring in a region E shown in FIG. 4.

FIG. 5 is an enlarged view of the joint ring 115 in a region E shown in FIG. 4.

The joint ring 115 is a short cylindrical member formed of a metal. The plurality of joint rings 115 are connected so that the internal spaces of the adjacent joint rings 115 become continuous spaces.

The joint ring 115 has a first joint ring 115*a* on the distal side and a second joint ring 115*b* on the proximal side. The first joint ring 115*a* and the second joint ring 115*b* are rotatably connected by a first rotation pin 115*p* in a vertical direction (also referred to as a "UD direction") perpendicular to the longitudinal direction A.

In the adjacent joint rings 115, the second joint ring 115*b* in the joint ring 115 on the distal side and the first joint ring 115*a* in the joint ring 115 on the proximal side are connected by a second rotation pin 115*q* in a left/right direction (an "LR direction") perpendicular to the longitudinal direction A and the UD direction.

The first joint ring 115*a* and the second joint ring 115*b* are alternately connected by the first rotation pin 115*p* and the second rotation pin 115*q*, and the bending portion 112 is freely bent in a desired direction.

FIG. 6 is a cross-sectional view of the bending portion 112 along line C1-C1 of FIGS. 4 and 5.

On the inner circumferential surface of the second joint ring 115*b*, the upper wire guide 115*u* and the lower wire guide 115*d* are formed. The upper wire guide 115*u* and the lower wire guide 115*d* are arranged on both sides between which a central axis O in the longitudinal direction A is sandwiched in the UD direction. On the inner circumferential surface of the first joint ring 115*a*, a left wire guide 1151 and a right wire guide 115*r* are formed. The left wire guide 1151 and the right wire guide 115*r* are arranged on both sides between which the central axis O in the longitudinal direction A is sandwiched in the LR direction.

On the upper wire guide 115*u*, the lower wire guide 115*d*, the left wire guide 1151, and the right wire guide 115*r*, a through-hole into which the bending wire 160 is inserted is formed in the longitudinal direction A.

The bending wire 160 is a wire for bending the bending portion 112. The bending wire 160 extends to the detachable portion 150 through the internal path 101. As shown in FIGS. 4 and 6, the bending wire 160 includes an upper bending wire 161*u*, a lower bending wire 161*d*, a left bending wire 1611, a right bending wire 161*r*, and four wire sheaths 161*s*.

As shown in FIG. 4, the upper bending wire 161*u*, the lower bending wire 161*d*, the left bending wire 1611, and the right bending wire 161*r* are inserted into the wire sheaths 161*s*. The distal end of the wire sheath 161*s* is attached to the joint ring 115 at the proximal end of the bending portion 112. The wire sheath 161*s* extends to the detachable portion 150.

The upper bending wire 161*u* and the lower bending wire 161*d* are wires for bending the bending portion 112 in the UD direction. The upper bending wire 161*u* is inserted into the upper wire guide 115*u*. The lower bending wire 161*d* is inserted into the lower wire guide 115*d*.

The distal ends of the upper bending wire 161*u* and the lower bending wire 161*d* are fixed to the distal end portion 116 of the distal end of the bending portion 112 as shown in FIG. 4. The distal ends of the upper bending wire 161*u* and the lower bending wire 161*d* fixed to the distal end portion 116 are arranged on both sides between which the central axis O in the longitudinal direction A is sandwiched in the UD direction.

The left bending wire 1611 and the right bending wire 161*r* are wires for bending the bending portion 112 in the LR direction. The left bending wire 1611 is inserted into the left wire guide 1151. The right bending wire 161*r* is inserted into the right wire guide 115*r*.

The distal ends of the left bending wire 1611 and the right bending wire 161*r* are fixed to the distal end portion 116 of the bending portion 112 as shown in FIG. 4. The distal ends of the left bending wire 1611 and the right bending wire 161*r* fixed to the distal end portion 116 are arranged on both sides between which the central axis O in the longitudinal direction A is sandwiched in the LR direction.

The bending portion 112 is freely bent in a desired direction by pulling or relaxing the bending wires 160 (the upper bending wire 161*u*, the lower bending wire 161*d*, the left bending wire 1611, and the right bending wire 161*r*).

As shown in FIG. 6, the bending wire 160, the channel tube 171, the imaging cable 173, the light guide 174, and the air/water supply tube 175 are inserted into the internal path 101 formed inside the bending portion 112.

The intracorporeal flexible portion 119 is a long and flexible tubular member. The bending wire 160, the channel tube 171, the imaging cable 173, the light guide 174, and the air/water supply tube 175 are inserted into the internal path 101 formed in the intracorporeal flexible portion 119.

[Connection Portion 120]

Figure 7:
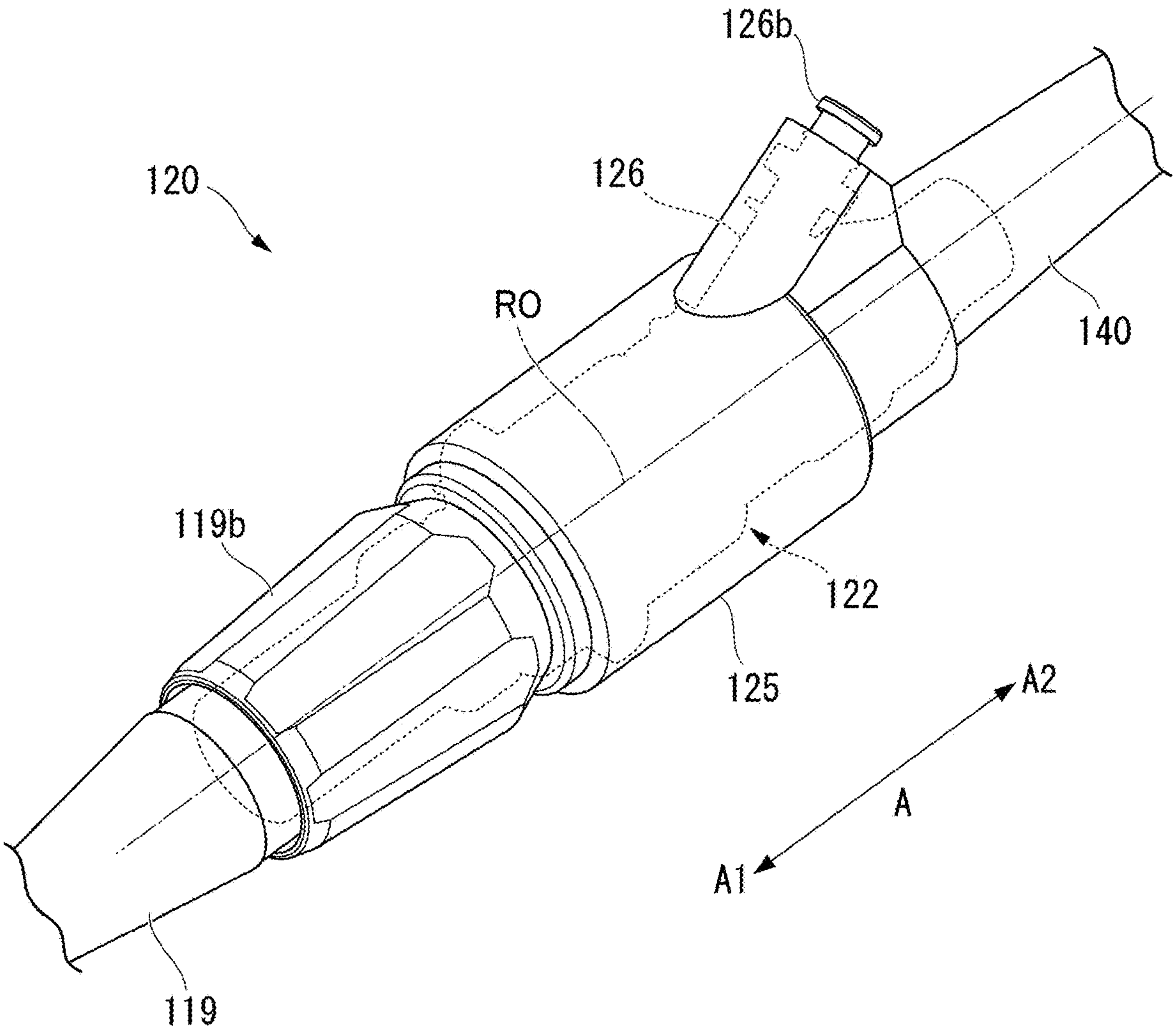
FIG. 7 illustrates an example of a perspective view of a connection portion of the endoscope.
Figure 8:
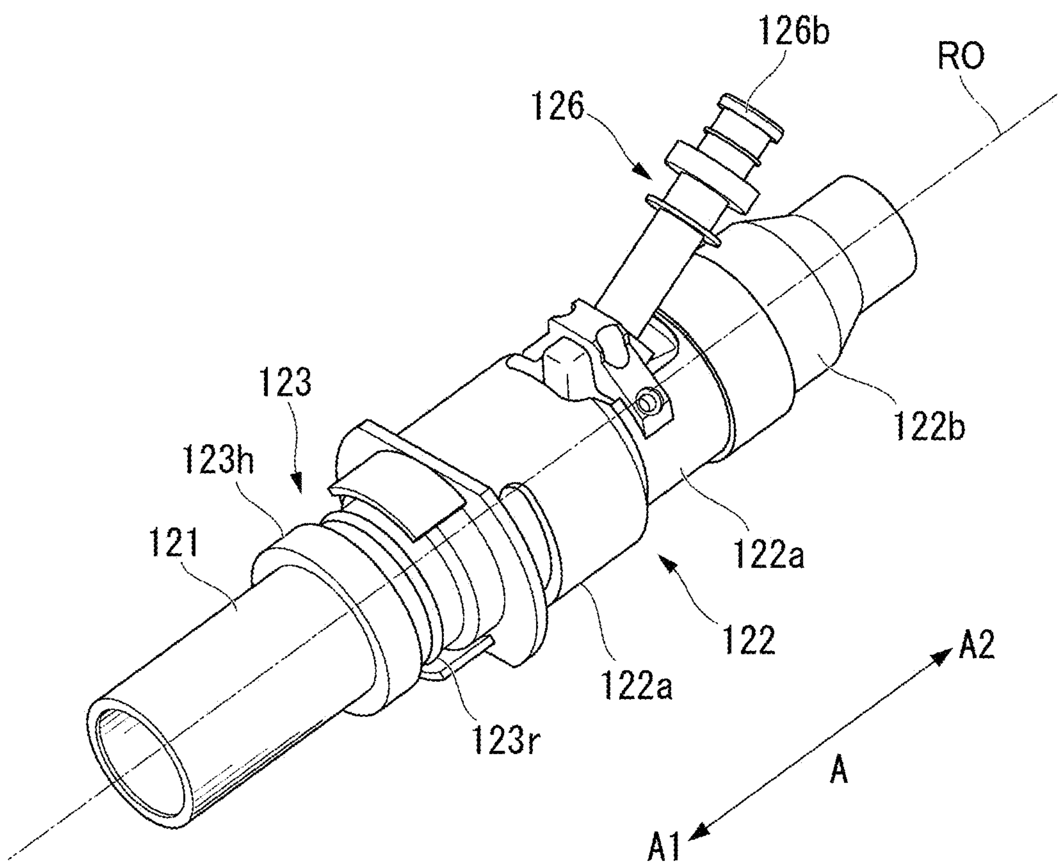
FIG. 8 illustrates an example of a perspective view of a part of the connection portion.

FIG. 7 is a perspective view of the connection portion 120. FIG. 8 is a perspective view of a part of the connection portion 120.

The connection portion 120 is a member that connects the intracorporeal flexible portion 119 and the extracorporeal flexible portion 140 of the insertion portion 110. The connection portion 120 includes a cylindrical member 121, a connection portion body 122, a sealing portion 123, a bearing portion 124, a cover member 125, an instruments port 126, and a trifurcated branch tube 127.

Figure 9:
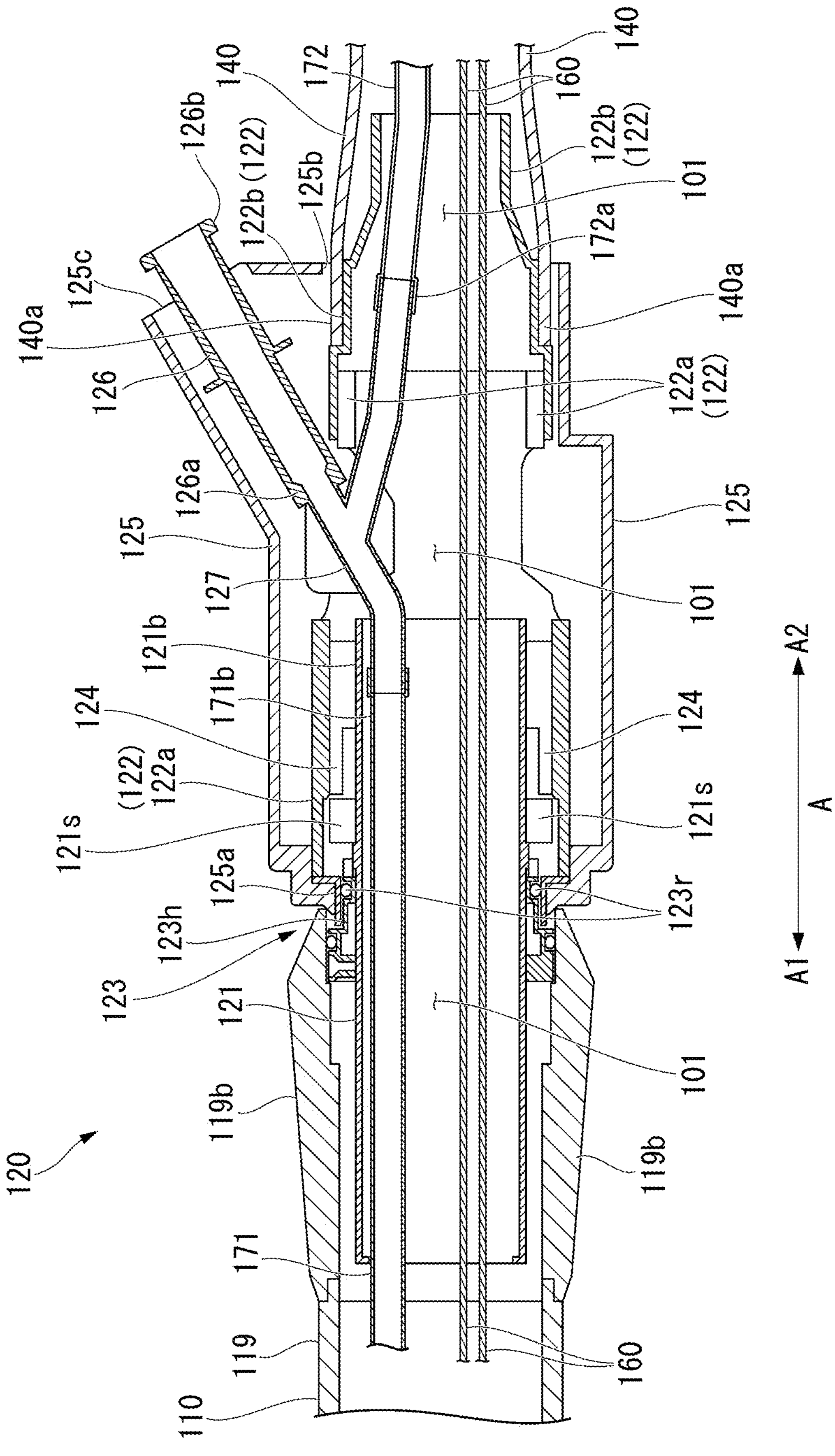
FIG. 9 illustrates an example of a cross-sectional view of the connection portion.

FIG. 9 is a cross-sectional view of the connection portion 120.

The cylindrical member 121 is formed in a cylindrical shape. The internal space of the cylindrical member 121 communicates with the internal space of the intracorporeal flexible portion 119 and forms a part of the internal path 101. The bending wire 160, the channel tube 171, the imaging cable 173, the light guide 174, and the air/water supply tube 175 are inserted into the internal space of the cylindrical member 121. A magnetic ring 121*s* is attached to an outer circumferential surface of the cylindrical member 121 in a circumferential direction.

The connection portion body 122 is formed in a substantially cylindrical shape. The connection portion body 122 has a distal end portion 122*a* and a proximal end portion 122*b*. A proximal end portion 121*b* of the cylindrical member 121 is inserted into a distal end opening of the distal end portion 122*a*. The distal end portion 140*a* of the extracorporeal flexible portion 140 is joined to the proximal end portion 122*b* by adhesive, heat fusion, or the like. The internal space of the connection portion body 122 communicates with the internal space of the extracorporeal flexible portion 140 and forms a part of the internal path 101.

The sealing portion 123 has a housing 123*h* and a ring 123*r*. The inner side of the housing 123*h* is fixed to the outer circumference of the cylindrical member 121. The outer side of the housing 123*h* is in contact with an inner circumferential surface of the distal end portion 125*a* of the cover member 125 via the ring 123*r*.

Figure 10:
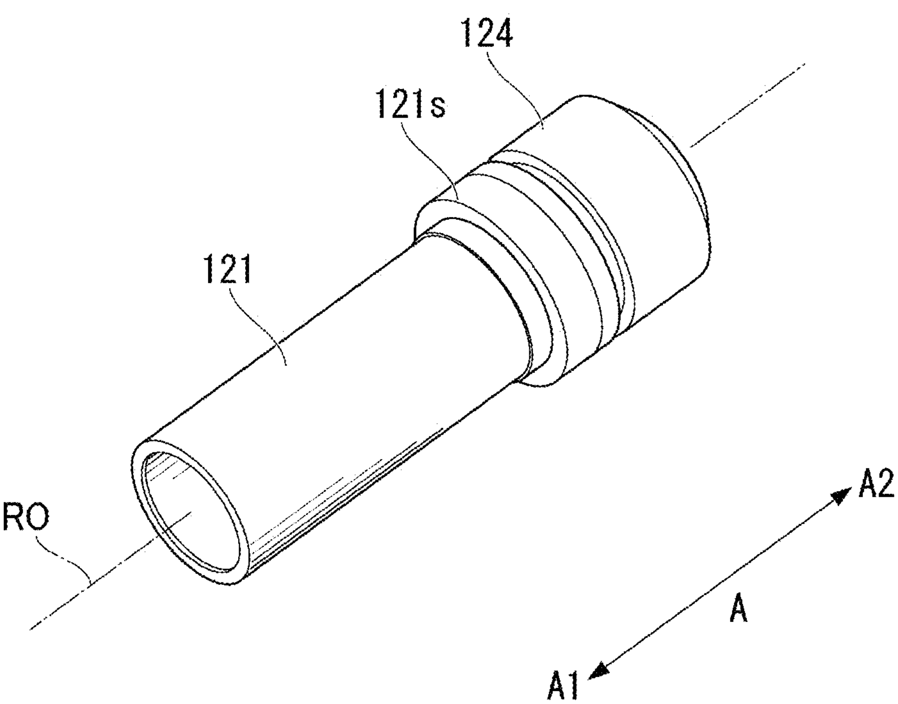
FIG. 10 illustrates an example of a perspective view of a cylindrical member and a bearing portion of the connection portion.

FIG. 10 is a perspective view of the cylindrical member 121 and the bearing portion 124.

The bearing portion 124 connects the connection portion body 122 and the cylindrical member 121 rotatably around a rotation axis RO extending in the longitudinal direction A. Specifically, the bearing portion 124 is fixed to the connection portion body 122. The bearing portion 124 supports the cylindrical member 121 rotatably around the rotation axis RO extending in the longitudinal direction A.

The connection portion body 122 has a magnetic sensor (not shown) that detects the rotation of the magnetic ring 121*s* and can detect a rotation angle of the cylindrical member 121 with respect to the connection portion body 122. The detected rotation angle is transmitted to the control device 600 via a transmission cable (not shown).

A proximal end portion 119*b* of the intracorporeal flexible portion 119 is fixed to the outer side of the housing 123*h*. Therefore, the intracorporeal flexible portion 119, the housing 123*h*, and the cylindrical member 121 are integrated and rotated with respect to the connection portion body 122. The proximal end portion 119*b* of the intracorporeal flexible portion 119, the housing 123*h*, and the cylindrical member 121 are also referred to as a "passive rotation portion."

The cover member 125 is a member that covers the outer circumference of the connection portion body 122. The cover member 125 has a first opening 125*b* through which the extracorporeal flexible portion 140 passes and a second opening 125*c* through which the instruments port 126 passes. A gap between the first opening 125*b* and the extracorporeal flexible portion 140 is sealed by a sealing member. A gap between the second opening 125*c* and the instruments port 126 is sealed by a sealing member.

The instruments port 126 is an insertion port into which the treatment tool 400 is inserted. The instruments port 126 is formed in a cylindrical shape and is attached to the cover member 125. A proximal end portion 126*b* of the instruments port 126 protrudes from the second opening 125*c* of the cover member 125.

The trifurcated branch tube 127 connects a proximal end portion 171*b* of the channel tube 171, a distal end portion 126*a* of the instruments port 126, and a distal end portion 172*a* of the suction tube 172. The channel tube 171 and the suction tube 172 are connected via the trifurcated branch tube 127. Moreover, the instruments port 126 and the channel tube 171 are connected via the trifurcated branch tube 127. The scopist S can insert the treatment tool 400 from the proximal end portion 126*b* of the instruments port 126 and insert the treatment tool 400 into the channel tube 171.

The intracorporeal flexible portion 119 and the extracorporeal flexible portion 140 are connected rotatably around the rotation axis RO extending in the longitudinal direction A by the connection portion 120. Therefore, as shown in FIG. 2, when the scopist S rotates the intracorporeal flexible portion 119 of the insertion portion 110 around the rotation axis RO extending in the longitudinal direction A, the extracorporeal flexible portion 140 extending to the vicinity of the drive device 200 is not rotated and only the intracorporeal flexible portion 119 can be rotated. Therefore, the scopist S can easily rotate and manipulate the intracorporeal flexible portion 119.

On the other hand, because a frictional force is generated between the intracorporeal flexible portion 119 and the extracorporeal flexible portion 140 when they rotate relative to each other, they do not rotate relative to each other unless a predetermined force or more is applied. The above-described friction force is adjusted so that the intracorporeal flexible portion 119 does not rotate with respect to the extracorporeal flexible portion 140 unless the scopist S rotates the intracorporeal flexible portion 119 of the insertion portion 110. Therefore, for example, even when the scopist S separates the right hand R from the intracorporeal flexible portion 119 to manipulate the treatment tool 400, the intracorporeal flexible portion 119 does not rotate with respect to the extracorporeal flexible portion 140.

Moreover, when the scopist S rotates the intracorporeal flexible portion 119 of the insertion portion 110 around the rotation axis RO extending in the longitudinal direction A, the instruments port 126 attached to the connection portion body 122, which is a portion that does not rotate in cooperation with the intracorporeal flexible portion 119, does not rotate. Because the position of the instruments port 126 into which the treatment tool 400 is inserted does not change, the scopist S can easily manipulate the treatment tool 400.

A proximal end portion 121*b* of the cylindrical member 121 is inserted into the connection portion body 122. Therefore, the bending wire 160 or the like inserted into the cylindrical member 121 and the connection portion body 122 mainly passes through the internal space of the cylindrical member 121 and is unlikely to come into contact with the connection portion body 122 rotating relative to the cylindrical member 121. Therefore, even when the cylindrical member 121 and the connection portion body 122 rotate relative to each other, the bending wire 160 or the like is twisted throughout the long internal path 101, and therefore torsional stress is unlikely to become concentrated.

[Extracorporeal Flexible Portion 140]

The extracorporeal flexible portion 140 is a long tubular member. The bending wire 160, the imaging cable 173, the light guide 174, the suction tube 172 (see FIG. 9), and the air/water supply tube 175 are inserted into the internal path 101 formed inside the extracorporeal flexible portion 140.

[Detachable Portion 150]

As shown in FIG. 1, the detachable portion 150 includes a first detachable portion 1501 attached to the drive device 200 and a second detachable portion 1502 attached to the video control device 500. In addition, the first detachable portion 1501 and the second detachable portion 1502 may be an integrated detachable portion.

The internal path 101 formed inside the extracorporeal flexible portion 140 branches into the first detachable portion 1501 and the second detachable portion 1502. The bending wire 160, the suction tube 172, and the air/water supply tube 175 are inserted into the first detachable portion 1501. The imaging cable 173 and the light guide 174 are inserted into the second detachable portion 1502.

Figure 11:
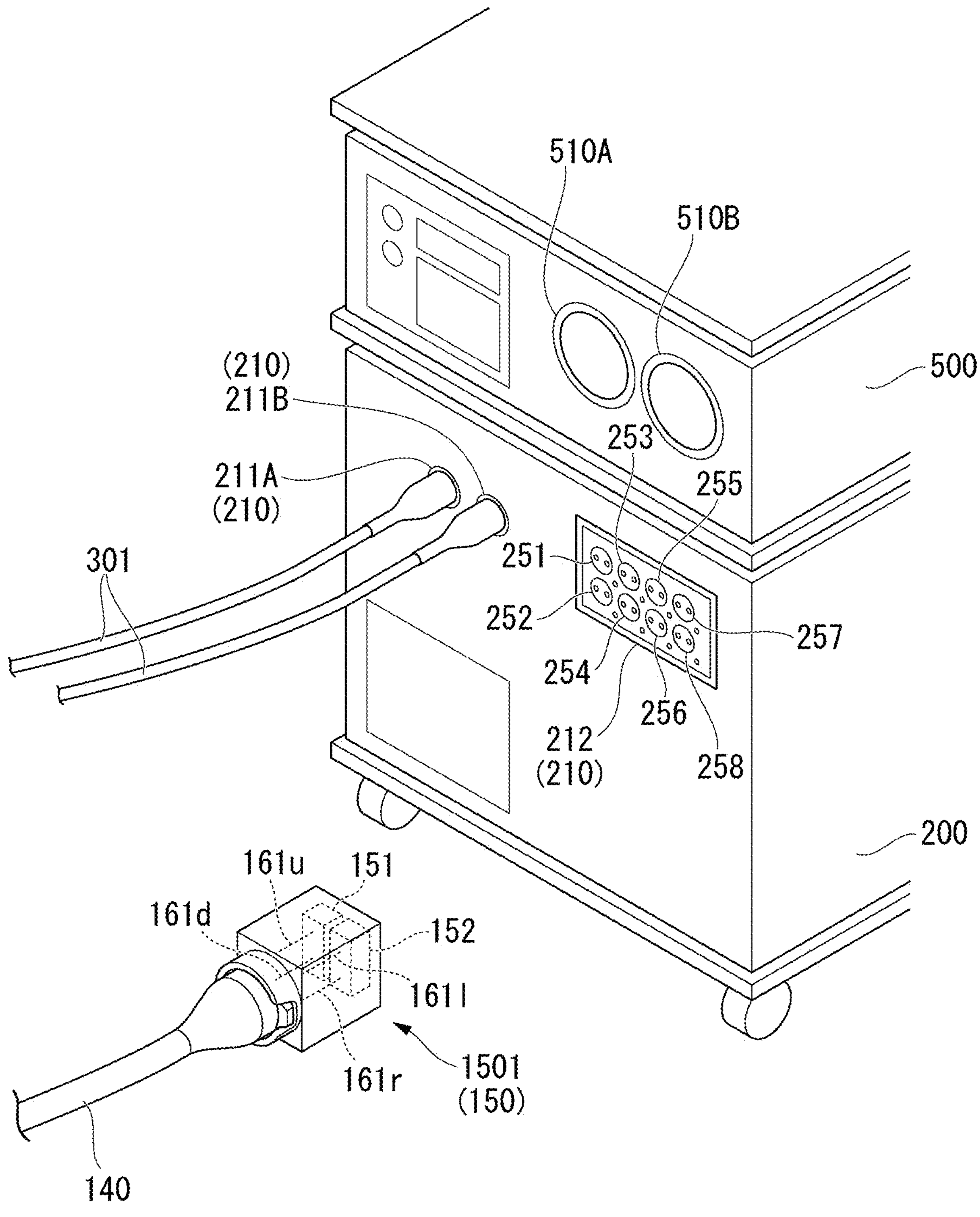
FIG. 11 illustrates an example of a view showing a first detachable portion of the endoscope before attachment to a drive device of the electric endoscope system.

FIG. 11 is a view showing the first detachable portion 1501 before attachment to the drive device 200.

The first detachable portion 1501 includes a detachable upper/lower bending wire portion 151, a detachable left/right bending wire portion 152, and a scope ID storage portion 158.

The detachable upper/lower bending wire portion 151 is a mechanism for detachably connecting wires (the upper bending wire 161*u* and the lower bending wire 161*d*) for bending the bending portion 112 in the UD direction to the drive device 200.

The detachable left/right bending wire portion 152 is a mechanism for detachably connecting wires (the left bending wire 1611 and the right bending wire 161*r*) for bending the bending portion 112 in the LR direction to the drive device 200.

Because the detachable left/right bending wire portion 152 has a structure equivalent to that of the detachable upper/lower bending wire portion 151, illustration and description thereof are omitted.

Figure 12:
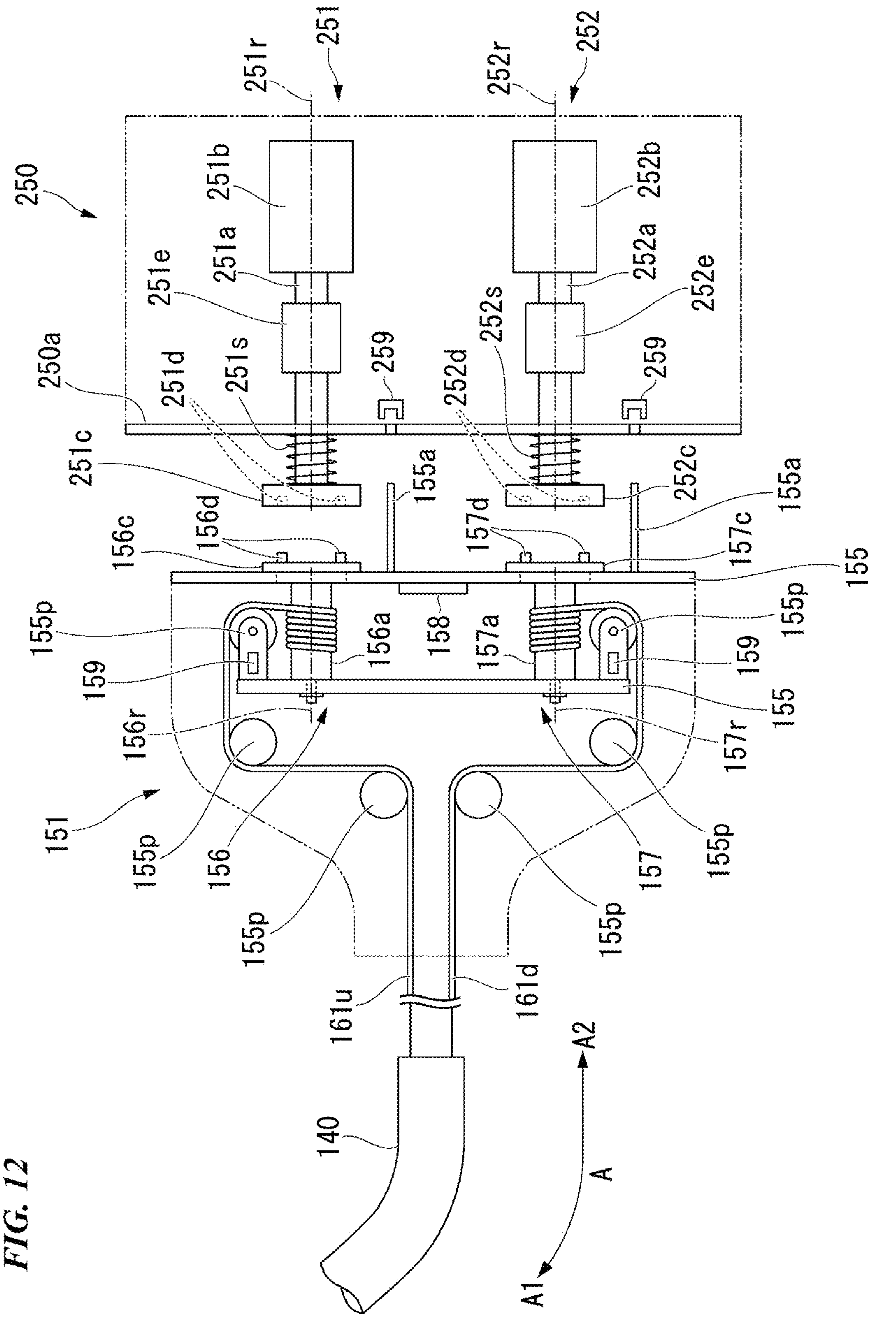
FIG. 12 illustrates an example of a view showing a detachable upper/lower bending wire portion of the first detachable portion before attachment to the drive device.
Figure 13:
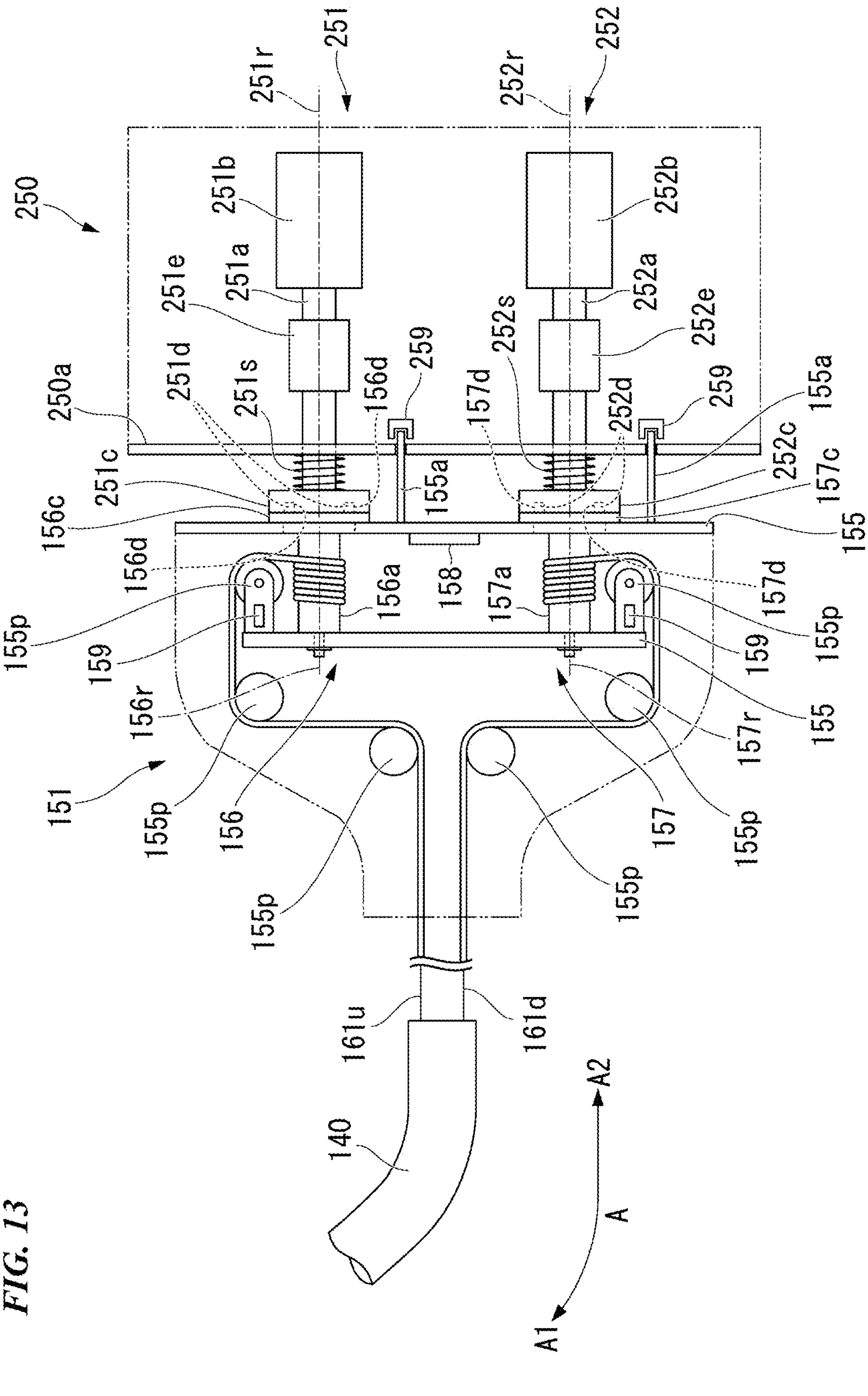
FIG. 13 illustrates an example of a view showing the detachable upper/lower bending wire portion attached to the drive device.

FIG. 12 is a view showing the detachable upper/lower bending wire portion 151 before attachment to the drive device 200. FIG. 13 is a view showing the detachable upper/lower bending wire portion 151 attached to the drive device 200. The detachable upper/lower bending wire portion 151 includes a support member 155, a first driven portion 156, a second driven portion 157, and a tension sensor 159.

The support member 155 supports the first driven portion 156, the second driven portion 157, and the scope ID storage portion 158. The support member 155 includes an attachment/detachment detection dog 155*a* arranged on the proximal side of the detachable upper/lower bending wire portion 151, and a plurality of bend pulleys 155*p*.

The bend pulley 155*p* changes a transport direction of the upper bending wire 161*u* inserted into the extracorporeal flexible portion 140 and guides the upper bending wire 161*u* to the first driven portion 156. Moreover, the bend pulley 155*p* changes the transport direction of the lower bending wire 161*d* inserted into the extracorporeal flexible portion 140 and guides the lower bending wire 161*d* to the second driven portion 157.

The first driven portion (driving force transmission portion) 156 is a member to which a driving force for driving the bending portion 112 (movable portion) is input. In the present embodiment, the first driven portion 156 is a rotation drum. The first driven portion 156 is supported by the support member 155 so that the first driven portion 156 can rotate around the first drum rotation axis 156*r* extending in the longitudinal direction A. The first driven portion 156 includes a first winding pulley 156*a* and a first coupling portion 156*c*. In addition, the first driven portion 156 is not limited to the rotation drum.

The first winding pulley 156*a* pulls or sends the upper bending wire 161*u* by rotating around the first drum rotation axis 156*r*. By rotating the first winding pulley 156*a* clockwise from the distal side to the proximal side, the upper bending wire 161*u* is wound around the first winding pulley 156*a* and pulled. In contrast, the first winding pulley 156*a* rotates counterclockwise, and therefore the upper bending wire 161*u* is sent from the first winding pulley 156*a*. With this configuration, even if an amount of advanceable and retractable movement of the upper bending wire 161*u* is large, a pulled portion is compactly stored and does not take up space.

The first coupling portion 156*c* is a disc member that rotates around the first drum rotation axis 156*r*. The first coupling portion 156*c* is fixed to the proximal end of the first winding pulley 156*a* and rotates integrally with the first winding pulley 156*a*. The first coupling portion 156*c* is exposed on the proximal side of the detachable upper/lower bending wire portion 151. Two first fitting convex portions 156*d* are formed on the surface of the proximal side of the first coupling portion 156*c*. The two first fitting convex portions 156*d* are formed on both sides between which the first drum rotation axis 156*r* is sandwiched.

The second driven portion 157 is a member to which a driving force driving the bending portion 112 (movable portion) is input. In the present embodiment, the second driven portion 157 is a rotation drum. The second driven portion 157 is supported by the support member 155 so that the second driven portion 157 can be rotated around the second drum rotation axis 157*r* extending along the longitudinal direction A. The second driven portion 157 includes a second winding pulley 157*a* and a second coupling portion 157*c*. In addition, the second driven portion 157 is not limited to the rotation drum.

The second winding pulley 157*a* pulls or sends the lower bending wire 161*d* by rotating around the second drum rotation axis 157*r*. By rotating the second winding pulley 157*a* counterclockwise from the distal side to the proximal side, the lower bending wire 161*d* is wound around the second winding pulley 157*a* and pulled. In contrast, the second winding pulley 157*a* rotates clockwise, and therefore the lower bending wire 161*d* is sent from the second winding pulley 157*a*.

The second coupling portion 157*c* is a disc member that rotates around the second drum rotation axis 157*r*. The second coupling portion 157*c* is fixed to the proximal end of the second winding pulley 157*a* and rotates integrally with the second winding pulley 157*a*. The second coupling portion 157*c* is exposed on the proximal side of the detachable upper/lower bending wire portion 151. Two second fitting convex portions 157*d* are formed on the surface of the proximal side of the second coupling portion 157*c*. The two second fitting convex portions 157*d* are formed on both sides between which the second drum rotation axis 157*r* is sandwiched.

In the following description, when the first driven portion 156 and the second driven portion 157 are not distinguished, they are referred to as "driven portions 15X." The number of driven portions 15X required to drive the endoscope 100 is four.

The scope ID storage portion 158 has a non-volatile memory that stores a scope ID of the endoscope 100. The scope ID is an ID indicating the type, specifications, and the like of the endoscope 100. The scope ID is acquired by a drive controller 260 via electrical wiring (not shown). On the basis of the acquired scope ID, the drive controller 260 can recognize the number of driven portions 15X that need to be driven in the first detachable portion 1501 that is attached, the arrangement of the driven portions 15X that need to be driven, and the like.

The tension sensor 159 detects the tension of the upper bending wire 161*u* and the lower bending wire 161*d*. A detection result of the tension sensor 159 is acquired by the drive controller 260 via electrical wiring (not shown).

[Drive Device 200]

Figure 14:
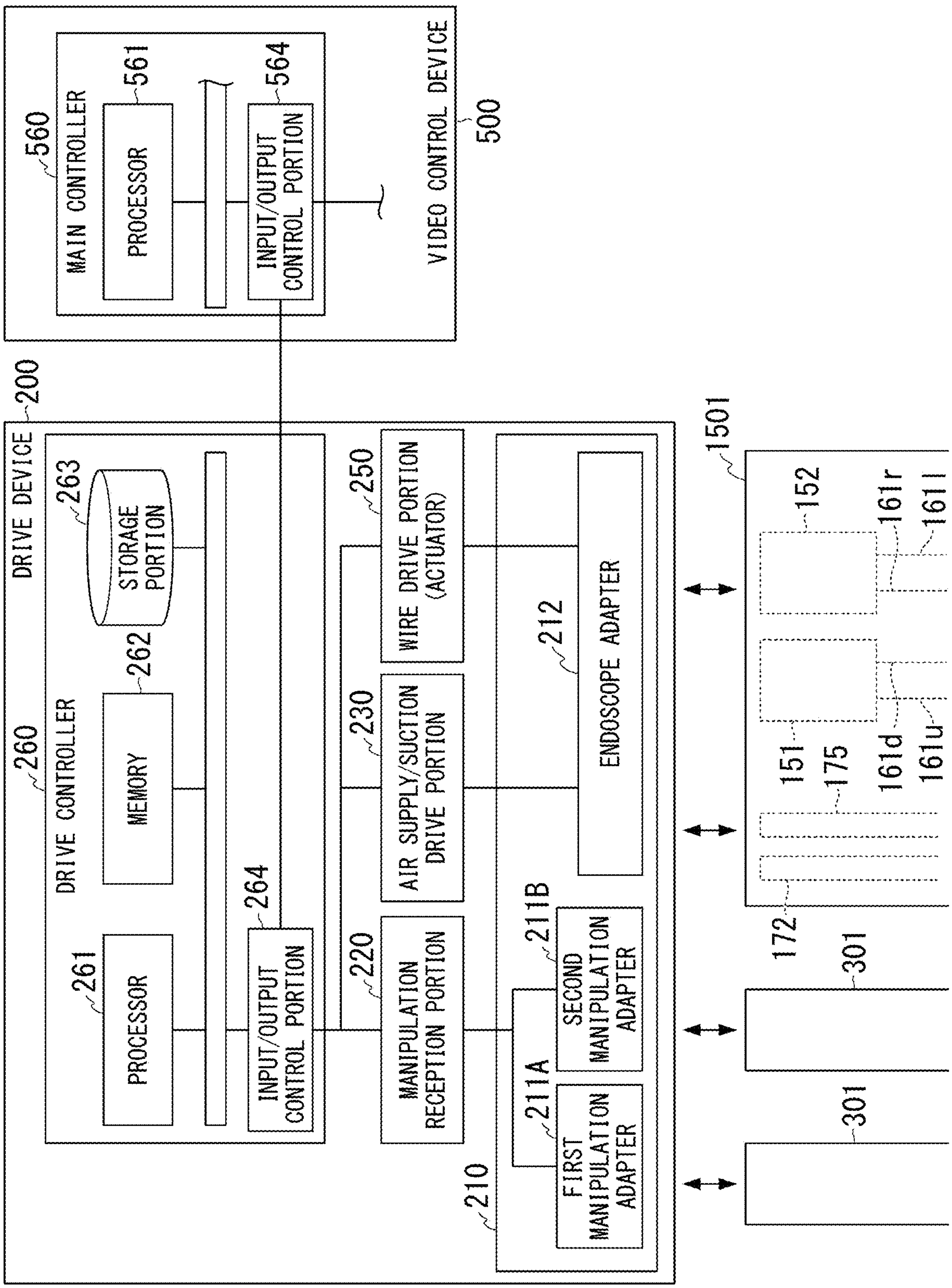
FIG. 14 illustrates an example of a functional block diagram of the drive device.

FIG. 14 is a functional block diagram of the drive device 200.

The drive device 200 includes an adapter 210, a manipulation reception portion 220, an air supply/suction drive portion 230, a wire drive portion (actuator) 250, and the drive controller 260.

The adapter 210 includes a first manipulation adapter 211A, a second manipulation adapter 211B, and an endoscope adapter 212, as shown in FIG. 11. The first manipulation adapter 211A and the second manipulation adapter are adapters to which the manipulation cable 301 is detachably connected.

Figure 15:
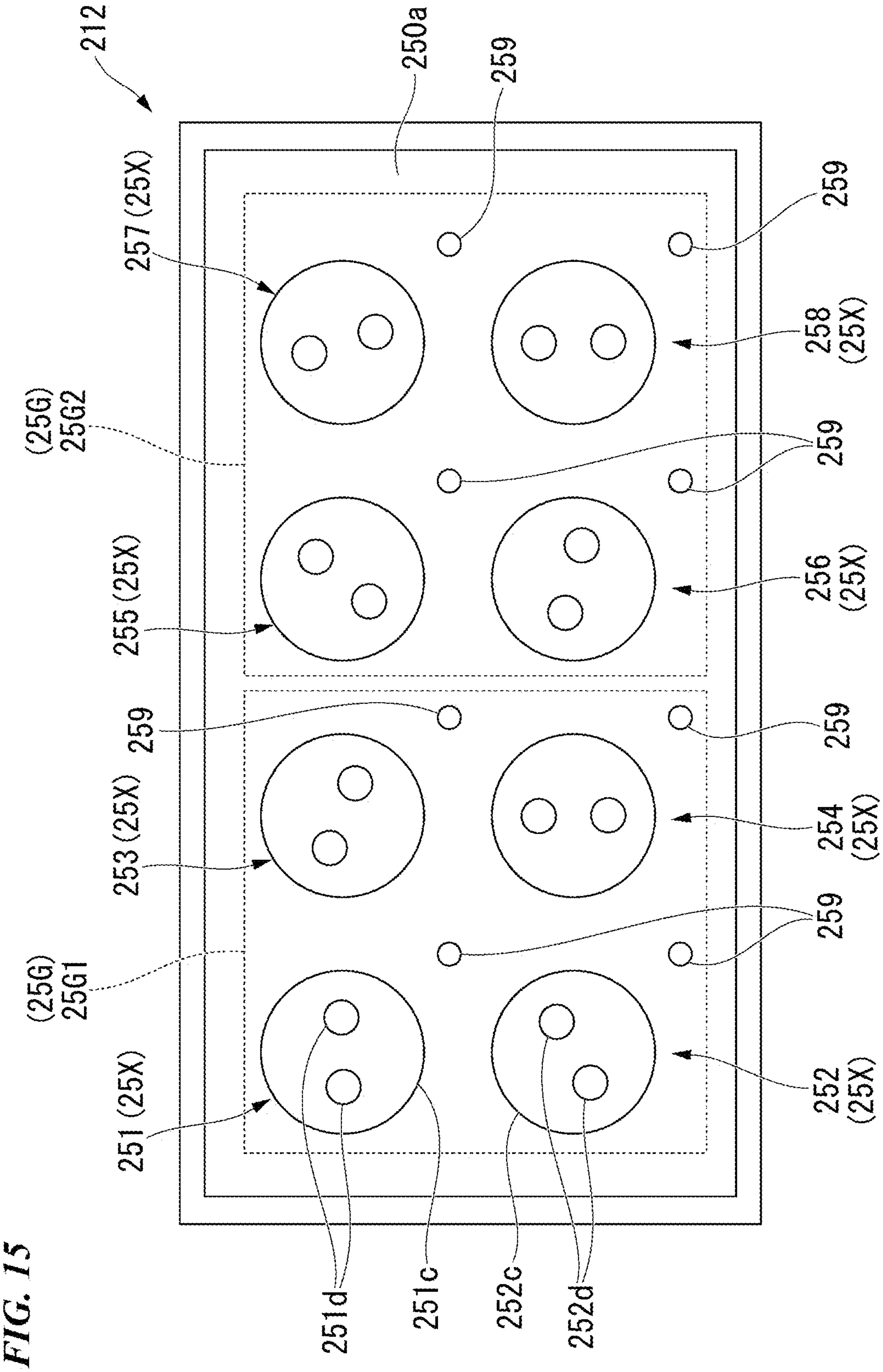
FIG. 15 illustrates an example of a view showing an endoscope adapter of the drive device.

FIG. 15 is a view showing the endoscope adapter 212.

The endoscope adapter 212 is an adapter to which the first detachable portion 1501 of the endoscope 100 is detachably connected. The endoscope adapter 212 is provided to surround the wire drive portion 250. When the first detachable portion 1501 is connected to the endoscope adapter 212, the detachable upper/lower bending wire portion 151 and the detachable left/right bending wire portions 152 can be coupled with the wire drive portion 250.

The manipulation reception portion 220 receives a manipulation input from the manipulation device 300 via the manipulation cable 301. When the manipulation device 300 and the drive device 200 perform communication according to wireless communication instead of wired communication, the manipulation reception portion 220 has a known wireless reception module.

The air supply/suction drive portion 230 is connected to the suction tube 172 and the air/water supply tube 175 inserted into the internal path 101 of the endoscope 100. The air supply/suction drive portion 230 includes a pump or the like and supplies air or water to the air/water supply tube 175. Moreover, the air supply/suction drive portion 230 suctions air from the suction tube 172.

The wire drive portion (actuator) 250 drives the bending wire 160 by coupling with the detachable upper/lower bending wire portion 151 and the detachable left/right bending wire portion 152.

As shown in FIGS. 10 and 12, the wire drive portion 250 includes a support member 250*a*, a first drive portion (first actuator) 251, a second drive portion (second actuator) 252, a third drive portion (third actuator) 253, a fourth drive portion (fourth actuator) 254, a fifth drive portion (fifth actuator) 255, a sixth drive portion (sixth actuator) 256, a seventh drive portion (seventh actuator) 257, an eighth drive portion (eighth actuator) 258, and a detachable sensor 259.

In the following description, when the first drive portion 251, the second drive portion 252, the third drive portion 253, the fourth drive portion 254, the fifth drive portion 255, the sixth drive portion 256, the seventh drive portion 257, and the eighth drive portion 258 are not distinguished, they are referred to as "drive portions 25X." The number of drive portions 25X (eight) is greater than the number of driven portions 15X required to drive the endoscope 100 (four). In addition, the number of drive portions 25X provided in the wire drive portion 250 is not limited to eight.

The plurality of drive portions 25X are arranged in a grid shape when viewed from the distal side A1. In the present embodiment, four drive portions 25X among the eight drive portions 25X are arrayed in a horizontal direction and two drive portions 25X are arrayed in a vertical direction. In addition, an array aspect of the plurality of drive portions 25X is not limited to this.

The endoscope adapter 212 can be connected to the first detachable portion 1501 in various aspects. The endoscope adapter 212 shown in FIG. 1 is connected to the first detachable portion 1501 so that the first drive portion 251, the second drive portion 252, the third drive portion 253, and the fourth drive portion 254 drive the bending wire 160. Moreover, the endoscope adapter 212 may be connected to the first detachable portion 1501 so that a fifth drive portion 255, a sixth drive portion 256, a seventh drive portion 257, and an eighth drive portion 258 drive the bending wire 160. That is, two first detachable portions 1501 may be simultaneously connected to the endoscope adapter 212.

A plurality of drive portions 25X to which one first detachable portion 1501 is attached are referred to as a "drive portion group 25G." In the present embodiment, the first drive portion 251, the second drive portion 252, the third drive portion 253, and the fourth drive portion 254 to which one of the two first detachable portions 1501 capable of being attached to the endoscope adapter 212 is attached are referred to as a "first drive portion group 25G1." Moreover, the fifth drive portion 255, the sixth drive portion 256, the seventh drive portion 257, and the eighth drive portion 258 to which the other first detachable portion 1501 is attached are referred to as a "second drive portion group 25G2."

In addition, a connection aspect between the endoscope adapter 212 and the first detachable portion 1501 is not limited to this. For example, the endoscope adapter 212 may be connected to the first detachable portion 1501 so that any four drive portions 25X selected from the eight drive portions 25X drive the bending wire 160.

The first drive portion 251 and the second drive portion 252 are provided adjacently in the vertical direction. The first drive portion 251 and the second drive portion 252, for example, can be coupled with the detachable upper/lower bending wire portion 151 to drive wires (the upper bending wire 161*u* and the lower bending wire 161*d*) for bending the bending portion 112 in the UD direction.

The third drive portion 253 and the fourth drive portion 254 are provided adjacently in the vertical direction. The third drive portion 253 and the fourth drive portion 254, for example, can be coupled with the detachable left/right bending wire portion 152 to drive wires (the left bending wire 1611 and the right bending wire 161*r*) for bending the bending portion 112 in the LR direction.

Because the third drive portion 253 and the fourth drive portion 254 have structures equivalent to those of the first drive portion 251 and the second drive portion 252, illustration and description thereof are omitted.

Because the fifth drive portion 255 and the sixth drive portion 256 have structures equivalent to those of the first drive portion 251 and the second drive portion 252, illustration and description thereof are omitted.

Because the seventh drive portion 257 and the eighth drive portion 258 have structures equivalent to those of the first drive portion 251 and the second drive portion 252, illustration and description thereof are omitted.

The first drive portion 251 shown in the example of FIG. 12 is coupled with the first driven portion 156 of the detachable upper/lower bending wire portion 151 to drive the upper bending wire 161*u*. The first drive portion 251 includes a first shaft 251*a*, a first motor portion 251*b*, a first coupled portion 251*c*, a first torque sensor 251*e*, and a first elastic member 251*s*.

The first shaft 251*a* is supported by the support member 250*a* so that the first shaft 251*a* can rotate around the first shaft rotation axis 251*r* and advance and retract in the longitudinal direction A. When the first detachable portion 1501 of the endoscope 100 is attached to the drive device 200, the first shaft rotation axis 251*r* coincides with the first drum rotation axis 156*r*.

The first motor portion 251*b* includes a first motor such as a DC motor, a first motor driver that drives the first motor, and a first motor encoder. The first motor rotates the first shaft 251*a* around the first shaft rotation axis 251*r*. The first motor driver is controlled by the drive controller 260.

The first coupled portion 251*c* is a disc member that rotates around the first shaft rotation axis 251*r*. The first coupled portion 251*c* is fixed to the distal end of the first shaft 251*a* and rotates integrally with the first shaft 251*a*. As shown in FIG. 12, the first coupled portion 251*c* is exposed on the distal side A1 of the wire drive portion 250. Two first fitting concave portions 251*d* are formed on the surface of the distal side A1 of the first coupled portion 251*c*. The two first fitting concave portions 251*d* are formed on both sides between which the first shaft rotation axis 251*r* is sandwiched.

As shown in FIG. 13, the first fitting convex portion 156*d* and the first fitting concave portion 251*d* are fitted and the first coupling portion 156*c* and the first coupled portion 251*c* are coupled. As a result, the rotation of the first shaft 251*a* by the first motor portion 251*b* is transmitted to the first driven portion 156. The upper bending wire 161*u* is pulled by rotating the first shaft 251*a* clockwise from the distal side A1 to the proximal side A2. In contrast, the first shaft 251*a* rotates counterclockwise, and therefore the upper bending wire 161*u* is sent.

The first torque sensor 251*e* detects rotational torque centered on the first shaft rotation axis 251*r* of the first shaft 251*a*. A detection result of the first torque sensor 251*e* is acquired by the drive controller 260.

The first elastic member 251*s* is, for example, a compression spring, and has a distal end portion in contact with the first coupled portion 251*c* and a proximal end portion in contact with the support member 250*a*. The first elastic member 251*s* biases the first coupled portion 251*c* to the distal side A1. As shown in FIG. 13, when the first coupling portion 156*c* is attached, the first coupled portion 251*c* moves to the proximal side A2 together with the first shaft 251*a*.

The second drive portion 252 exemplified in FIG. 12 is coupled with the second driven portion 157 of the detachable upper/lower bending wire portion 151 to drive the lower bending wire 161*d*. The second drive portion 252 includes a second shaft 252*a*, a second motor portion 252*b*, a second coupled portion 252*c*, a second torque sensor 252*e*, and a second elastic member 252*s*.

The second shaft 252*a* is supported by the support member 250*a* so that second shaft 252*a* can rotate around the second shaft rotation axis 252*r* and can advance and retract in the longitudinal direction A. When the first detachable portion 1501 of the endoscope 100 is attached to the drive device 200, the second shaft rotation axis 252*r* coincides with the second drum rotation axis 157*r*.

The second motor portion 252*b* includes a second motor such as a DC motor, a second motor driver that drives the second motor, and a second motor encoder. The second motor rotates the second shaft 252*a* around the second shaft rotation axis 252*r*. The second motor driver is controlled by the drive controller 260.

The second coupled portion 252*c* is a disc member that rotates around the second shaft rotation axis 252*r*. The second coupled portion 252*c* is fixed to the distal end of the second shaft 252*a* and rotates integrally with the second shaft 252*a*. As shown in FIG. 12, the second coupled portion 252*c* is exposed on the distal side A1 of the wire drive portion 250. Two second fitting concave portions 252*d* are formed on the surface of the distal side A1 of the second coupled portion 252*c*. The two second fitting concave portions 252*d* are formed on both sides between which the second shaft rotation axis 252*r* is sandwiched.

As shown in FIG. 13, the second fitting convex portion 157*d* and the second fitting concave portion 252*d* are fitted and the second coupling portion 157*c* and the second coupled portion 252*c* are coupled. As a result, the rotation of the second shaft 252*a* by the second motor portion 252*b* is transmitted to the second driven portion 157. The second shaft 252*a* rotates counterclockwise when viewed from the distal side A1 to the proximal side A2, and therefore the lower bending wire 161*d* is pulled. In contrast, the second shaft 252*a* rotates clockwise, and therefore the lower bending wire 161*d* is sent.

The second torque sensor 252*e* detects rotational torque centered on the second shaft rotation axis 252*r* of the second shaft 252*a*. A detection result of the second torque sensor 252*e* is acquired by the drive controller 260.

The second elastic member 252*s* is, for example, a compression spring, and has a distal end portion in contact with the second coupled portion 252*c* and a proximal end portion in contact with the support member 250*a*. The second elastic member 252*s* biases the second coupled portion 252*c* to the distal side A1. As shown in FIG. 13, when the second coupling portion 157*c* is attached, the second coupled portion 252*c* moves to the proximal side A2 together with the second shaft 252*a*.

As shown in FIG. 13, the detachable sensor 259 detects the attachment and detachment of the first detachable portion 1501 for the wire drive portion 250 by detecting the engagement and non-engagement with the attachment/detachment detection dog 155*a*. The detachable sensor 259 is individually provided for the eight drive portions 25X and can detect the drive portion 25X used by the first detachable portion 1501 that is attached. A detection result of the detachable sensor 259 is acquired by the drive controller 260.

According to the above-described mechanism, when the detachable upper/lower bending wire portion 151 is attached to the first drive portion 251 and the second drive portion 252, the first drive portion 251 can independently drive the upper bending wire 161*u* and the second drive portion 252 can independently drive the lower bending wire 161*d*. Likewise, when the detachable left/right bending wire portion 152 is attached to the third drive portion 253 and the fourth drive portion 254, the third drive portion 253 can independently drive the left bending wire 1611 and the fourth drive portion 254 can independently drive the right bending wire 161*r*. Therefore, even if a distance from the bending portion 112 of the endoscope 100 to the drive device 200 is longer than that of a conventional flexible endoscope, a bending manipulation on the bending portion 112 can be controlled with high accuracy.

The drive controller 260 controls the entire drive device 200. The drive controller 260 acquires a manipulation input received by the manipulation reception portion 220. The drive controller 260 controls the air supply/suction drive portion 230 and the wire drive portion 250 on the basis of the acquired manipulation input.

The drive controller 260 is a computer capable of executing a program. The computer includes a processor 261, a memory 262, a storage portion 263 capable of storing programs and data, and an input/output control portion 264. Functions of the drive controller 260 are implemented by the processor 261 executing the program. At least some of the functions of the drive controller 260 may be implemented by a dedicated logic circuit.

Because the drive controller 260 controls a plurality of motors that drive a plurality of bending wires 160 with high accuracy, the drive controller 260 desirably has high calculation performance.

The program that controls the drive controller 260 stored in the storage portion 263 can independently drive a plurality of endoscopes 100 connected to the wire drive portion 250.

The storage portion 263 stores a database of the endoscope 100 in which the scope ID of the endoscope 100 and information of the endoscope 100 such as the type and specifications of the endoscope 100 are associated. The drive controller 260 can recognize the information of the endoscope 100 from the scope ID with reference to the database.

In addition, the drive controller 260 may further include constituent elements other than the processor 261, the memory 262, the storage portion 263, and the input/output control portion 264. For example, the drive controller 260 may further include an image calculation portion that performs a part or all of image processing and image recognition processing. The image calculation portion is further included, and therefore the drive controller 260 can execute specific image processing and image recognition processing at a high speed. The image calculation portion may be mounted in a separate hardware device connected by a communication circuit.

[Manipulation Device 300]

Figure 16:
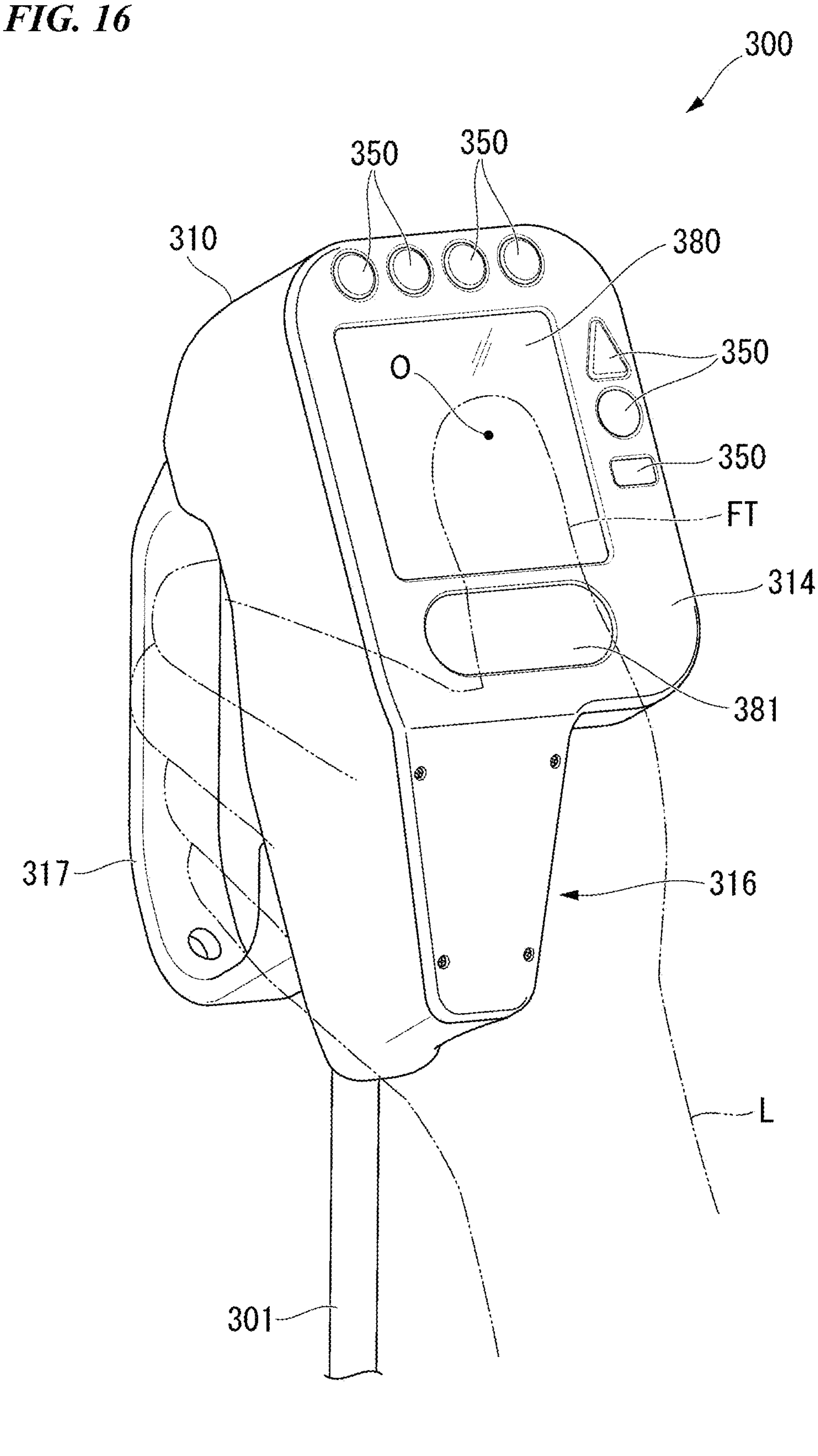
FIG. 16 illustrates an example of a perspective view of the manipulation device.

FIG. 16 is a perspective view of the manipulation device 300.

The manipulation device 300 is a device to which a manipulation for driving the endoscope 100 is input. The input manipulation input is transmitted to the drive device 200 via the manipulation cable 301. The manipulation device 300 may be able to communicate with the drive device 200 according to wireless communication instead of wired communication.

Figure 17:
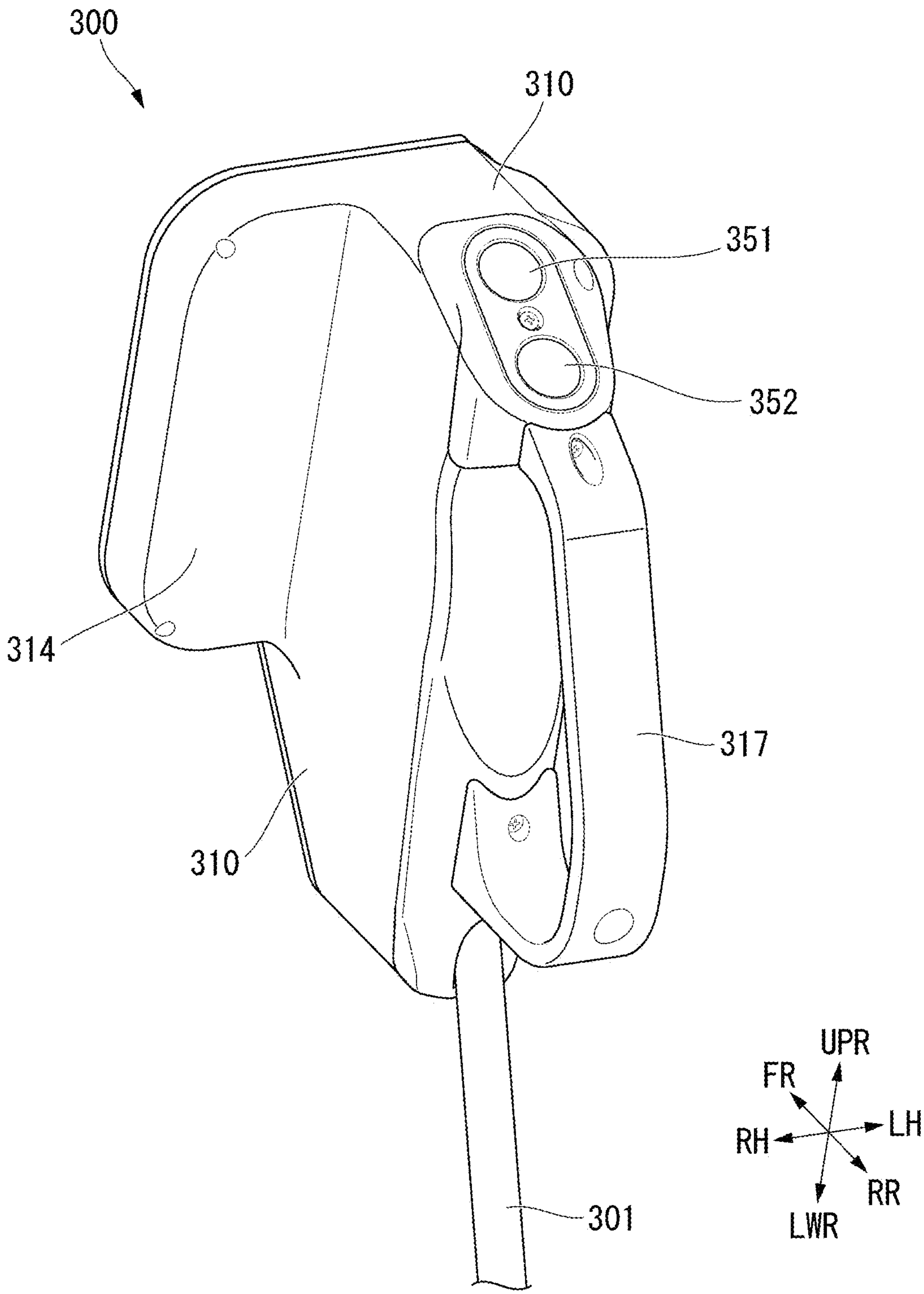
FIG. 17 illustrates an example of a perspective view of the manipulation device viewed from the rear.

FIG. 17 is a perspective view of the manipulation device 300 viewed from the rear.

The manipulation device 300 includes a manipulation portion body 310, an air/water supply button 351, a suction button 352, various buttons 350, a touchpad 380, and a touch sensor 381.

The manipulation portion body 310 is formed in a substantially prismatic shape that can be held by the scopist S with the left hand L. The manipulation portion body 310 includes a touchpad support portion 314 provided above, a grip portion 316 provided below, and a handle 317 provided at the rear. As shown in FIG. 16, the scopist S can manipulate the touchpad 380 with a thumb finger FT of the left hand L while gripping the grip portion 316 with the left hand L.

The touchpad 380 is a touch-sensitive interface to which a bending manipulation or the like on the bending portion 112 is input. The touchpad 380 may be a touch panel.

[Video Control Device 500]

Figure 18:
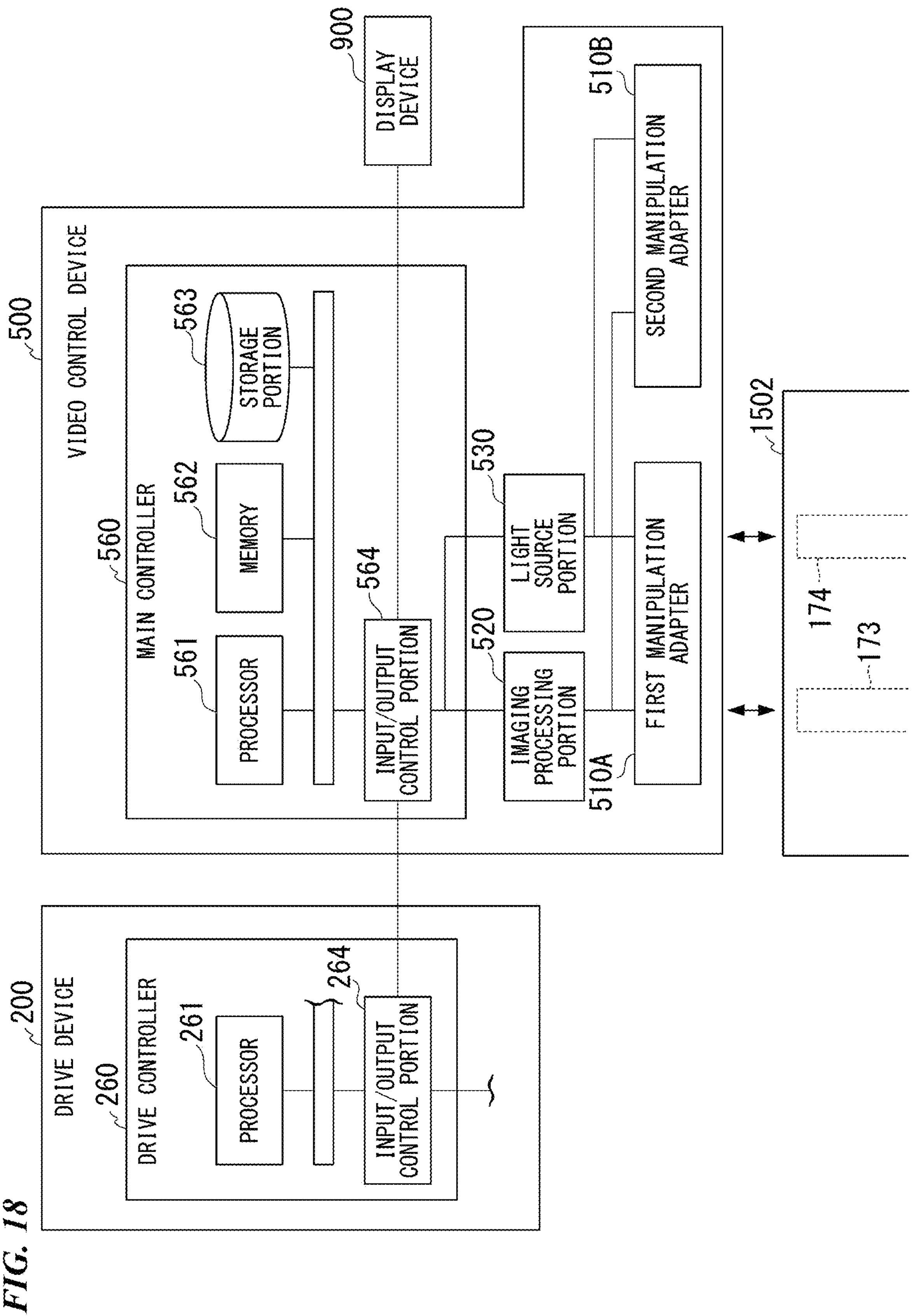
FIG. 18 illustrates an example of a functional block diagram of a video control device of the electric endoscope system.

FIG. 18 is a functional block diagram of the video control device 500.

The video control device 500 controls the electric endoscope system 1000. The video control device 500 includes a first endoscope adapter 510A, a second endoscope adapter 510B, an imaging processing portion 520, a light source portion 530, and a main controller 560.

The first endoscope adapter 510A and the second endoscope adapter 510B are adapters to which the second detachable portion 1502 of the endoscope 100 is detachably connected.

The imaging processing portion 520 converts an imaging signal acquired from the imaging portion 111*c* of the distal end portion 111 into a captured image via the imaging cable 173.

The light source portion 530 generates illumination light radiated to an imaging target. The illumination light generated by the light source portion 530 is guided to the illumination portion 111*b* of the distal end portion 111 via the light guide 174.

The main controller 560 includes a computer capable of executing a program. The computer includes a processor 561, a memory 562, a storage portion 563 capable of storing programs and data, and an input/output control portion 564. Functions of the main controller 560 is implemented by the processor 561 executing a program. At least some of the functions of the main controller 560 may be implemented by a dedicated logic circuit.

The main controller 560 includes the processor 561, the memory 562 from which a program can be read, the storage portion 563, and the input/output control portion 564.

The storage portion 563 is a non-volatile recording medium that stores the above-described programs and necessary data. The storage portion 563 includes, for example, a ROM, a hard disk, or the like. The program recorded in the storage portion 563 is read into the memory 562 and executed by the processor 561.

The input/output control portion 564 is connected to an imaging processing portion 520, a light source portion 530, a drive device 200, a display device 900, an input device (not shown), and a network device (not shown). The input/output control portion 564 performs the transmission/reception of data and/or the transmission/reception of control signals for the connected device on the basis of the control of the processor 561.

The main controller 560 can perform image processing on the captured image acquired by the imaging processing portion 520. The main controller 560 can generate a GUI image or a CG image for the purpose of providing information to the scopist S. The main controller 560 can cause the display device 900 to display a captured image, a GUI image, or a CG image.

The main controller 560 is not limited to an integrated hardware device. For example, the main controller 560 may be configured by separating its part as a separate hardware device and then connecting the separated hardware device with a communication circuit. For example, the main controller 560 may be a cloud system in which the separated storage portion 563 is connected by the communication circuit.

The main controller 560 may further include constituent elements other than the processor 561, the memory 562, the storage portion 563, and the input/output control portion 564. For example, the main controller 560 may further include an image calculation portion that performs a part or all of the image processing and image recognition processing performed by the processor 561. The image calculation portion is further provided, and therefore the main controller 560 can execute specific image processing and image recognition processing at a high speed. The image calculation portion may be mounted in a separate hardware device connected by the communication circuit.

[Operation of Electric Endoscope System 1000]

Next, the operation of the electric endoscope system 1000 of the present embodiment will be described. Specifically, the operation of the drive controller 260 of the control device 600 of the electric endoscope system 1000 will be described.

Figure 19:
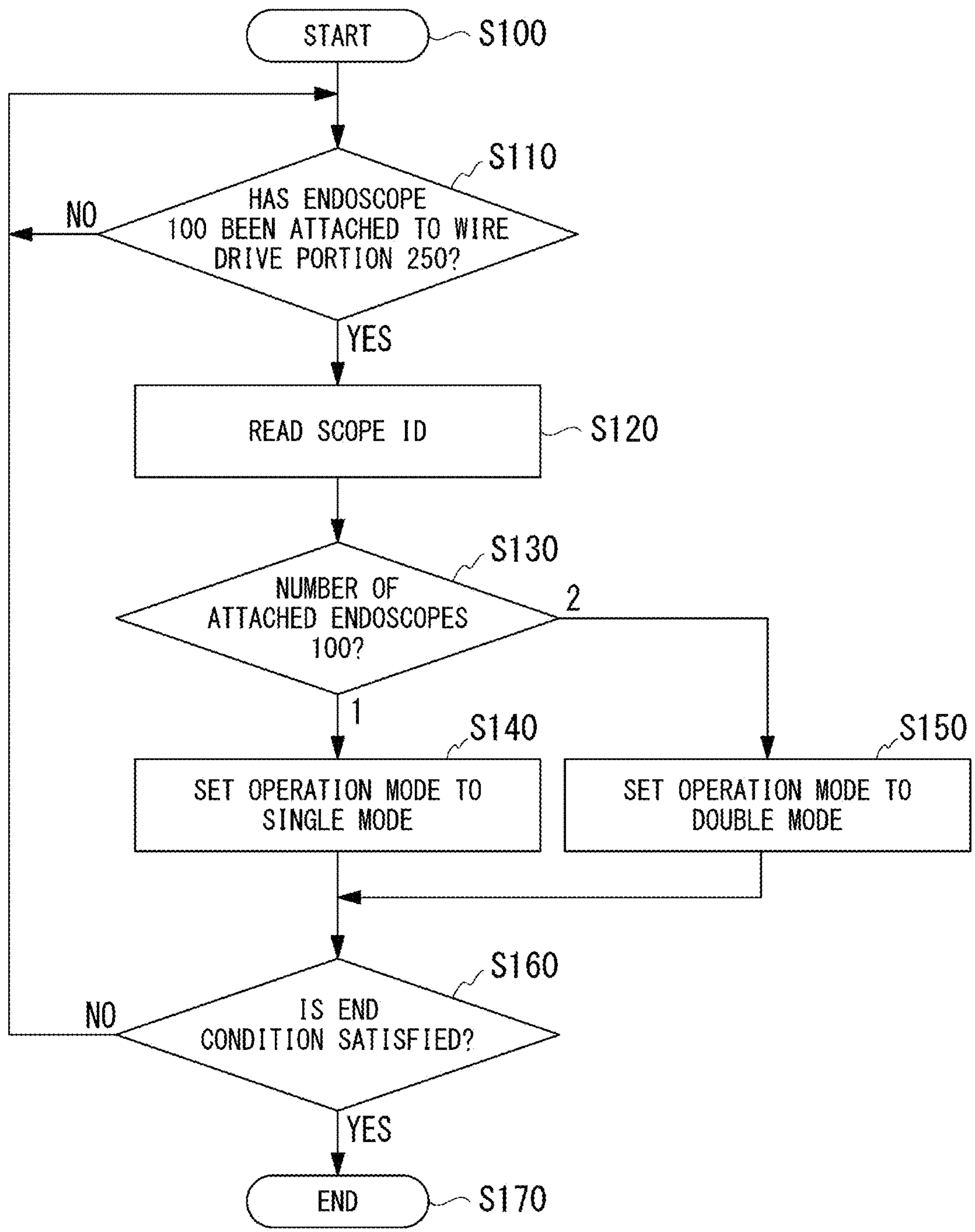
FIG. 19 illustrates an example of a control flowchart of a drive controller of the drive device.

Hereinafter, description will be given according to a control flowchart of the drive controller 260 of the control device 600 shown in FIG. 19. When the control device 600 is activated, the drive controller 260 starts a control flow shown in FIG. 19 after initialization (step S100). Subsequently, the drive controller 260 (mainly, the processor 261) executes step S110.

<Step S110>

In step S110, the drive controller 260 detects whether the first detachable portion 1501 of the endoscope 100 has been attached to the wire drive portion 250. When the first detachable portion 1501 of the endoscope 100 is attached to the wire drive portion 250, the drive controller 260 subsequently executes step S120.

<Step S120>

In step S120, the drive controller 260 reads a scope ID stored in the first detachable portion 1501 of the attached endoscope 100. When a plurality of endoscopes 100 are attached to the wire drive portion 250, the drive controller 260 reads scope IDs from all endoscopes 100. The drive controller 260 subsequently executes step S130.

<Step S130>

In step S130, the drive controller 260 recognizes a type of attached endoscope 100, the number of attached endoscopes 100, and the like on the basis of the acquired scope ID. When the number of attached endoscopes 100 is one, the drive controller 260 subsequently executes step S140. When the number of attached endoscopes 100 is two, the drive controller 260 subsequently executes step S150.

<Step S140: Single Mode>

The drive controller 260 sets an operation mode to a "single mode" in step S140. The drive controller 260 operating in the single mode drives one endoscope 100 attached to the drive device 200 on the basis of a manipulation input acquired from the manipulation device 300.

One endoscope 100 and one manipulation device 300 are attached to the drive device 200 shown in FIG. 1. The first detachable portion 1501 of the endoscope 100 is attached to the first drive portion group 25G1 (the first drive portion 251, the second drive portion 252, the third drive portion 253, and the fourth drive portion 254). The manipulation device 300 is connected to the first manipulation adapter 211A.

The drive controller 260 controls the first drive portion 251 and the second drive portion 252 on the basis of an input to the touchpad 380 of the manipulation device 300 so that wires (the upper bending wire 161*u* and the lower bending wire 161*d*) for bending the bending portion 112 of the endoscope 100 in the UD direction are driven. Moreover, the drive controller 260 controls the third drive portion 253 and the fourth drive portion 254 on the basis of an input to the touchpad 380 of the manipulation device 300 so that wires (the left bending wire 1611 and the right bending wire 161*r*) for bending the bending portion 112 of the endoscope 100 in the LR direction are driven.

<Step S150: Double Mode>

Figure 20:
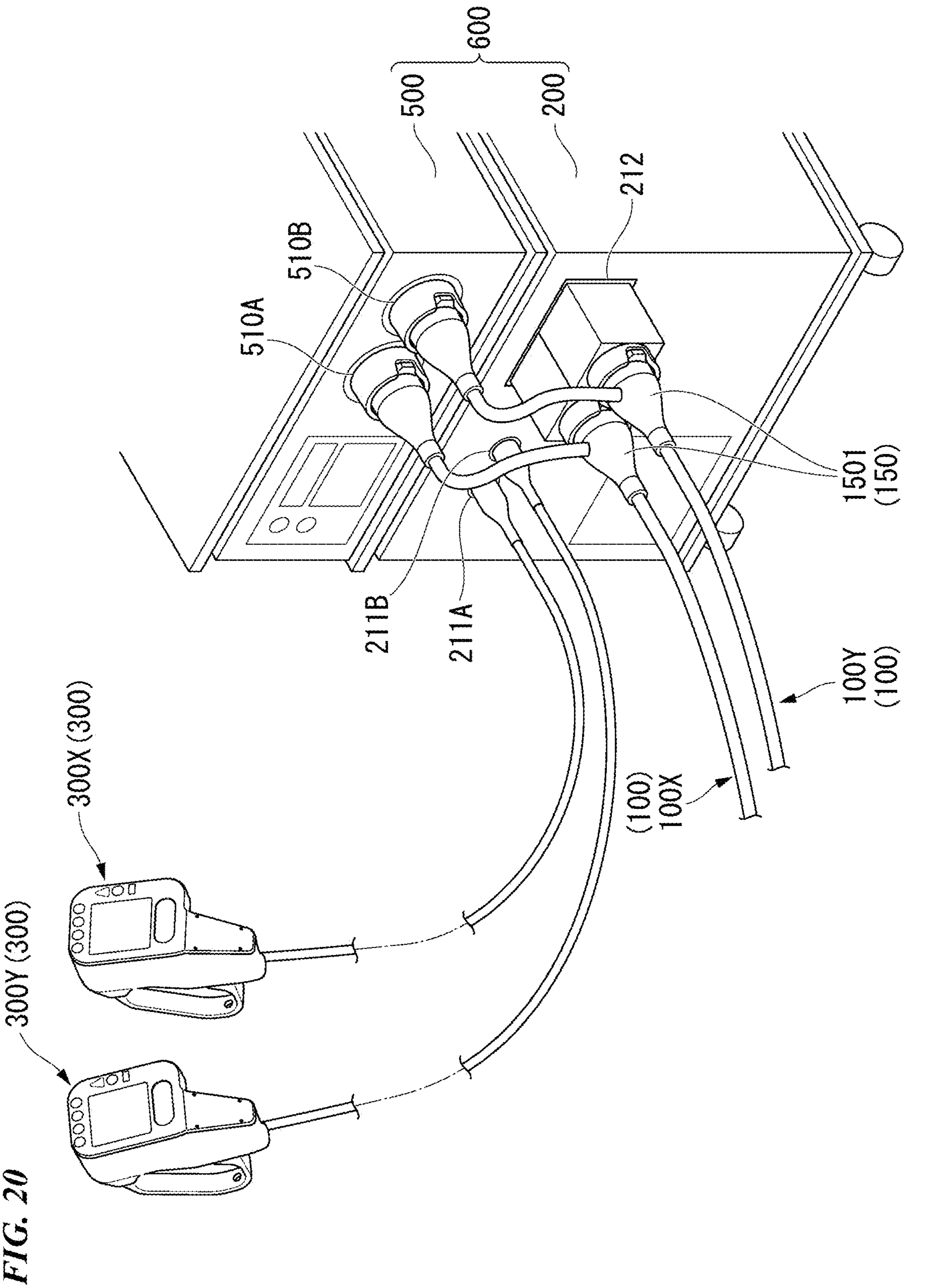
FIG. 20 illustrates an example of a view showing the drive device operating in a double mode.

FIG. 20 is a view showing the drive device 200 operating in a double mode.

The drive controller 260 sets the operation mode to the "double mode" in step S150. The drive controller 260 operating in the double mode separately and independently drives the two endoscopes 100 attached to the drive device 200 on the basis of manipulation inputs acquired from the two different manipulation devices 300.

Two endoscopes 100 and two manipulation devices 300 are attached to the drive device 200 shown in FIG. 20. In the following description, one of the two endoscopes 100 is referred to as a first endoscope 100X and the other is referred to as a second endoscope 100Y. Moreover, one of the two manipulation devices 300 is referred to as a first manipulation device 300X and the other is referred to as a second manipulation device 300Y.

When the second endoscope 100Y is further attached to the drive device 200 to which only the first endoscope 100X is attached, the drive controller 260 changes the operation mode from "single mode" to the "double mode" (step S150).

The first detachable portion 1501 of the first endoscope 100X is attached to the first drive portion group 25G1 (the first drive portion 251, the second drive portion 252, the third drive portion 253, and the fourth drive portion 254). The first detachable portion 1501 of the second endoscope 100Y is attached to the second drive portion group 25G2 (the fifth drive portion 255, the sixth drive portion 256, the seventh drive portion 257, and the eighth drive portion 258). The first manipulation device 300X is connected to the first manipulation adapter 211A. The second manipulation device 300Y is connected to the second manipulation adapter 211B.

The drive controller 260 controls the first drive portion 251 and the second drive portion 252 on the basis of an input to the touchpad 380 of the first manipulation device 300X so that wires (the upper bending wire 161*u* and the lower bending wire 161*d*) for bending the bending portion 112 of the endoscope 100X in the UD direction are driven. Moreover, the drive controller 260 controls the third drive portion 253 and the fourth drive portion 254 on the basis of an input to the touchpad 380 of the first manipulation device 300X so that wires (the left bending wire 1611 and the right bending wire 161*r*) for bending the bending portion 112 of the first endoscope 100X in the LR direction are driven.

Furthermore, the drive controller 260 controls the fifth drive portion 255 and the sixth drive portion 256 on the basis of an input to the touchpad 380 of the second manipulation device 300Y so that wires (the upper bending wire 161*u* and the lower bending wire 161*d*) for bending the bending portion 112 of the second endoscope 100Y in the UD direction are driven. Moreover, the drive controller 260 controls the seventh drive portion 257 and the eighth drive portion 258 on the basis of an input to the touchpad 380 of the second manipulation device 300Y so that wires (the left bending wire 1611 and the right bending wire 161*r*) for bending the bending portion 112 of the second endoscope 100Y in the LR direction are driven.

<Step S160>

The drive controller 260 subsequently executes step S160. In step S160, the drive controller 260 determines whether to end a control flow. When the control flow does not end, the drive controller 260 performs step S110 again. When the control flow ends, the drive controller 260 subsequently performs step S170 to end the control flow.

Figure 21:
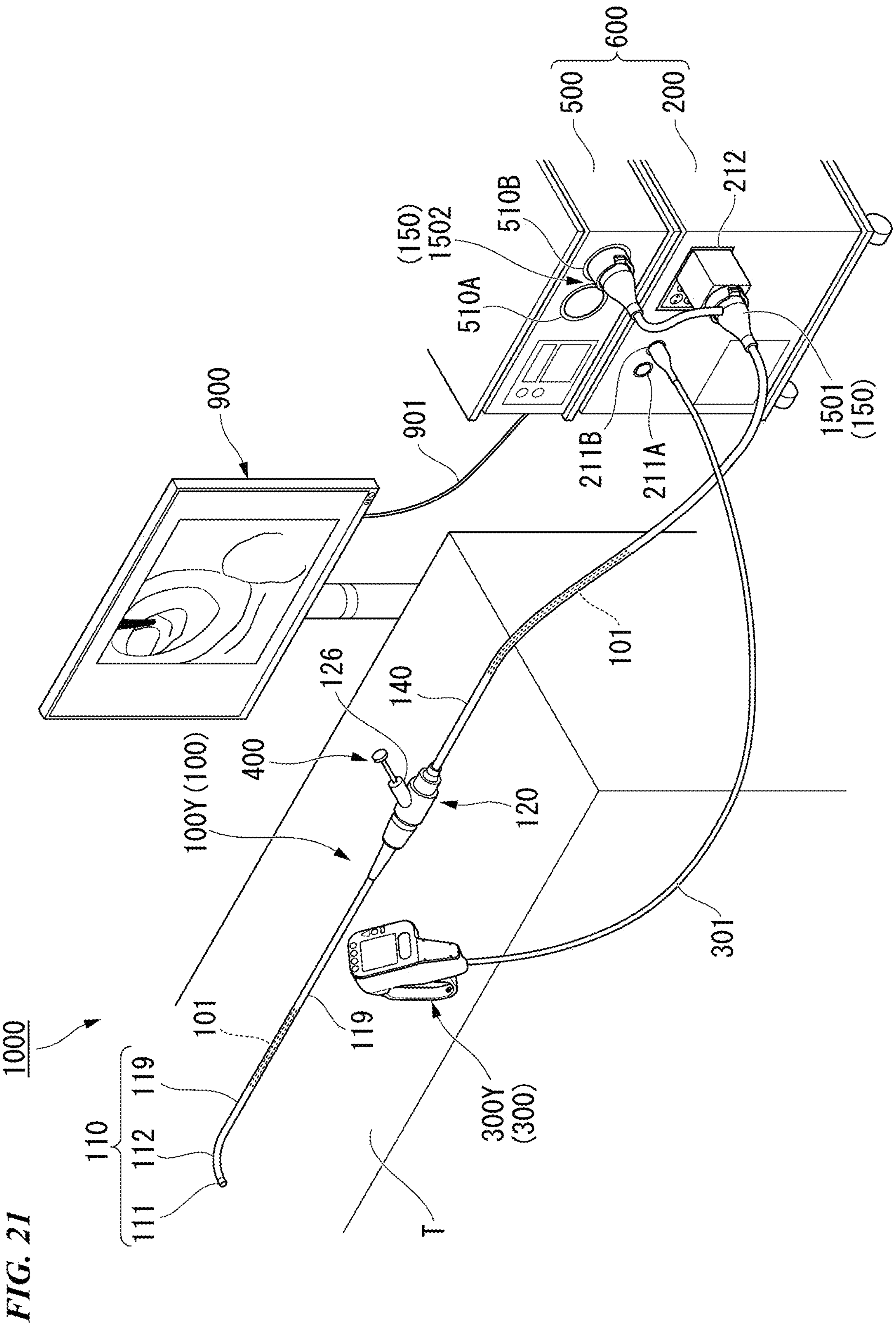
FIG. 21 illustrates an example of a view showing the drive device from which a first endoscope has been removed.

FIG. 21 is a view showing the drive device 200 from which the first endoscope 100X has been removed.

When the first endoscope 100X is removed, the drive controller 260 changes the operating mode from the “double mode” to the “single mode” (step S140). The drive controller 260 operating in the single mode drives the second endoscope 100Y on the basis of a manipulation input acquired from the second manipulation device 300Y.

Usage Example 1 of Electric Endoscope System 1000

Next, a usage example of the electric endoscope system 1000 will be described. Specifically, the usage example in which one of the two endoscopes 100 is used in treating the patient P and the other is used in a pre-use device check process will be described.

First, the scopist treats a first patient P as shown in FIG. 2 using the first endoscope 100X attached to the first drive portion group 25G1 of the drive device 200. The drive controller 260 operates in the single mode. The drive controller 260 controls the drive portion 25X of the first drive portion group 25G1 with a “normal operation program.” The normal operation program is a program for driving the endoscope 100 on the basis of a manipulation input acquired from the manipulation device 300.

Subsequently, an assistant further attaches the second endoscope 100Y to the second drive portion group 25G2 of the drive device 200. The drive controller 260 changes the operation mode from the “single mode” to the “double mode.” The drive controller 260 controls the drive portion 25X of the second drive portion group 25G2 with a “check program.” The assistant performs a pre-use device check process for the second endoscope 100Y by executing the check program. The check program is a program for performing various types of pre-use checks, an initialization operation for the connected second endoscope 100Y and the drive device 200, a calibration process of a bending manipulation, and the like.

When the treatment for the first patient P ends, the assistant removes the first endoscope 100X from the first drive portion group 25G1 of the drive device 200 for reprocessing. The drive controller 260 changes the operation mode from the “double mode” to the “single mode.” The drive controller 260 changes a program for controlling the drive portion 25X of the second drive portion group 25G2 to a “normal operation program.” In addition, when the operation mode is changed from the “double mode” to the “single mode,” the drive controller 260 may select whether to change the program for controlling the drive portion 25X to the “normal operation program” or whether to use the “check program” as it is on the basis of an instruction input from the user (the scopist S or the assistant).

The assistant prepares for the treatment of a second patient P. Because the pre-use device check process for the second endoscope 100Y for use in treating the second patient P is performed in parallel with the treatment of the first patient P, a preparation time for treating the second patient P is significantly reduced.

The second endoscope 100Y can be used in treating the second patient P without removing it from the second drive portion group 25G2 attached during the pre-use device check process. Therefore, the scopist can use the second endoscope 100Y attached to the second drive portion group 25G2 subjected to the pre-use device check process for the treatment of the second patient P as it is.

Usage Example 2 of Electric Endoscope System 1000

Next, another usage example of the electric endoscope system 1000 will be described. Specifically, a usage example for changing the drive portion group 25G when an abnormality of the drive portion 25X is detected will be described.

Hereinafter, description will be given according to the control flowchart of the drive controller 260 of the control device 600 shown in FIG. 22. When the control device 600 detects an abnormality of the endoscope 100, the drive controller 260 starts the control flow shown in FIG. 22 (step S200). The scopist or assistant may start the control flow shown in FIG. 22 when an abnormality of the endoscope 100 is felt during surgery or during the pre-use device check process. The drive controller 260 (mainly, the processor 261) subsequently executes step S210.

<Step S210>

In step S210, the drive controller 260 changes a motor command value for the motor of the wire drive portion 250. For example, the drive controller 260 changes the motor command value and transmits a test pattern to the motor of the wire drive portion 250. The drive controller 260 subsequently executes step S220.

<Step S220>

The drive controller 260 acquires an output of the tension sensor 159 in step S220. The drive controller 260 confirms whether or not the output of the tension sensor 159 has changed normally in correspondence with a change in the motor command value. When the output of the tension sensor 159 has not changed normally, there is a high possibility that an abnormality has occurred in the drive portion 25X to which the endoscope 100 is attached. In this case, the drive controller 260 subsequently executes step S230. When the output of the tension sensor 159 has changed normally, there is a possibility that an abnormality has not occurred or that an abnormality has occurred in a portion other than the drive portion 25X (for example, the endoscope 100). In this case, the drive controller 260 subsequently executes step S250.

<Step S230>

In step S230, the drive controller 260 displays a GUI image for issuing an instruction (notification) for allowing the user to change the drive portion group 25G to which the endoscope 100 is attached for the scopist and the assistant on the display device 900 in cooperation with the main controller 560. For example, when the endoscope 100 is attached to the first drive portion group 25G1 when an abnormality is detected, the drive controller 260 displays a GUI image for instructing the user to attach the endoscope 100 to the second drive portion group 25G2 on the display device 900. The scopist or assistant attaches the endoscope 100 to the second drive portion group 25G2 in accordance with the instruction. The drive controller 260 subsequently executes step S240.

<Step S240>

In step S240, the drive controller 260 switches the drive portion group 25G for driving the endoscope 100 from the first drive portion group 25G1 to the second drive portion group 25G2. Information necessary to drive the endoscope 100 (a control parameter, a current position of the motor encoder, and the like) is transferred from a program for controlling the first drive portion group 25G1 to a program for controlling the second drive portion group 25G2. Therefore, the scopist can immediately use the endoscope 100 attached to the second drive portion group 25G2 and does not burden the patient P. The drive controller 260 subsequently executes step S250.

<Step S250>

Figure 22:
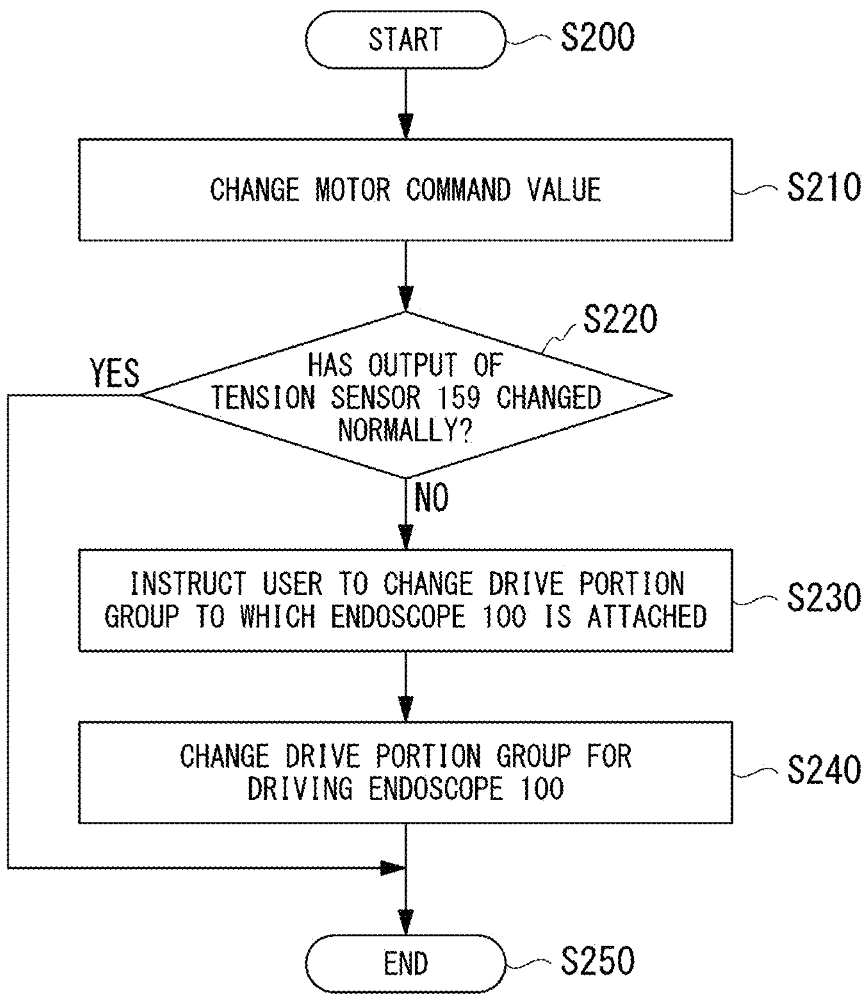
FIG. 22 illustrates an example of another control flowchart of the drive controller.

The drive controller 260 ends the control flow shown in FIG. 22 in step S250. In addition, the drive controller 260 may detect a motor current value of the wire drive portion 250 and an output of the motor encoder to perform further investigation of the cause of the abnormality.

The electric endoscope system 1000 according to the present embodiment can more efficiently perform observation and treatment using the endoscope 100. Because a plurality of endoscopes 100 can be attached to the drive device 200, a period of time required for a pre-use device check process or a device replacement process at the time of abnormality detection is significantly reduced.

Although the first embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Second Embodiment

An electric endoscope system 1000B according to a second embodiment of the present disclosure will be described with reference to FIGS. 23 to 24. In the following description, constituent elements identical to those described above are denoted by the same reference signs and redundant description thereof will be omitted.

[Electric Endoscope System 1000B]

Figure 23:
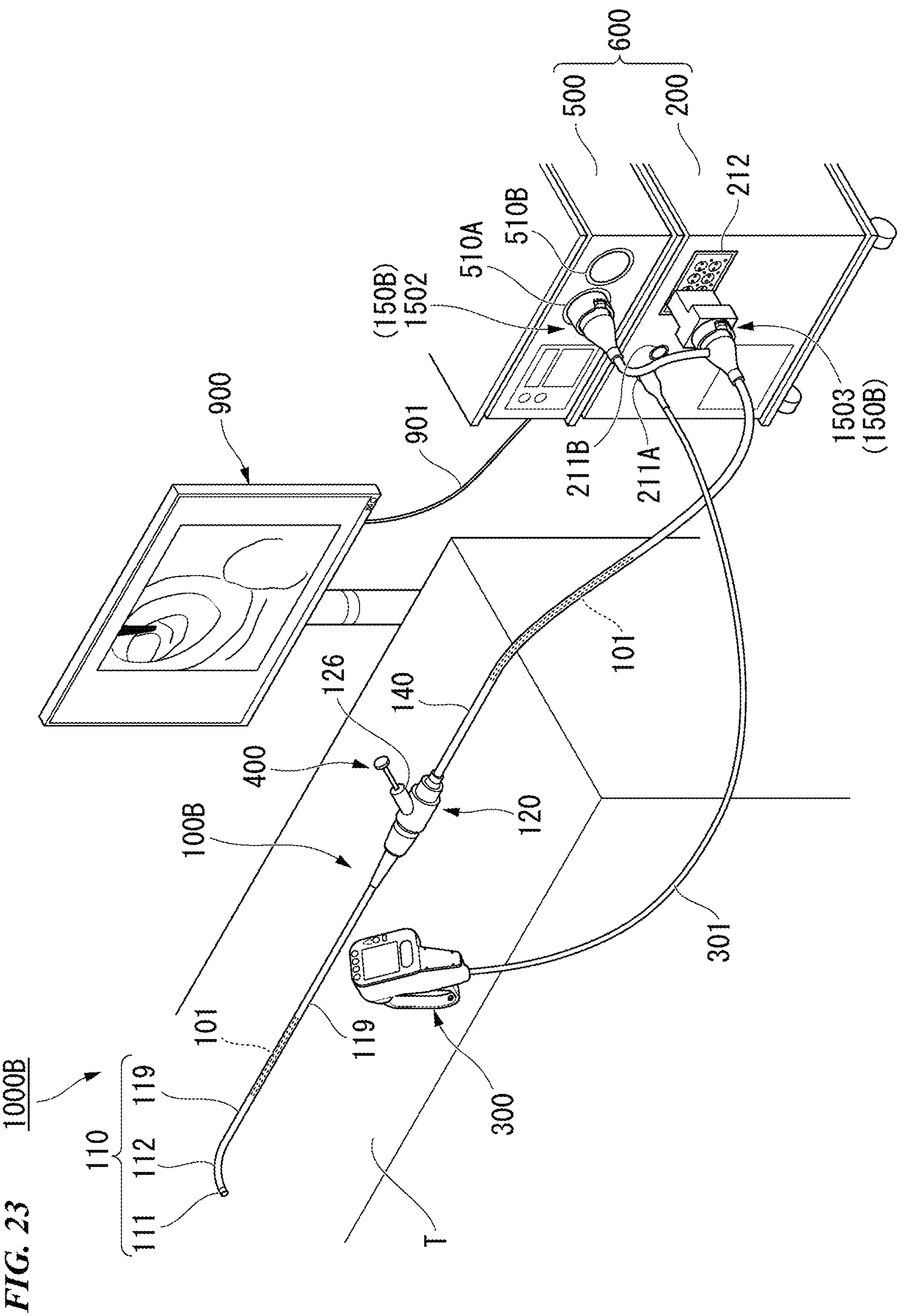
FIG. 23 illustrates an example of an overall view of an electric endoscope system according to a second embodiment.

FIG. 23 is an overall view of the electric endoscope system 1000B according to the present embodiment.

The electric endoscope system 1000B includes an endoscope 100B, a drive device 200, a manipulation device 300, a treatment tool 400, a video control device 500, and a display device 900.

[Endoscope 100B]

The endoscope 100B includes an insertion portion 110, a connection portion 120, an extracorporeal flexible portion 140, a detachable portion 150B, a bending wire 160, and a built-in object 170.

[Detachable Portion 150B]

Figure 24:
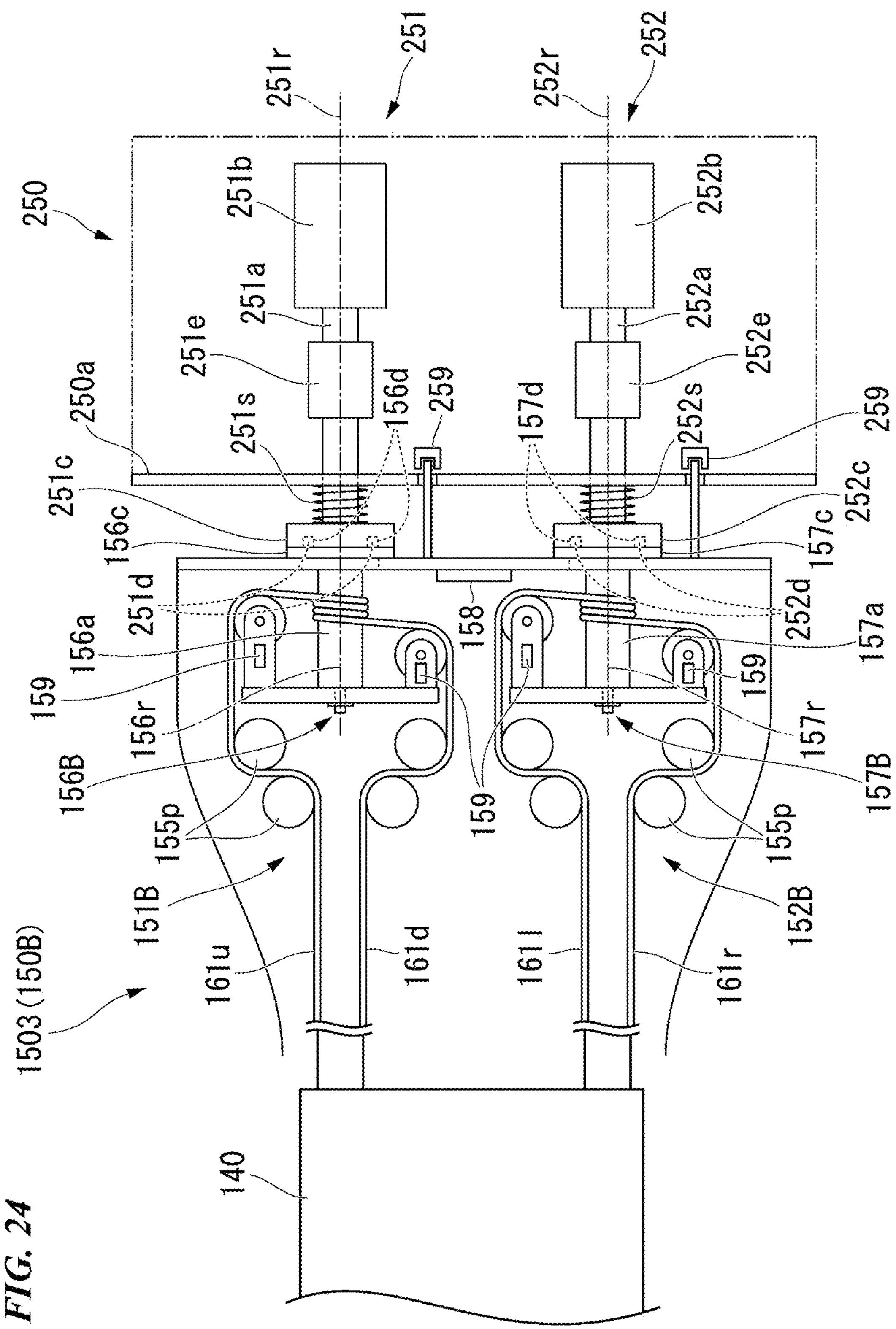
FIG. 24 illustrates an example of a view showing a first detachable portion of an endoscope of the electric endoscope system.

FIG. 24 is a view showing the first detachable portion 1503.

The detachable portion 150B includes a first detachable portion 1503 attached to the drive device 200 and a second detachable portion 1502 attached to the video control device 500. The first detachable portion 1503 includes a detachable upper/lower bending wire portion 151B, a detachable left/right bending wire portion 152B, and a scope ID storage portion 158.

The detachable upper/lower bending wire portion 151B is a mechanism for detachably connecting wires (an upper bending wire 161*u* and a lower bending wire 161*d*) for bending the bending portion 112 in the UD direction to the drive device 200.

The detachable upper/lower bending wire portion 151B includes a support member 155, a first driven portion 156B, and a tension sensor 159.

The support member 155 supports the first driven portion 156B. The support member 155 includes the attachment/detachment detection dog 155*a* exposed on the proximal side of the detachable upper/lower bending wire portions 151B and a plurality of bend pulleys 155*p*.

The bend pulley 155*p* changes a transport direction of the upper bending wire 161*u* inserted into the extracorporeal flexible portion 140 and guides the upper bending wire 161*u* to the first driven portion 156B. Moreover, the bend pulley 155*p* changes a transport direction of the lower bending wire 161*d* inserted into the extracorporeal flexible portion 140 and guides the lower bending wire 161*d* to the first driven portion 156B.

The first driven portion 156B has a member to which a driving force for driving the bending portion 112 (a movable portion) is input. In the present embodiment, the first driven portion 156B is a rotation drum. The first driven portion 156B is supported by the support member 155 so that the first driven portion 156B can rotate around the first drum rotation axis 156*r* extending in a longitudinal direction A. The first driven portion 156B includes a first winding pulley 156*a* and a first coupling portion 156*c*.

The first winding pulley 156*a* pulls or sends the upper bending wire 161*u* and the lower bending wire 161*d* by rotating around the first drum rotation axis 156*r*. The first winding pulley 156*a* rotates clockwise when viewed from the distal side A1 to the proximal side A2, and therefore the upper bending wire 161*u* is wound around the first winding pulley 156*a* and pulled and the lower bending wire 161*d* is sent from the first winding pulley 156*a*. In contrast, the first winding pulley 156*a* rotates counterclockwise, and therefore the upper bending wire 161*u* is sent from the first winding pulley 156*a* and the lower bending wire 161*d* is wound around the first winding pulley 156*a* and pulled.

The detachable left/right bending wire portion 152B is a mechanism for detachably connecting wires (the left bending wire 1611 and the right bending wire 161*r*) for bending the bending portion 112 in the LR direction to the drive device 200.

The detachable left/right bending wire portion 152B includes a support member 155, a second driven portion 157B, and a tension sensor 159.

The support member 155 supports the second driven portion 157B. The support member 155 includes the attachment/detachment detection dog 155*a* exposed on the proximal side of the detachable left/right bending wire portion 152B and the plurality of bend pulleys 155*p*.

The bend pulley 155*p* changes a transport direction of the left bending wire 1611 inserted into the extracorporeal flexible portion 140 and guides the left bending wire 1611 to the second driven portion 157B. Moreover, the bend pulley 155*p* changes a transport direction of the right bending wire 161*r* inserted into the extracorporeal flexible portion 140 and guides the right bending wire 161*r* to the second driven portion 157B.

The second driven portion 157B is a member to which a driving force for driving the bending portion 112 is input. In the present embodiment, the second driven portion 157B is a rotation drum. The second driven portion 157B is supported by the support member 155 so that the second driven portion 157B can rotate around the second drum rotation axis 157*r* extending in the longitudinal direction A. The second driven portion 157B includes a second winding pulley 157*a* and a second coupling portion 157*c*.

The second winding pulley 157*a* pulls or sends the left bending wire 1611 and the right bending wire 161*r* by rotating around the second drum rotation axis 157*r*. The second winding pulley 157*a* rotates clockwise when viewed from the distal side A1 to the proximal side A2, and therefore the left bending wire 1611 is wound around the second winding pulley 157*a* and pulled and the right bending wire 161*r* is sent from the second winding pulley 157*a*. In contrast, the second winding pulley 157*a* rotates counter-clockwise, and therefore the left bending wire 1611 is sent from the second winding pulley 157*a* and the right bending wire 161*r* is wound around the second winding pulley 157*a* and pulled.

In the following description, when the first driven portion 156B and the second driven portion 157B are not distinguished, they are referred to as "driven portions 15X." The number of driven portions 15X required to drive the endoscope 100B is two.

The endoscope adapter 212 can be connected to the first detachable portion 1501 in various aspects. The endoscope adapter 212 shown in FIG. 23 is connected to the first detachable portion 1503 so that the first drive portion 251 and the second drive portion 252 drive the bending wire 160. Moreover, the endoscope adapter 212 may be connected to the first detachable portion 1503 so that the third drive portion 253 and the fourth drive portion 254 drive the bending wire 160. Moreover, the endoscope adapter 212 may be connected to the first detachable portion 1503 so that the fifth drive portion 255 and the sixth drive portion 256 drive the bending wire 160. Moreover, the endoscope adapter 212 may be connected to the first detachable portion 1503 so that the seventh drive portion 257 and the eighth drive portion 258 drive the bending wire 160. That is, four first detachable portions 1503 may be connected to the endoscope adapter 212 at the same time.

The electric endoscope system 1000B according to the present embodiment can more efficiently perform observation and treatment using the endoscope 100. The electric endoscope system 1000B can be used by attaching an endoscope 100B, which has a difference in the number of driven portions 15X or the like from the endoscope 100, to the drive device 200. Moreover, as in the first embodiment, because a plurality of endoscopes 100B can be attached to the drive device 200, a period of time required for a pre-use device check process or a device replacement process at the time of abnormality detection is significantly reduced.

Although the second embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Third Embodiment

An electric endoscope system 1000C according to the third embodiment of the present disclosure will be described with reference to FIGS. 25 to 28. In the following description, constituent elements identical to those described above are denoted by the same reference signs and redundant description thereof will be omitted.

[Electric Endoscope System 1000C]

Figure 25:
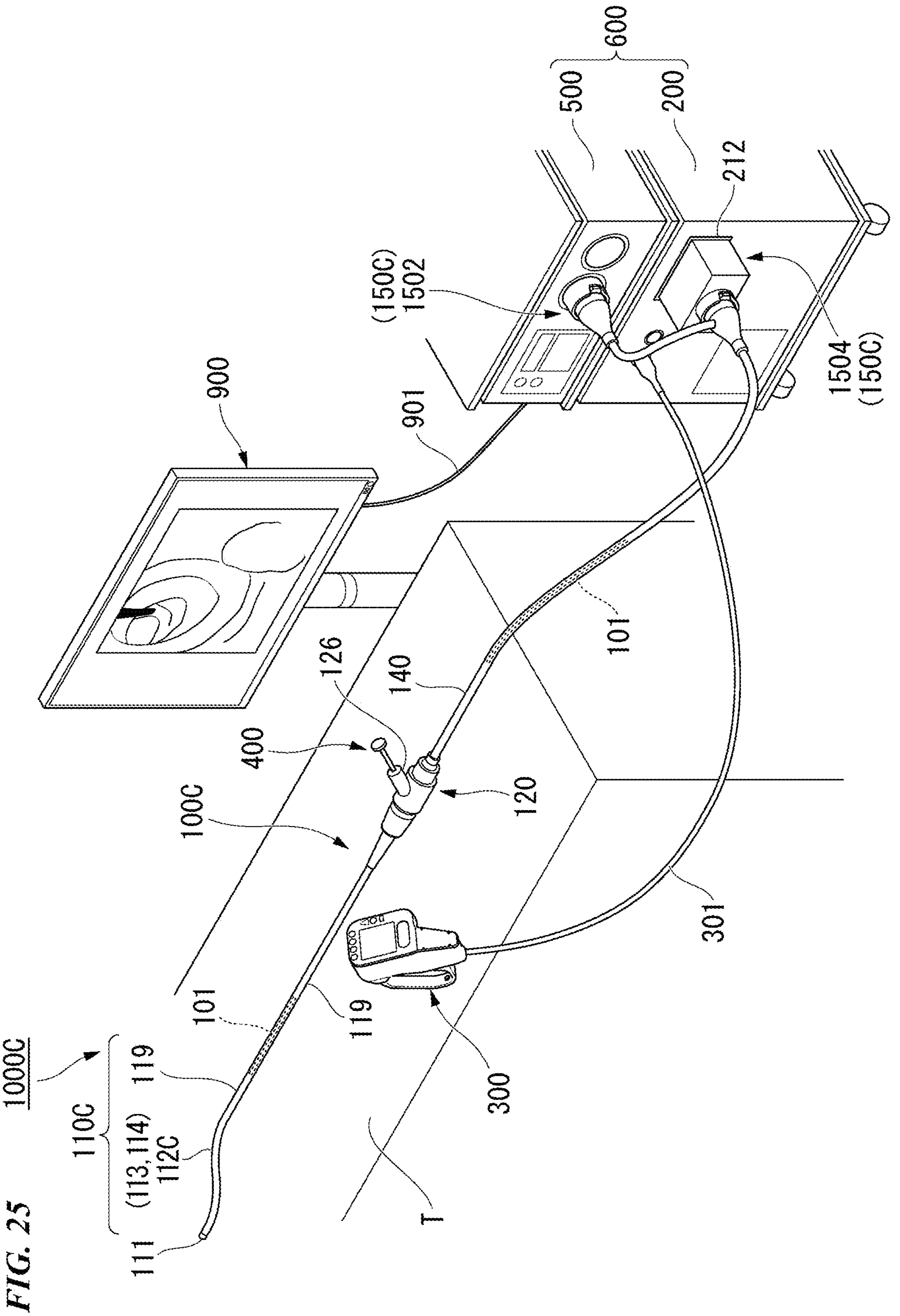
FIG. 25 illustrates an example of an overall view of an electric endoscope system according to a third embodiment.

FIG. 25 is an overall view of the electric endoscope system 1000C according to the present embodiment.

The electric endoscope system 1000C includes an endoscope 100C, a drive device 200, a manipulation device 300, a treatment tool 400, a video control device 500, and a display device 900.

[Endoscope 100C]

The endoscope 100C includes an insertion portion 110C, a connection portion 120, an extracorporeal flexible portion 140, a detachable portion 150C, a bending wire 160C, and a built-in object 170.

Figure 26:
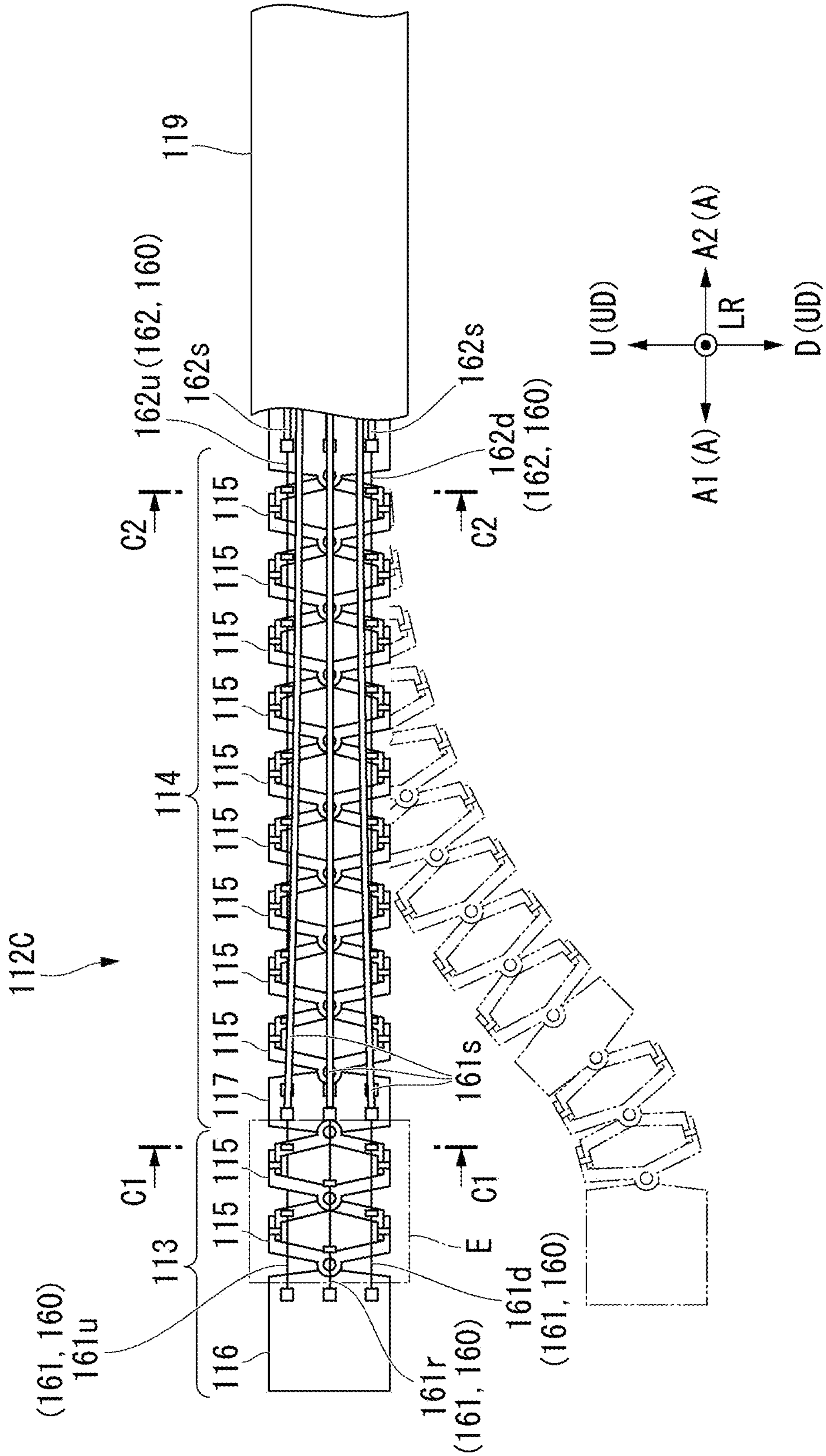
FIG. 26 illustrates an example of a view showing a part of a bending portion of an endoscope of the electric endoscope system in a cross-sectional view.

FIG. 26 is a view showing a part of the bending portion 112C in a cross-sectional view.

The insertion portion 110C includes a distal end portion 111, a bending portion 112C, and an intracorporeal flexible portion 119. The bending portion 112C includes a first bending portion 113 on a distal side A1 of the bending portion 112C, a second bending portion 114 on a proximal side A2 of the bending portion 112C, and an outer sheath 118. The first bending portion 113 and the second bending portion 114 can be bent in different directions.

The first bending portion (distal side bending portion) 113 includes a plurality of joint rings (also referred to as bending pieces) 115 and a first distal end portion 116 connected to the distal ends of the plurality of joint rings 115. The plurality of joint rings 115 and the first distal end portion 116 are connected in a longitudinal direction A inside the outer sheath 118. In addition, the shapes and number of joint rings 115 provided in the first bending portion 113 are not limited to the shapes and number of joint rings 115 shown in FIG. 26.

The second bending portion (proximal side bending portion) 114 includes a plurality of joint rings (also referred to as bending pieces) 115 and a second distal end portion 117 connected to the distal ends of the plurality of joint rings 115. The plurality of joint rings 115 and the second distal end portion 117 are connected in the longitudinal direction A inside the outer sheath 118. The second distal end portion 117 is connected to the joint ring 115 at the proximal end of the first bending portion 113. The joint ring 115 at the proximal end of the second bending portion 114 is attached to the distal end of the intracorporeal flexible portion 119.

The bending wire 160C is a wire for bending the bending portion 112C. The bending wire 160C has a first bending wire 161 for bending the first bending portion 113 and a second bending wire 162 for bending the second bending portion 114. The first bending wire 161 and the second bending wire 162 extend to the detachable portion 150C through the internal path 101.

As shown in FIG. 26, the first bending wire 161 has a first upper bending wire 161*u*, a first lower bending wire 161*d*, a first left bending wire 1611, a first right bending wire 161*r*, and four first wire sheaths 161*s*.

As shown in FIG. 26, the first upper bending wire 161*u*, the first lower bending wire 161*d*, the first left bending wire 1611, and the first right bending wire 161*r* are inserted into the first wire sheaths 161*s*. The distal end of the first wire sheath 161*s* is attached to the second distal end portion 117. The first wire sheath 161*s* extends to the detachable portion 150C.

Figure 27:
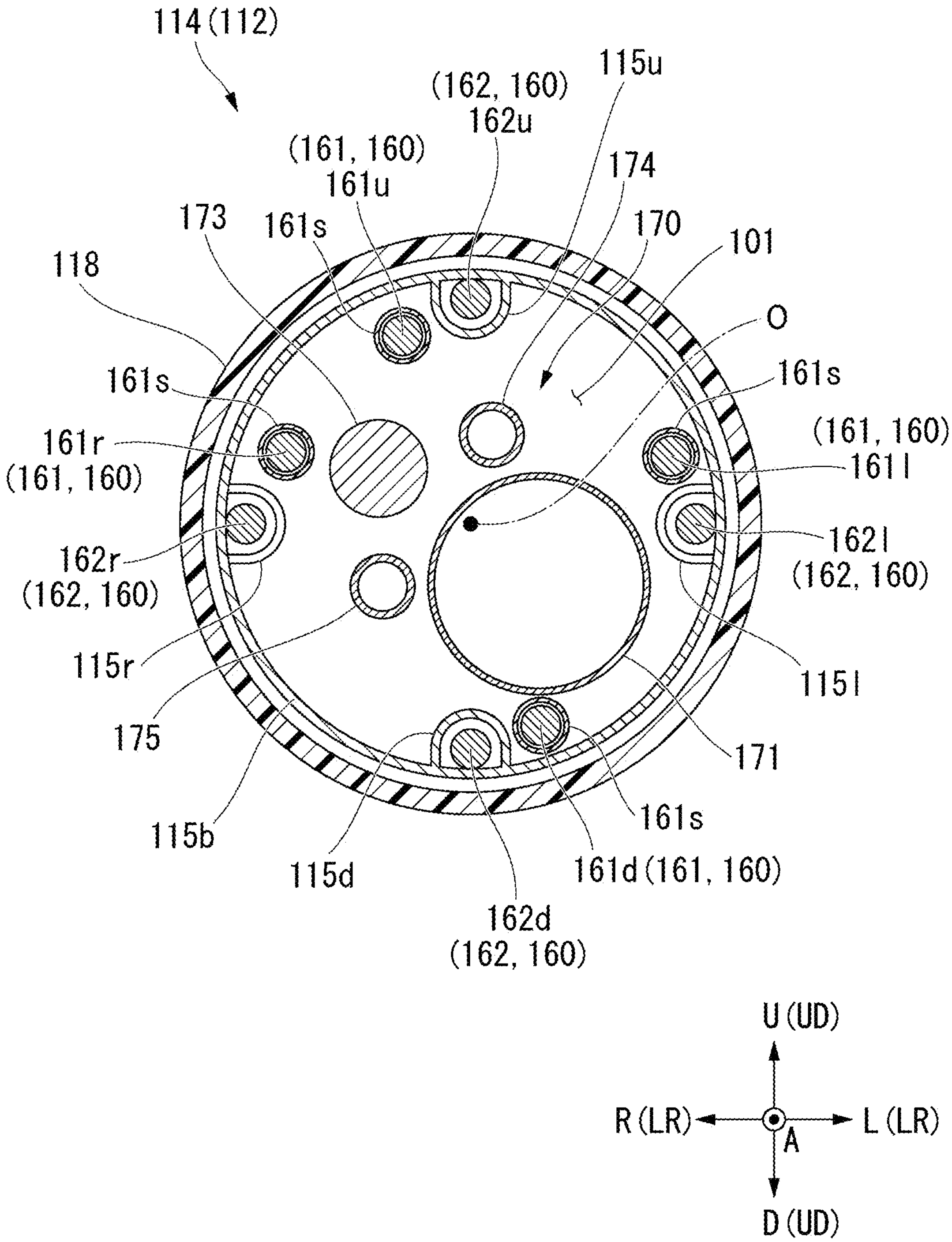
FIG. 27 illustrates an example of a cross-sectional view of a second bending portion of the bending portion along line C2-C2 of FIG. 26.

FIG. 27 is a cross-sectional view of the second bending portion 114 along line C2-C2 of FIG. 26.

Like the first bending wire 161, the second bending wire 162 has a second upper bending wire 162*u*, a second lower bending wire 162*d*, a second left bending wire 1621, and a second right bending wire 162*r*.

The second upper bending wire 162*u*, the second lower bending wire 162*d*, the second left bending wire 1621, and the second right bending wire 162*r* are inserted into the second wire sheaths 162$s$ as shown in FIG. 26. The distal end of the second wire sheath 162$s$ is attached to the joint ring 115 at the proximal end of the second bending portion 114. The second wire sheath 162$s$ extends to the detachable portion 150C.

The second upper bending wire 162$u$ and the second lower bending wire 162$d$ are wires for bending the second bending portion 114 in the UD direction. As shown in FIG. 27, in the second bending portion 114, the second upper bending wire 162$u$ is inserted into the upper wire guide 115$u$. Moreover, in the second bending portion 114, the second lower bending wire 162$d$ is inserted into the lower wire guide 115$d$.

The distal ends of the second upper bending wire 162$u$ and the second lower bending wire 162$d$ are fixed to the second distal end portion 117 of the distal end of the second bending portion 114 as shown in FIG. 26. The distal ends of the second upper bending wire 162$u$ and the second lower bending wire 162$d$ fixed to the second distal end portion 117 are arranged on both sides between which a central axis O in the longitudinal direction A is sandwiched in the UD direction.

The second left bending wire 1621 and the second right bending wire 162$r$ are wires for bending the second bending portion 114 in the LR direction. As shown in FIG. 27, in the second bending portion 114, the second left bending wire 1621 is inserted into the left wire guide 1151. Moreover, in the second bending portion 114, the second right bending wire 162$r$ is inserted into the right wire guide 115$r$.

The distal ends of the second left bending wire 1621 and the second right bending wire 162$r$ are fixed to the second distal end portion 117 of the distal end of the second bending portion 114 as shown in FIG. 26. The distal ends of the second left bending wire 1621 and the second right bending wire 162$r$ fixed to the second distal end portion 117 are arranged on both sides between which the central axis O in the longitudinal direction A is sandwiched in the LR direction.

The second bending portion 114 is freely bent in a desired direction by pulling or relaxing each of the second bending wires 162 (the second upper bending wire 162$u$, the second lower bending wire 162$d$, the second left bending wire 1621, and the second right bending wire 162$r$).

Figure 28:
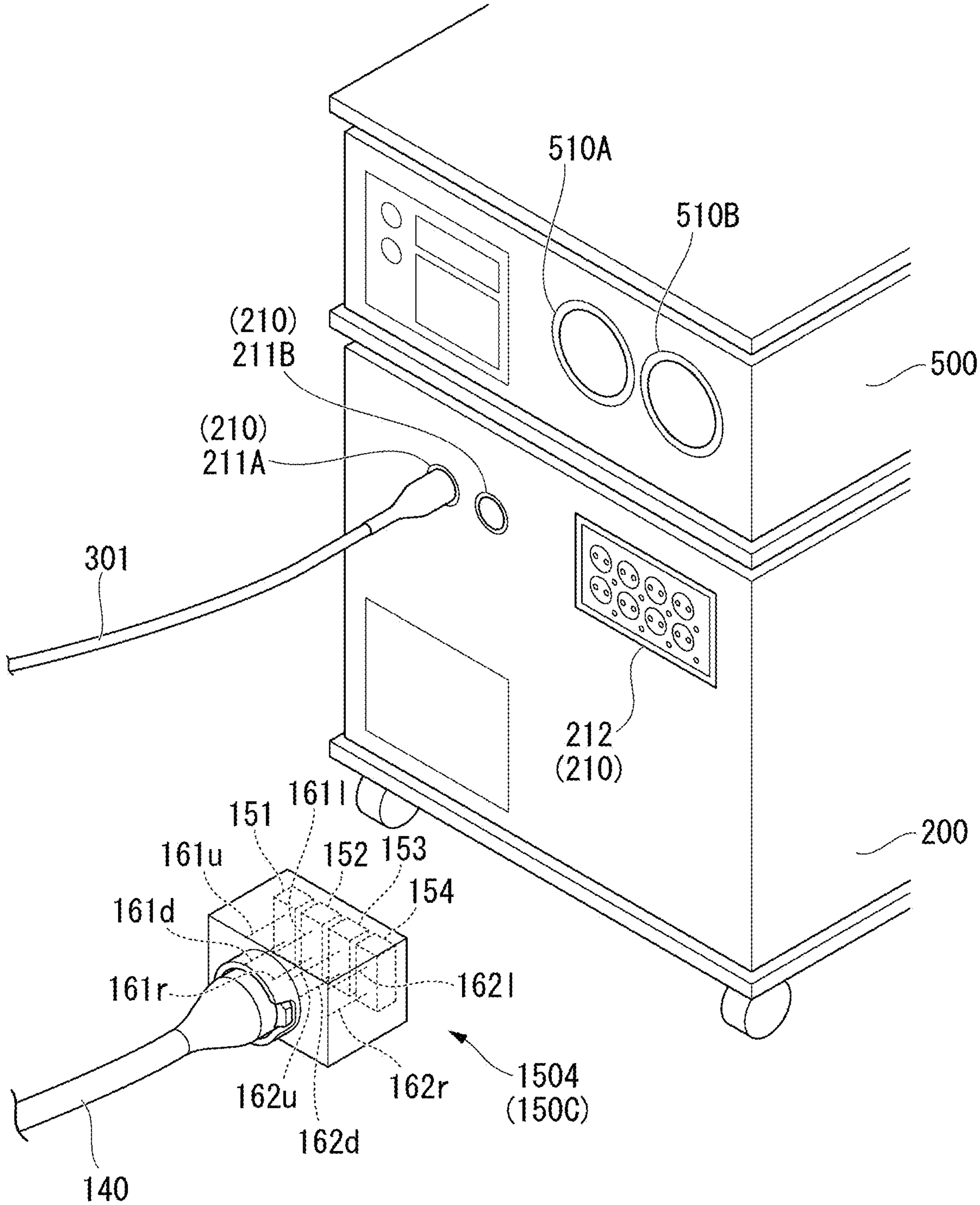
FIG. 28 illustrates an example of a view showing a first detachable portion of the endoscope before attachment to a drive device.

FIG. 28 is a view showing the first detachable portion 1504 before attachment to the drive device 200C.

The detachable portion 150C includes a first detachable portion 1504 attached to the drive device 200 and a second detachable portion 1502 attached to the video control device 500. The first detachable portion 1504 includes a first detachable upper/lower bending wire portion 151, a first detachable left/right bending wire portion 152, a second detachable upper/lower bending wire portion 153, and a second detachable left/right bending wire portion 154.

The first detachable upper/lower bending wire portion 151 is a mechanism for detachably connecting wires (the first upper bending wire 161$u$ and the first lower bending wire 161$d$) for bending the first bending portion 113 in the UD direction to the drive device 200.

The first detachable left/right bending wire portion 152 is a mechanism for detachably connecting wires (the first left bending wire 1611 and the first right bending wire 161$r$) for bending the first bending portion 113 in the LR direction to the drive device 200.

The second detachable upper/lower bending wire portion 153 has a mechanism similar to that of the first detachable upper/lower bending wire portion 151 and is a mechanism for detachably connecting wires (the second upper bending wire 162$u$ and the second lower bending wire 162$d$) for bending the second bending portion 114 in the UD direction to the drive device 200.

The second detachable left/right bending wire portion 154 has a mechanism similar to that of the first detachable left/right bending wire portion 152 and is a mechanism for detachably connecting wires (the second left bending wire 1621 and the second right bending wire 162$r$) for bending the second bending portion 114 in the LR direction to the drive device 200.

The number of driven portions 15X required to drive the endoscope 100C is 8.

The endoscope adapter 212 is connected to the first detachable portion 1504 so that the first drive portion 251, the second drive portion 252, the third drive portion 253, the fourth drive portion 254, the fifth drive portion 255, the sixth drive portion 256, the seventh drive portion 257, and the eighth drive portion 258 drive the bending wire 160.

The first drive portion 251 and the second drive portion 252 can be coupled with the first detachable upper/lower bending wire portion 151 to drive wires (the first upper bending wire 161$u$ and the first lower bending wire 161$d$) for bending the first bending portion 113 in the UD direction.

The third drive portion 253 and the fourth drive portion 254 can be coupled with the first detachable left/right bending wire portion 152 to drive wires (the first left bending wire 1611 and the first right bending wire 161$r$) for bending the first bending portion 113 in the LR direction.

The fifth drive portion 255 and the sixth drive portion 256 can be coupled with the second detachable upper/lower bending wire portion 153 to drive wires (the second upper bending wire 162$u$ and the second lower bending wire 162$d$) for bending the second bending portion 114 in the UD direction.

The seventh drive portion 257 and the eighth drive portion 258 can be coupled with the second detachable left/right bending wire portion 154 to drive wires (the second left bending wire 1621 and the second right bending wire 162$r$) for bending the second bending portion 114 in the LR direction.

The electric endoscope system 1000C according to the present embodiment can be used by attaching the endoscope 100C, which has a difference in the number of driven portions 15X or the like from the endoscope 100, to the drive device 200.

Although the third embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Fourth Embodiment

An electric endoscope system 1000D according to the fourth embodiment of the present disclosure will be described with reference to FIGS. 29 to 45.

[Electric Endoscope System 1000D]

Figure 29:
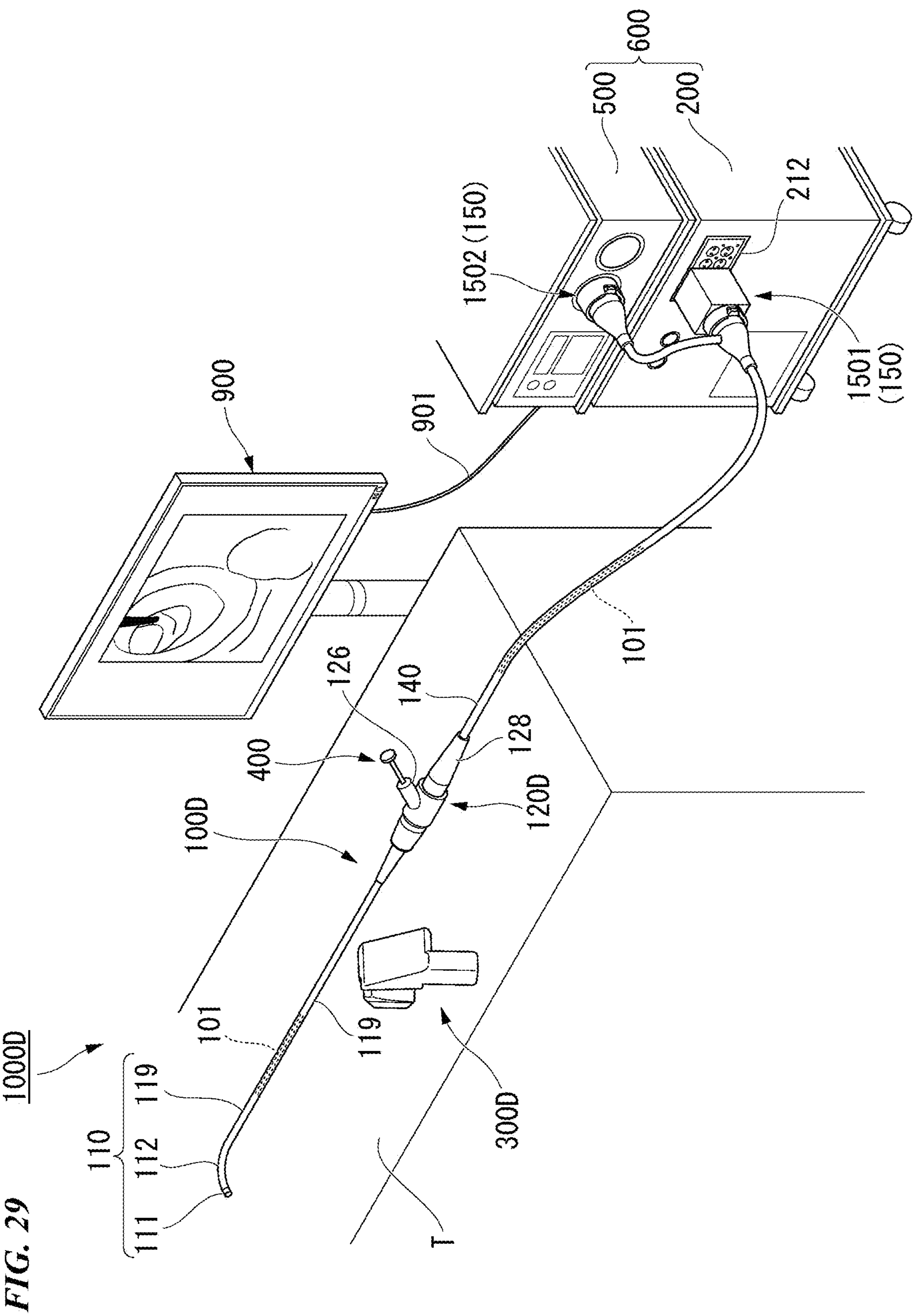
FIG. 29 illustrates an example of an overall view of an electric endoscope system according to a fourth embodiment.

FIG. 29 is an overall view of the electric endoscope system 1000D according to the present embodiment.

The electric endoscope system 1000D includes an endoscope 100D, a drive device 200, a manipulation device 300D, a treatment tool 400, a video control device 500, and a display device 900.

[Endoscope 100D]

The endoscope 100D includes an insertion portion 110, a connection portion 120D, an extracorporeal flexible portion 140, a detachable portion 150, a bending wire 160, and a built-in object 170.

Figure 30:
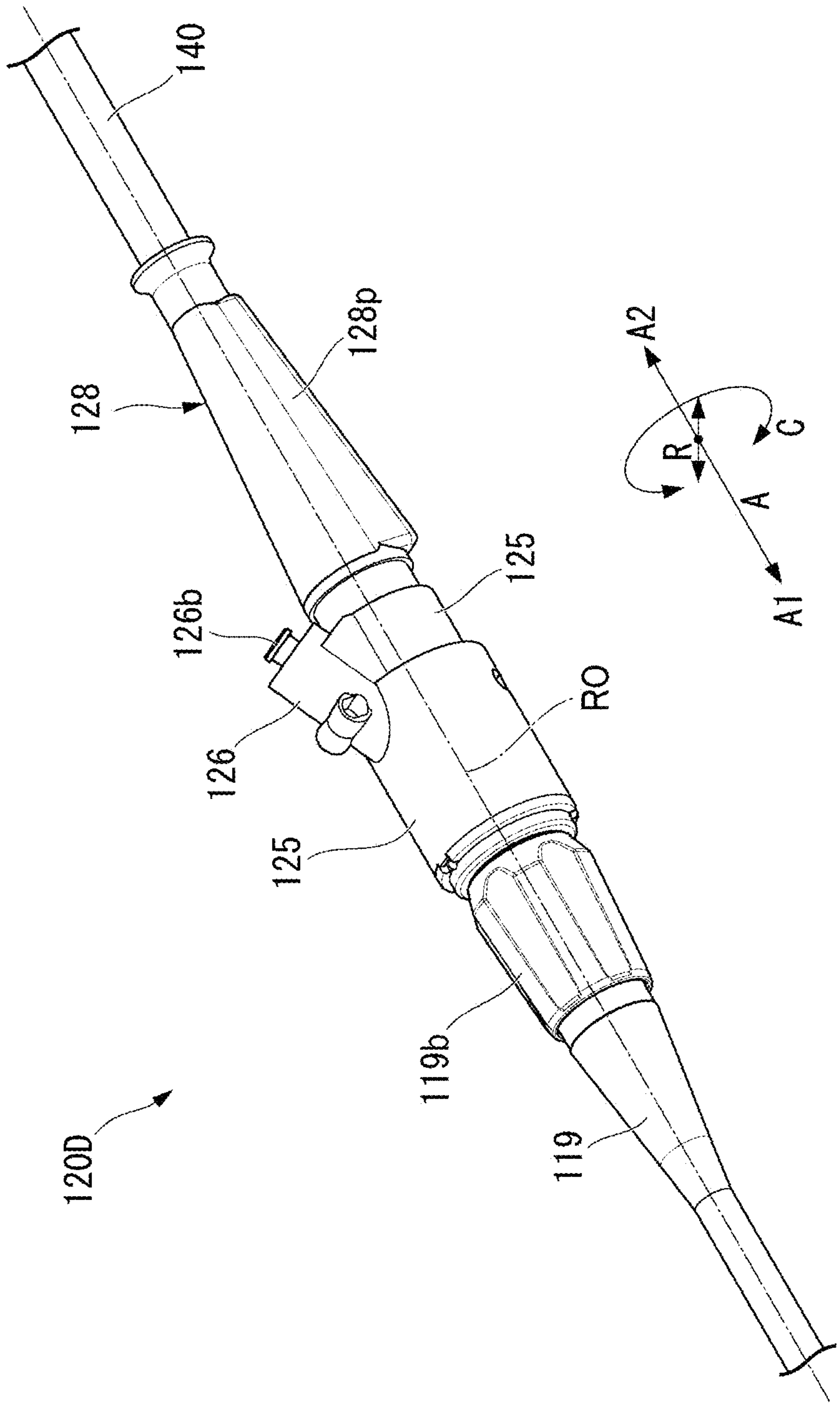
FIG. 30 illustrates an example of a perspective view of a connection portion of an endoscope in the electric endoscope system.
Figure 31:
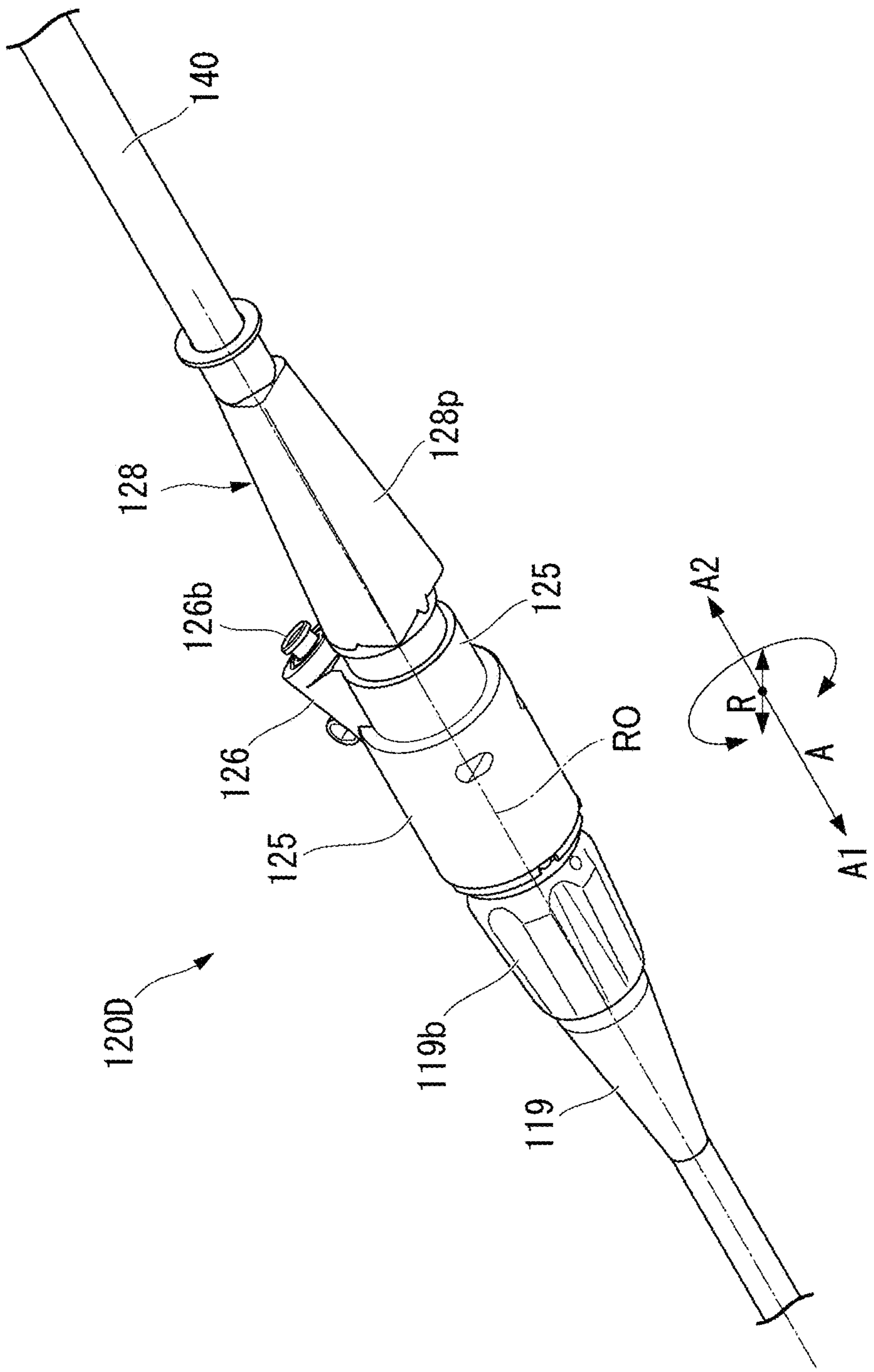
FIG. 31 illustrates an example of a perspective view of the connection portion.

FIGS. 30 and 31 are perspective views of the connection portion 120D.

The connection portion 120D further includes a fitting portion 128 as compared with the connection portion 120 of the first embodiment. The fitting portion 128 is a portion to which the manipulation device 300D is fitted.

The fitting portion 128 is attached to a proximal side A2 of a cover member 125. The fitting portion 128 is formed in a substantially tubular shape and the extracorporeal flexible portion 140 is inserted into an internal space. An outer circumferential surface of the fitting portion 128 is formed in a tapered shape in which a diameter dimension increases from the proximal side A2 to a distal side A1. The outer circumferential surface of the fitting portion 128 is formed in a D-shape in a cross-section perpendicular to a longitudinal direction A (see FIG. 39).

As shown in FIG. 31, a planar portion 128*p* is formed on the outer circumferential surface of the fitting portion 128. The planar portion 128*p* is a surface facing in a radial direction R perpendicular to the longitudinal direction A. The planar portion 128*p* is provided on the opposite side of an instruments port 126 with respect to a rotation axis RO of a cylindrical member 121 extending in a longitudinal direction A.

[Manipulation Device 300D]

Figure 32:
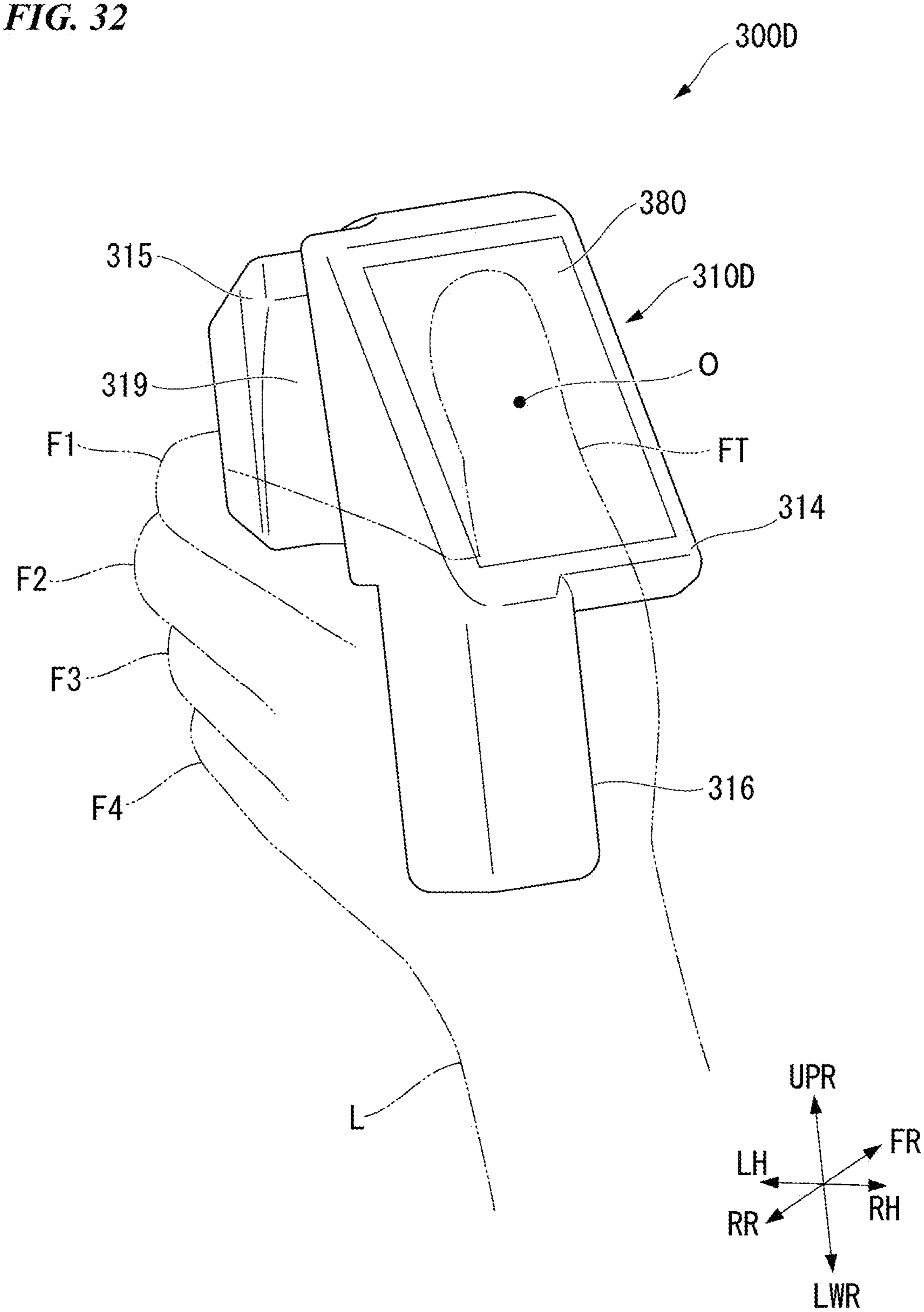
FIG. 32 illustrates an example of a perspective view of a manipulation device in the electric endoscope system.
Figure 33:
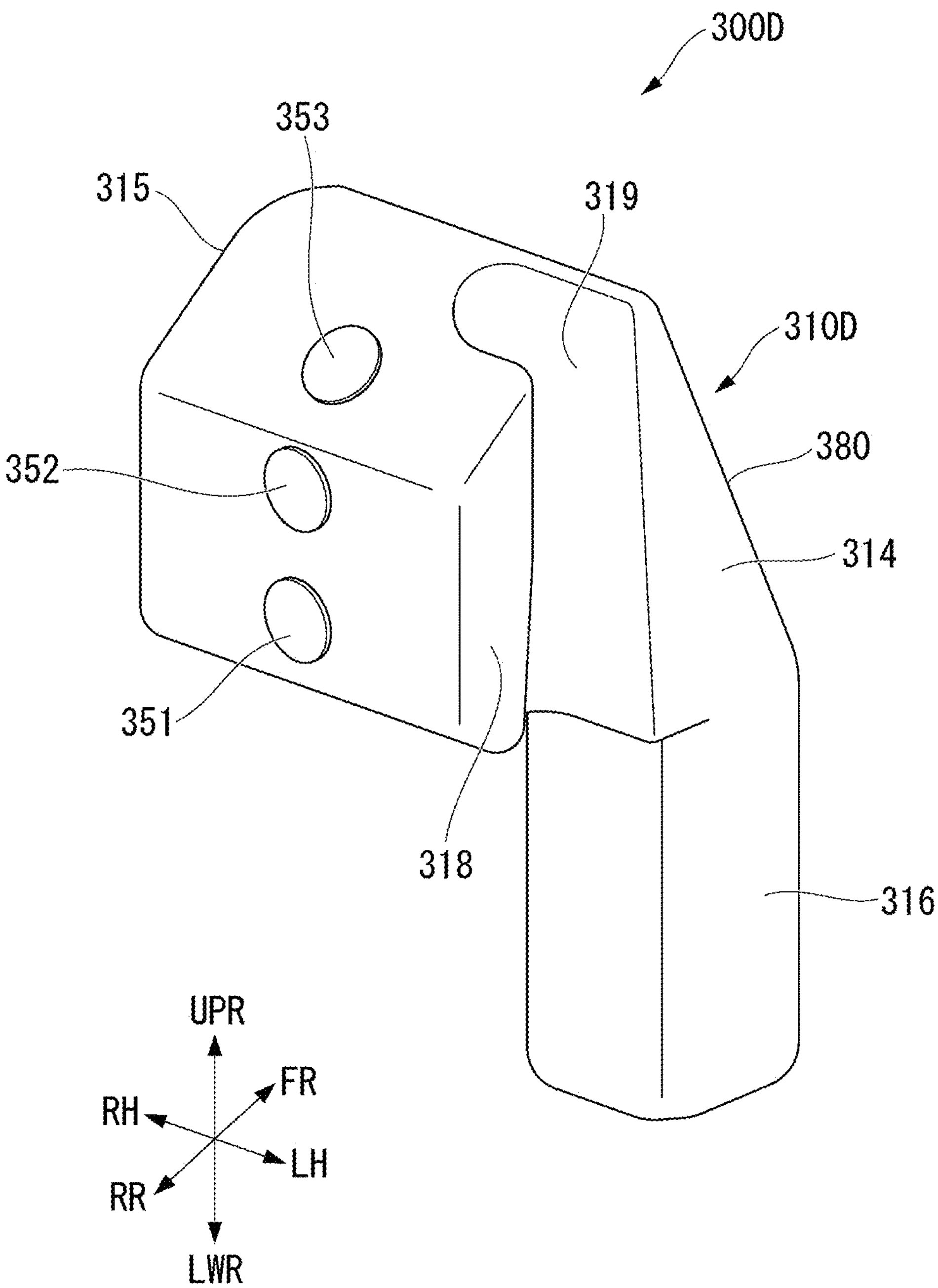
FIG. 33 illustrates an example of a perspective view of the manipulation device.

FIGS. 32 and 33 are perspective views of the manipulation device 300D.

The manipulation device (controller) 300D is a device to which a manipulation of a scopist S who controls the electric endoscope system 1000D (in particular, a manipulation for driving the endoscope 100D) is input. The input manipulation input is transmitted to the drive device 200 or the like through wireless communication.

The manipulation device 300D includes a manipulation portion body 310D, an air/water supply button 351, a suction button 352, a release button 353, and a touchpad 380.

In the following description, a direction perpendicular to the touchpad 380 is defined as a "advanceable and retractable direction" and an orientation in which the touchpad 380 is provided on the manipulation portion body 310D is defined as a "front FR." An orientation opposite to the "front FR" is defined as a "rear RR." Moreover, a longitudinal direction of the manipulation portion body 310D is defined as a "vertical direction" and an orientation in which the touchpad 380 is attached to the manipulation portion body 310D is defined as an "upper side UPR." An orientation opposite to the "upper side UPR" is defined as a "lower side LWR." A right orientation toward the rear RR is defined as "right RH." An orientation opposite to the "right RH" is defined as "left LH." A direction toward the right RH or the left LH is defined as a "left/right direction."

The manipulation portion body 310D is formed in a shape capable of being held by the scopist S with a left hand L. The manipulation portion body 310 includes a touchpad support portion 314 provided on the upper side UPR, a button support portion 315 provided on the rear RR, a grip member 316 provided on the lower side LWR, and a guide groove 319 provided on the left LH.

The touchpad support portion 314 is formed in a substantially rectangular shape when viewed from the front FR to the rear RR and supports the touchpad 380.

The button support portion 315 is a convex portion protruding from the touchpad support portion 314 to the rear RR. The button support portion 315 supports the air/water supply button 351, the suction button 352, and the release button 353.

Figure 34:
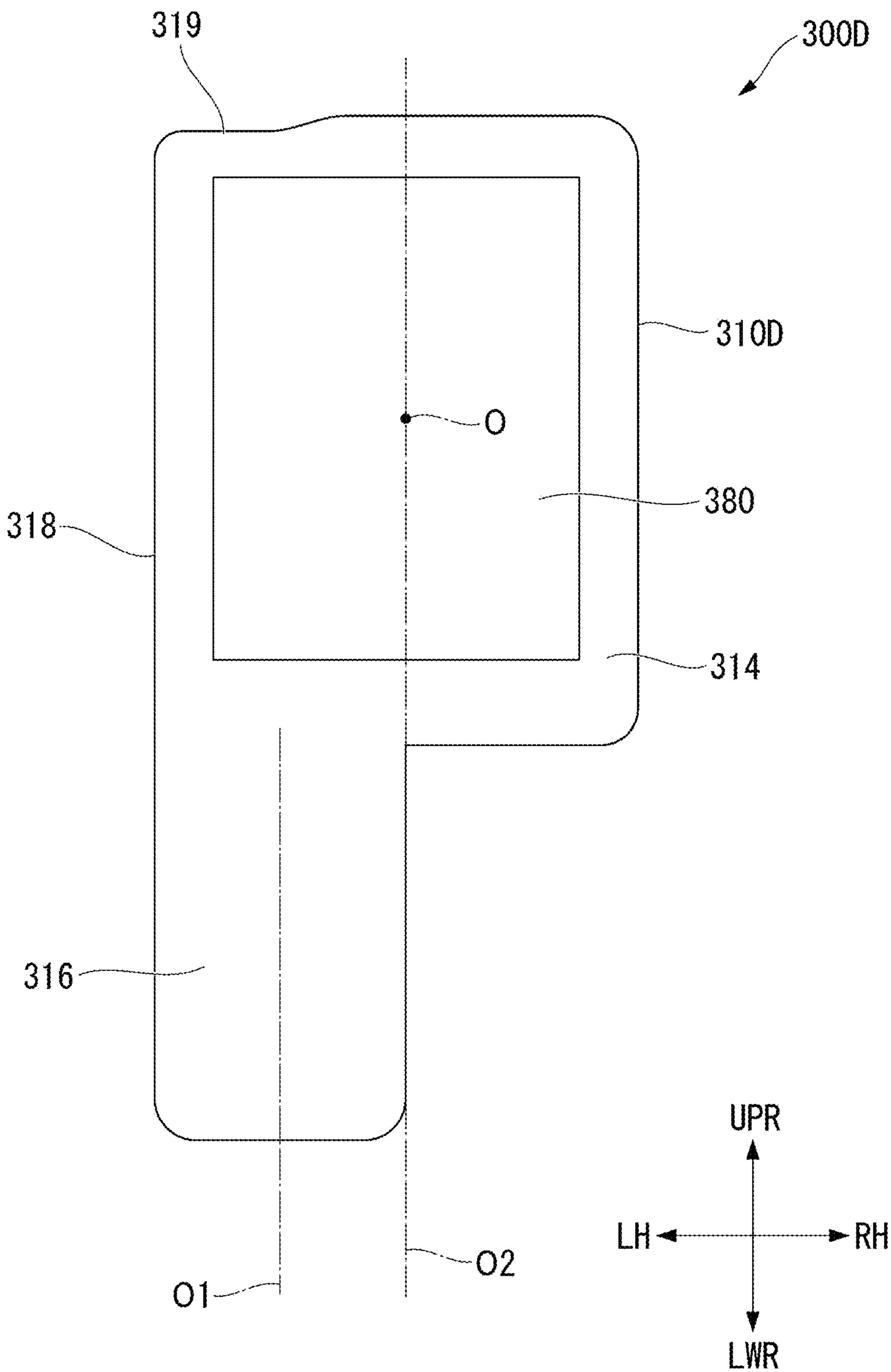
FIG. 34 illustrates an example of a front view of the manipulation device.

FIG. 34 is a front view of the manipulation device 300D.

The grip member (grip portion) 316 is formed in a substantially rectangular shape extending in the vertical direction and gripped by a ring finger (third finger) F3 and a little finger (fourth finger) F4 of the left hand L of the scopist S. A first central axis O1 of the grip member 316 in the vertical direction is arranged to be offset to the left LH from a second central axis O2 in the vertical direction passing through a center O of the touchpad 380 when viewed from the front FR. Therefore, as shown in FIG. 32, the scopist S causes a palm of the left hand L to come into contact with the grip member 316 and easily manipulates the touchpad 380 with a thumb finger FT of the left hand L.

Figure 35:
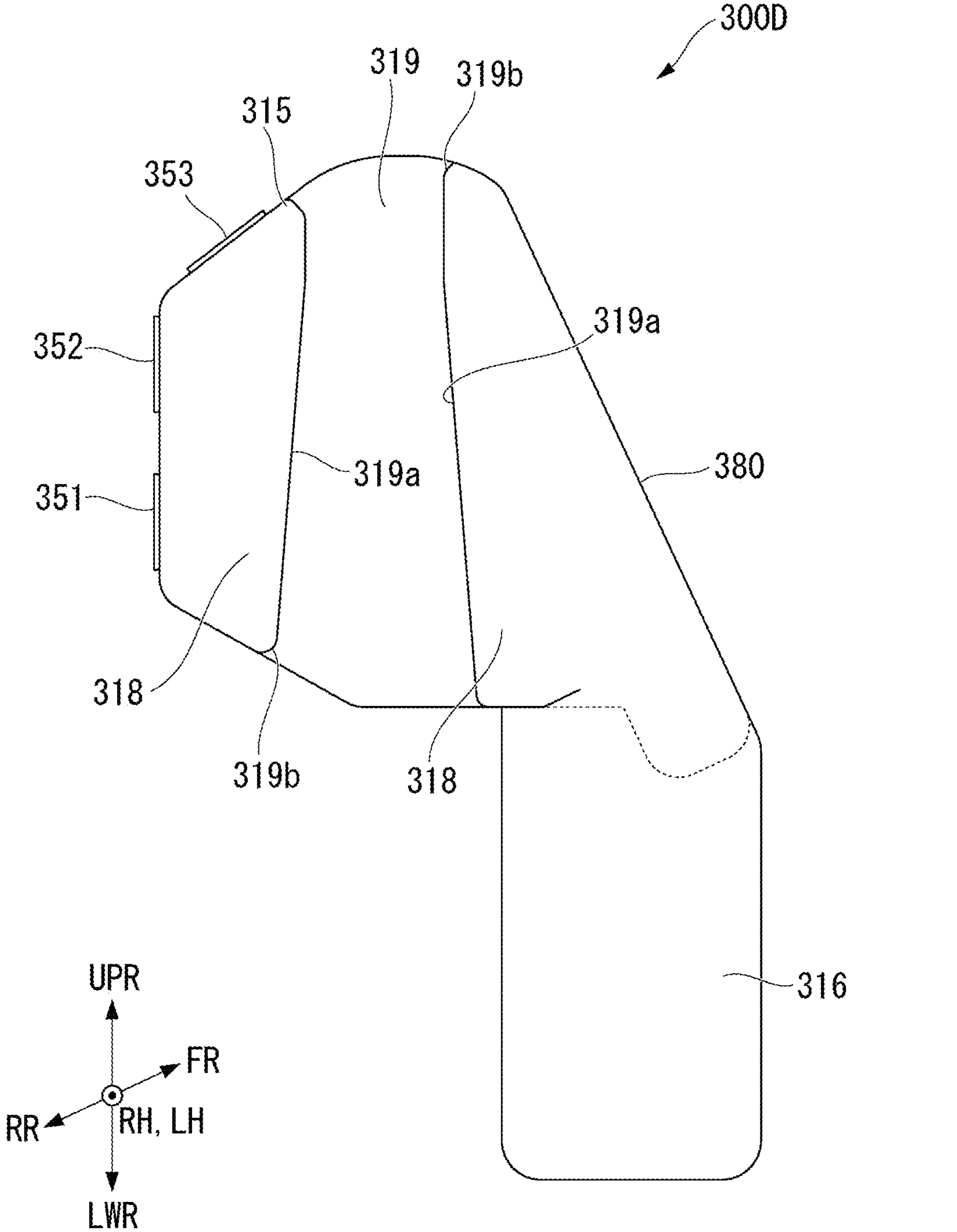
FIG. 35 illustrates an example of a left-side view of the manipulation device.

FIG. 35 is a left-side view of the manipulation device 300D.

The guide groove 319 is a groove formed on a left surface 318 facing the left LH of the manipulation portion body 310D and extends in the vertical direction. The guide groove 319 has a taper portion 319*a* extending in the vertical direction and an opening 319*b* formed at both ends of the taper portion 319*a* in the vertical direction. The taper portion 319*a* is formed in a tapered shape in which a diameter dimension increases from the upper side UPR to the lower side LWR. The taper portion 319*a* can be fitted to the outer circumferential surface of the fitting portion 128.

Figure 36:
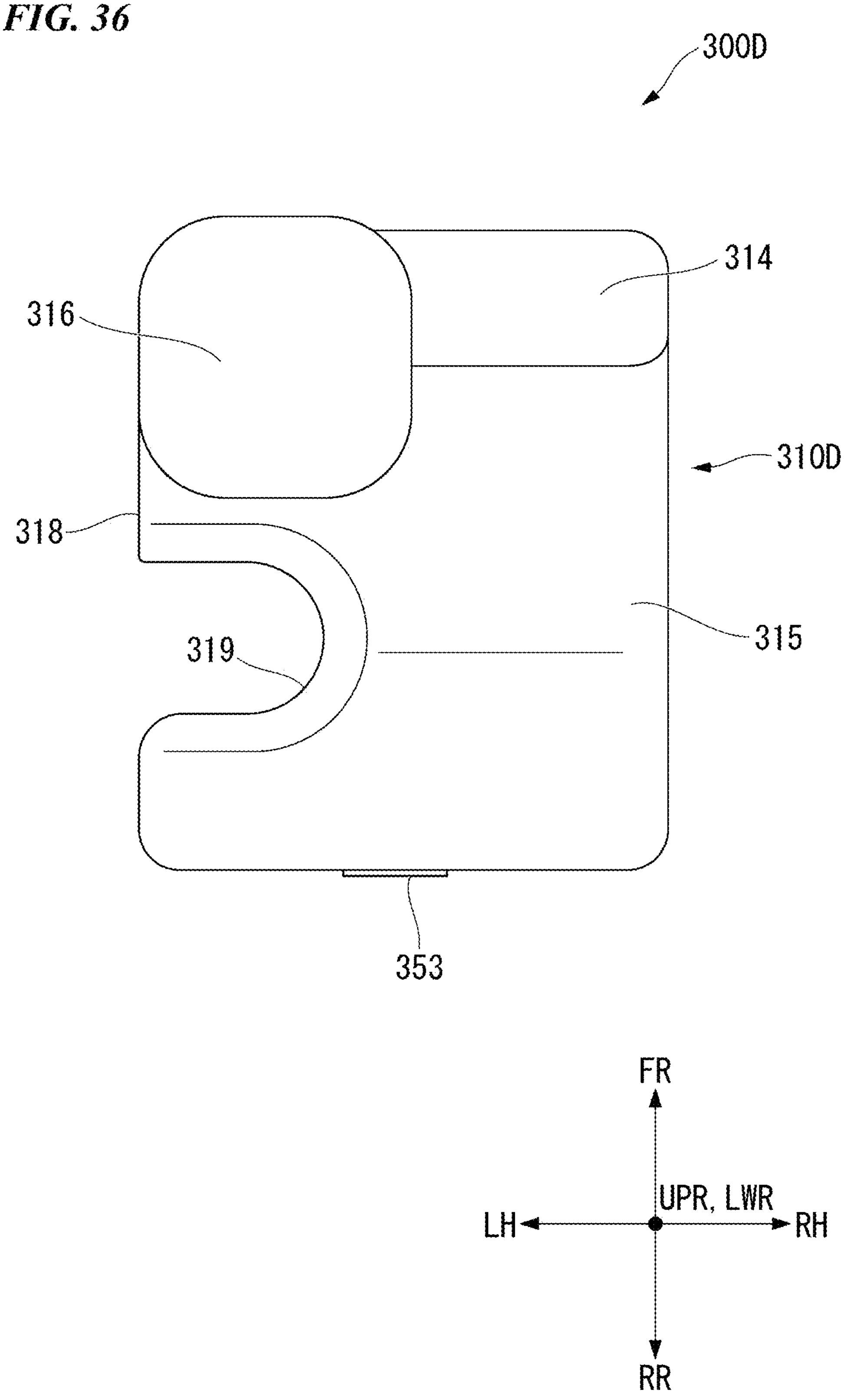
FIG. 36 illustrates an example of a bottom view of the manipulation device.

FIG. 36 is a bottom view of the manipulation device 300D.

The guide groove 319 is a groove formed in a D-shape when viewed in the vertical direction. The guide groove 319 extending in the vertical direction is arranged side by side with the grip member 316 in the advanceable and retractable direction when viewed in the vertical direction and is provided at a position that does not overlap the grip member 316.

The air/water supply button 351 is attached to the rear RR of the button support portion 315 and is a push button for inputting a manipulation of performing air/water supply from the opening 111*a* of the distal end portion 111 of the endoscope 100D. When the air/water supply button 351 is pressed, the manipulation device 300D transmits a manipulation input for performing air/water supply to the drive device 200.

The suction button 352 is attached to the rear RR of the button support portion 315 and is a push button for inputting a manipulation of performing suction from the opening 111*a* of the distal end portion 111 of the endoscope 100D. When the suction button 352 is pressed, the manipulation device 300D transmits a manipulation input for performing suction to the drive device 200.

The release button 353 is attached to the upper side UPR of the button support portion 315 and is a push button for inputting a manipulation of saving a captured image acquired from the imaging portion 111*c* of the endoscope 100D in the video control device 500. When the release button 353 is pressed, the manipulation device 300D transmits a manipulation input for saving the captured image to the drive device 200.

The touchpad 380 is a touch-sensitive interface to which a bending manipulation or the like on the bending portion 112 is input. The touchpad 380 may be a touch panel.

As shown in FIG. 32, the scopist S can manipulate the touchpad 380 with the thumb finger FT of the left hand L while gripping the grip member 316 with the ring finger F3 and the little finger F4 of the left hand L. Moreover, the scopist S can manipulate the air/water supply button 351, the suction button 352, and the release button 353 with an index finger (first finger) F1 or a middle finger (second finger) F2 of the left hand L.

[Operation of Electric Endoscope System 1000D]

Next, an operation of the electric endoscope system 1000D of the present embodiment will be described. Specifically, a usage method of fitting the manipulation device 300D of the electric endoscope system 1000D to the connection portion 120D will be described.

Figure 37:
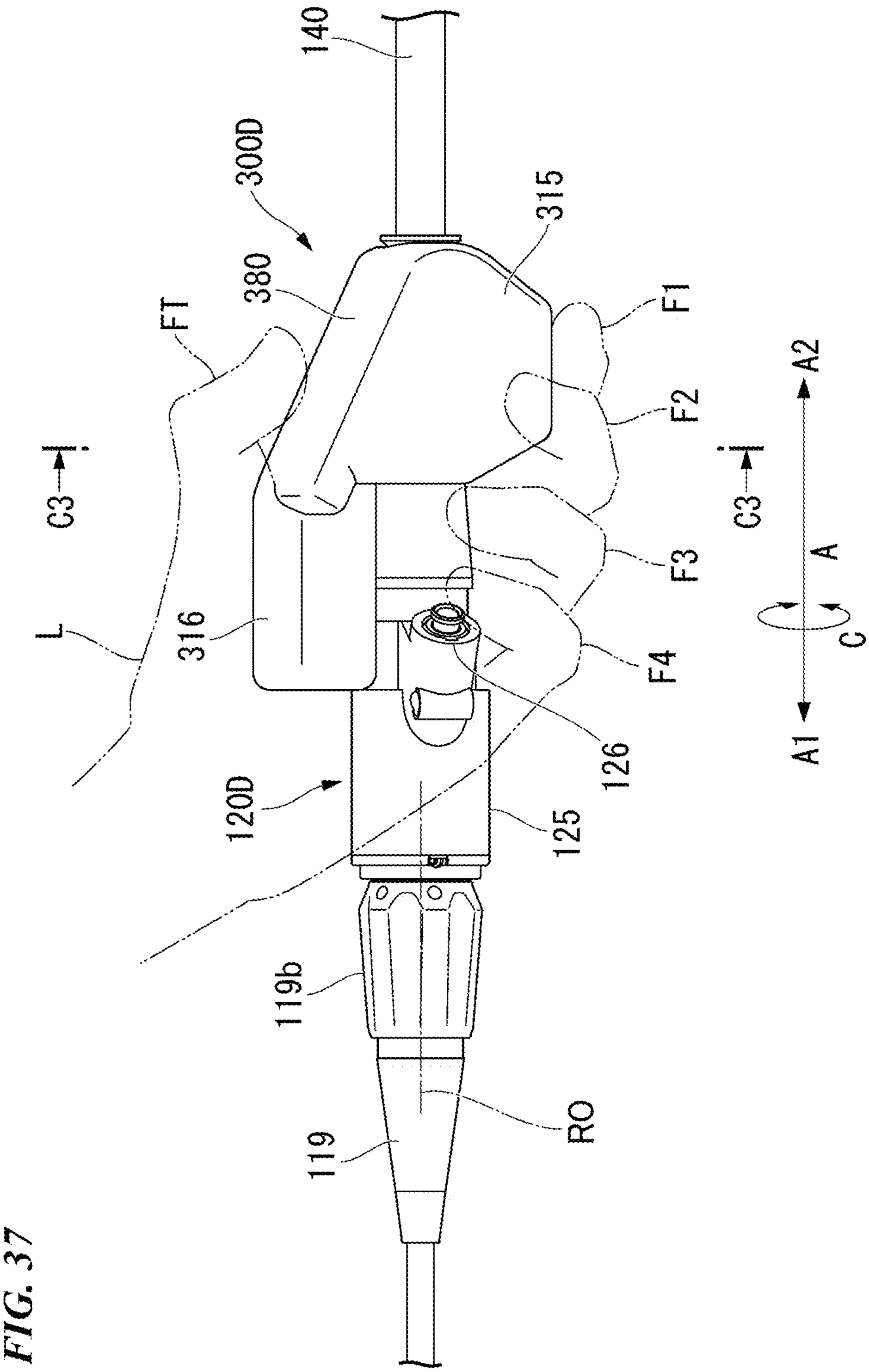
FIG. 37 illustrates an example of a view showing the manipulation device fitted with the connection portion.
Figure 38:
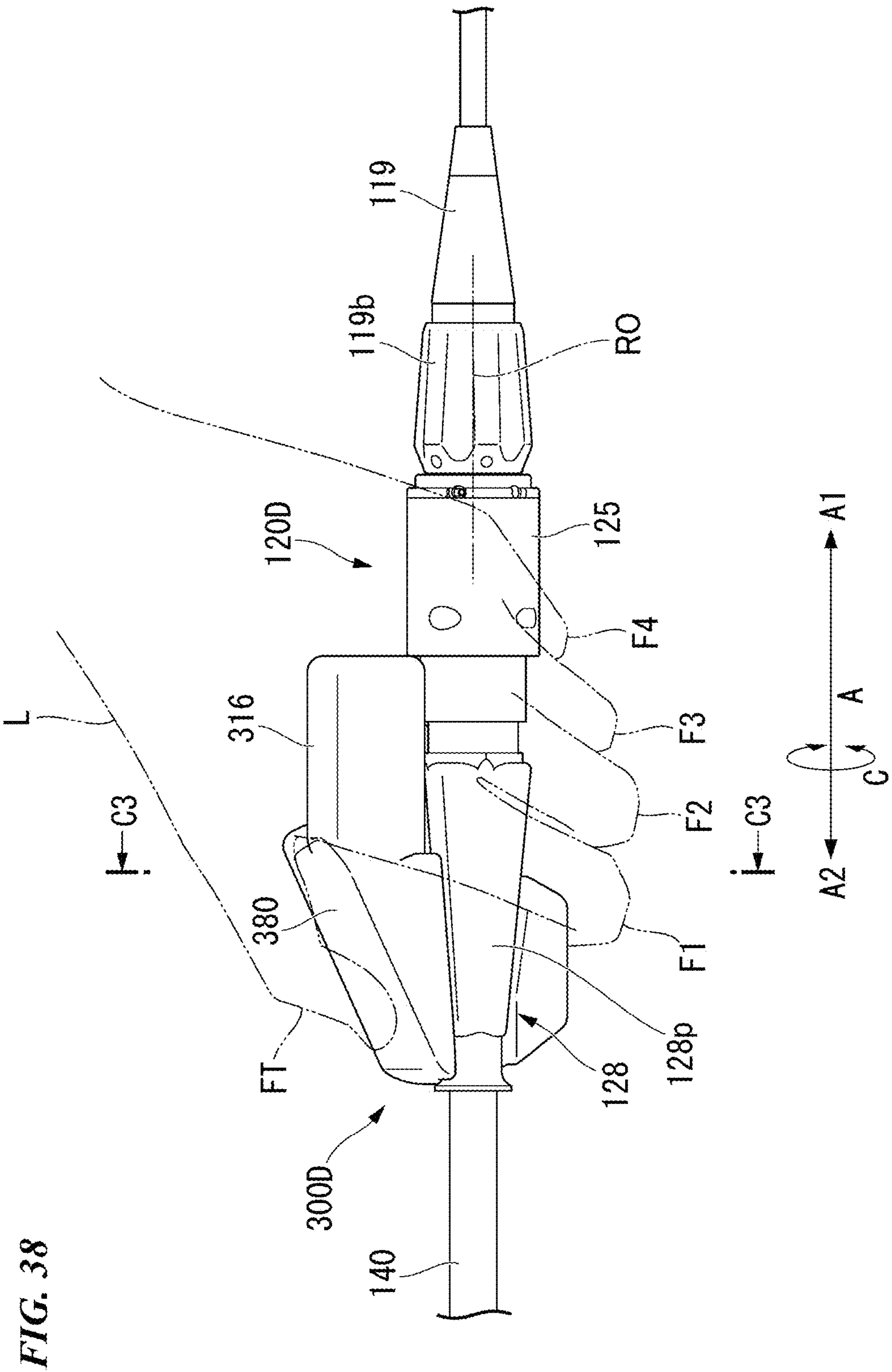
FIG. 38 illustrates an example of a view showing the manipulation device fitted with the connection portion.

FIGS. 37 and 38 are views showing the manipulation device 300D fitted with the connection portion 120D. The scopist S holds the manipulation device 300D and the connection portion 120D with the left hand L in a state in which the guide groove 319 of the manipulation device 300D is fitted to the fitting portion 128 of the connection portion 120D.

Specifically, the scopist S causes the vertical direction of the manipulation device 300D to substantially coincide with the longitudinal direction A of the connection portion 120D and causes the guide groove 319 of the manipulation device 300D to be fitted to the fitting portion 128 of the connection portion 120D. The upper side UPR of the manipulation device 300D faces the proximal side A2 of the connection portion 120D. The lower side LWR of the manipulation device 300D faces the distal side A1 of the connection portion 120D.

The guide groove 319 is a groove formed on the left surface 318 facing the left LH of the manipulation portion body 310D. Therefore, the scopist S can firmly hold the manipulation device 300D and the connection portion 120D without using the right hand R by simply fitting the fitting portion 128 from the left LH to the guide groove 319 and holding the manipulation device 300D from the left LH with the left hand L.

The guide groove 319 and the fitting portion 128 are formed in a tapered shape as described above. Therefore, the scopist S can easily fit the guide groove 319 to the fitting portion 128 by sliding and moving the manipulation device 300D to the distal side A1 while arranging the guide groove 319 of the manipulation device 300D along the extracorporeal flexible portion 140.

The guide groove 319 extending in the vertical direction is arranged side by side with the grip member 316 in the advanceable and retractable direction when viewed in the vertical direction, and is provided at a position that does not overlap other portions of the manipulation device 300D including the grip member 316. Therefore, when the guide groove 319 is fitted to the fitting portion 128, the connection portion 120D is arranged side by side with the grip member 316 of the manipulation device 300D in the advanceable and retractable direction. Therefore, the scopist S can collectively hold the grip member 316 of the manipulation device 300D and the connection portion 120D with the ring finger F3 and the little finger F4 of the left hand L. In addition, the grip member 316 is desirably arranged adjacent to the connection portion 120D.

Figure 39:
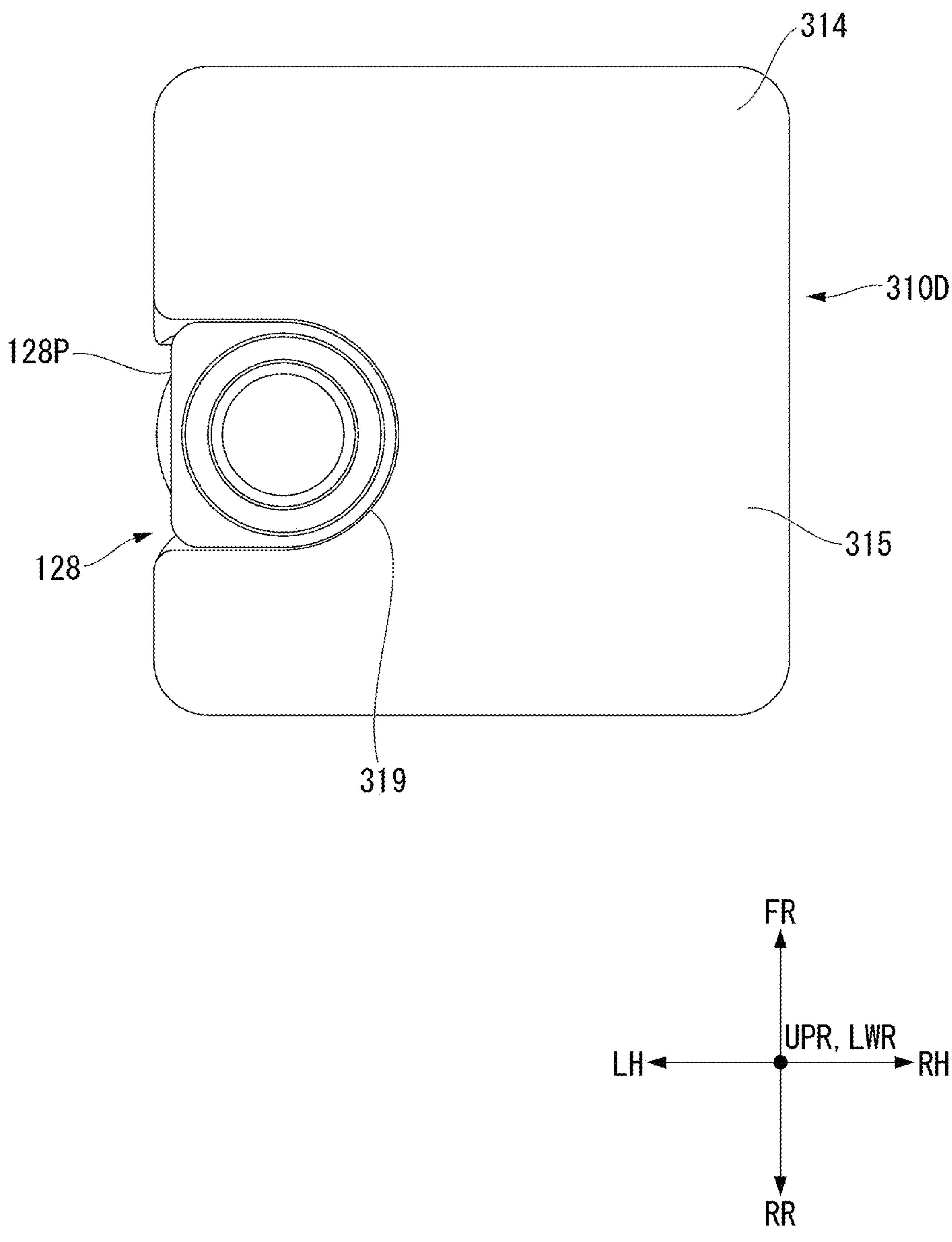
FIG. 39 illustrates an example of a cross-sectional view of the manipulation device along line C3-C3 shown in FIGS. 37 and 38.

FIG. 39 is a cross-sectional view of the manipulation device 300D along line C3-C3 shown in FIGS. 37 and 38. The scopist S fits the fitting portion 128 to the guide groove 319 so that the planar portion 128*p* of the fitting portion 128 faces the left LH of the manipulation device 300D. As a result, the outer circumferential surface other than the planar portion 128*p* of the fitting portion 128 is fitted with the inner circumferential surface of the guide groove 319 formed in a D-shape when viewed in the vertical direction. The outer circumferential surface other than the planar portion 128*p* of the fitting portion 128 is fitted with the inner circumferential surface of the guide groove 319, for example, with a tight fit. As shown in FIG. 39, in a cross-section perpendicular to the longitudinal direction A, the outer circumferential surface of the fitting portion 128 is formed in a D-shape. Therefore, when the guide groove 319 is fitted to the fitting portion 128, the manipulation device 300D does not rotate in a circumferential direction C with respect to the connection portion 120D. In addition, the fitting portion 128 may further have an elastic member such as rubber so that the guide groove 319 can be press-fitted to the fitting portion 128.

When the guide groove 319 of the manipulation device 300D is fitted to the fitting portion 128 of the connection portion 120D, the manipulation device 300D is attached to the connection portion 120D. Therefore, the scopist S simply moves the manipulation device 300D to the right RH with the right hand R by separating the ring finger F3 and the little finger F4 of the left hand L from the grip member 316, and therefore the manipulation device 300D can be easily removed from the connection portion 120D.

<First Manipulation Position OP1>

Figure 40:
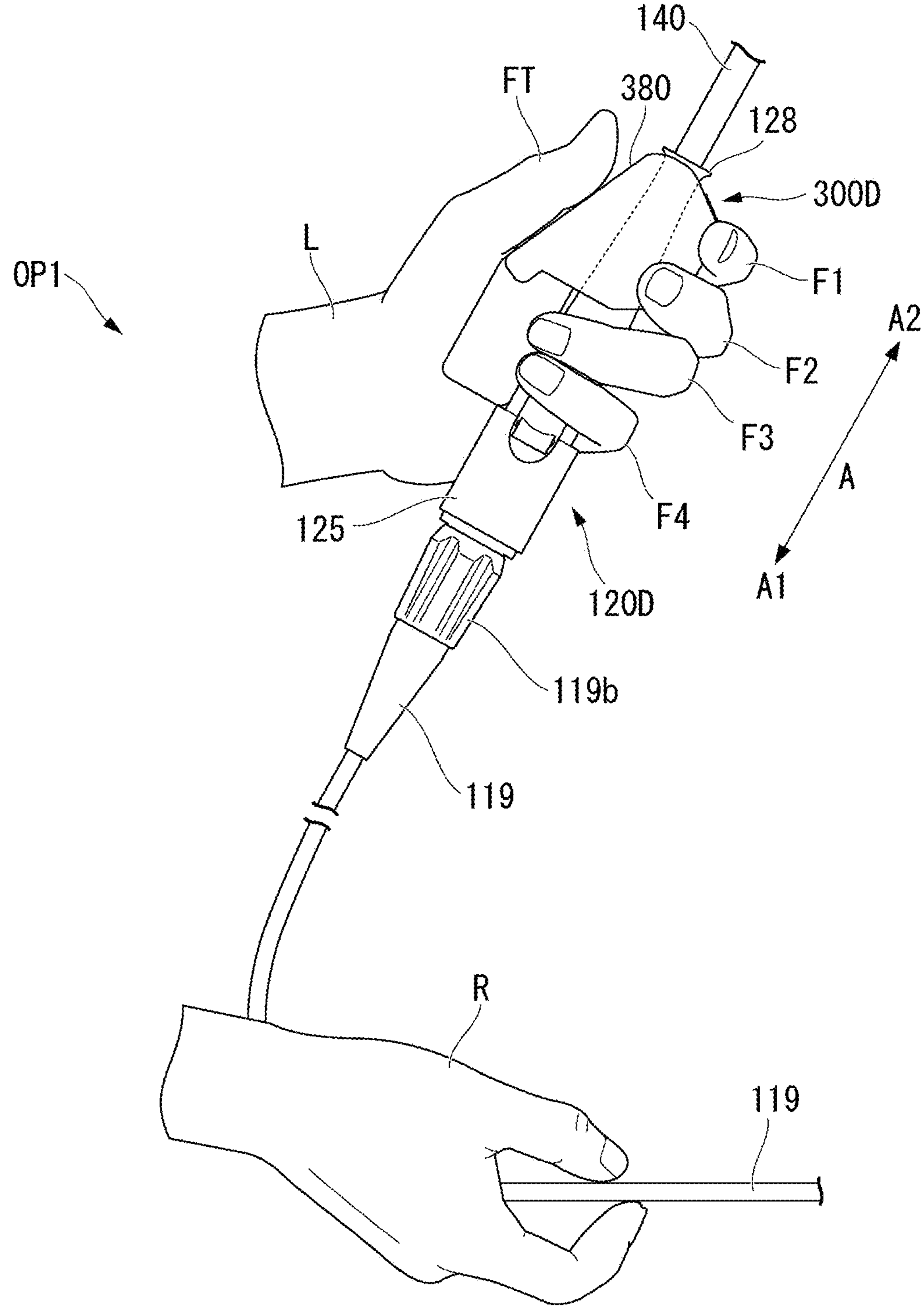
FIG. 40 illustrates an example of a view showing a first manipulation position of the manipulation device.

FIG. 40 is a view showing a first manipulation position OP1 of the manipulation device 300D.

An arrangement position of the manipulation device 300D obtained by fitting the guide groove 319 of the manipulation device 300D to the fitting portion 128 of the connection portion 120D is referred to as the "first manipulation position OP1." The manipulation device 300D arranged at the first manipulation position OP1 fits the guide groove 319 of the manipulation device 300D to the fitting portion 128 of the connection portion 120D by causing the vertical direction of the manipulation device 300D to substantially coincide with the longitudinal direction A of the connection portion 120D. The upper side UPR of the manipulation device 300D faces the proximal side A2 of the connection portion 120D. The lower side LWR of the manipulation device 300D faces the distal side A1 of the connection portion 120D.

As shown in FIG. 40, the scopist S collectively holds the manipulation device 300D and the connection portion 120D arranged at the first manipulation position OP1 with the left hand L and holds the intracorporeal flexible portion 119 with the right hand R. While observing a captured image displayed on the display device 900, the scopist S moves the insertion portion 110 while manipulating the intracorporeal flexible portion 119 with the right hand R (an advanceable and retractable movement manipulation and a torsion manipulation). Moreover, the scopist S manipulates the touchpad 380 of the manipulation device 300D with the left hand L (an angle manipulation) and bends the bending portion 112 as necessary.

When the scopist S moves the insertion portion 110 while manipulating the intracorporeal flexible portion 119 with the right hand R, the connection portion 120D is held with the left hand L. Therefore, the scopist S can perform the torsion manipulation on the intracorporeal flexible portion 119 with the left hand L. Moreover, the scopist S can advance and retract the connection portion 120D with the left hand L and support the advanceable and retractable movement manipulation on the intracorporeal flexible portion 119 with the right hand R. As a result, the scopist S can appropriately manipulate the intracorporeal flexible portion 119 as compared with a case where the intracorporeal flexible portion 119 is manipulated only with the right hand R.

The first manipulation position OP1 is an arrangement position of the manipulation device 300D that is particularly effective when the insertion portion 110 is inserted into the patient P.

Figure 41:
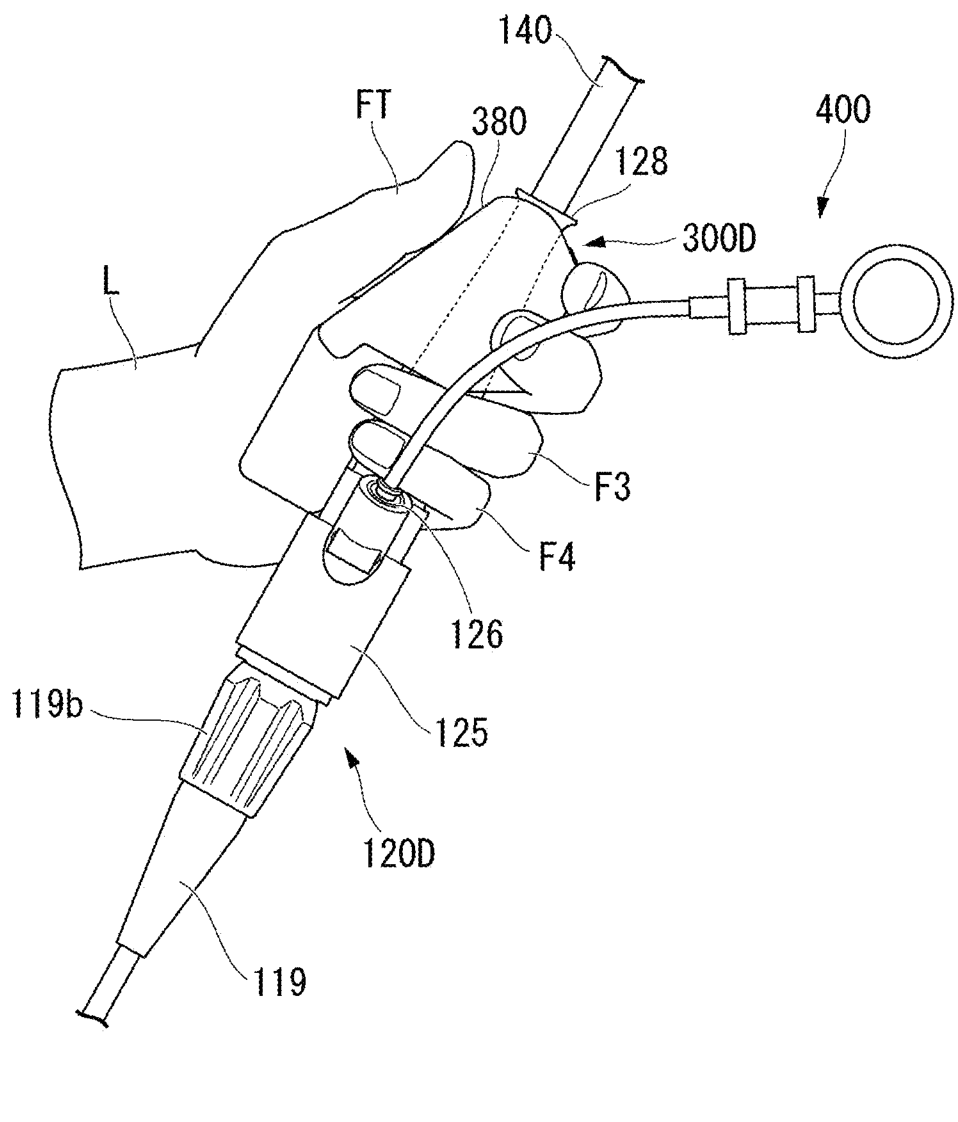
FIG. 41 illustrates an example of a view showing the connection portion in which a treatment tool is inserted into an instruments port.

FIG. 41 is a view showing the connection portion 120D in which the treatment tool 400 is inserted into the instruments port 126. The instruments port 126 of the connection portion 120D and the planar portion 128*p* of the fitting portion 128 are provided on both sides between which the rotation axis RO of the cylindrical member 121 extending in the longitudinal direction A is sandwiched. Therefore, when the manipulation device 300D is arranged at the first manipulation position OP1, the instruments port 126 is arranged at the lower right of the manipulation device 300D. Therefore, the scopist S can manipulate the manipulation device 300D with the left hand L and manipulate the treatment tool 400 inserted into the instruments port 126 with the right hand R as in an existing method of manipulating the endoscope and the treatment tool.

Figure 42:
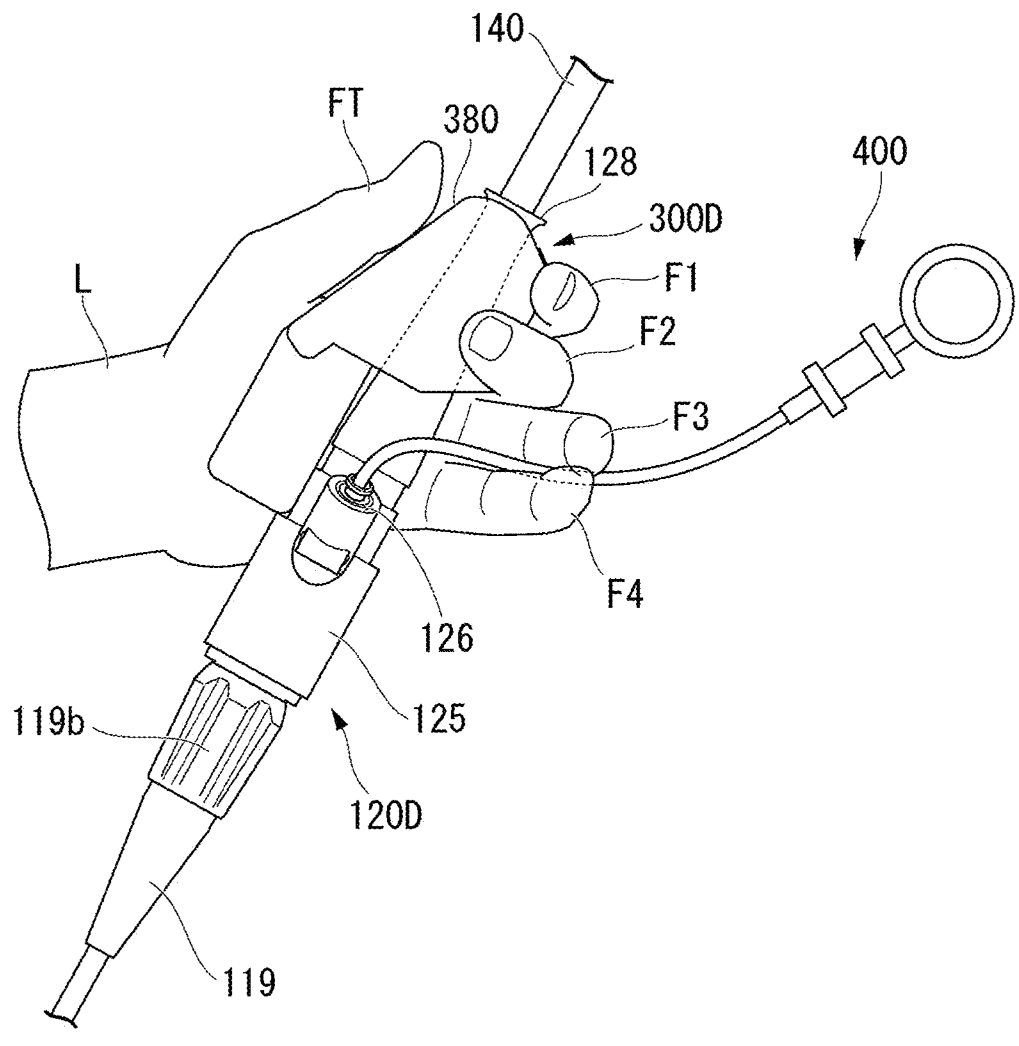
FIG. 42 illustrates an example of a view showing a guide tool to be manipulated by a left hand.

FIG. 42 is a view showing a treatment tool manipulated by the left hand L.

The scopist S may manipulate the treatment tool 400 inserted into the instruments port 126 with the ring finger F3 and the little finger F4 of the left-hand holding the manipulation device 300D. The scopist S can manipulate the treatment tool 400 with the left hand L while manipulating the touchpad 380 of the manipulation device 300D with the left hand L (an angle manipulation).

<Second Manipulation Position OP2>

Figure 43:
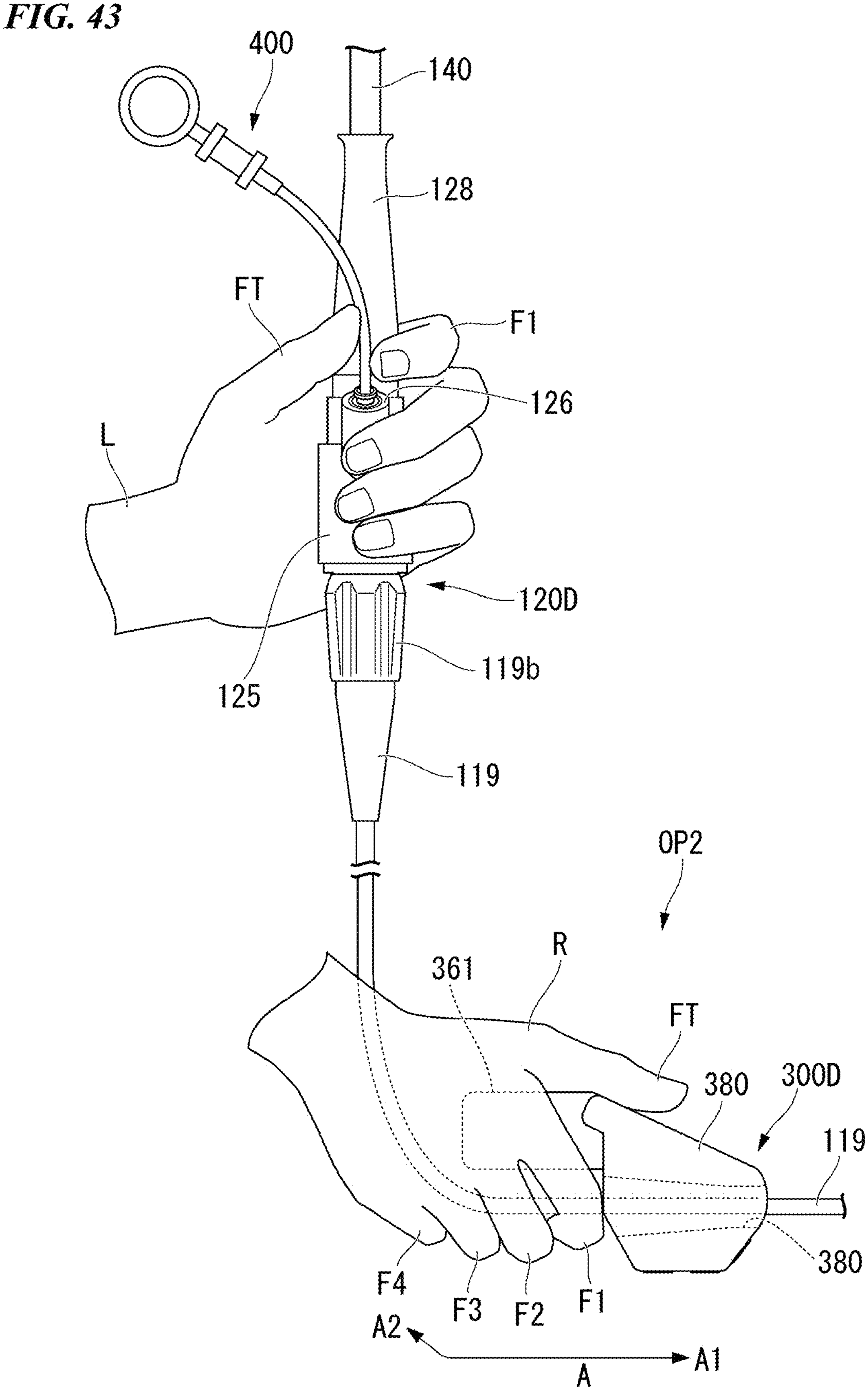
FIG. 43 illustrates an example of a view showing a second manipulation position of the manipulation device.

FIG. 43 is a view showing a second manipulation position OP2 of the manipulation device 300D.

The scopist S can engage the guide groove 319 of the manipulation device 300D with the intracorporeal flexible portion 119. An arrangement position of the manipulation device 300D at which the manipulation device 300D is engaged with the intracorporeal flexible portion 119 is referred to as the “second manipulation position OP2.” The manipulation device 300D arranged at the second manipulation position OP2 causes the vertical direction of the manipulation device 300D to substantially coincide with the longitudinal direction A of the intracorporeal flexible portion 119, and the guide groove 319 of the manipulation device 300D is engaged with the intracorporeal flexible portion 119. The upper side UPR of the manipulation device 300D faces the distal side A1 of the intracorporeal flexible portion 119. The lower side LWR of the manipulation device 300D faces the proximal side A2 of the intracorporeal flexible portion 119.

As shown in FIG. 43, the scopist S holds the connection portion 120D with the left hand L and collectively holds the manipulation device 300D and the intracorporeal flexible portion 119 arranged at the second manipulation position OP2 with the right hand R. The scopist S causes the intracorporeal flexible portion 119 to come into contact with the manipulation device 300D with the ring finger F3 and the little finger F4 of the right hand R. While observing the imaging image displayed on the display device 900, the scopist S moves the insertion portion 110 while manipulating the intracorporeal flexible portion 119 with the right hand R (a advanceable and retractable movement manipulation). Moreover, the scopist S manipulates the touchpad 380 of the manipulation device 300D with the right hand R (an angle manipulation) and bends the bending portion 112 as necessary.

The scopist S can manipulate the treatment tool 400 inserted into the instruments port 126 with the left hand L in a state in which the connection portion 120D is held with the left hand L. Therefore, the scopist S can perform the manipulation of the insertion portion 110 (an advanceable and retractable movement manipulation and an angle manipulation) and the manipulation of the treatment tool 400 in cooperation. Moreover, because the scopist S holds the connection portion 120D with the left hand L, it is possible to perform a torsion manipulation on the intracorporeal flexible portion 119 with the left hand L.

The second manipulation position OP2 is an arrangement position of the manipulation device 300D that is particularly effective when the patient P is treated by the treatment tool 400.

<Third Manipulation Position OP3>

Figure 44:
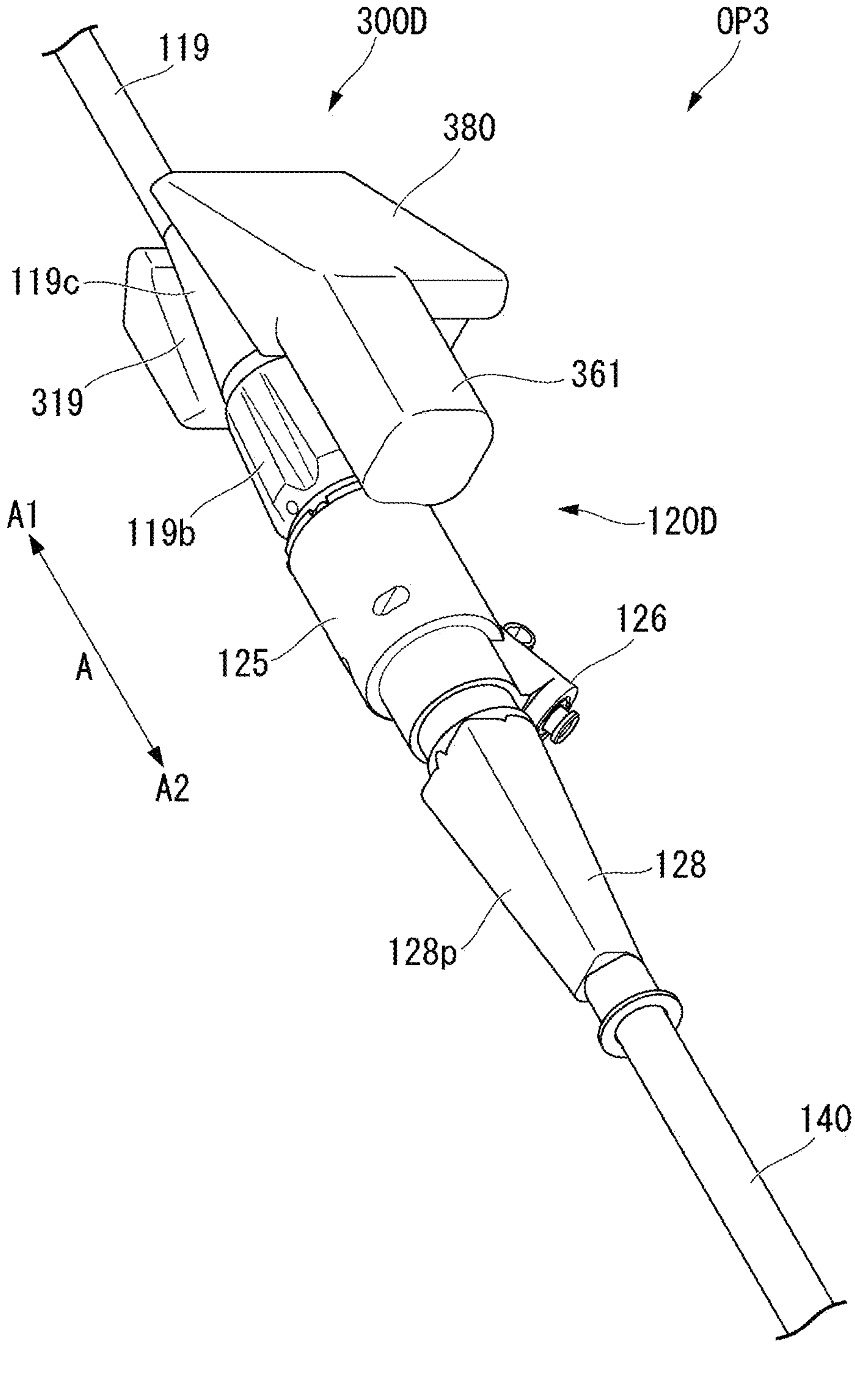
FIG. 44 illustrates an example of a view showing a third manipulation position of the manipulation device.

FIG. 44 is a view showing a third manipulation position OP3 of the manipulation device 300D.

The scopist S can cause the guide groove 319 of the manipulation device 300D to be engaged with the anti-bending portion 119*c* provided at the end of the proximal side A2 of the intracorporeal flexible portion 119. An arrangement position of the manipulation device 300D at which the manipulation device 300D is engaged with the anti-bending portion 119*c* of the intracorporeal flexible portion 119 is referred to as the “third manipulation position OP3.” The manipulation device 300D arranged at the third manipulation position OP3 causes the vertical direction of the manipulation device 300D to substantially coincide with the longitudinal direction A of the intracorporeal flexible portion 119, and the guide groove 319 of the manipulation device 300D is engaged with the anti-bending portion 119*c* of the intracorporeal flexible portion 119. The upper side UPR of the manipulation device 300D faces the distal side A1 of the intracorporeal flexible portion 119. The lower side LWR of the manipulation device 300D faces the proximal side A2 of the intracorporeal flexible portion 119.

Figure 45:
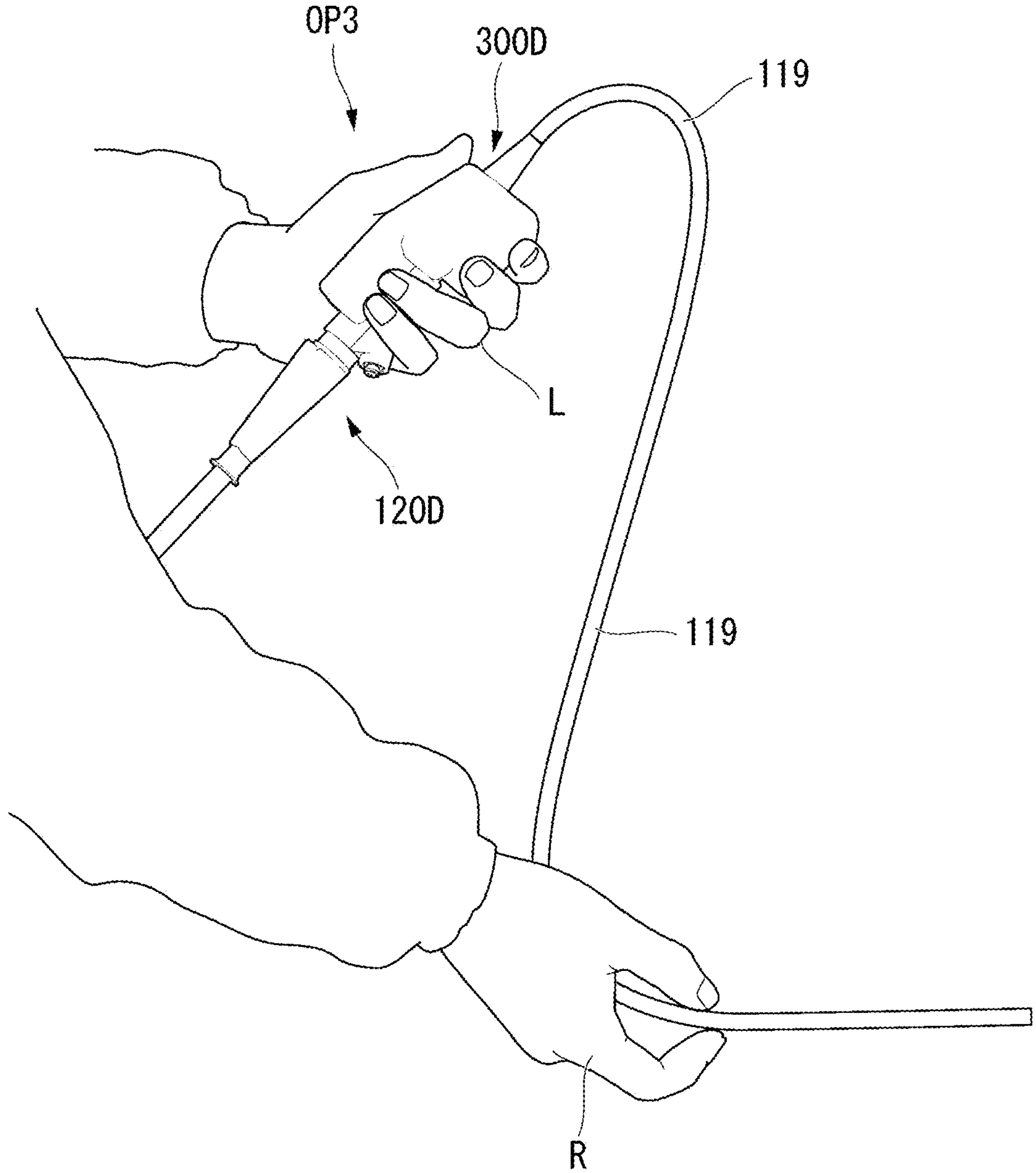
FIG. 45 illustrates an example of a view showing the manipulation device arranged at the third manipulation position.

FIG. 45 is a view showing the manipulation device 300D arranged at the third manipulation position OP3.

As shown in FIG. 45, the scopist S collectively holds the manipulation device 300D and the connection portion 120D arranged at the third manipulation position OP3 with the left hand L and holds the intracorporeal flexible portion 119 with the right hand R. Even if the insertion portion 110 is inserted into the patient P to near the root thereof, the scopist S can hold the manipulation device 300D arranged at the third manipulation position OP3 in a natural state.

Figure 46:
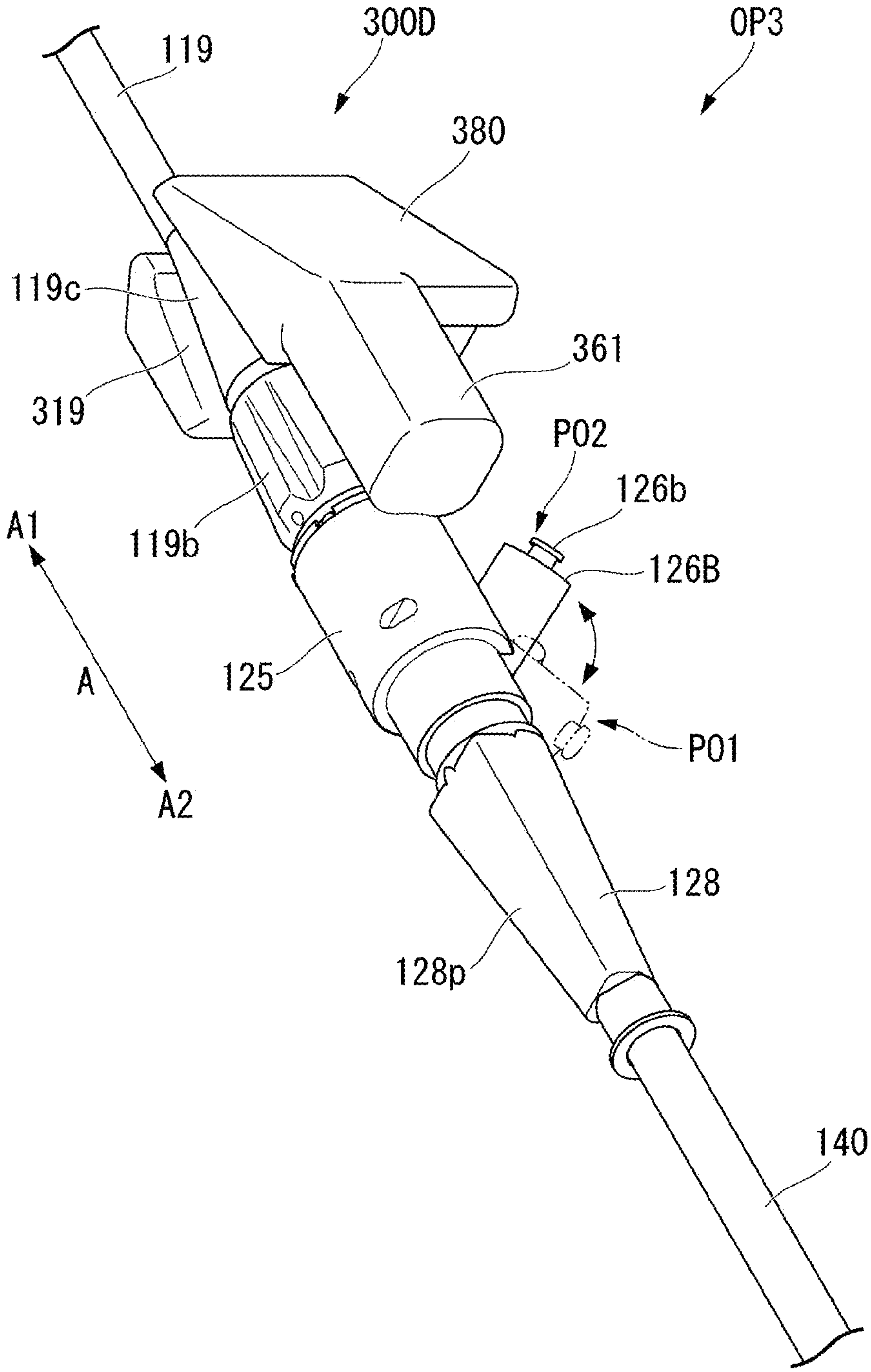
FIG. 46 illustrates an example of a view showing a modified example of the instruments port.

FIG. 46 is a view showing an instruments port 126B, which is a modified example of the instruments port 126.

The instruments port 126B is rotatably attached to the cover member 125. The instruments port 126B can be rotated from a first position PO1 where the proximal end portion 126*b* faces the proximal side A2 to a second position PO2 where the proximal end portion 126*b* faces the distal side A1. When the manipulation device 300D is arranged at the first manipulation position OP1 as shown in FIG. 40, the instruments port 126B is arranged at the first position PO1. On the other hand, when the manipulation device 300D is arranged at the third manipulation position OP3 as shown in FIG. 46, the instruments port 126B is arranged at the second position PO2. The instruments port 126B is rotated so that the proximal end portion 126*b* faces a position where the manipulation device 300D is arranged according to a position where the manipulation device 300D is arranged. As a result, the scopist S can manipulate the manipulation device 300D with the left hand L and manipulate the treatment tool 400 inserted into the instruments port 126 with the right hand R as in the existing method of manipulating the endoscope and the treatment tool.

The electric endoscope system 1000D according to the present embodiment can more efficiently perform observation and treatment using the endoscope 100D. By arranging the manipulation device 300D at various positions, the scopist S can coordinate various manipulations (an advanceable and retractable movement manipulation, an angle manipulation, and a torsion manipulation).

Although the fourth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Fifth Embodiment

An electric endoscope system 1000E according to a fifth embodiment of the present disclosure will be described with reference to FIGS. 47 to 51.

[Electric Endoscope System 1000E]

Figure 47:
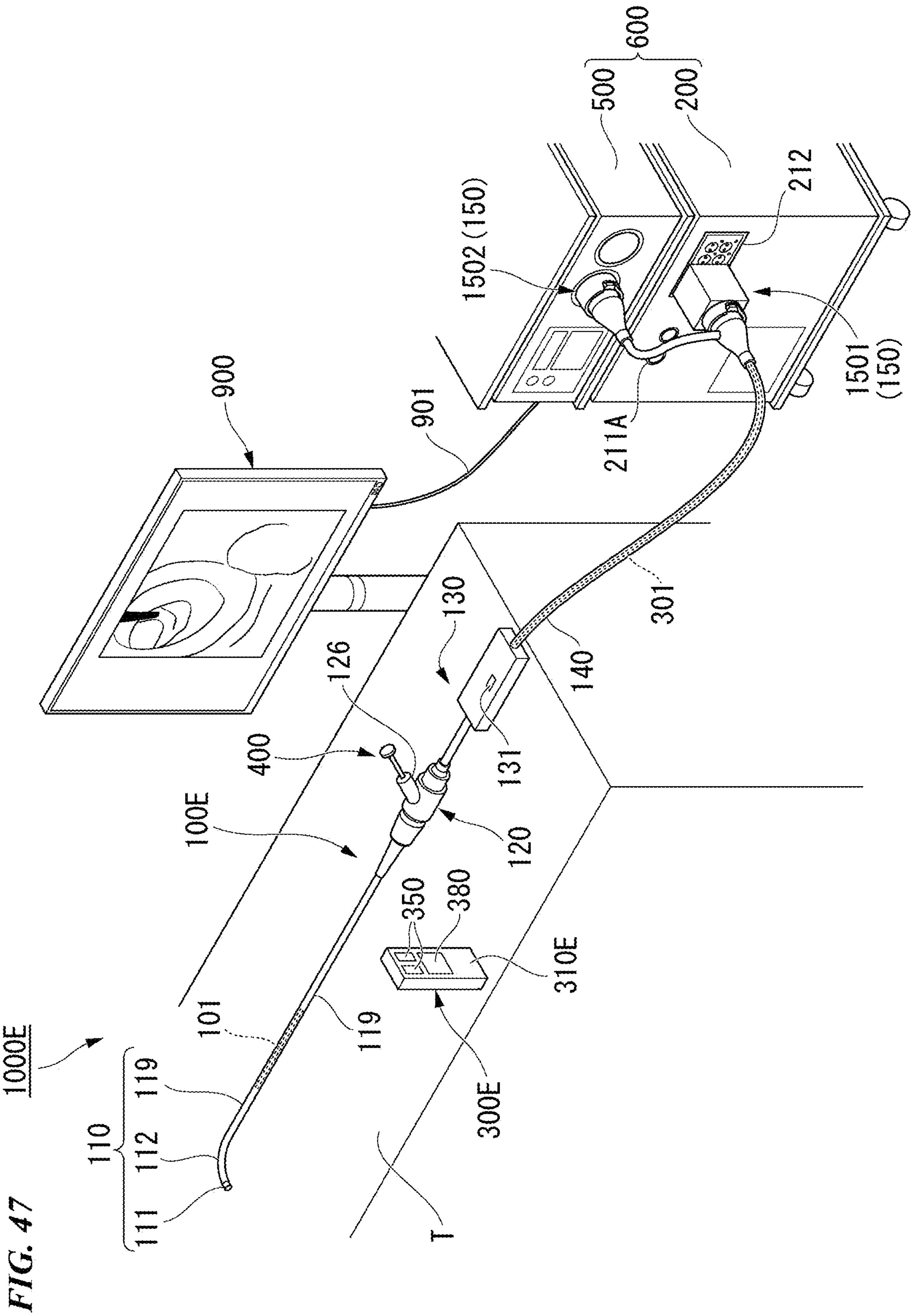
FIG. 47 illustrates an example of an overall view of the electric endoscope system according to a fifth embodiment.

FIG. 47 is an overall view of the electric endoscope system 1000E according to the present embodiment.

The electric endoscope system 1000E includes an endoscope 100E, a drive device 200, a manipulation device 300E, a treatment tool 400, a video control device 500, and a display device 900.

[Endoscope 100E]

The endoscope 100E includes an insertion portion 110, a connection portion 120, a detachable manipulation device portion 130, an extracorporeal flexible portion 140, a detachable portion 150, a bending wire 160, and a built-in object 170.

The detachable manipulation device portion 130 can be attached and detached to and from the manipulation device 300E and is provided in the extracorporeal flexible portion 140. The detachable manipulation device portion 130 has an electrical contact point 131 that electrically connects the attached manipulation device 300E to the manipulation cable 301.

The manipulation cable 301 is inserted into an internal path of the extracorporeal flexible portion 140. A distal end portion of the manipulation cable 301 is connected to the electrical contact point 131. A proximal end portion of the manipulation cable 301 is connected to the manipulation reception portion 220 via the endoscope adapter 212.

[Manipulation Device 300E]

The manipulation device (controller) 300E is a device to which a manipulation of the scopist S who controls the electric endoscope system 1000E (in particular, a manipulation for driving the endoscope 100E) is input. The manipulation device 300E includes a manipulation portion body 310E, various buttons 350, and a touchpad 380.

Figure 48:
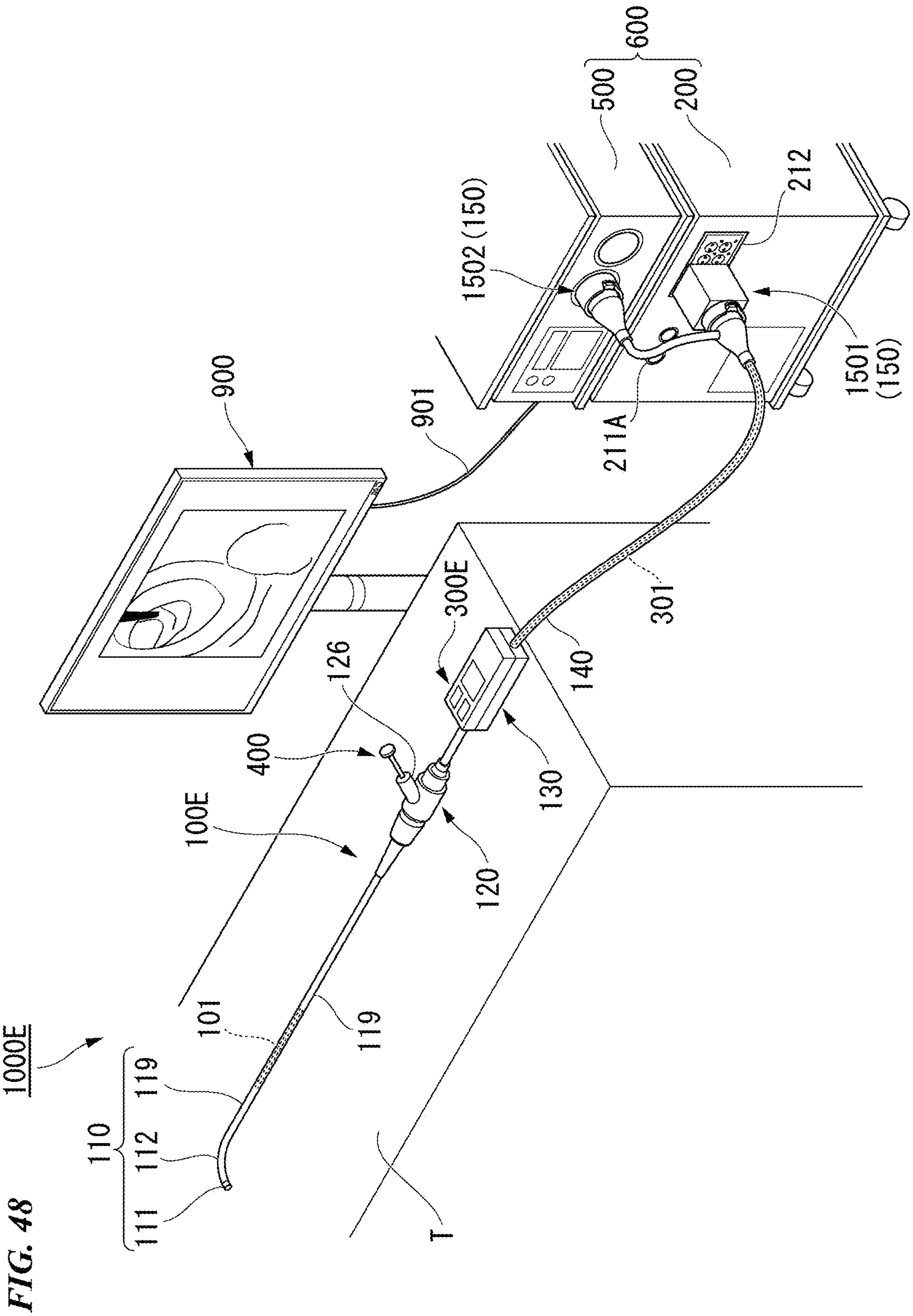
FIG. 48 illustrates an example of a view showing a detachable manipulation device portion to which a manipulation device is attached in the electric endoscope system.

FIG. 48 is a view showing the detachable manipulation device portion 130 to which the manipulation device 300E is attached. The manipulation device 300E is attached to the detachable manipulation device portion 130, and therefore can communicate with the drive device 200 and the like via the manipulation cable 301. The manipulation cable 301 is inserted into the internal path of the extracorporeal flexible portion 140 and is not externally exposed. Therefore, the manipulation cable 301 does not interfere with the work of the scopist S.

When the manipulation device 300E can communicate with the drive device 200 or the like through wireless communication, the manipulation device 300E can communicate with the drive device 200 or the like regardless of attachment or detachment to or from the detachable manipulation device portion 130. In this case, the manipulation cable 301 and the electrical contact point 131 are unnecessary.

Figure 49:
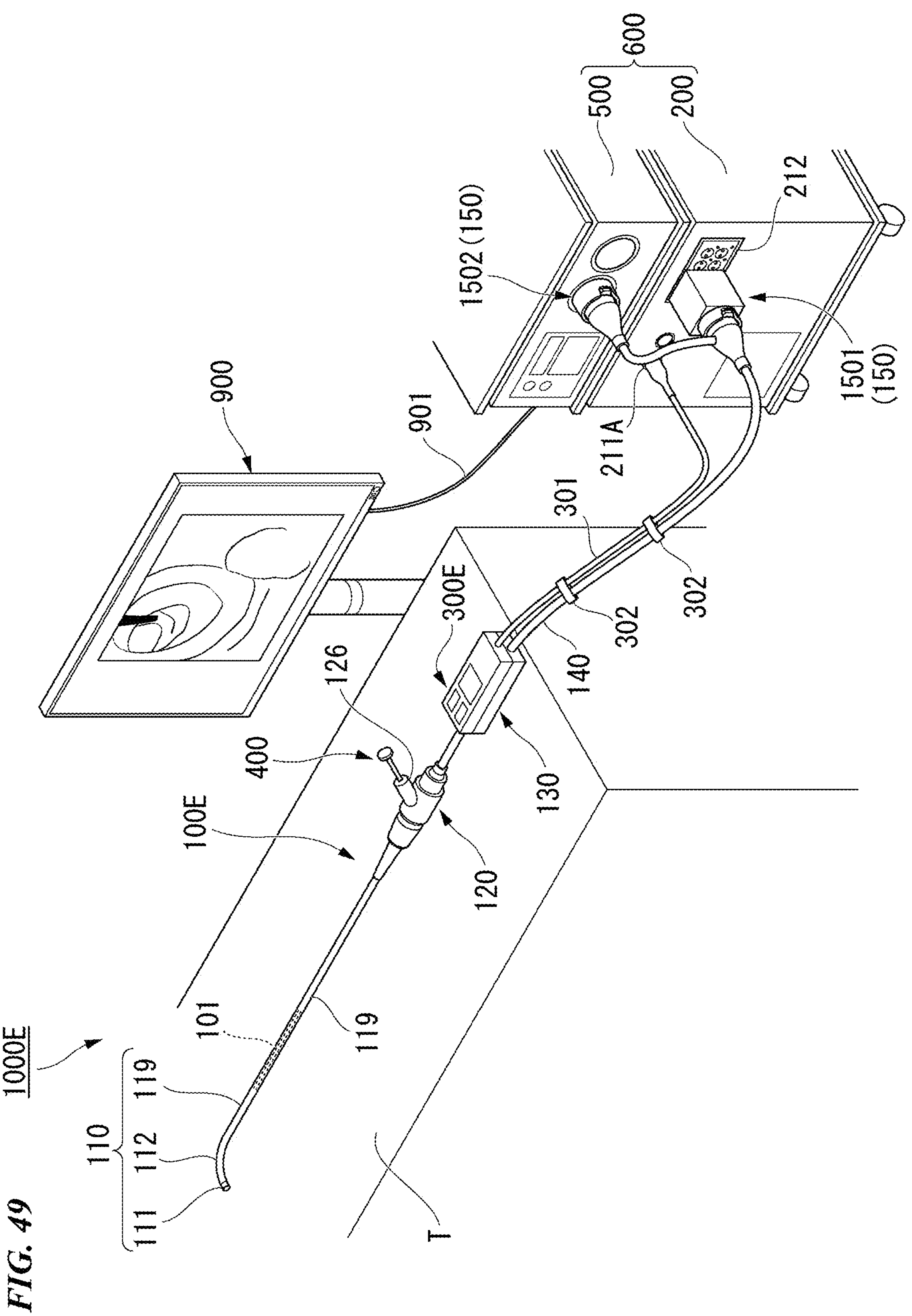
FIG. 49 illustrates an example of a view showing a manipulation cable restrained by an extracorporeal flexible portion.

FIG. 49 is a view showing the manipulation cable 301 restrained by the extracorporeal flexible portion 140.

When the manipulation cable 301 is fixed to the manipulation device 300E, the manipulation cable 301 arranged outside the extracorporeal flexible portion 140 may be restrained by the extracorporeal flexible portion 140 and a restraint band 302.

Figure 50:
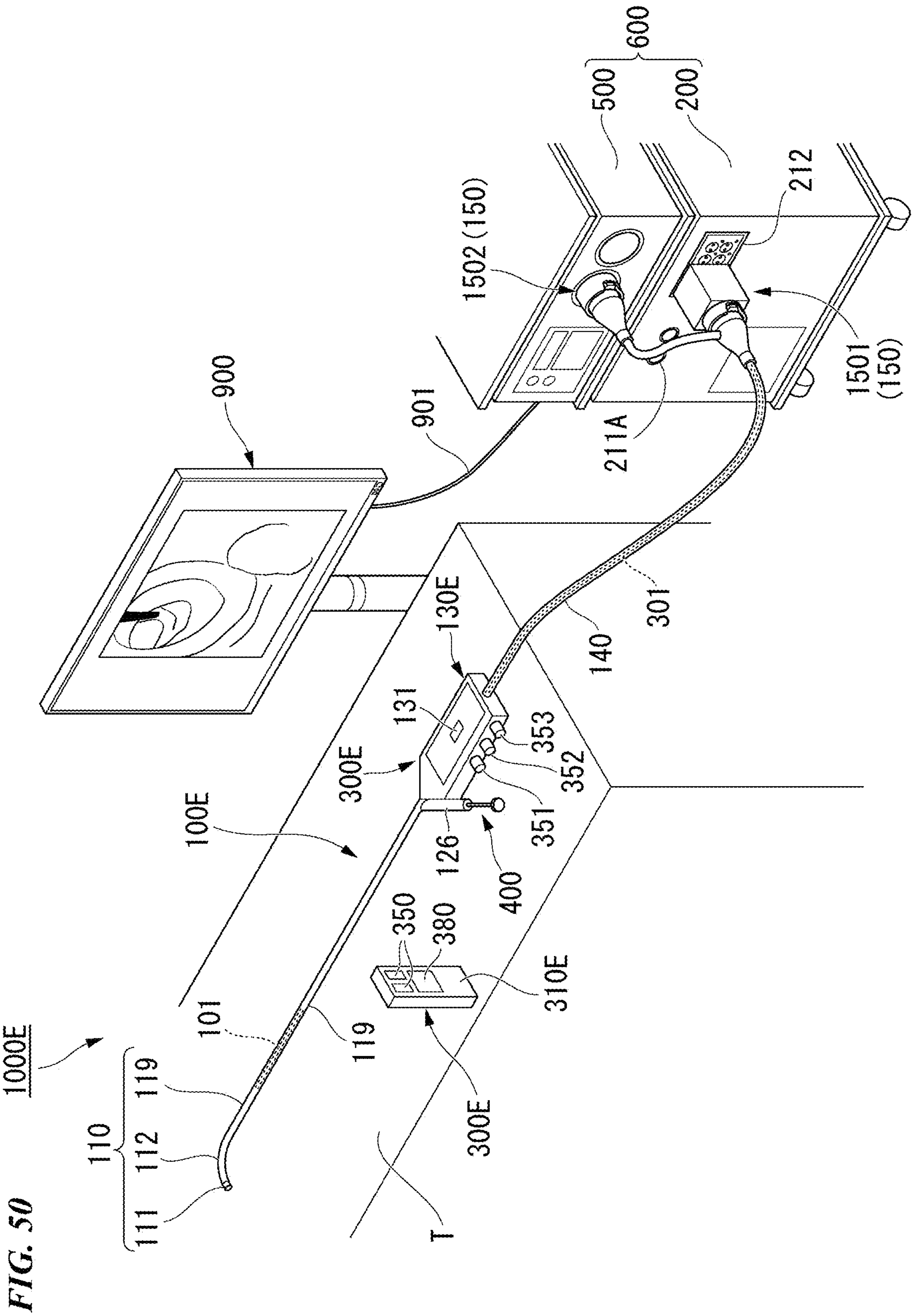
FIG. 50 illustrates an example of a view showing a modified example of the detachable manipulation device portion.

FIG. 50 is a view showing the detachable manipulation device portion 130E, which is a modified example of the detachable manipulation device portion 130. The detachable manipulation device portion 130E further includes an air/water supply button 351, a suction button 352, a release button 353, and an instruments port 126.

The air/water supply button 351 and the suction button 352 are physical buttons for physically opening and closing the internal path of the suction tube 172 and the air/water supply tube 175 inserted into the internal path 101 of the endoscope 100E. The air/water supply button 351 and the suction button 352 can control air supply and suction without communicating with the drive device 200.

Like the instruments port 126 of the first embodiment, the instruments port 126 is an insertion port for inserting the treatment tool 400 into the internal path 101 of the endoscope 100E.

Figure 51:
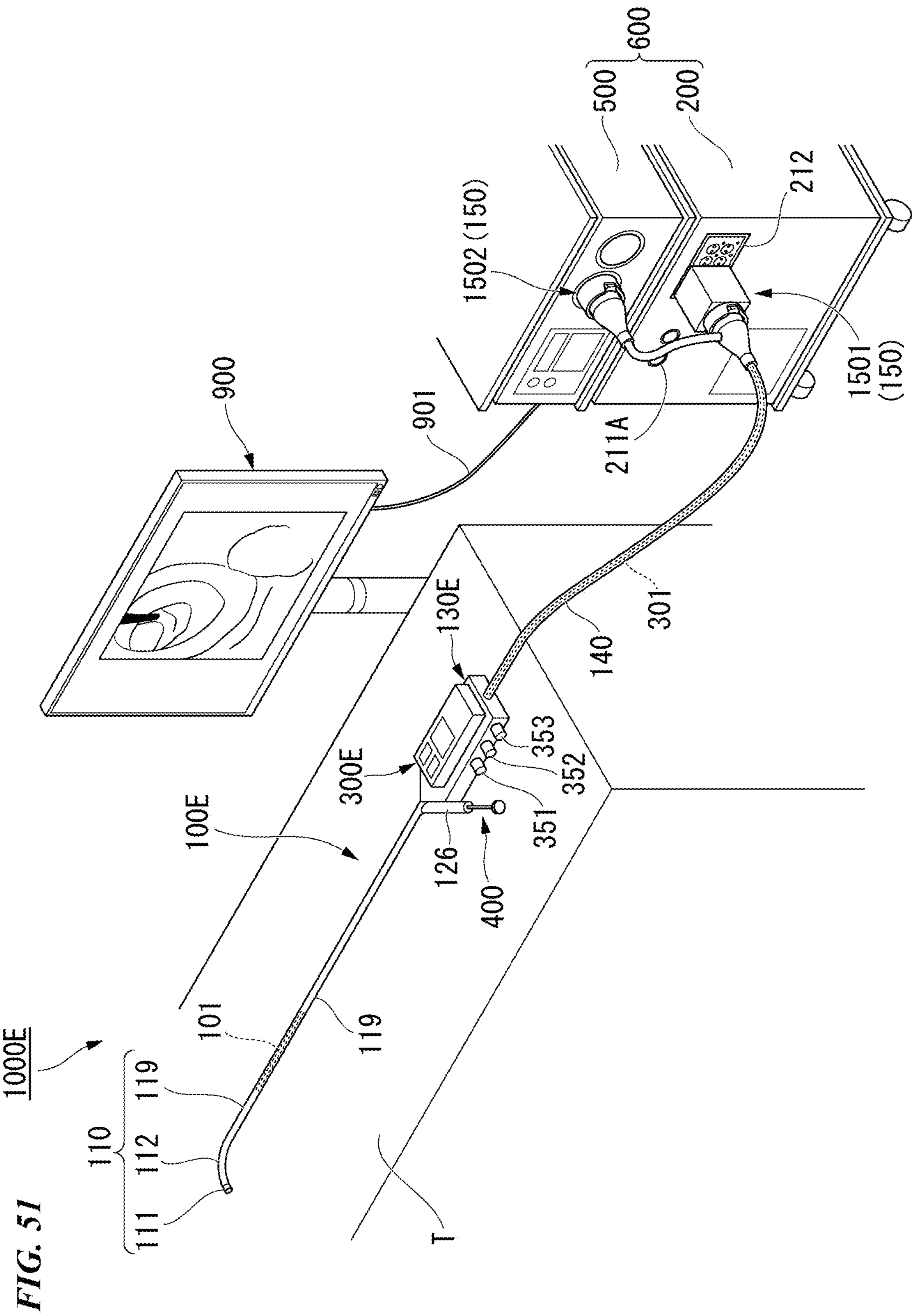
FIG. 51 illustrates an example of a view showing the modified example of the detachable manipulation device portion to which the manipulation device is attached.

FIG. 51 is a view showing the detachable manipulation device portion 130E to which the manipulation device 300E is attached. When the manipulation device 300E is attached to the detachable manipulation device portion 130E, the air/water supply button 351, the suction button 352, and the release button 353 are provided on the right RH of the manipulation device 300E. Moreover, the instruments port 126 is provided on the lower right of the manipulation device 300E. Therefore, the scopist S can manipulate the manipulation device 300E and the treatment tool 400 as in the existing method of manipulating the endoscope and the treatment tool.

The electric endoscope system 1000E according to the present embodiment can more efficiently perform observation and treatment using the endoscope 100E.

Although the fifth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Sixth Embodiment

An electric endoscope system 1000F according to the sixth embodiment of the present disclosure will be described with reference to FIGS. 52 to 55.

[Electric Endoscope System 1000F]

Figure 52:
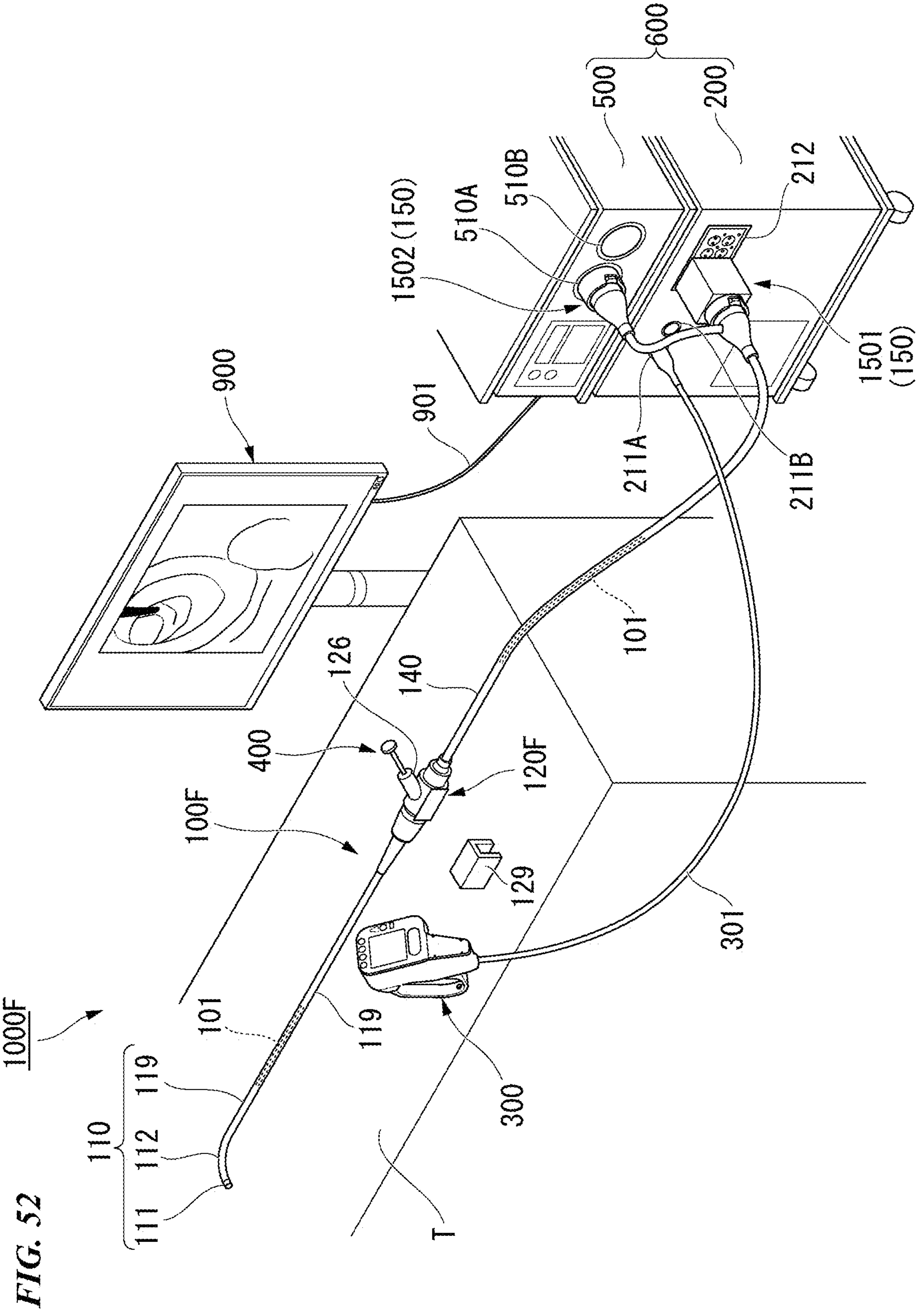
FIG. 52 illustrates an example of an overall view of an electric endoscope system according to a sixth embodiment.

FIG. 52 is an overall view of the electric endoscope system 1000F according to the present embodiment.

The electric endoscope system 1000F includes an endoscope 100F, a drive device 200, a manipulation device 300, a treatment tool 400, a video control device 500, and a display device 900.

[Endoscope 100F]

The endoscope 100F includes an insertion portion 110, a connection portion 120F, a stopper 129, an extracorporeal flexible portion 140, a detachable portion 150, a bending wire 160, and a built-in object 170.

Figure 53:
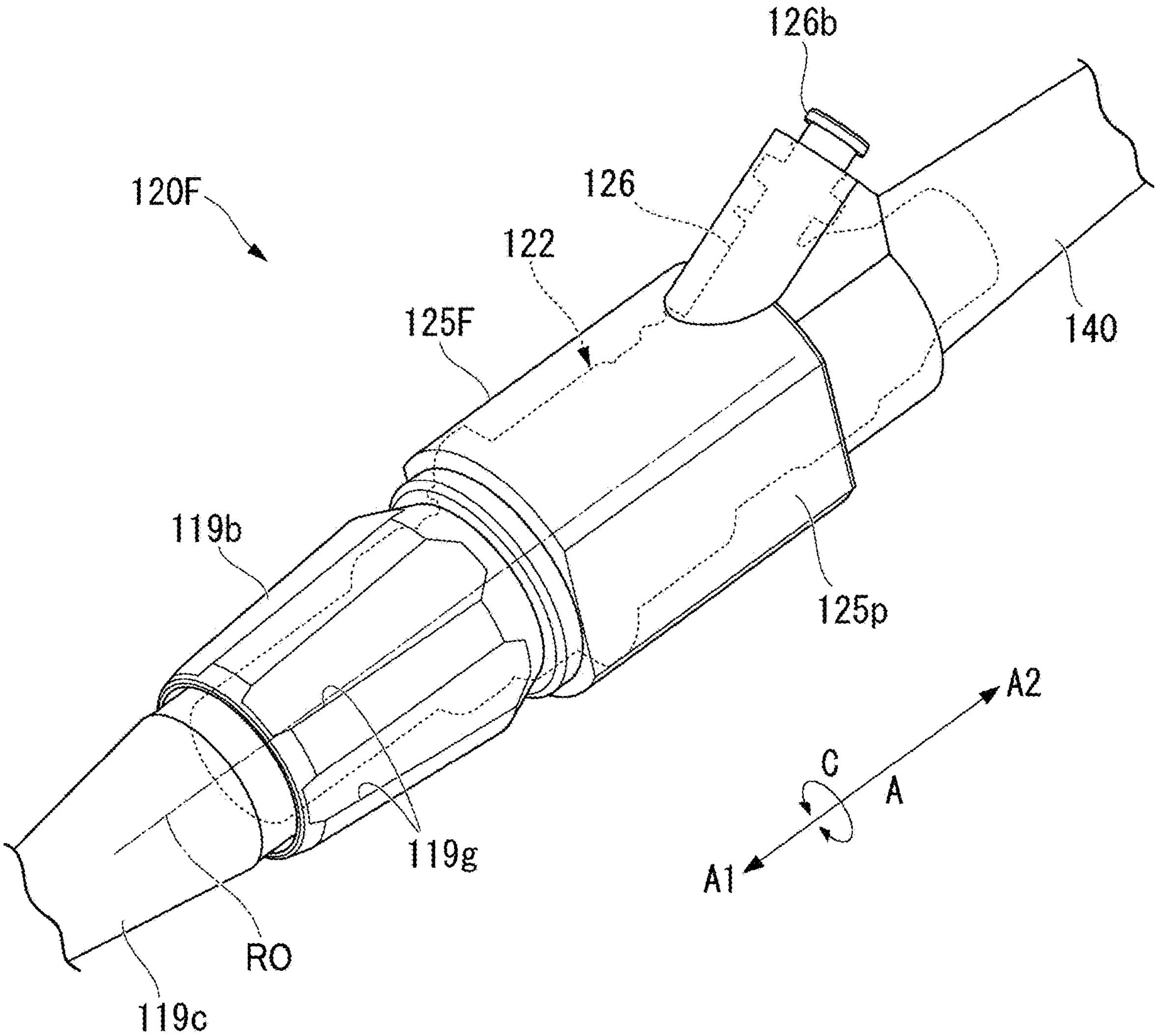
FIG. 53 illustrates an example of a perspective view of a connection portion of the electric endoscope system.

FIG. 53 is a perspective view of the connection portion 120F.

The connection portion 120F includes a cylindrical member 121, a connection portion body 122, a sealing portion 123, a bearing portion 124, a cover member 125F, an instruments port 126, and a trifurcated branch tube 127.

The cover member 125F is a member that covers the outer circumference of the connection portion body 122. The cover member 125F has a planar portion 125*p* horizontal to a rotation axis RO extending in a longitudinal direction A. An outer circumferential surface of the cover member 125F is formed in a D-shape in a cross-section perpendicular to the longitudinal direction A.

Figure 54:
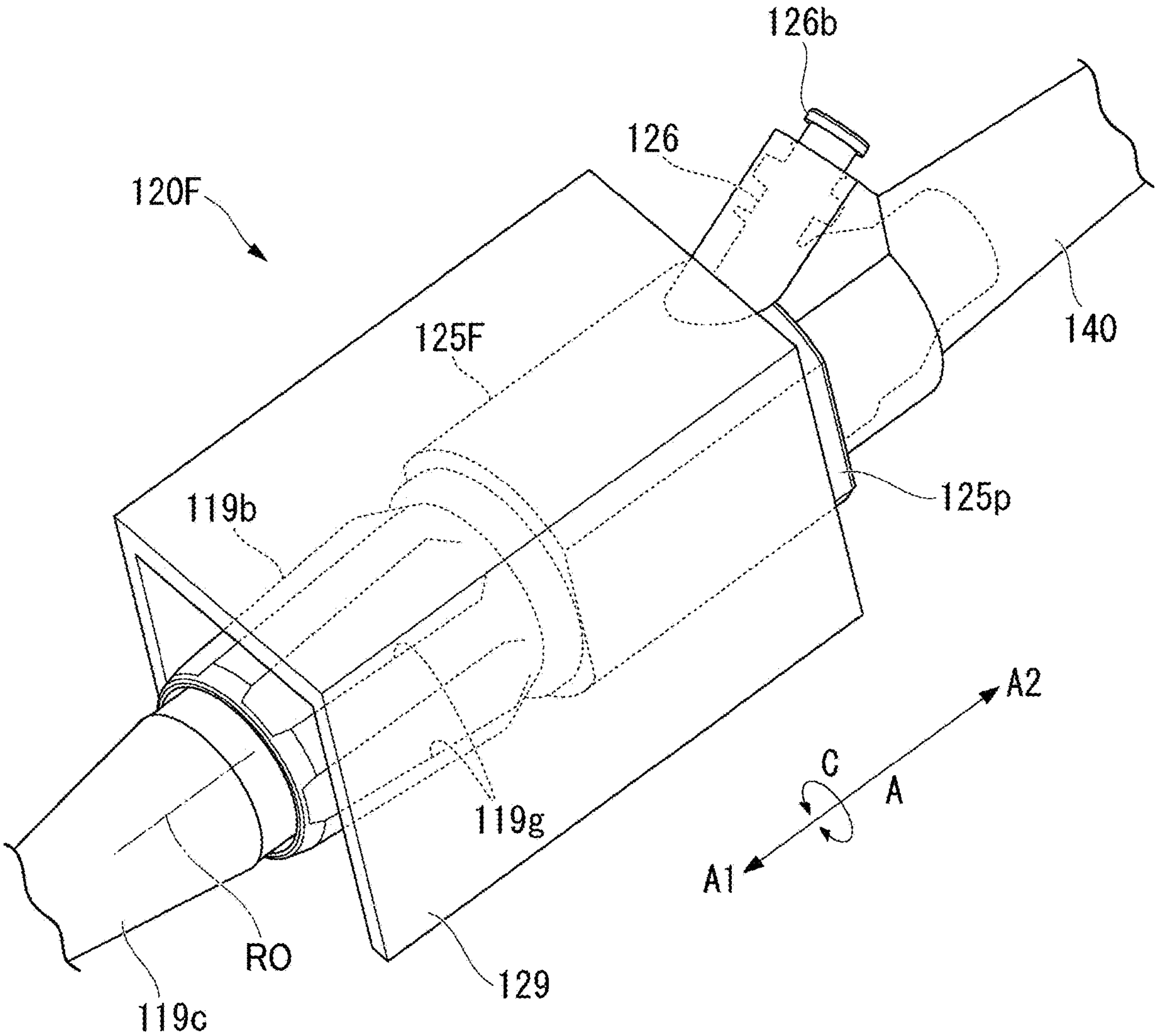
FIG. 54 illustrates an example of a view showing the connection portion to which a stopper is attached.

FIG. 54 is a view showing the connection portion 120F to which the stopper 129 is attached.

The stopper 129 is formed in a U-shape and can be detached from the connection portion 120F. The stopper 129 attached to the connection portion 120F is engaged with a planar portion 125*p* of the cover member 125F and a groove 119*g* formed on a proximal end portion 119*b* of the intracorporeal flexible portion 119. Therefore, when the stopper 129 is attached to the connection portion 120F, a passive rotation portion (the proximal end portion 119*b* of the intracorporeal flexible portion 119, a housing 123*h*, and the cylindrical member 121) does not rotate in a circumferential direction C with respect to the cover member 125F.

The passive rotation portion (the proximal end portion 119*b* of the intracorporeal flexible portion 119, the housing 123*h*, and the cylindrical member 121) does not rotate in the circumferential direction C with respect to the cover member 125F unless a force greater than a predetermined force is applied. However, when a torsional reaction force from the insertion portion 110 inserted into the body of a patient P is large, a predetermined force or more is applied to the passive rotation portion and the passive rotation portion rotates. In this case, a scopist S can regulate that the passive rotation portion rotates in the circumferential direction C with respect to the cover member 125F by attaching the stopper 129 to the connection portion 120F.

Figure 55:
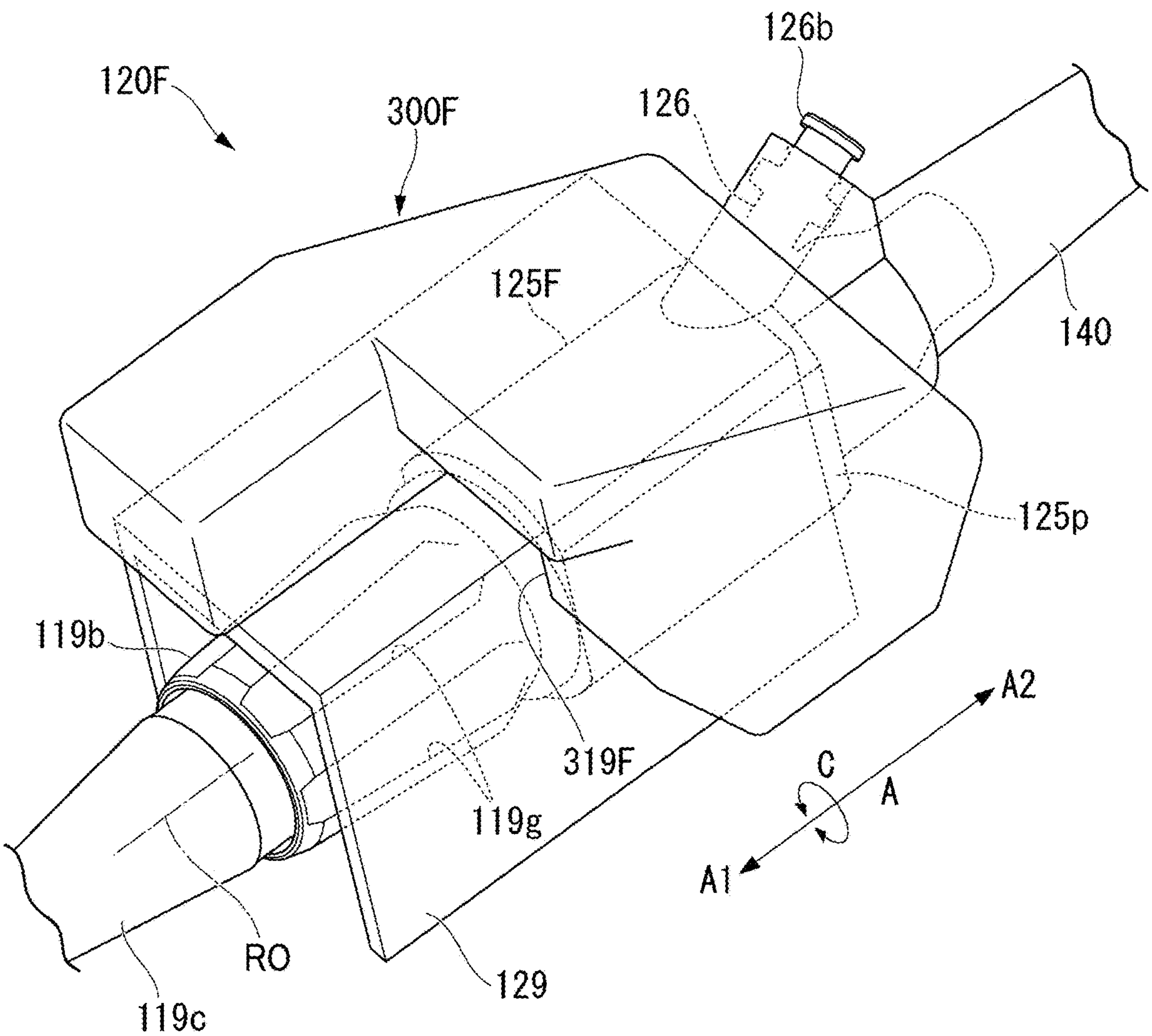
FIG. 55 illustrates an example of a view showing a modified example of the stopper.

FIG. 55 is a view showing a modified example of the stopper 129.

A manipulation device 300F having a groove 319F having a structure similar to that of the stopper 129 may be used as a stopper. As shown in FIG. 55, the manipulation device 300F is attached to the connection portion 120F, and therefore it is possible to regulate that the passive rotation portion rotates in the circumferential direction C with respect to the cover member 125F.

Figure 56:
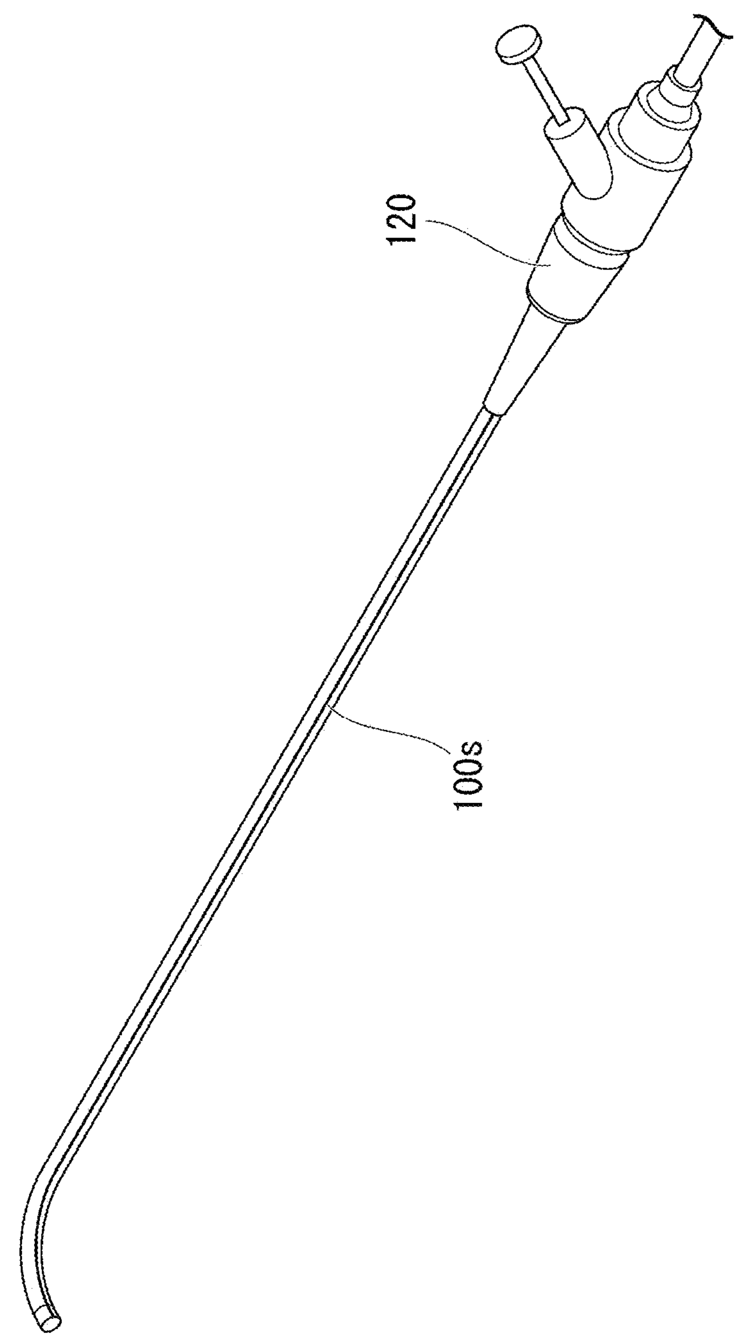
FIG. 56 illustrates an example of a view showing a modified example of an endoscope.

FIG. 56 is a view showing a modified example of the endoscope 100.

In the endoscope shown in FIG. 56, a line 100*s* is provided in the insertion portion 110. The line 100*s* is provided, for example, in a U direction. By looking at the line 100*s*, the scopist S can roughly ascertain a direction in which the bending portion 112 is facing. The line 100*s* may be a straight-line shape or a dashed-line shape.

The electric endoscope system 1000F according to the present embodiment can more efficiently perform observation and treatment using the endoscope 100F.

Although the sixth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Seventh Embodiment

An electric endoscope system 1000G according to a seventh embodiment of the present disclosure will be described with reference to FIGS. 57 to 60.

[Electric Endoscope System 1000G]

Figure 57:
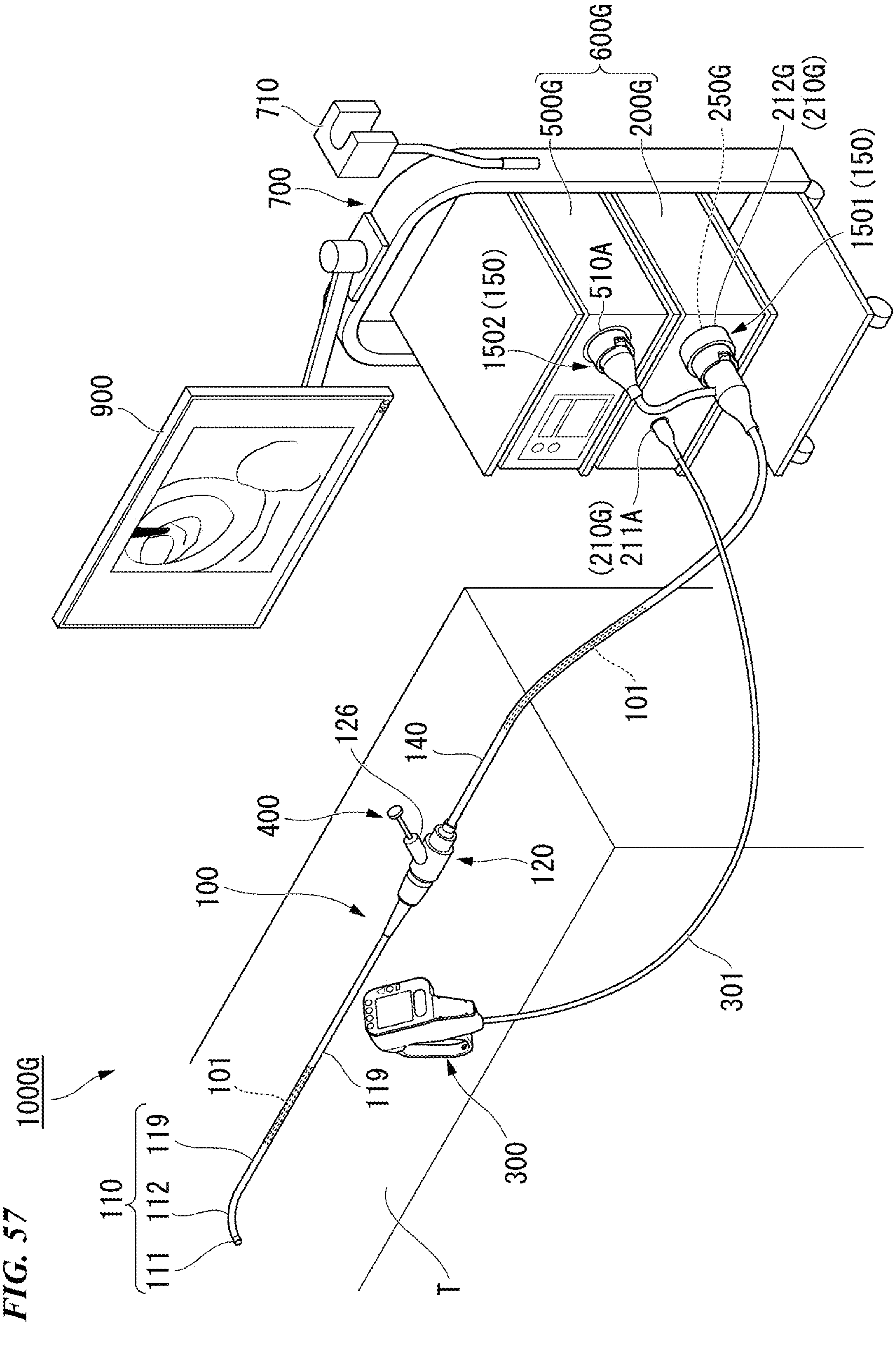
FIG. 57 illustrates an example of an overall view of an electric endoscope system according to a seventh embodiment.

FIG. 57 is an overall view of the electric endoscope system 1000G according to the present embodiment.

The electric endoscope system 1000G includes an endoscope 100, a drive device 200G, a manipulation device 300, a treatment tool 400, a video control device 500G, a storage rack 700, and a display device 900.

The drive device 200G includes an adapter 210G, a manipulation reception portion 220, an air supply/suction drive portion 230, a wire drive portion (actuator) 250G, and a drive controller 260.

The adapter 210G includes a first manipulation adapter 211A and an endoscope adapter 212G. The adapter 210G does not have a second manipulation adapter 211B.

The endoscope adapter 212G is an adapter detachably connected to a first detachable portion 1501 of the endoscope 100. The endoscope adapter 212G is provided to surround the wire drive portion 250G. One first detachable portion 1501 is connected to the endoscope adapter 212G.

The wire drive portion (actuator) 250G includes a support member 250*a*, a first drive portion (first actuator) 251, a second drive portion (second actuator) 252, a third drive portion (third actuator) 253, a fourth drive portion (fourth actuator) 254, and a detachable sensor 259.

The video control device 500G includes a first endoscope adapter 510A, an imaging processing portion 520, a light source portion 530, and a main controller 560. The video control device 500G does not have a second endoscope adapter 510B.

The drive device 200G and the video control device 500G constitute a control device 600G that controls the electric endoscope system 1000G. The control device 600G may further include a peripheral device such as a video printer. The drive device 200G and the video control device 500G may be an integrated device.

The drive device 200G, the video control device 500G, and the display device 900 are stored in a storage rack 700. The storage rack 700 is equipped with tires and is easily moved. The storage rack 700 includes a hanger (trolley) 710 that can be installed by hanging the endoscope 100.

[Operation of Electric Endoscope System 1000G]

Next, an operation of the electric endoscope system 1000G of the present embodiment will be described. Specifically, an operation related to a pre-use device check process of the endoscope 100 will be described.

Figure 58:
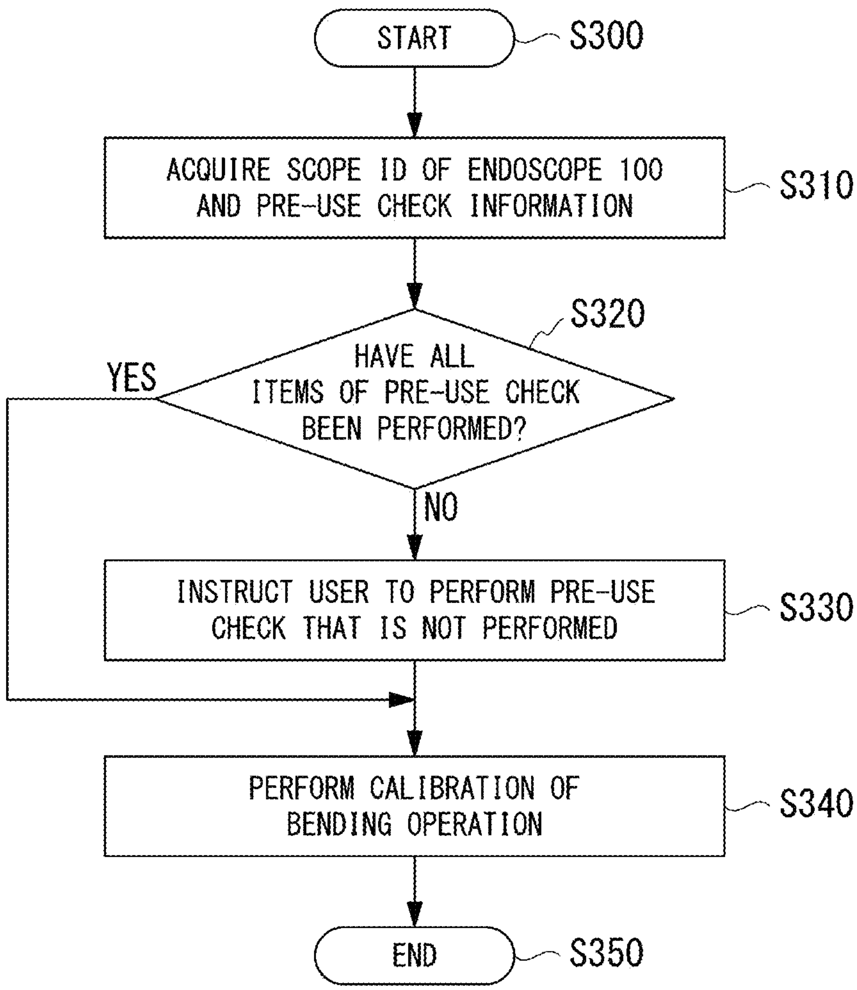
FIG. 58 illustrates an example of a control flowchart of a main controller of a control device of the electric endoscope system.

Hereinafter, description will be given according to a control flowchart of the main controller 560 of the control device 600G shown in FIG. 58. When a user activates a "check program" in the control device 600G so that the pre-use device check process is performed, the main controller 560 starts the control flow shown in FIG. 58 (step S300). Subsequently, the main controller 560 (mainly, the processor 561) executes step S310.

<Step S310>

In step S310, the main controller 560 communicates with the drive controller 260 to acquire a scope ID and pre-use check information stored in a scope ID storage portion 158 of the first detachable portion 1501 of the endoscope 100 attached to the drive device 200G. The main controller 560 subsequently executes step S320.

"Pre-use check information" is information about the progress of the pre-use check process of the endoscope 100 or the like. For example, when at least a part of the pre-use check process is performed by another control device 600G in the backyard or the like, the progress of the pre-use check process, a check result, and the like are stored as pre-use check information in the scope ID storage portion 158.

<Step S320>

The main controller 560 confirms the pre-use check information of the endoscope 100 in step S320. When some items of the pre-use check process have not been performed, the main controller 560 subsequently executes step S330. When all items of the pre-use check process have been performed, the main controller 560 skips the pre-use check process in step S320 and subsequently executes step S340.

<Step S330>

In step S330, the main controller 560 instructs (notifies) the user to perform the pre-use check process that has not yet been performed. Specifically, the main controller 560 displays a GUI image for issuing an instruction (notification) for allowing the user to perform the pre-use check process exemplified below on the display device 900.

The main controller 560, for example, instructs the user to input a manipulation for bending the bending portion 112 from the manipulation device 300. The main controller 560 confirms whether or not the bending manipulation indicated in the instruction has been input.

The main controller 560, for example, instructs the user to input a manipulation of performing air supply from the manipulation device 300 with the air/water supply button 351 and a manipulation of performing suction with the suction button 352. The main controller 560 confirms whether or not the manipulation of performing the air/water supply and the manipulation of performing the suction indicated in the instruction have been input.

The main controller 560, for example, instructs the user to input a manipulation of performing functions assigned to various buttons 350 in the manipulation device 300. The main controller 560 confirms whether or not a manipulation for performing the function indicated in the instruction has been input.

The main controller 560, for example, instructs the user to input a manipulation of bending the bending portion 112 from the manipulation device 300. The main controller 560 confirms whether or not the bending manipulation indicated in the instruction has been performed by the drive device 200G on the basis of the tension sensor 159 or the like. When there is a defect such as a failure, the main controller 560 presents details of the defect to the user.

The main controller 560, for example, instructs the user to input a manipulation of performing air supply from the manipulation device 300 with the air/water supply button 351 and a manipulation of performing suction with the suction button 352. The main controller 560 confirms whether or not the air supply or suction indicated in the instruction has been performed by the drive device 200G on the basis of a flow rate sensor or the like. When there is a defect such as a failure, the main controller 560 presents details of the defect to the user.

The main controller 560, for example, instructs the user to input a manipulation of performing functions assigned to the various buttons 350 in the manipulation device 300. The main controller 560 confirms whether or not the function indicated in the instruction is being performed. When there is a defect such as a failure, the main controller 560 presents details of the defect to the user.

The main controller 560, for example, confirms whether or not display content of the display device 900 that is changed with the above-described manipulation input has been correctly changed.

The main controller 560 may cause the user to perform the above-described confirmation. The main controller 560 displays a message for issuing a confirmation instruction (notification) to the user on the display device 900. The main controller 560 acquires the user's confirmation result by displaying a GUI image necessary for an input of a confirmation result of the user and allowing the user to input the confirmation result.

<Step S340>

In step S340, the main controller 560 performs a calibration of the bending manipulation by communicating with the drive controller 260. In addition, the calibration of the bending manipulation may not be performed necessarily for each use or may be performed periodically.

Figure 59:
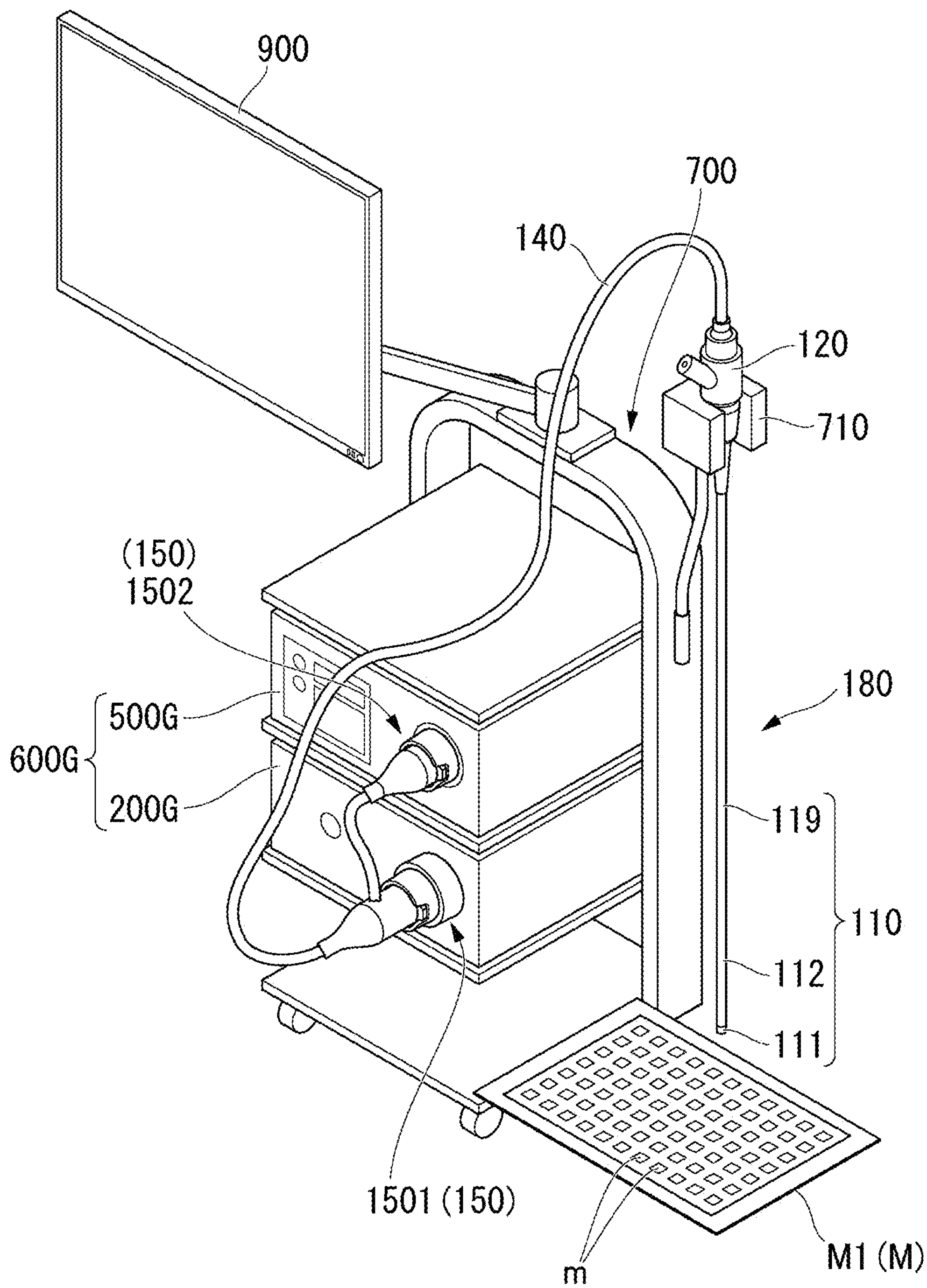
FIG. 59 illustrates an example of a view showing a suspended endoscope.

FIG. 59 is a view showing the suspended endoscope 100 or the like.

The main controller 560 displays a GUI image for instructing the user to hang the endoscope 100 on the hanger 710 and suspend the distal end portion 180 including the bending portion 112 within the endoscope 100 from the hanger 710 on the display device 900. The user suspends the distal end portion 180 from the hanger 710 in accordance with the instruction displayed in the GUI image.

Figure 60:
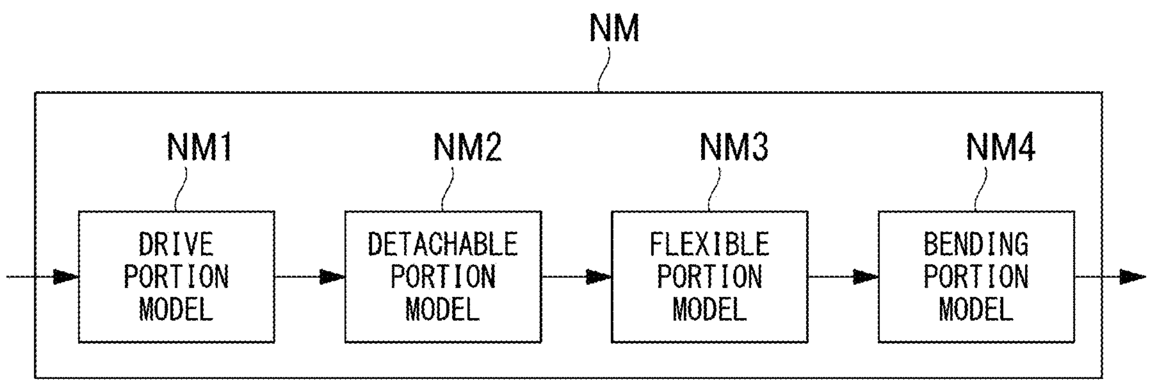
FIG. 60 illustrates an example of a diagram showing a normative model used by a drive controller of the control device.

FIG. 60 is a diagram showing a normative model NM used by the drive controller 260.

The main controller 560 updates parameters of the normative model NM by calibrating the bending manipulation. The normative model NM is a model for estimating a bending operation of the endoscope 100. The normative model NM includes a drive portion model NM1 obtained by modeling the drive portion 25X, a detachable portion model NM2 obtained by modeling the first detachable portion 1501, a flexible portion model NM3 obtained by modeling the extracorporeal flexible portion 140 and the intracorporeal flexible portion 119, and a bending portion model NM4 obtained by modeling the bending portion 112.

The main controller 560 may use a marker M to calibrate the bending manipulation. The marker M shown in FIG. 59 is a marker board M1. The marker M has known marker patterns m for identifying relative position information. The marker patterns m are patterns for identifying the relative position information by performing observation from different locations.

The electric endoscope system 1000G according to the present embodiment can more efficiently perform observation and treatment using the endoscope 100. The user can efficiently perform a pre-use device check process.

Although the seventh embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Eighth Embodiment

An electric endoscope system 1000H according to an eighth embodiment of the present disclosure will be described with reference to FIGS. 61 to 75.

[Electric Endoscope System 1000H]

Figure 61:
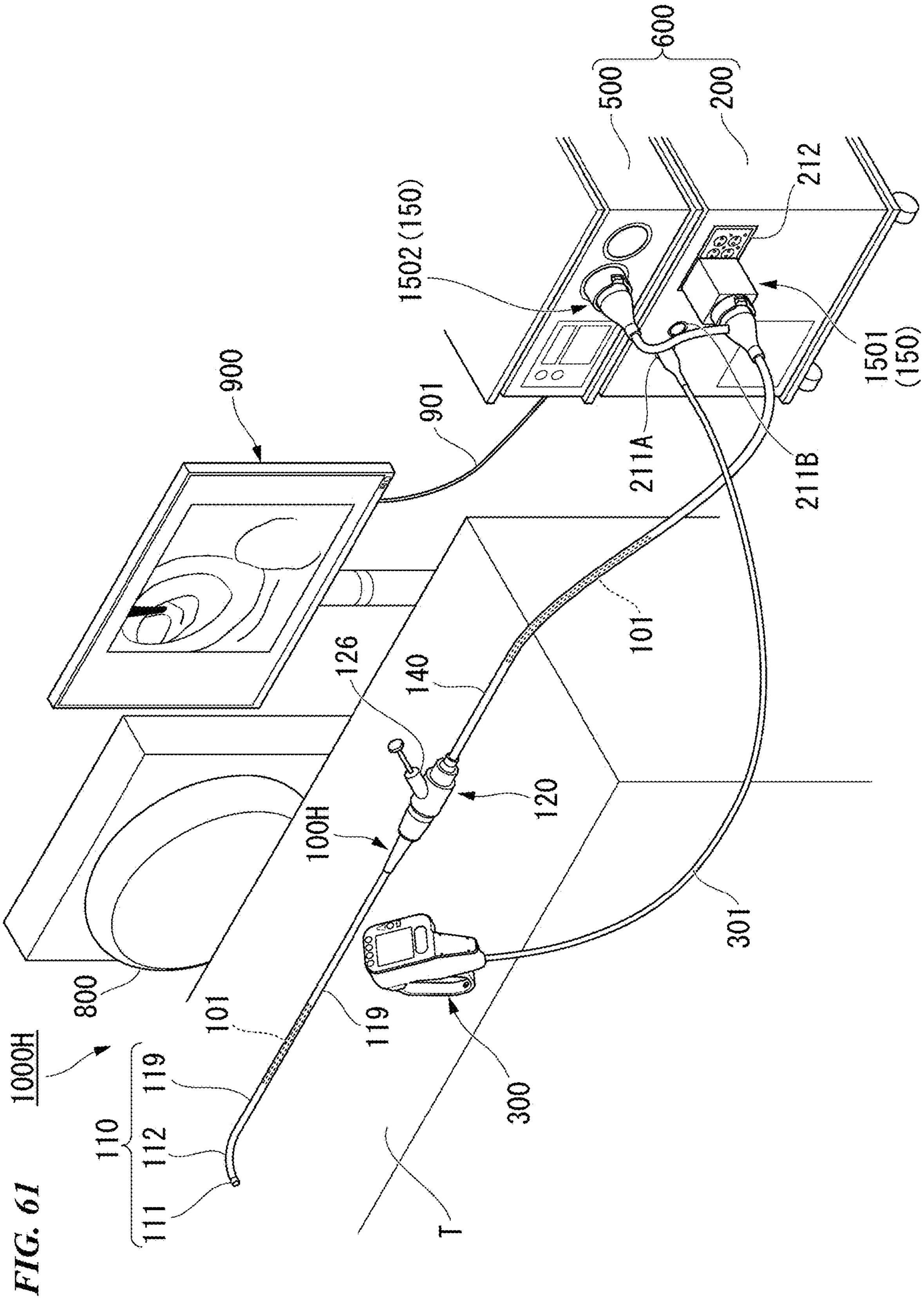
FIG. 61 illustrates an example of an overall view of an electric endoscope system according to an eighth embodiment.

FIG. 61 is an overall view of the electric endoscope system 1000H according to the present embodiment.

The electric endoscope system 1000H includes an endoscope 100H, a drive device 200, a manipulation device 300, a treatment tool 400, a video control device 500, an observation device 800, and a display device 900.

The endoscope 100H is the same as the endoscope 100 of the first embodiment, except that the insertion portion 110 has a built-in magnetic coil (not shown) in the longitudinal direction A. The magnetic coil, for example, is attached in a spiral shape along the inner circumferential surface in the internal path 101 of the insertion portion 110.

The observation device 800 is a device for observing an insertion shape of the endoscope 100H using a magnetic field. The observation device 800 receives magnetism generated from the magnetic coil built into the insertion portion 110 of the endoscope 100H with an antenna. An observation result of the observation device 800 is also acquired by the main controller 560.

FIGS. 62 to 66 are views showing a pair of bending wires 160 inserted into an insertion portion 110 that is bent. Hereinafter, the pair of bending wires (the upper bending wire 161*u* and the lower bending wire 161*d*) for bending the bending portion 112 in the UD direction will be described. A virtual marker VM1 and a virtual marker VM2 are virtual markers indicating positions that are predetermined distances from the beginning of the bending wires (the upper bending wire 161*u* and the lower bending wire 161*d*). In addition, a pair of bending wires 160 (the left bending wire 1611 and the right bending wire 161*r*) for bending the bending portion 112 in the LR direction have similar structures, and therefore illustration and description thereof are omitted.

Figure 62:
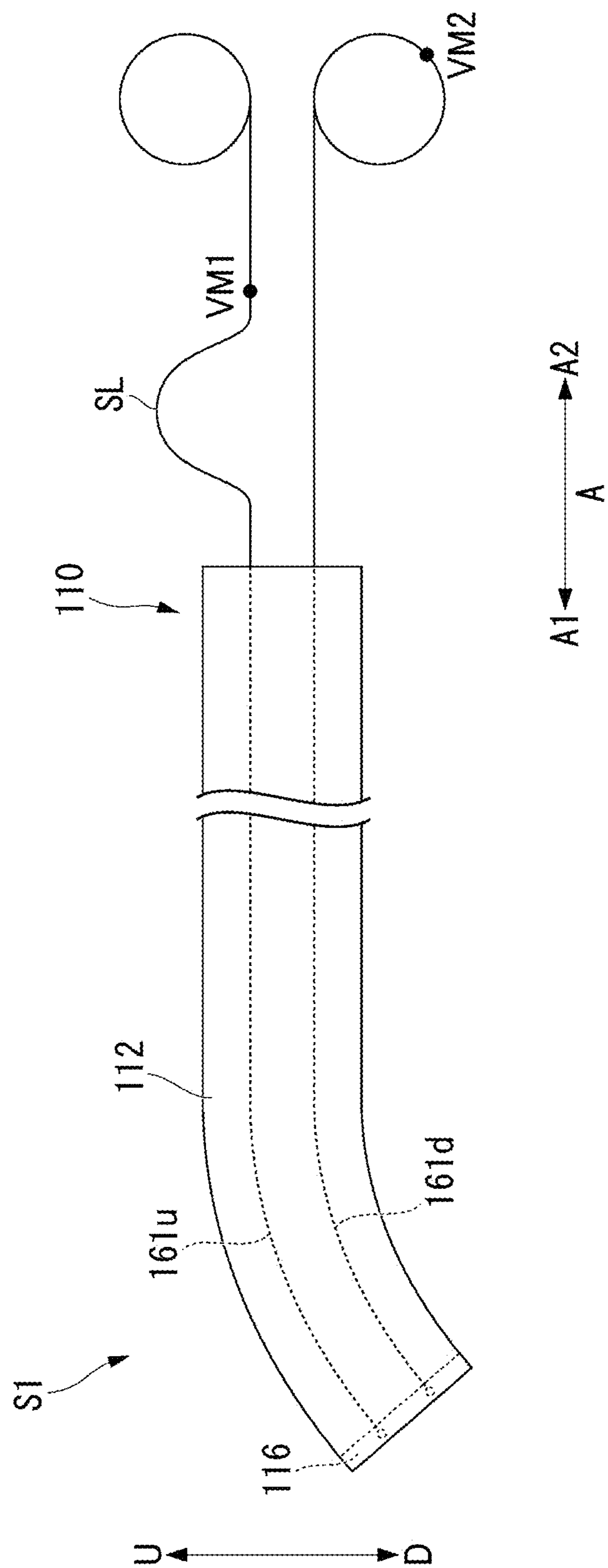
FIG. 62 illustrates an example of a view showing a pair of bending wires for inserting an insertion portion that is bent inside of an endoscope of the electric endoscope system.

The pair of bending wires 160 shown in FIG. 62 are in a state in which the lower bending wire 161*d* is most bent in the D direction of the bending portion 112 (also referred to as a first state S1).

Figure 63:
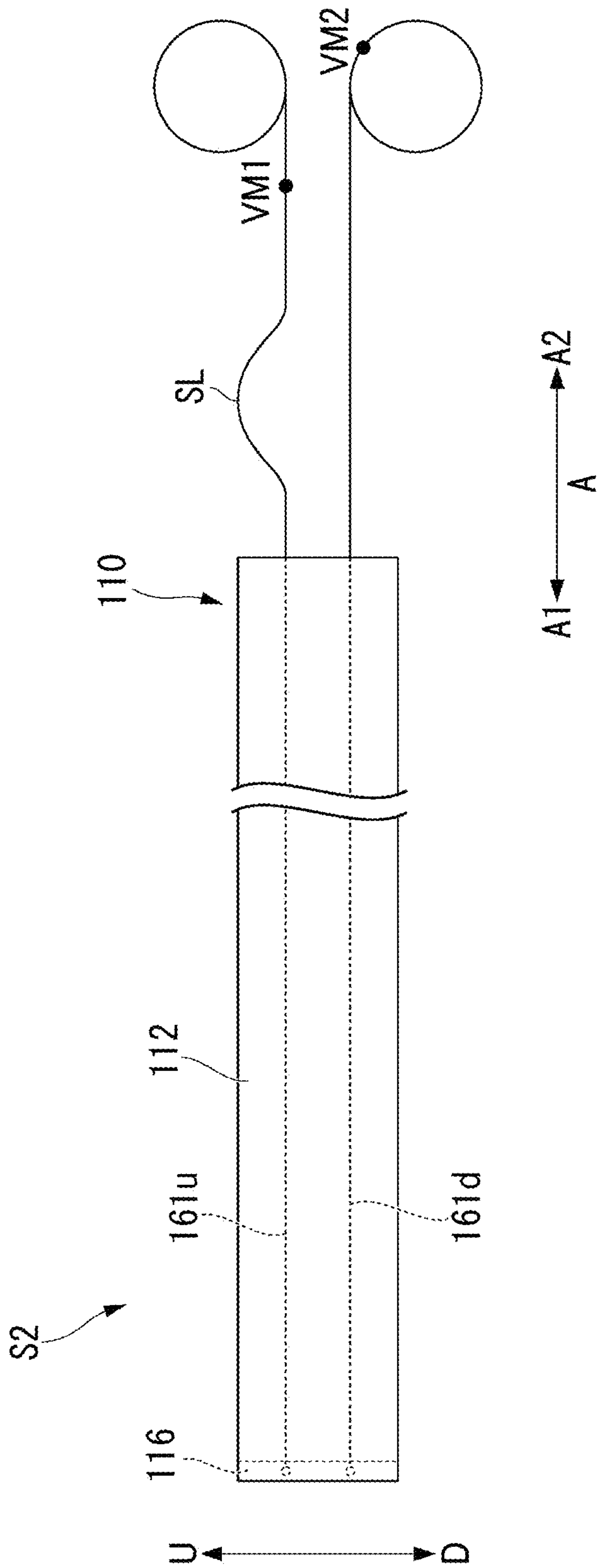
FIG. 63 illustrates an example of a view showing the pair of bending wires.

The pair of bending wires 160 shown in FIG. 63 are in a state in which the lower bending wire 161*d* begins to bend the bending portion 112 in the D direction (also referred to as a second state S2).

Figure 64:
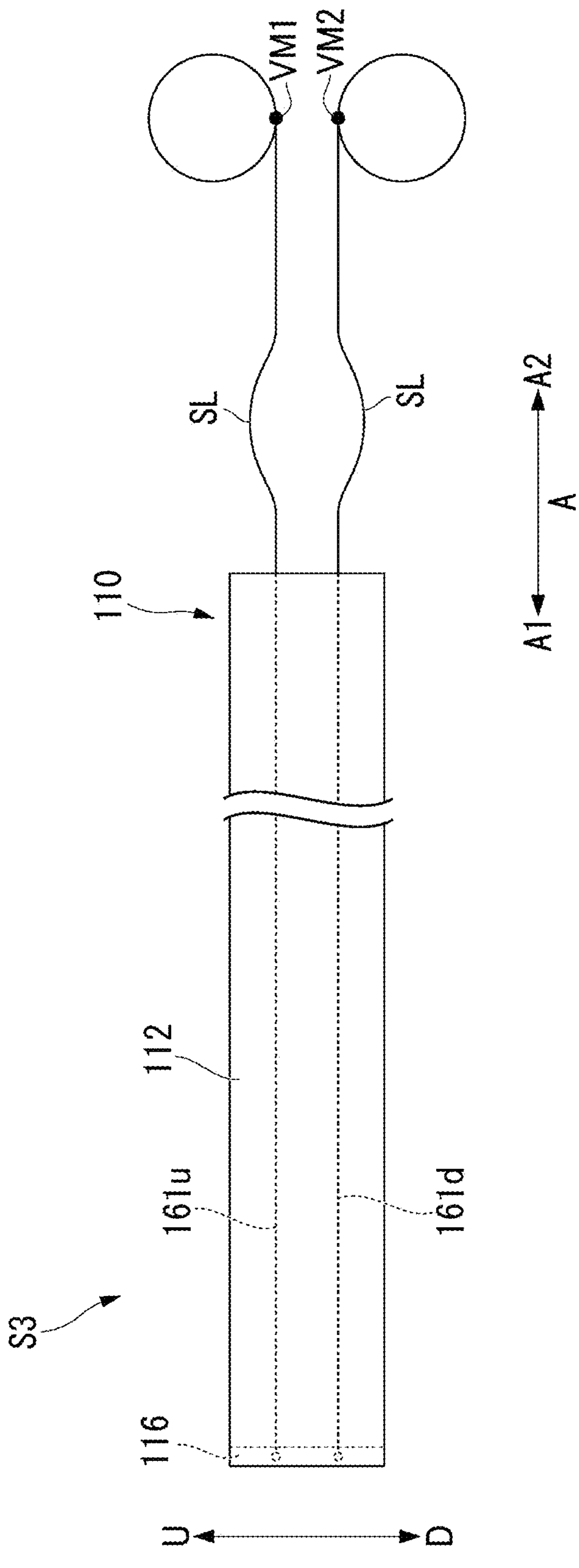
FIG. 64 illustrates an example of a view showing the pair of bending wires.

The pair of bending wires 160 shown in FIG. 64 are in a state in which the pair of bending wires 160 have a non-bending linear shape of the bending portion 112 (also referred to as a third state S3).

Figure 65:
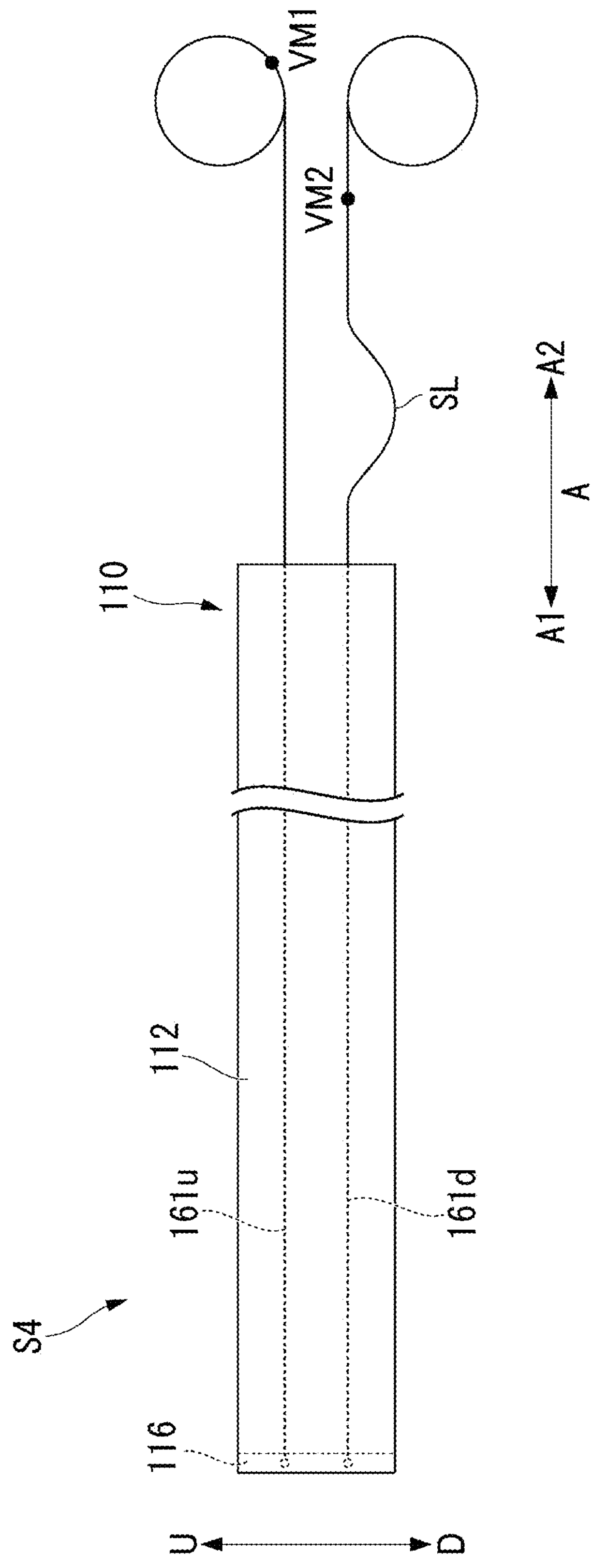
FIG. 65 illustrates an example of a view showing the pair of bending wires.

The pair of bending wires 160 shown in FIG. 65 are in a state in which the upper bending wire 161*u* begins to bend the bending portion 112 in the U direction (also referred to as a fourth state S4).

Figure 66:
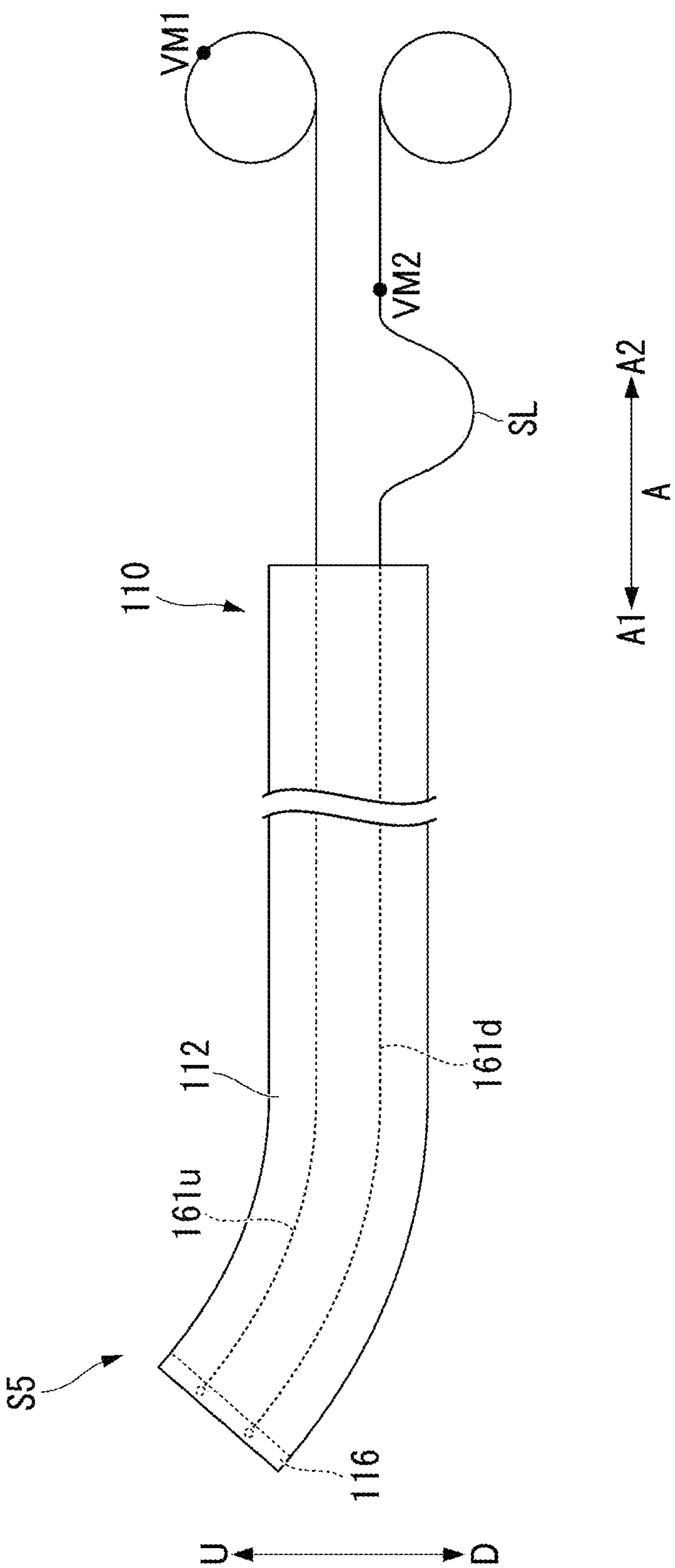
FIG. 66 illustrates an example of a view showing the pair of bending wires.

The pair of bending wires 160 shown in FIG. 66 are in a state in which the upper bending wire 161*u* bends the bending portion 112 most in the U direction (also referred to as a fifth state S5).

A path length of the pair of bending wires 160 changes with the bending of the flexible portions (the insertion portion 110 and the extracorporeal flexible portion 140). Therefore, the pair of bending wires 160 have a surplus length for absorbing a change in the path length and have "slack SL" in the third state S3 shown in FIG. 64.

[Operation of Electric Endoscope System 1000H]

Next, an operation of the electric endoscope system 1000H of the present embodiment will be described. Specifically, bending control (first bending control, second bending control, and third bending control) for bending the bending portion 112 will be described.

[First Bending Control]

Figure 67:
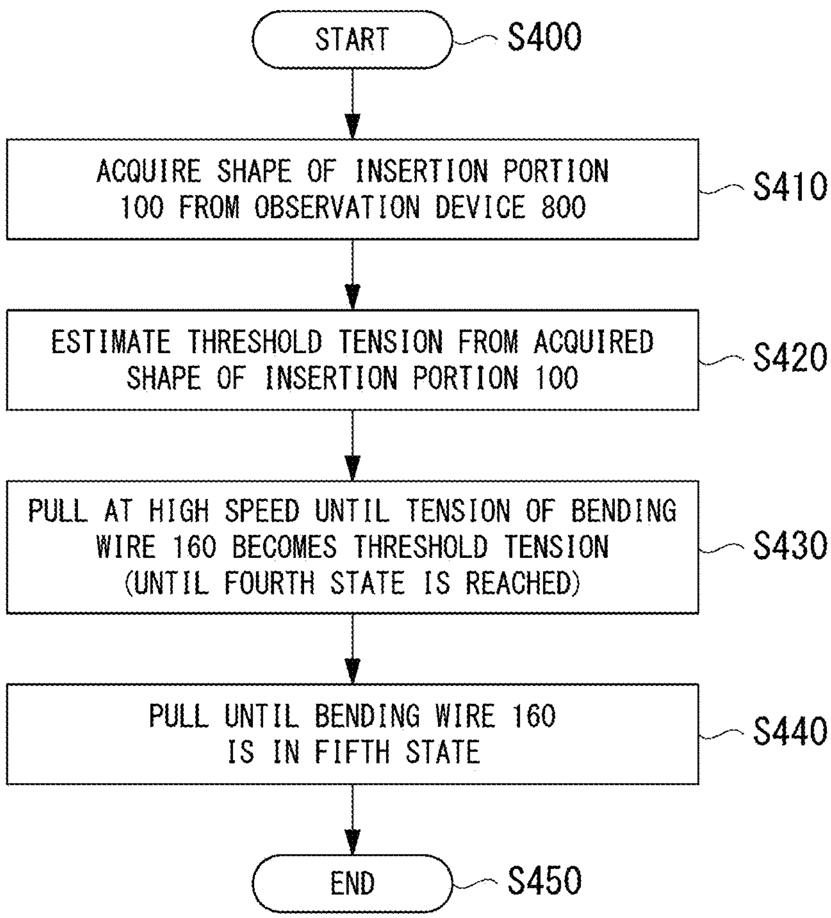
FIG. 67 illustrates an example of a control flowchart of first bending control.

FIG. 67 is a control flowchart of the first bending control.

As shown in FIGS. 62 to 66, the drive controller 260 (mainly, the processor 261) performs the first bending control shown in FIG. 67 when the bending portion 112 facing in the D direction is bent by the upper bending wire 161*u* in the U direction. In addition, because the first bending control in which the drive controller 260 bends the bending portion 112 facing in the U direction with the lower bending wire 161*d* in the D direction is similar control, description thereof is omitted.

<Step S410>

In step S410, the drive controller 260 communicates with the main controller 560 to acquire a shape of the insertion portion 110, which is an observation result of the observation device 800. The drive controller 260 subsequently executes step S420.

<Step S420>

Figure 68:
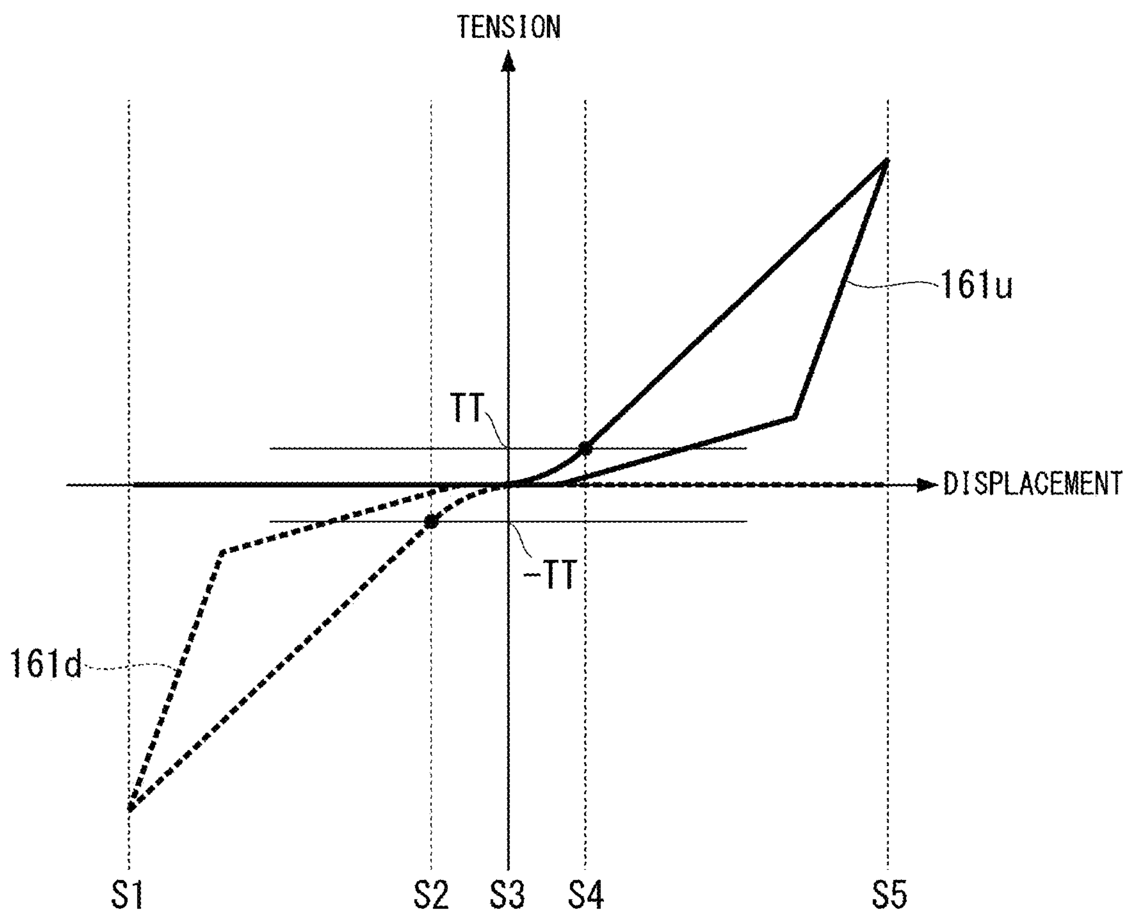
FIG. 68 illustrates an example of a diagram showing a relationship between the displacement and tension of the pair of bending wires.

FIG. 68 is a diagram showing a relationship between the displacement and tension of the pair of bending wires 160.

In step S420, the drive controller 260 estimates a threshold tension TT from the acquired shape of the insertion portion 110. As shown in FIG. 65, the threshold tension TT is a tension of the upper bending wire 161*u* in a state in which the upper bending wire 161*u* begins to bend the bending portion 112 in the U direction (the fourth state S4).

The drive controller 260 subsequently executes step S430.

<Step S430>

In step S430, the drive controller 260 pulls the upper bending wire 161*u* at a high speed until the tension of the upper bending wire 161*u* acquired from the tension sensor 159 becomes the threshold tension TT. The upper bending wire 161*u* is slackened (surplus) until the tension of the upper bending wire 161*u* becomes the threshold tension TT. Therefore, the drive controller 260 can shorten a period during which the bending portion 112 does not operate (a dead period) by pulling the upper bending wire 161*u* at a high speed. The drive controller 260 subsequently executes step S440.

<Step S440>

In step S440, the drive controller 260 pulls the upper bending wire 161*u* at a normal speed until it reaches the fifth state S5. The bending portion 112 bends in the U direction.

According to the first bending control, the bending responsiveness of the bending portion 112 is improved by driving the bending wire 160 at a high speed to compensate for an amount of movement corresponding to a surplus length of the bending wire 160.

[Second Bending Control]

Figure 69:
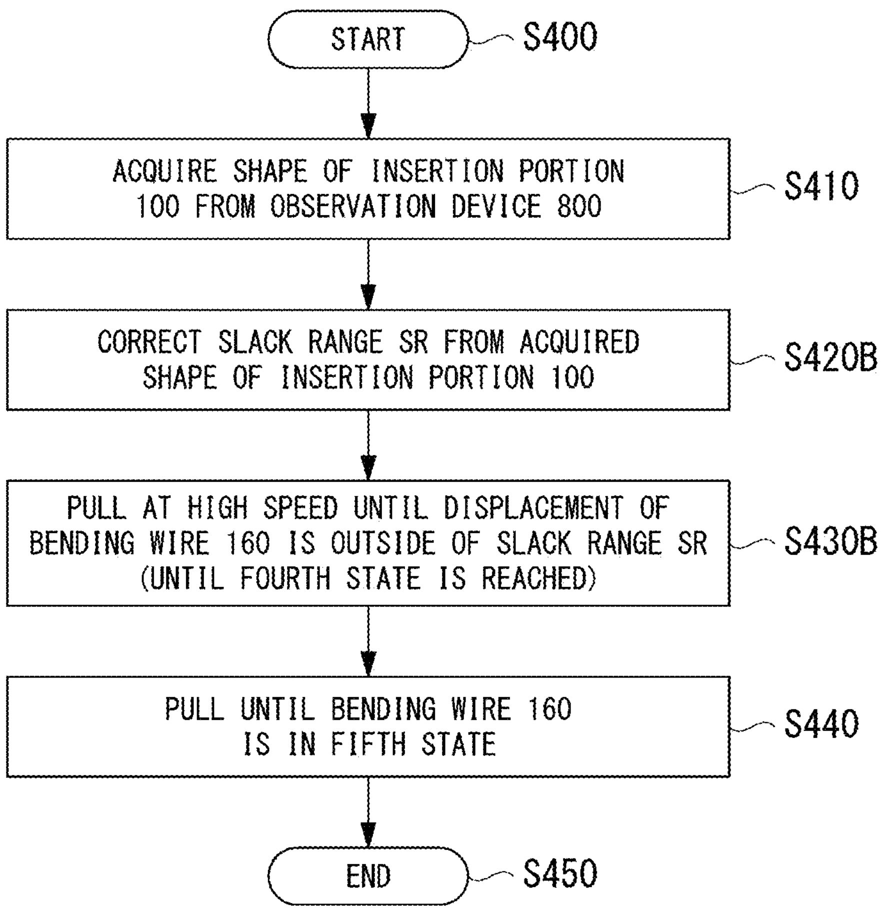
FIG. 69 illustrates an example of a control flowchart of second bending control.

FIG. 69 is a control flowchart of the second bending control.

The drive controller 260 (mainly, the processor 261) performs the second bending control shown in FIG. 69 when the bending portion 112 facing in the D direction is bent by the upper bending wire 161*u* in the U direction as shown in FIGS. 62 to 66. In addition, because the second bending control in which the drive controller 260 bends the bending portion 112 facing in the U direction with the lower bending wire 161*d* in the D direction is similar control, description thereof is omitted.

<Step S410>

In step S410, the drive controller 260 communicates with the main controller 560 to acquire a shape of the insertion portion 110, which is an observation result of the observation device 800. The drive controller 260 subsequently executes step S420B.

<Step S420B>

Figure 70:
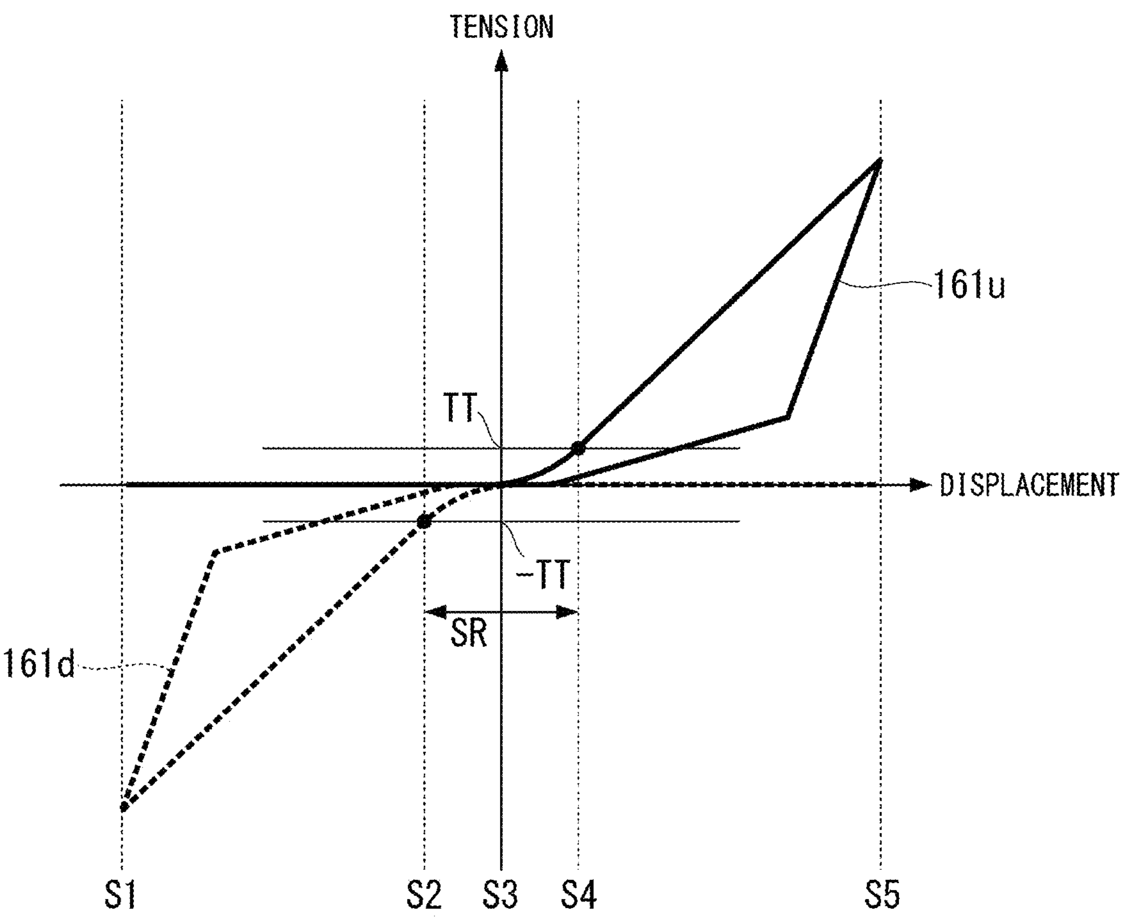
FIG. 70 illustrates an example of a diagram showing a relationship between the displacement and tension of the pair of bending wires.

FIG. 70 is a diagram showing a relationship between the displacement and tension of a pair of bending wires 160.

In step S420B, the drive controller 260 estimates an amount of change in a path length from the acquired shape of the insertion portion 110 and corrects a slack range SR. As shown in FIGS. 63 to 65, the slack range (dead zone) SR is a range in which the bending wire 160 to be pulled is slack. The length of the slack range SR becomes a surplus length of the bending wire 160. The drive controller 260 subsequently executes step S430B.

<Step S430B>

In step S430B, the drive controller 260 pulls the upper bending wire 161*u* at a high speed until the displacement of the upper bending wire 161*u* is outside of the slack range SR. The upper bending wire 161*u* is slack (surplus) until the displacement of the upper bending wire 161*u* is outside of the slack range SR. Therefore, the drive controller 260 can shorten a period during which the bending portion 112 does not operate (a dead period) by pulling the upper bending wire 161*u* at a high speed. The drive controller 260 subsequently executes step S440.

<Step S440>

In step S440, the drive controller 260 pulls the upper bending wire 161*u* at a normal speed until it reaches the fifth state S5. The bending portion 112 bends in the U direction.

According to the second bending control, the bending responsiveness of the bending portion 112 is improved by driving the bending wire 160 at a high speed to compensate for an amount of movement corresponding to a surplus length of the bending wire 160.

[Third Bending Control]

Figure 71:
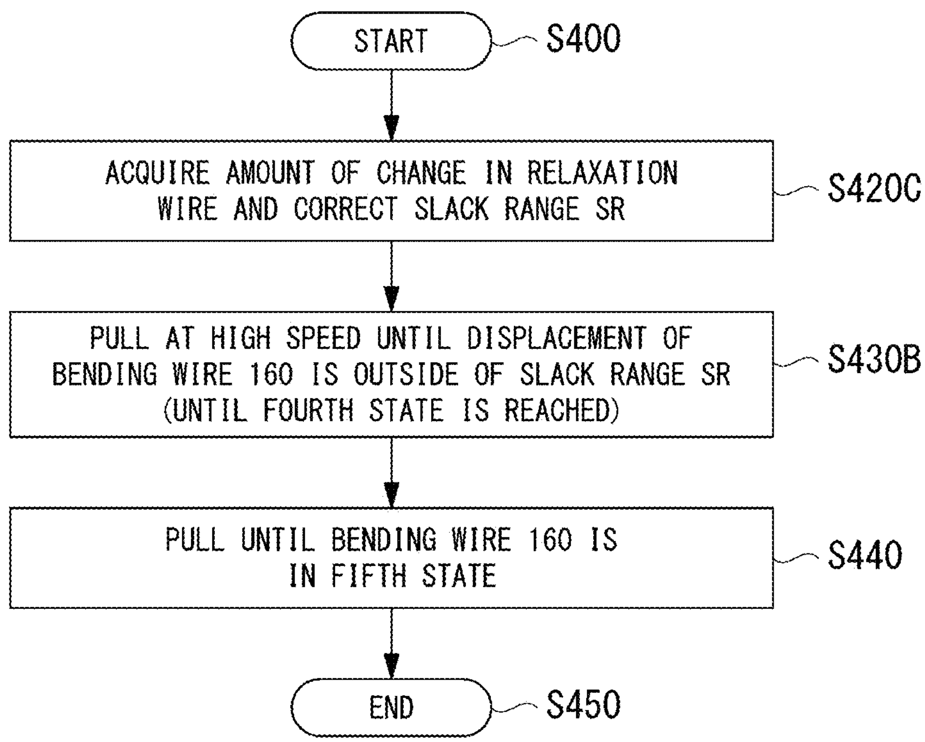
FIG. 71 illustrates an example of a control flowchart of third bending control.

FIG. 71 is a control flowchart of the third bending control.

As shown in FIGS. 62 to 66, the drive controller 260 (mainly, the processor 261) performs the third bending control shown in FIG. 71 when the bending portion 112 facing in the D direction is bent by the upper bending wire 161*u* in the U direction. In addition, the third bending control in which the drive controller 260 bends the bending portion 112 facing in the U direction with the lower bending wire 161*d* in the D direction is similar control, description thereof is omitted.

<Step S420C>

In step S420C, the drive controller 260 corrects the slack range SR on the basis of amounts of changes in the displacement and tension when relaxing the lower bending wire 161*d*, which is a relaxation wire. The drive controller 260 corrects the slack range SR by estimating an amount of change in the slack of the upper bending wire 161*u*, which is a pulling wire, on the basis of the amount of change in the slack of the lower bending wire 161*d*, which is the relaxation wire. Specifically, the drive controller 260 acquires the amount of change in the slack SL for an initial state of the lower bending wire 161*d* (the amount of change in the surplus length) when the tension of the upper bending wire 161*u* is below the threshold tension TT and estimates the amount of change in the slack SL (the amount of change in the surplus length) for an initial state of the upper bending wire 161*u*. The upper bending wire 161*u* and the lower bending wire 161*d* use the characteristic of slack to the same extent with respect to the initial state. The subsequent control is similar to the second bending control.

According to the third bending control, the bending responsiveness of the bending portion 112 is improved by driving the bending wire 160 at a high speed to compensate for an amount of movement corresponding to the surplus length of the bending wire 160.

[Slack Amount Control]

Figure 72:
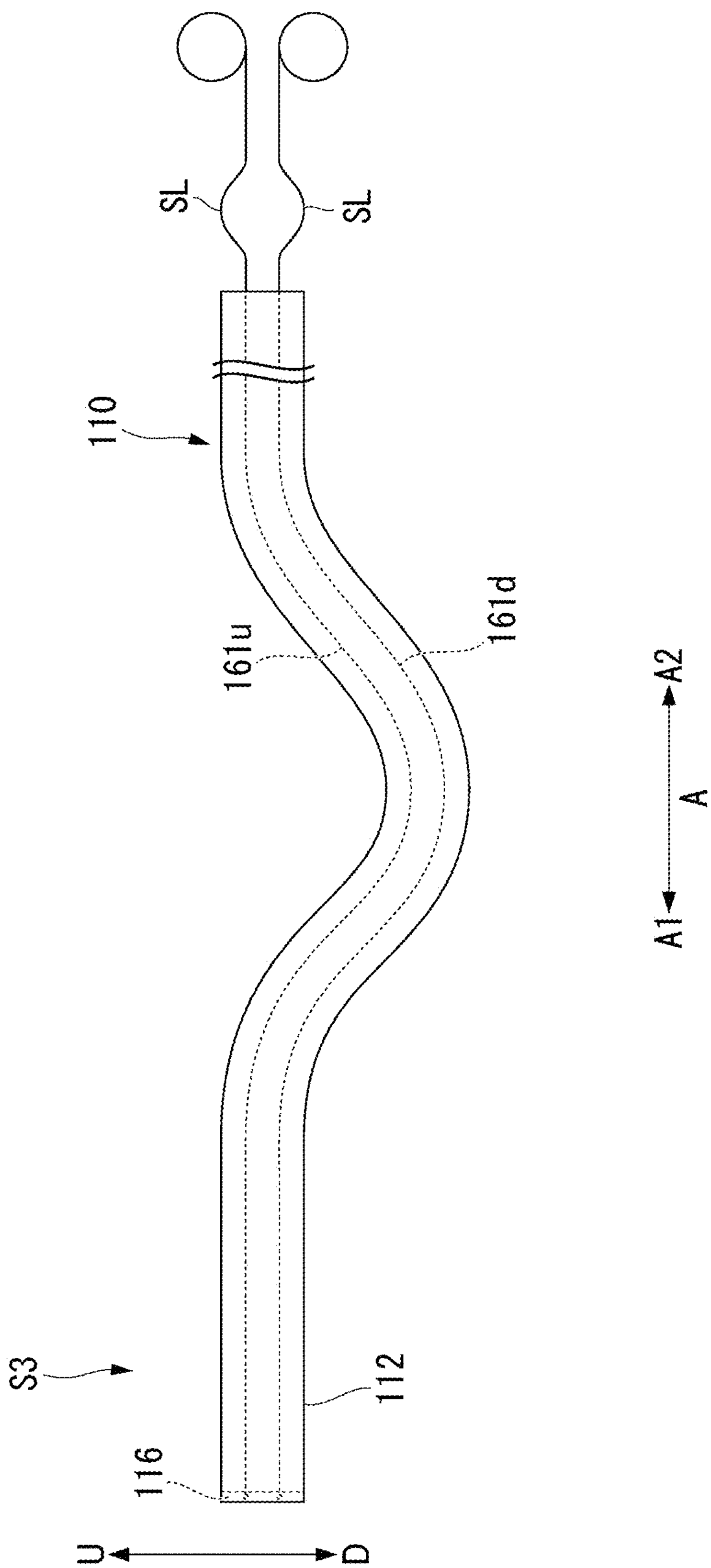
FIG. 72 illustrates an example of a view showing the pair of bending wires in a third state of another aspect.

FIG. 72 is a view showing a pair of bending wires 160 in the third state S3 of another aspect.

The drive controller 260 may perform slack amount control for controlling an amount of slack of the pair of bending wires 160 according to the bending control (the first bending control, the second bending control, and the third bending control). The drive controller 260 adjusts the amount of slack of the pair of bending wires 160 by pulling or sending the pair of bending wires 160 in the slack amount control.

For example, when the drive controller 260 estimates the threshold tension TT and the slack range SR in the first bending control, the second bending control, and the third bending control, the path lengths of the pair of bending wires 160 are lengthened according to the bending of the flexible portion (the insertion portion 110 and the extracorporeal flexible portion 140), and it is possible to detect that the "slack SL" is reduced in the third state S3. In this case, the drive controller 260 may send the pair of bending wires 160 to cause the "amount of slack" of each of the pair of bending wires 160 to coincide with an "amount of slack" of a predetermined state (for example, an initial state as shown in FIG. 64). The drive controller 260 can execute bending control with a uniform surplus length of the bending wire 160, regardless of the bending shape of the flexible portion (the insertion portion 110 and the extracorporeal flexible portion 140).

The initial state of the pair of bending wires 160 as shown in FIG. 64 is a state in which the flexible portion (the insertion portion 110 and the extracorporeal flexible portion 140) is not bent and the path length is the shortest. The amount of slack of each of the pair of bending wires 160 in the initial state is desirably 0.1% or more and less than 1% of the wire length of each of the pair of bending wires 160.

The "amount of slack" of each of the pair of bending wires 160 is preferably an "amount of slack" that does not generate a tension in the bending piece 115 even if the flexible portion (the insertion portion 110 and the extracorporeal flexible portion 140) has the most bending and the longest path length.

[Parameter Control]

Figure 73:
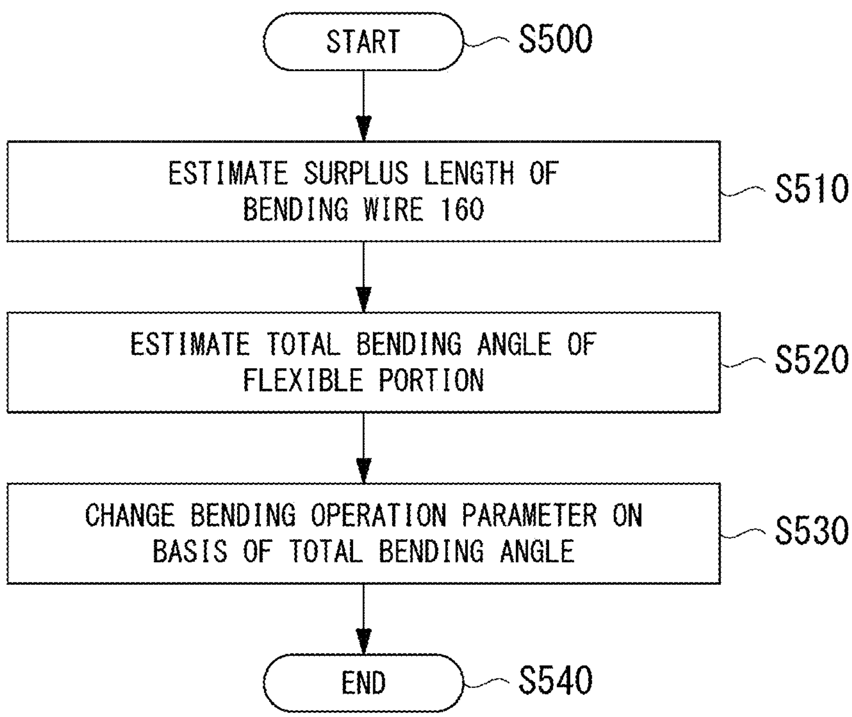
FIG. 73 illustrates an example of a control flowchart of parameter control.

FIG. 73 is a control flowchart of parameter control.

The drive controller 260 may perform parameter control for controlling bending operation parameters of the bending portion 112 with the pair of bending wires 160 in accordance with the bending control (the first bending control, the second bending control, and the third bending control).

<Step S510>

The drive controller 260 estimates a surplus length of the bending wire 160 by estimating the threshold tension TT and the slack range SR in the first bending control, the second bending control, and the third bending control. The drive controller 260 subsequently executes step S520.

<Step S520>

Figure 74:
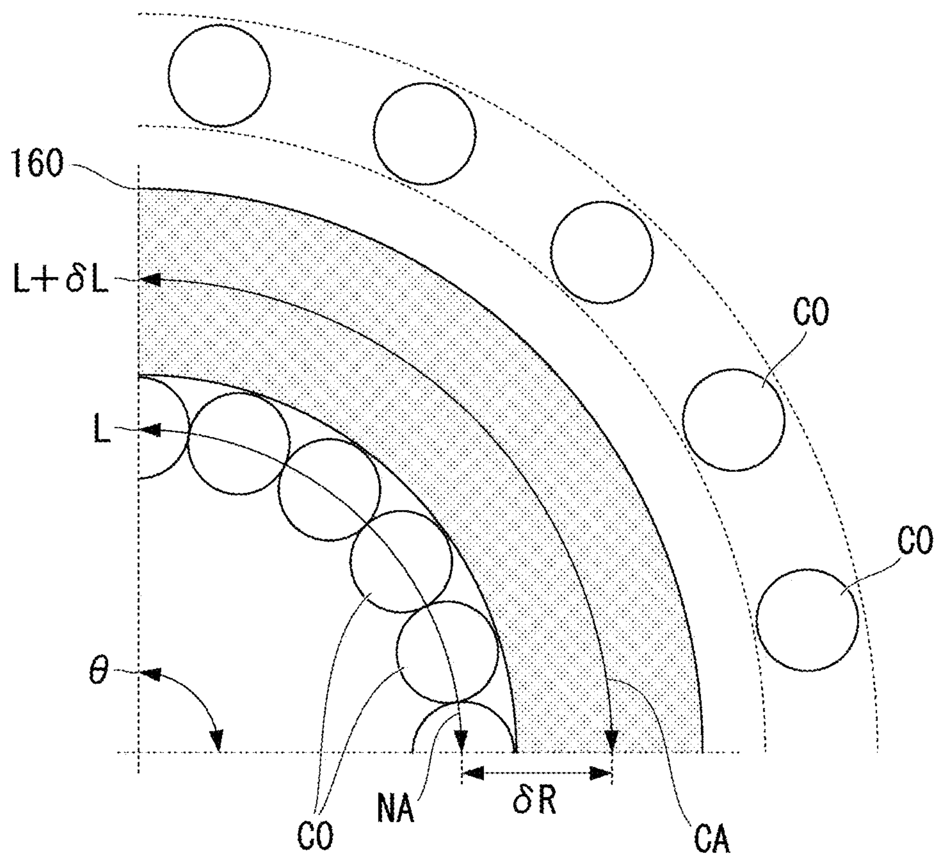
FIG. 74 illustrates an example of a view showing a model of a flexible portion in which a sheath is a coil.
Figure 75:
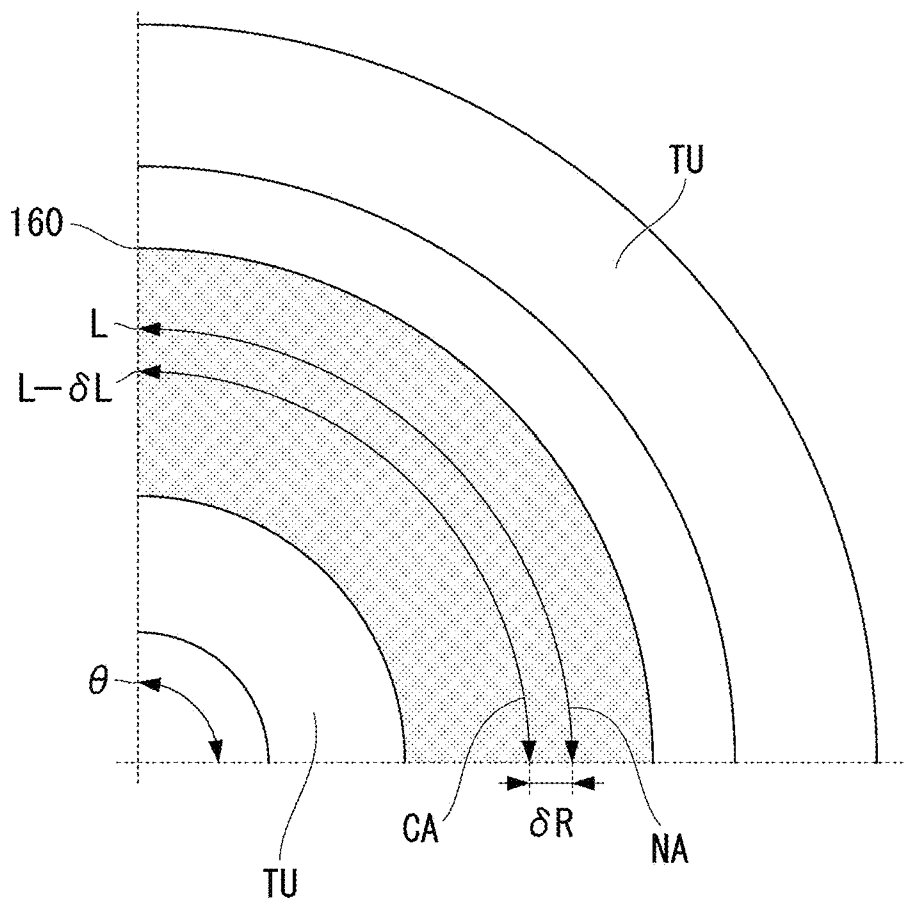
FIG. 75 illustrates an example of a view showing a model of a flexible portion in which the sheath is a tube.

FIG. 74 is a view showing a model of a flexible portion in which the sheath is a coil CO. FIG. 75 is a view showing a model of a flexible portion in which the sheath is a tube TU.

The drive controller 260 estimates a total bending angle of the flexible portion (the insertion portion 110 and the extracorporeal flexible portion 140) in step S520. The total bending angle is calculated by Eq. (1). The drive controller 260 subsequently executes step S530.

$$\delta L = \delta R \times \vartheta \quad \text{Eq. (1)}$$

In Eq. (1), δL denotes a change in the path length of the bending wire 160. δR denotes a distance between a neutral axis NA of the bending wire 160 and a central axis CA of the bending wire 160. Here, the central axis CA is an axis having a length equal to that of the bent bending wire 160 in a straight state. 0 denotes a total bending angle of the flexible portion (the insertion portion 110 and the extracorporeal flexible portion 140).

In the drive controller 260, because 8R is determined by dimensions of the bending wire 160 and the sheath, the total bending angle θ can be estimated from the change δL in the path length. As shown in FIGS. 74 and 75, even when the sheath is the coil CO (for example, a round wire coil) or even when the sheath is the tube TU, the drive controller 260 can estimate the total bending angle θ.

<Step S530>

In step S520, the drive controller 260 changes bending operation parameters (an amount of bending limit, an amount of hysteresis compensation, and the like) on the basis of an estimated total bending angle.

The electric endoscope system 1000H according to the present embodiment can more efficiently perform observation and treatment using the endoscope 100H. The electric endoscope system 1000H improves the bending responsiveness of the bending portion 112 by controlling the bending wire 160 according to the bending shape of the flexible portion (the insertion portion 110 and the extracorporeal flexible portion 140).

Although the eighth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Ninth Embodiment

An electric endoscope system 1000I according to a ninth embodiment of the present disclosure will be described with reference to FIGS. 76 to 89. In the following description, constituent elements identical to those described above are denoted by the same reference signs and redundant description thereof will be omitted.

[Electric Endoscope System 1000I]

Figure 76:
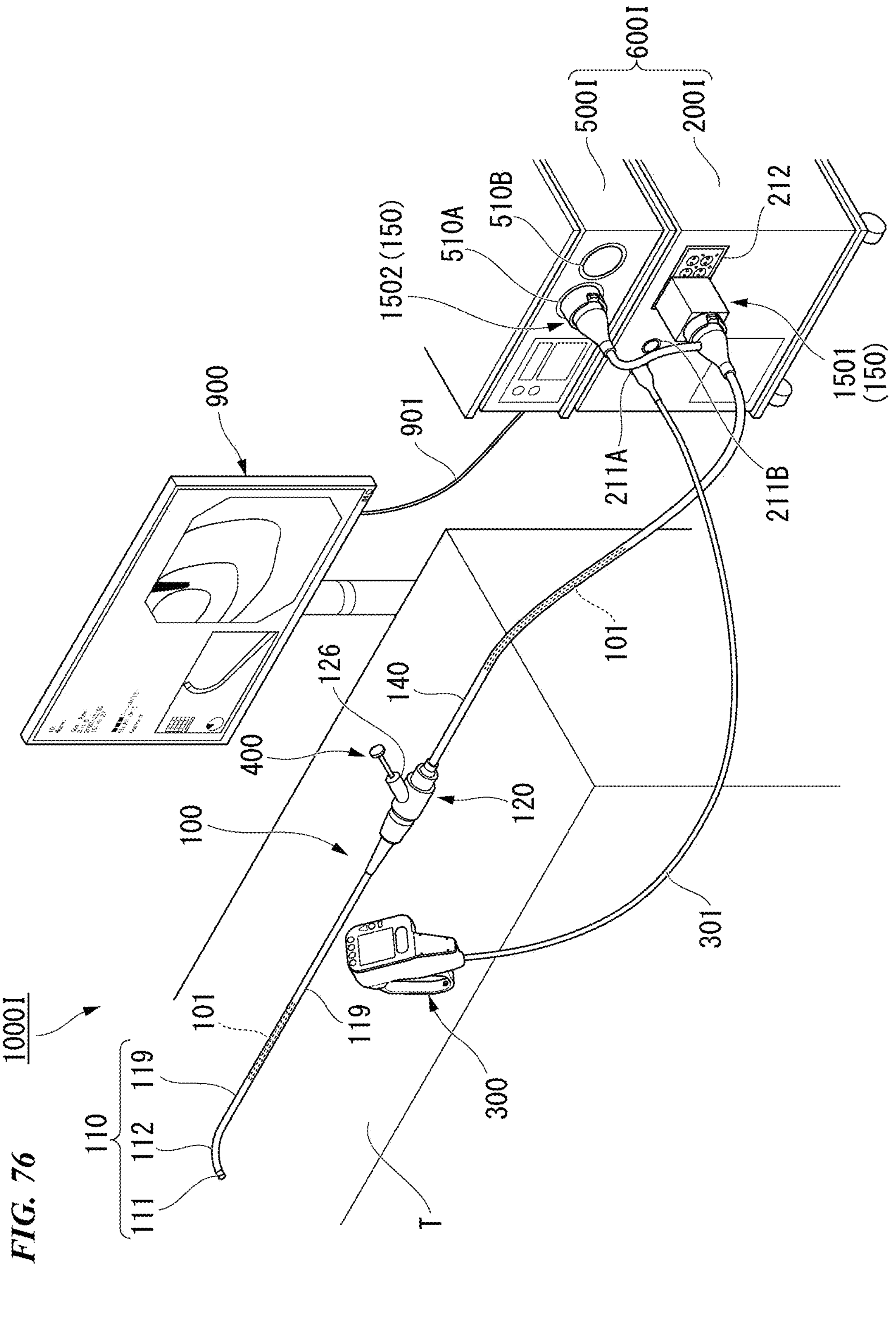
FIG. 76 illustrates an example of an overall view of an electric endoscope system according to a ninth embodiment.

FIG. 76 is an overall view of the electric endoscope system 1000I according to the present embodiment.

The electric endoscope system 1000I includes an endoscope 100, a drive device 200I, a manipulation device 300, a treatment tool 400, a video control device 500I, and a display device 900. The drive device 200I and the video control device 500I constitute a control device 600I that controls the electric endoscope system 1000I.

The drive device 200I is the same as the drive device 200 of the first embodiment, except that the drive device 200I has a plurality of input modes related to the manipulation input received from the manipulation device 300. A drive controller 260 of the drive device 200I has two input modes, i.e., a first input mode and a second input mode. On the basis of the selected input mode, the drive controller 260 associates the manipulation input received from the manipulation device 300 with the bending manipulation on a bending portion 112 or the like. Moreover, the drive controller 260 switches the input mode on the basis of a manipulation input for switching the input mode from the manipulation device 300.

Figure 77:
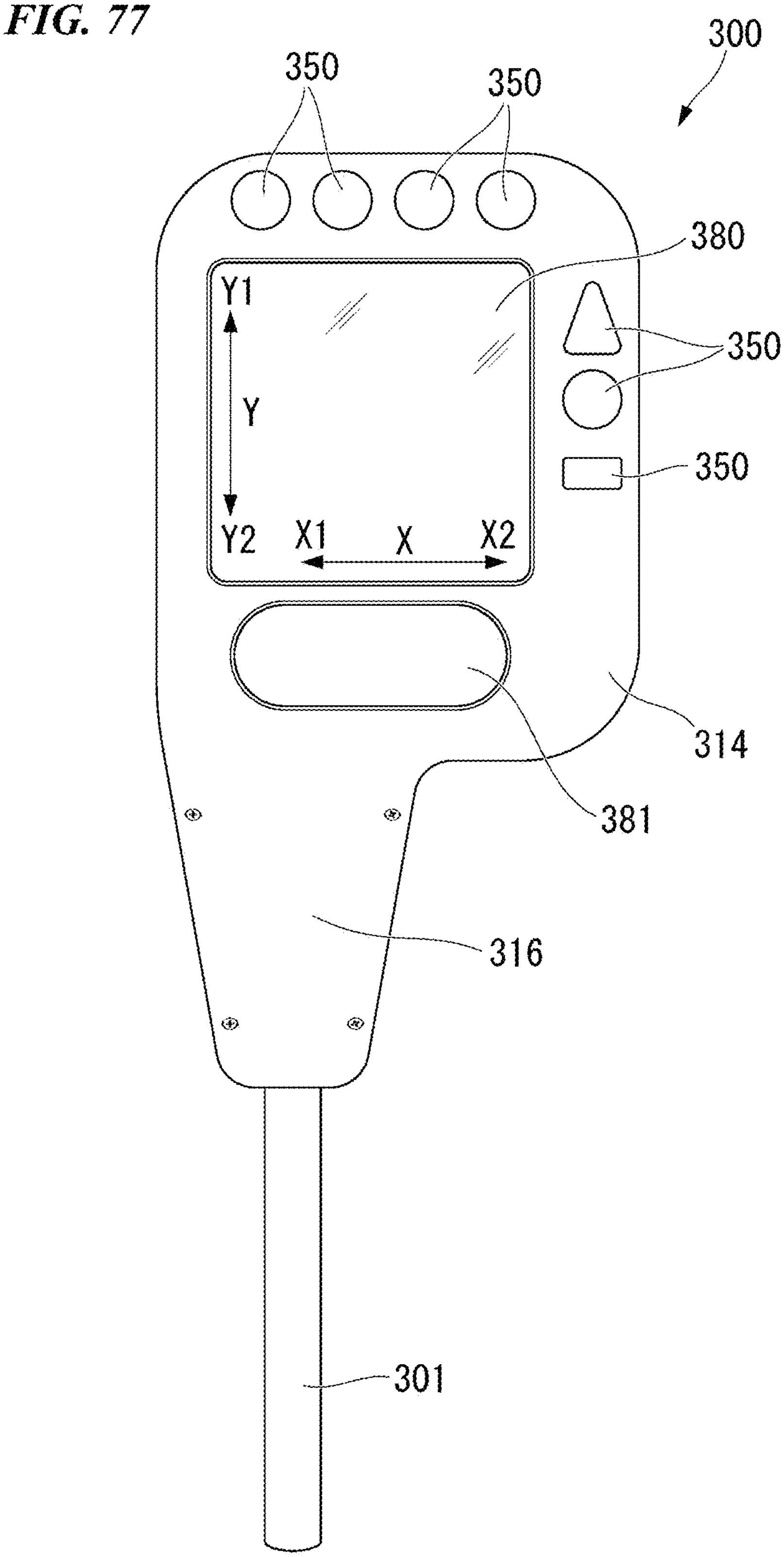
FIG. 77 illustrates an example of a front view of a manipulation device of the electric endoscope system.

FIG. 77 is a front view of the manipulation device 300.

The manipulation device 300 includes a manipulation portion body 310, an air/water supply button 351, a suction button 352, various buttons 350, a touchpad 380, and a touch sensor 381.

The touchpad 380 is a touch-sensitive interface to which a bending manipulation on the bending portion 112 or the like is input. For example, an input for an upward direction (Y1 direction) of a longitudinal direction (Y direction) in the touchpad 380 is associated with a manipulation of bending the bending portion 112 in a U direction. An input for a downward direction (Y2 direction) of the longitudinal direction (Y direction) in the touchpad 380 is associated with a manipulation of bending the bending portion 112 in a D direction. An input for a left direction (X1 direction) of a lateral direction (X direction) in the touchpad 380 is associated with a manipulation of bending the bending portion 112 in an L direction. An input for a right direction (X2 direction) of the lateral direction (X direction) in the touchpad 380 is associated with a manipulation of bending the bending portion 112 in an R direction.

The touch sensor 381 is a touch-sensitive interface to which any manipulation is input. The touch sensor 381 is used, for example, to adjust a ratio of an amount of drive of the bending portion 112 to an amount of manipulation input of the touchpad 380 (hereinafter also referred to as a "motion scale").

The manipulation device 300 includes a button for switching an input mode of the drive device 200I (hereinafter also referred to as an "input mode switching button"). The input mode switching button is, for example, various buttons 350 assigned as input mode switching buttons. When the touchpad 380 is a pressure-sensitive touchpad, the touchpad 380 may be assigned as an input mode switching button that detects pressing if the touchpad 380 is pressed with predetermined strength or more.

The drive controller 260 may switch the input mode by detecting that the input mode switching button has been pressed or may switch the input mode only while the input mode switching button is pressed.

The video control device 500I is the same as the video control device 500 of the first embodiment, except that the video control device 500I generates a display image IMG.

Figure 78:
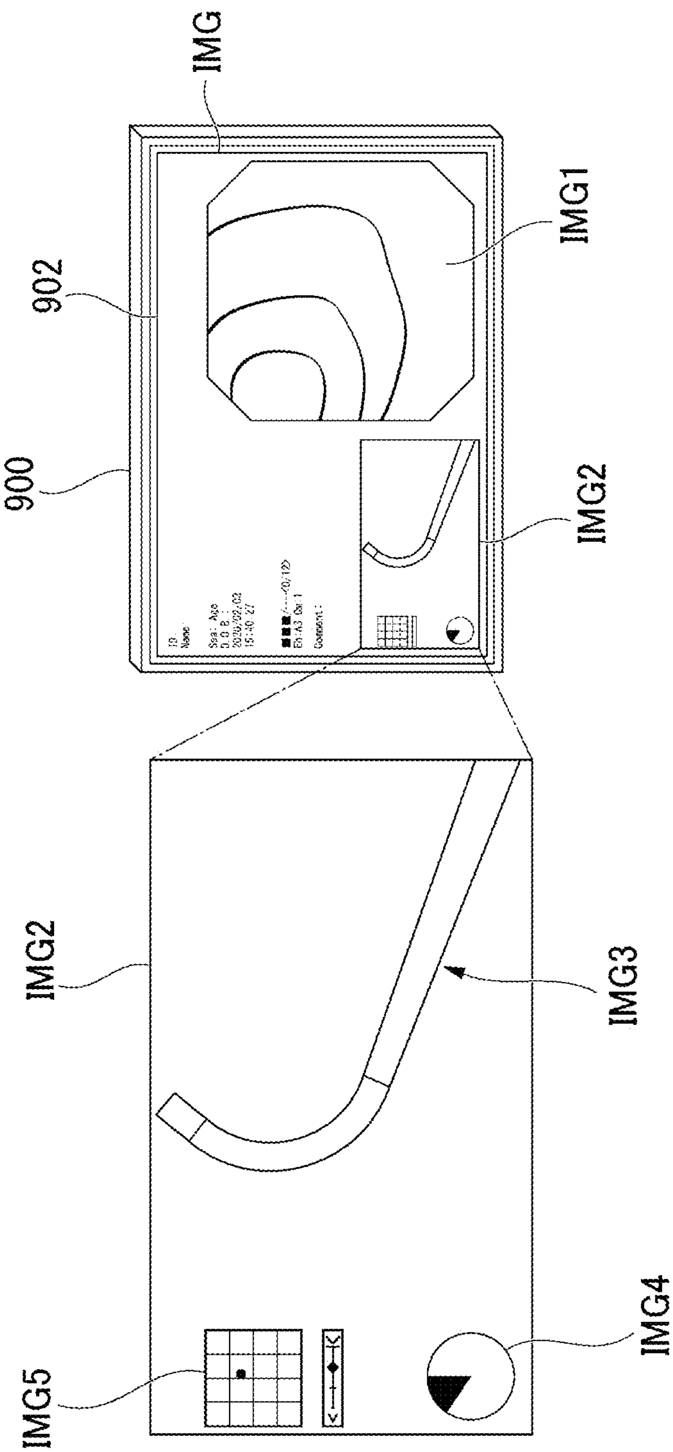
FIG. 78 illustrates an example of a view showing a display image output to a display device by a video control device of the electric endoscope system.

FIG. 78 is a view showing the display image IMG output by the video control device 500I to the display device 900. The video control device 500I generates the display image IMG and outputs the generated display image IMG to the display device 900. The display image IMG includes an imaging image IMG1 acquired from the endoscope 100 and a guide image IMG2. The display device 900 displays the display image IMG on a screen 902.

The guide image IMG2 is an image that supports a manipulation on the endoscope 100 by a scopist S. The guide image IMG2 is generated by a main controller 560 (mainly, a processor 561) of the video control device 500I. The guide image IMG2 includes a CG image IMG3, a passive rotation information image IMG4, and a manipulation information image IMG5.

The CG image IMG3 is a CG image of the insertion portion 110 including the bending portion 112. The main controller 560 generates the CG image IMG3 on the basis of a drive state of the bending wire 160 acquired from the drive controller 260. The scopist S can visually recognize a shape of the bending portion 112 in the body of a patient P by viewing the CG image IMG3.

The passive rotation information image IMG4 is an image in which a rotation angle of a passive rotation portion (a proximal end portion 119*b* of an intracorporeal flexible portion 119, a housing 123*h*, and a cylindrical member 121) in the connection portion 120 is displayed with a circle gauge. The main controller 560 generates the passive rotation information image IMG4 on the basis of a rotation angle of a magnetic ring 121*s* acquired from the magnetic sensor of the connection portion 120. The scopist S can intuitively ascertain an angle at which the passive rotation portion is rotating in a circumferential direction C with respect to a cover member 125F by viewing the passive rotation information image IMG4.

Figure 79:
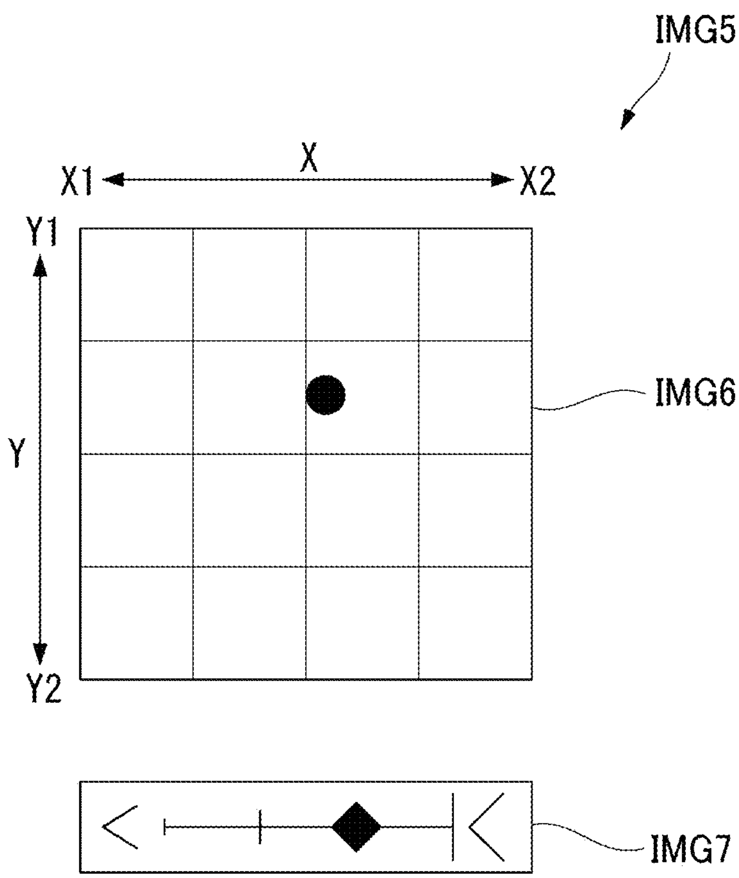
FIG. 79 illustrates an example of a view showing a manipulation information image.
Figure 80:
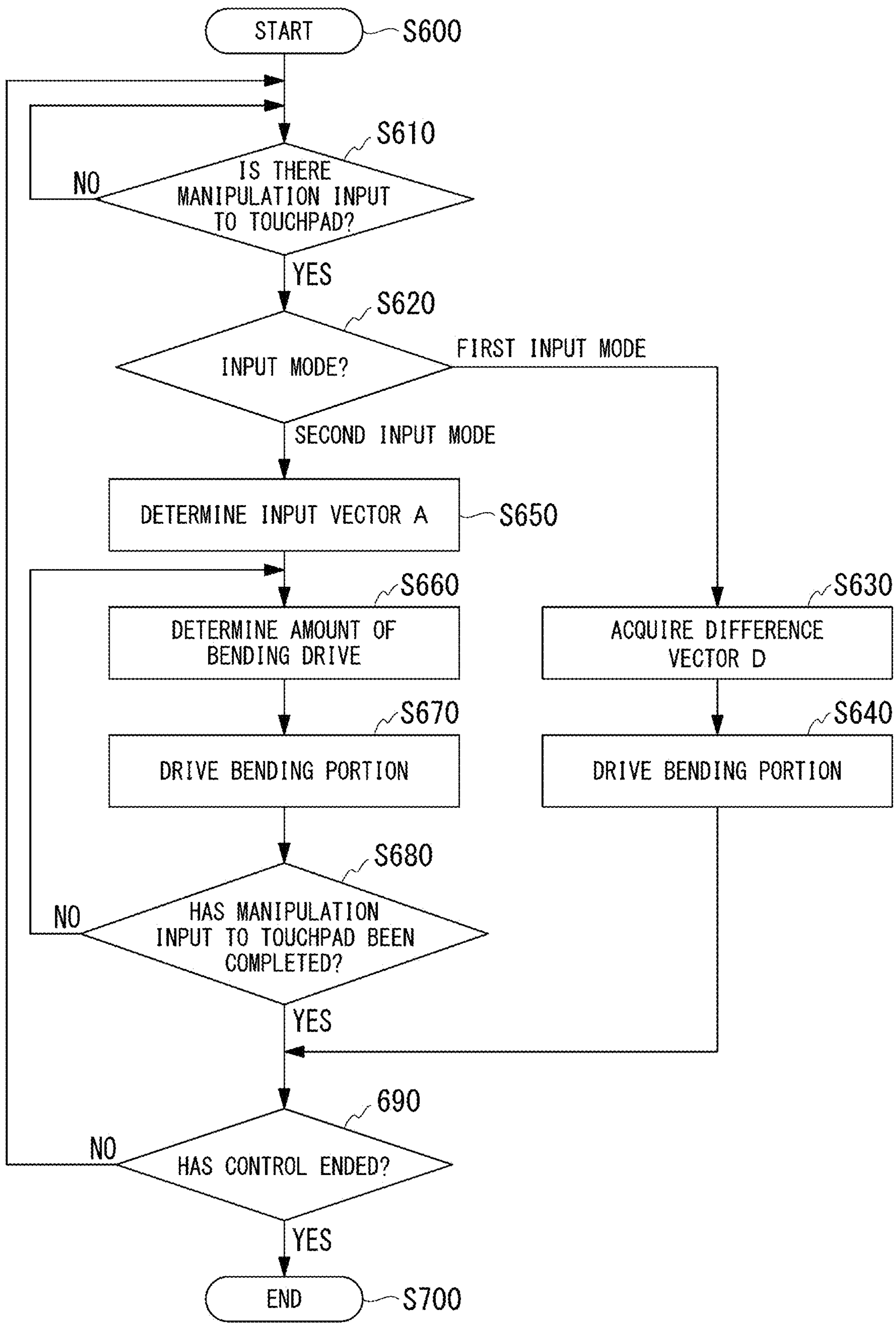
FIG. 80 illustrates an example of a control flowchart of a drive controller of a control device of the electric endoscope system.

FIG. 79 is a view showing a manipulation information image IMG5.

The manipulation information image IMG5 is an image in which the manipulation input of the manipulation device 300 by the scopist S is visualized. The main controller 560 generates the passive rotation information image IMG4 on the basis of the manipulation input received from the manipulation device 300. The manipulation information image IMG5 includes a first manipulation information image IMG6 displaying a position input to the touchpad 380 and a second manipulation information image IMG7 displaying a position input to the touch sensor 381. The scopist S can visualize the manipulation input to the manipulation device 300 by viewing the manipulation information image IMG5. By viewing the second manipulation information image IMG7, the scopist S can ascertain the currently set motion scale without actually performing a manipulation of bending the bending portion 112.

[Operation of Electric Endoscope System 1000I]

Next, an operation of the electric endoscope system 1000I of the present embodiment will be described. Hereinafter, description will be given in accordance with a control flowchart of the drive controller 260 of the control device 600I shown in FIG. 80. When the control device 600I is activated, the drive controller 260 starts a control flow shown in FIG. 80 (step S600). Subsequently, the drive controller 260 (mainly, the processor 261) executes step S610.

<Step S610: Determination of Start of Bending Drive>

In step S610, the drive controller 260 periodically confirms the manipulation input to the touchpad 380 and determines the start of the bending drive of the bending portion 112. When there is a manipulation input to the touchpad 380, the drive controller 260 subsequently executes step S620.

<Step S620: Determination of Input Mode>

The drive controller 260 determines a selected input mode in step S620. When a first input mode is selected, the drive controller 260 subsequently executes step S630. When a second input mode is selected, the drive controller 260 subsequently executes step S650.

<Step S630: Acquisition of Difference Vector D>

Figure 81:
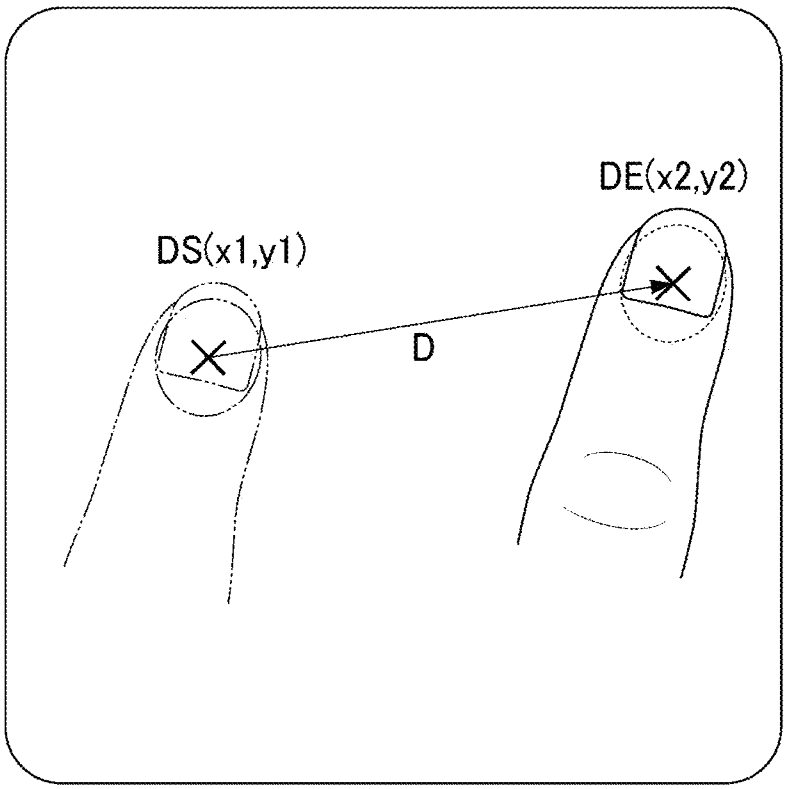
FIG. 81 illustrates an example of a view showing a difference vector.

FIG. 81 is a view showing a difference vector D.

In step S630, the drive controller 260 acquires a difference vector D from a difference between a start position DS and an end position DE. The start position DS is a position of a thumb finger FT on the touchpad 380 when a manipulation input is started in a manipulation input within a predetermined period. The end position DE is a position of the thumb finger FT on the touchpad 380 when the manipulation input is completed in the manipulation input within a predetermined period. At the time of a start position DS (x1, y1) and an end position DE (x2, y2), the difference vector D (dx, dy) is (x2-x1, y2-y1). The drive controller 260 subsequently executes step S640.

<Step S640: Bending Portion Drive>

The drive controller 260 drives the bending portion 112 on the basis of the determined difference vector D in step S640. Specifically, the drive controller 260 drives the bending portion 112 by an amount of bending drive proportional to a magnitude of the difference vector D with respect to the direction of the difference vector D. The drive controller 260 subsequently executes step S690.

When the input mode is the first input mode, a direction of the difference vector D is not limited to a specific direction. Therefore, when the input mode is the first input mode, the drive controller 260 can drive the bending portion 112 in the direction of the difference vector D acquired from the manipulation input. By selecting the first input as the input mode, for example, the scopist S can easily input a manipulation in which the distal end of the bending portion 112 is operated to draw a circle so that every corner of the lumen is observed.

<Step S650: Determination of Input Vector A>

In step S650, the drive controller 260 determines an input direction DI on the basis of the manipulation input to the touchpad 380. Specifically, the drive controller 260 determines an input vector A on the basis of a movement start direction of the thumb finger FT along the touchpad 380.

Figure 82:
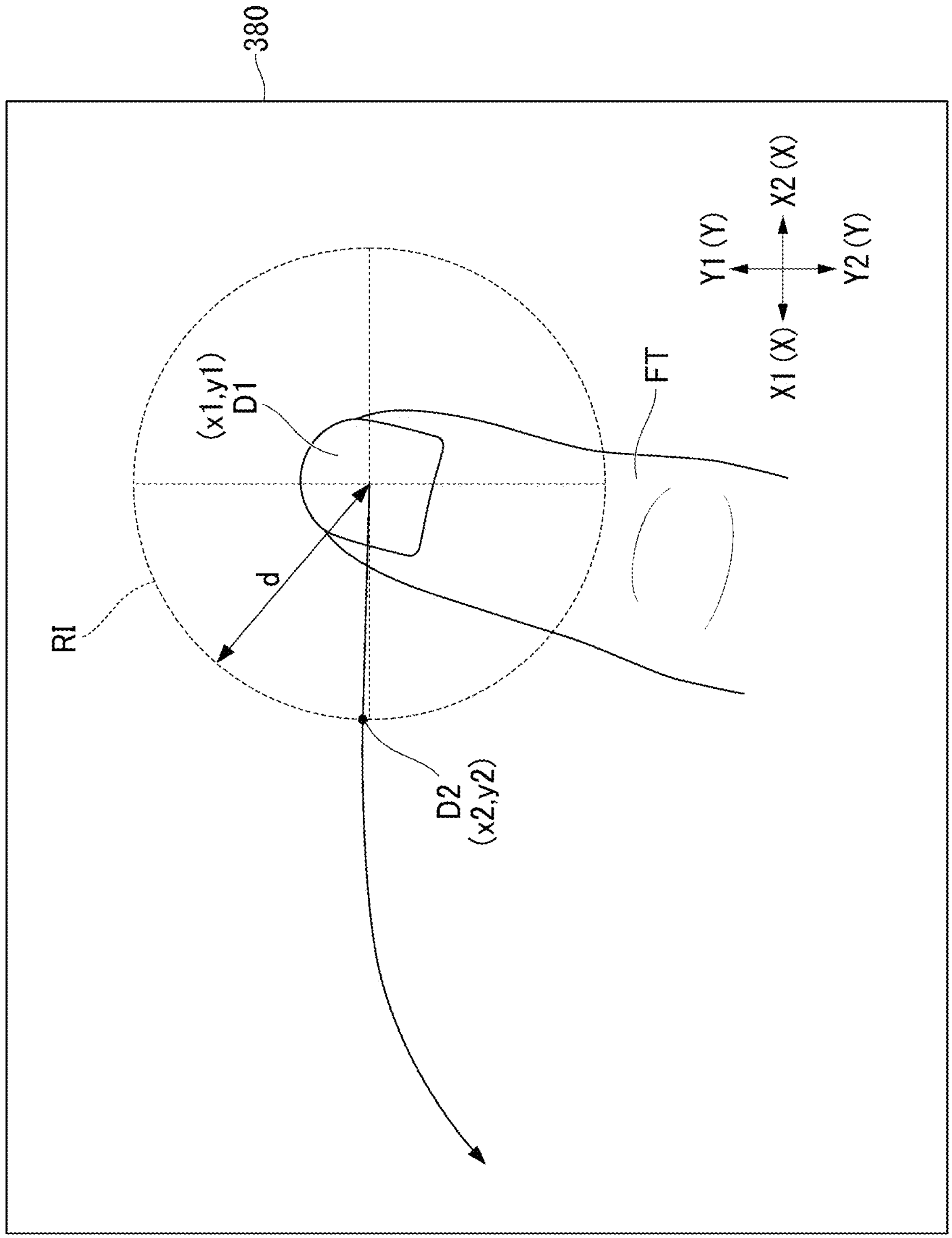
FIG. 82 illustrates an example of a view showing an input vector.

FIG. 82 is a view showing the input vector A.

The drive controller 260 determines the input vector A from a difference between a first position D1 and a second position D2. The first position D1 is the position of the thumb finger FT on the touchpad 380 when the manipulation input is started in one manipulation input. The second position D2 is the position of the thumb finger FT on the touchpad 380 immediately after the manipulation input is started (immediately after the start of movement) in one manipulation input. At the time of the first position D1 (*x*1, y1) and the second position D2 (*x*2, y2), the input vector A (dx, dy) is (x2-x1, y2-y1).

The second position D2 is, for example, the position of the thumb finger FT on the touchpad 380 immediately after the start of movement and is a position that is a predetermined distance d from the first position D1. The predetermined distance d is, for example, 1 mm to 10 mm. The predetermined distance d may be 5 mm to 10 mm, which corresponds to 50% to 100% of the width of the thumb finger FT. The predetermined distance d may be a length corresponding to 15% to 25% of the width (40 mm to 60 mm) of the touchpad 380.

The second position D2 is, for example, a position of the thumb finger FT on the touchpad 380 immediately after the start of movement, and is a position of the thumb finger FT when a predetermined time t has elapsed. The predetermined time t is, for example, 0.5 seconds to 1 second.

A range from the first position D1 as a starting point to the second position D2 or a range in which the thumb finger FT is located when a predetermined time t has elapsed with the first position D1 as the starting point is an "input start range RI." The input vector A is determined from the movement of the thumb finger FT in the input start range RI.

When the drive controller 260 determines the input direction DI in step S650, step S660 is subsequently executed.

<Step S660: Determination of Amount of Bending Drive>

The drive controller 260 determines an amount of bending drive in step S660. The drive controller 260 determines the amount of bending drive in a vector method or a touch method.

<<Vector Method>

Figure 83:
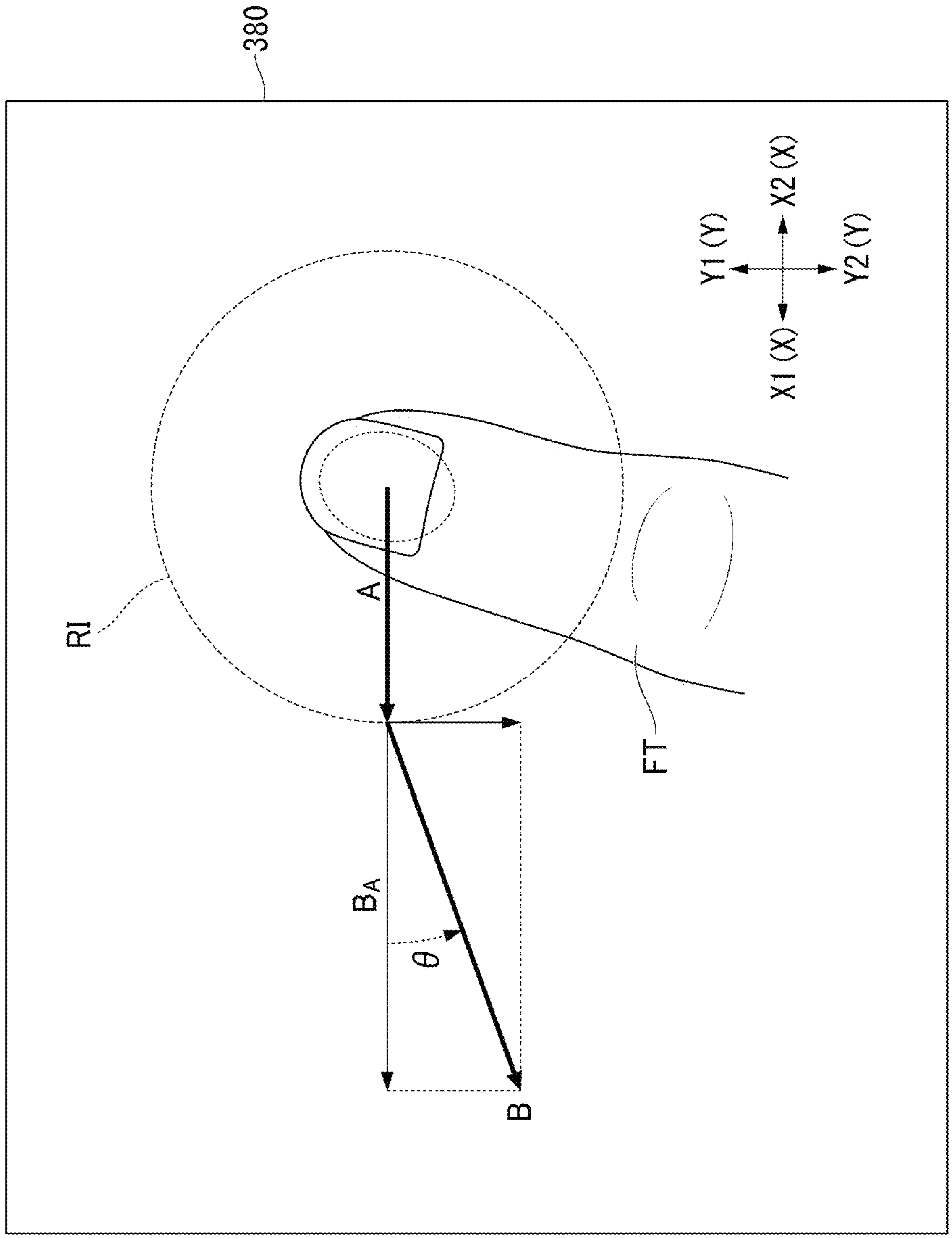
FIG. 83 illustrates an example of an explanatory view of the determination of an amount of bending drive based on a vector method.

FIG. 83 is a view showing the determination of the amount of bending drive in the vector method.

In the vector method, the drive controller 260 determines an input vector B on the basis of movement of the thumb finger FT along the touchpad 380 outside the input start range RI. The drive controller 260 determines the input vector B in a method similar to a method of determining the input vector A. The drive controller 260 calculates an amount of bending drive V according to Eq. (2) and Eq. (3). In Eq. (2), $e_A$ denotes a unit vector of the input vector A. In Eq. (3), θ denotes an angle formed by the input vector A and the input vector B. In Eq. (3), sgn (α) is a sign function. If the input α is positive, +1 is output. If the input a is negative, −1 is output. If the input α is zero, zero is output.

$$B_A=B\cdot e_A \quad \text{Eq. (2)}$$

$$V=|B_A|\text{sgn}(\cos\theta) \quad \text{Eq. (3)}$$

The amount of bending drive V in the vector method corresponds to the amount of movement of the thumb finger FT when it is assumed that the thumb finger FT continues to move in the direction of the input vector A immediately after the manipulation input is started (immediately after the start of movement).

<<Touch Method>

In the touch method, the drive controller 260 increases the amount of bending drive V in proportion to a period during which the thumb finger FT is touching the touchpad 380.

When the drive controller 260 determines the amount of bending drive V in step S660, the drive controller 260 subsequently executes step S670.

<Step S670: Bending Portion Drive>

In step S670, the drive controller 260 drives the bending portion 112 on the basis of the determined input vector A and the determined amount of bending drive V. Specifically, the drive controller 260 drives the bending portion 112 by the amount of bending drive V with respect to a direction of the input vector A. That is, the drive controller 260 drives the bending portion 112 only in the direction of the input vector A immediately after the manipulation input is started (immediately after the start of movement). The drive controller 260 subsequently executes step S680.

<Step S680: Completion Determination>

The drive controller 260 determines whether or not one manipulation input has been completed in step S680. The drive controller 260 determines that one manipulation input has been completed when the thumb finger FT is released from the touchpad 380. Moreover, when the touchpad 380 detects a manipulation input in which pressing by the thumb finger FT is performed or a manipulation input in which some of the various buttons 350 are pressed, the drive controller 260 may determine that one manipulation input has been completed. When the drive controller 260 determines that one manipulation input has been completed, the drive controller 260 subsequently executes step S690. When the drive controller 260 determines that the one manipulation input has not been completed, the drive controller 260 executes steps from step S660 again.

When the input mode is the second input mode, the input vector A is not changed in steps S660 and S670 to be executed again. Therefore, when the input mode is the second input mode, the drive controller 260 continuously drives the bending portion 112 only in the direction of the input vector A immediately after the manipulation input is started (immediately after the start of movement). By selecting the second input mode as the input mode, the scopist S can easily input a manipulation of moving the distal end of the bending portion 112 straight, for example, when a submucosal layer is removed in endoscopic submucosal dissection (ESD).

<Step S690>

The drive controller 260 determines whether or not to continuously control the bending drive of the bending portion 112 in step S690. When the bending drive of the bending portion 112 is continuously controlled, the drive controller 260 subsequently executes step S610. When the bending drive of the bending portion 112 is not controlled, the drive controller 260 subsequently executes step S700 to end a control flow shown in FIG. 80.

[Limitation of Direction of Input Vector A]

Figure 84:
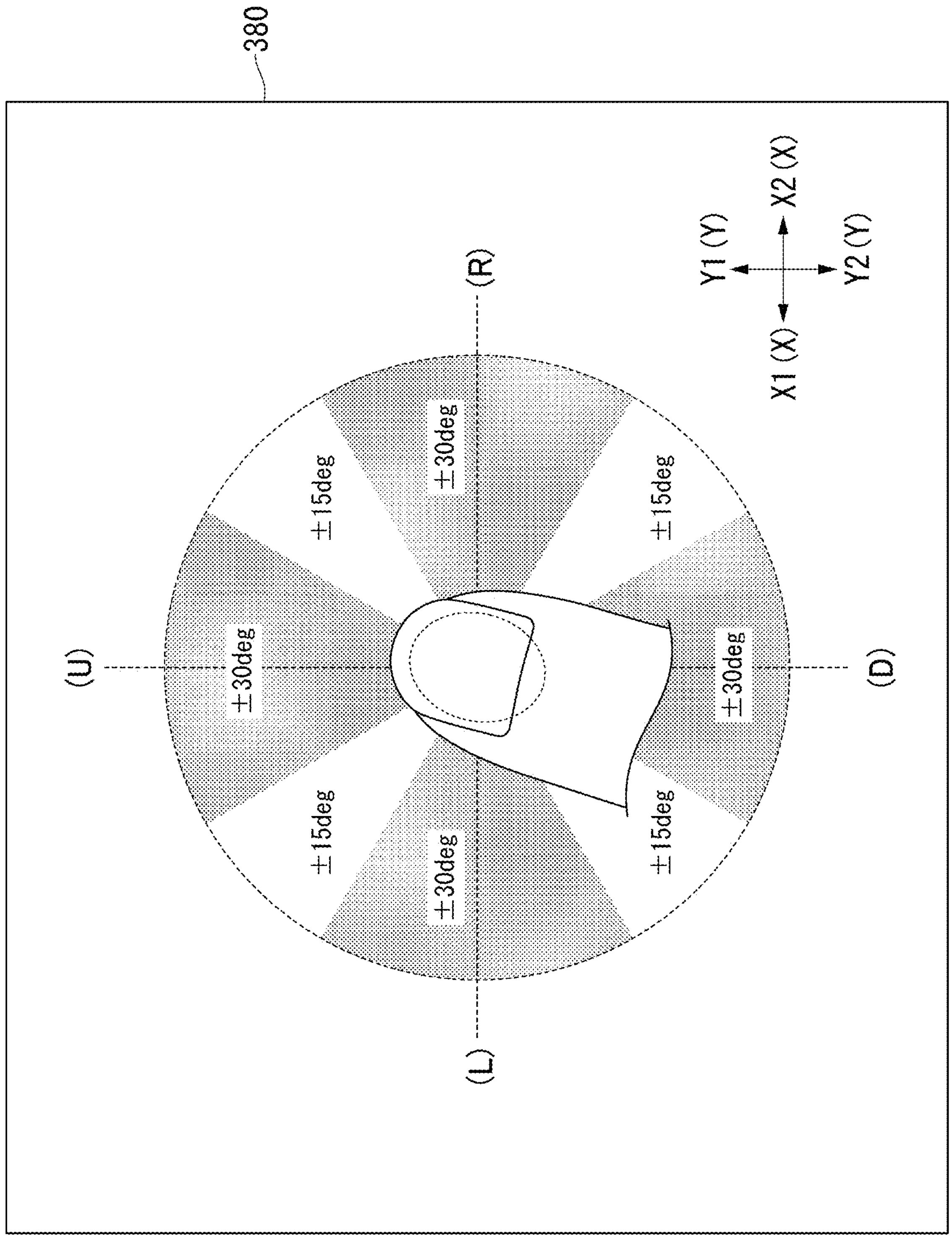
FIG. 84 illustrates an example of a view showing the limitation of a direction of the input vector.

FIG. 84 is a view showing the limitation of the direction of the input vector A.

By moving the thumb finger FT along the touchpad 380, the scopist S can intuitively input a manipulation of bending the bending portion 112 in any direction to the touchpad 380. On the other hand, it is difficult for the scopist S to input a manipulation of bending the bending portion 112 in any one of the U, D, L, and R directions to the touchpad 380. A manipulation portion of a conventional endoscope with an angle knob can easily input a manipulation of bending the bending portion only in any one of the U, D, L, and R directions. Therefore, desirably, a manipulation of bending the bending portion 112 only in any one of the U, D, L, and R directions can be easily input to the touchpad 380. Therefore, the drive controller 260 can limit the direction of the input vector A to several directions.

For example, as shown in FIG. 84, the drive controller 260 limits the direction of the input vector A to eight directions. For example, when the direction of the input vector A is Y1 direction±30 degrees, the drive controller 260 considers the direction of the input vector A as "Y1 direction±0 degrees." For example, when the direction of the input vector A is X1 direction±30 degrees, the drive controller 260 considers the direction of the input vector A as "X1 direction±0 degrees." In addition, the drive controller 260 may limit the direction of the input vector A to four directions or sixteen directions.

The Y1 direction of the touchpad is associated with the U direction of the bending portion 112. By increasing an angular range of the input vector A considered to be the Y1 direction of the touchpad, it is easy to input a manipulation in which the bending portion 112 is bent only in the U direction.

The Y2 direction of the touchpad is associated with the D direction of the bending portion 112. By increasing an angular range of the input vector A considered to be the Y2 direction of the touchpad, it is easy to input a manipulation in which the bending portion 112 is bent only in the D direction.

The X1 direction of the touchpad is associated with the L direction of the bending portion 112. By increasing the angular range of the input vector A considered to be the X1 direction of the touchpad, it is easy to input a manipulation of bending the bending portion 112 only in the L direction.

The X2 direction of the touchpad is associated with the R direction of the bending portion 112. By increasing an angular range of the input vector A considered to be the X2 direction of the touchpad, it is easy to input a manipulation of bending the bending portion 112 only in the R direction.

For example, as shown in FIG. 84, the angular range (30 degrees) of the input vector A considered in the Y1 direction, the Y2 direction, the X1 direction, and the X2 direction of the touchpad is larger than the angular range (15 degrees) of the input vector considered in the other direction. In this case, the scopist S can more easily input a manipulation of bending the bending portion 112 only in any one of the U, D, L, and R directions to the touchpad 380.

[Bending Limit Display]

Figure 85:
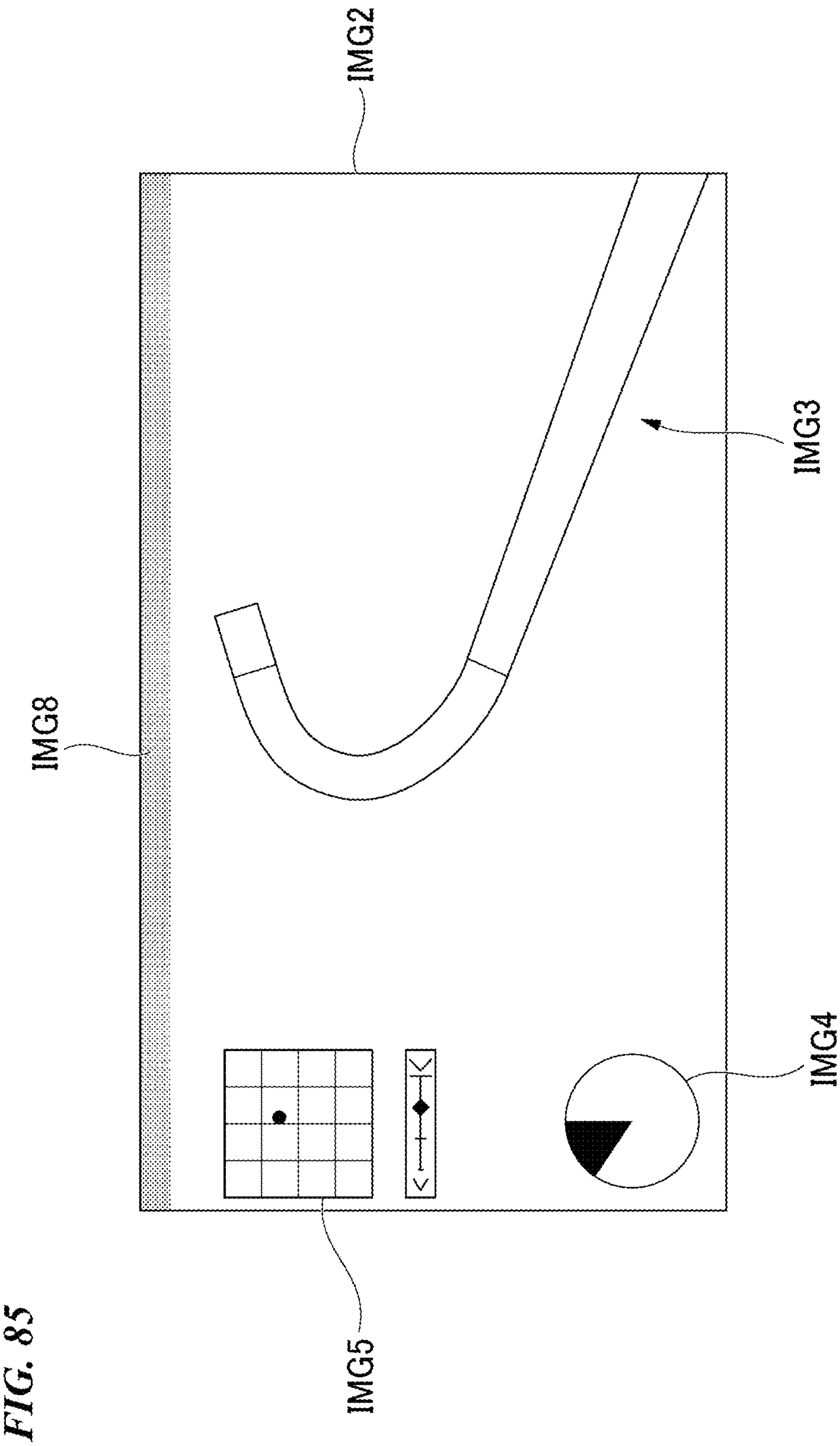
FIG. 85 illustrates an example of a view showing a guide image including bending limit display.

FIG. 85 is a view showing a guide image IMG2 including a bending limit display IMG8.

The guide image IMG2 may include bending limit display IMG8. The bending limit display IMG8 is display for notifying that the bending portion 112 is maximally bent. The main controller 560 generates the bending limit display IMG8 on the basis of the drive state of the bending wire 160 acquired from the drive controller 260.

The bending limit display IMG8 is display in which a noticeable color (for example, a fluorescent color) is colored in strip-like areas of the upper, lower, left, and right ends of the guide image IMG2 and indicates that the bending portion 112 is maximally bent in at least one of the U, D, L, and R directions.

When the bending portion 112 is maximally bent in the U direction, the bending limit display IMG8 is displayed in the strip-like area at the upper end of the guide image IMG2 as shown in FIG. 85.

When the bending portion 112 is maximally bent in the D direction, the bending limit display IMG8 is displayed in the strip-like area at the lower end of the guide image IMG2.

When the bending portion 112 is maximally bent in the L direction, the bending limit display IMG8 is displayed in the strip-like area at the left end of the guide image IMG2.

When the bending portion 112 is maximally bent in the R direction, the bending limit display IMG8 is displayed in the strip-like area at the right end of the guide image IMG2.

The scopist S can easily ascertain that the bending portion 112 is maximally bent in at least one of the U, D, L, and R directions by viewing the bending limit display IMG8. The main controller 560 may display the bending limit display IMG8 even when the bending portion 112 approaches a maximally bent state.

[Manipulation Guide]

Figure 86:
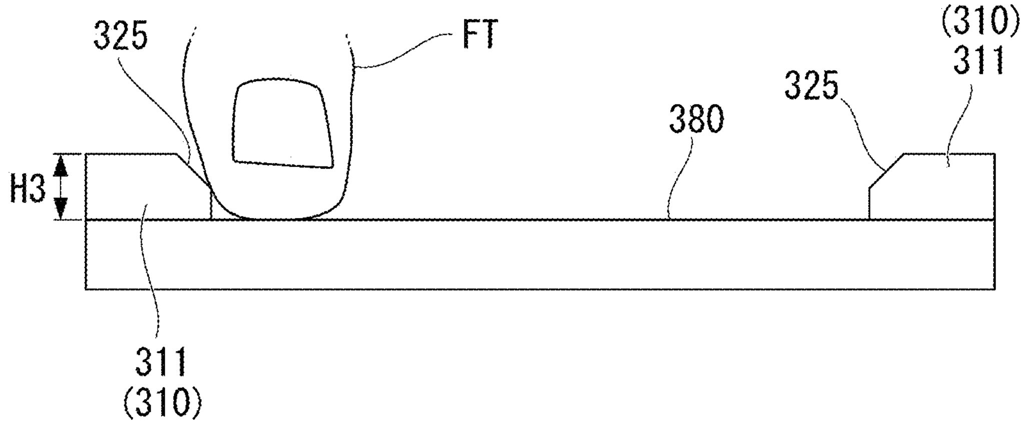
FIG. 86 illustrates an example of a view showing a manipulation guide of a manipulation portion body of the manipulation device.

FIG. 86 is a view showing a manipulation guide 325 of the manipulation portion body 310.

The manipulation portion body 310 of the manipulation device 300 may have the manipulation guide 325 in a frame 311 surrounding the touchpad 380. The manipulation guide 325 is formed in a shape in which the scopist S can feel a height difference from the touchpad 380 with a sense of touch. A height H3 of the manipulation guide 325 from the touchpad 380 is, for example, 0.5 mm to 2 mm.

Figure 87:
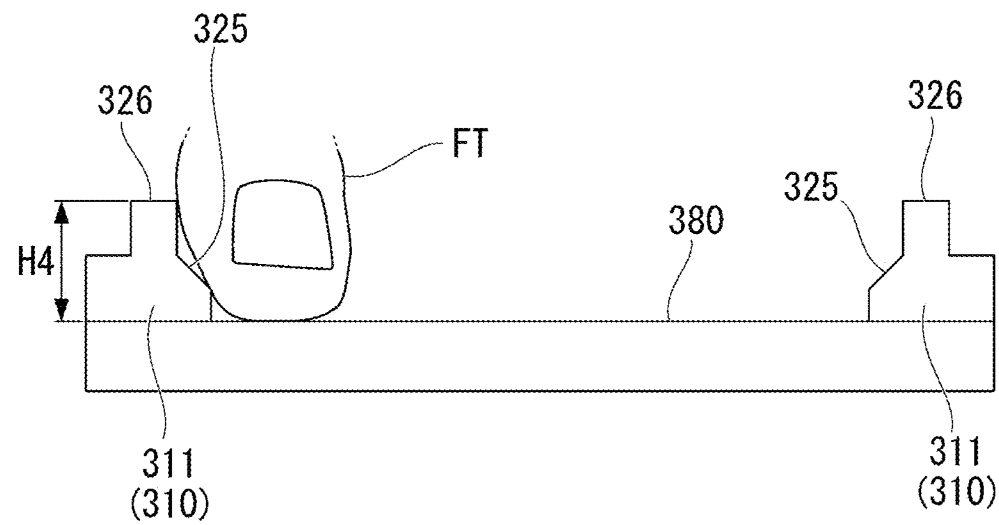
FIG. 87 illustrates an example of a view showing another aspect of the manipulation guide.

FIG. 87 is a view showing another aspect of the manipulation guide 325.

The manipulation guide 325 may further include a convex portion 326. The convex portion 326 is a convex portion protruding from the manipulation guide 325 in a direction away from the touchpad 380. A height H4 of the manipulation guide 325 including the convex portion 326 is, for example, 2 mm to 4 mm.

Even if the input mode is the first mode, the scopist S can easily input a straight manipulation to the touchpad 380 by placing the touchpad 380 along the manipulation guide 325 and the convex portion 326 with the thumb finger FT as a guide. Moreover, the scopist S can rest the thumb finger FT by causing the thumb finger FT to be in contact with the convex portion 326 and releasing the finger FT from the touchpad 380. In addition, in FIGS. 86 and 87, the illustration of the gloves worn by the scopist S is omitted.

Figure 88:
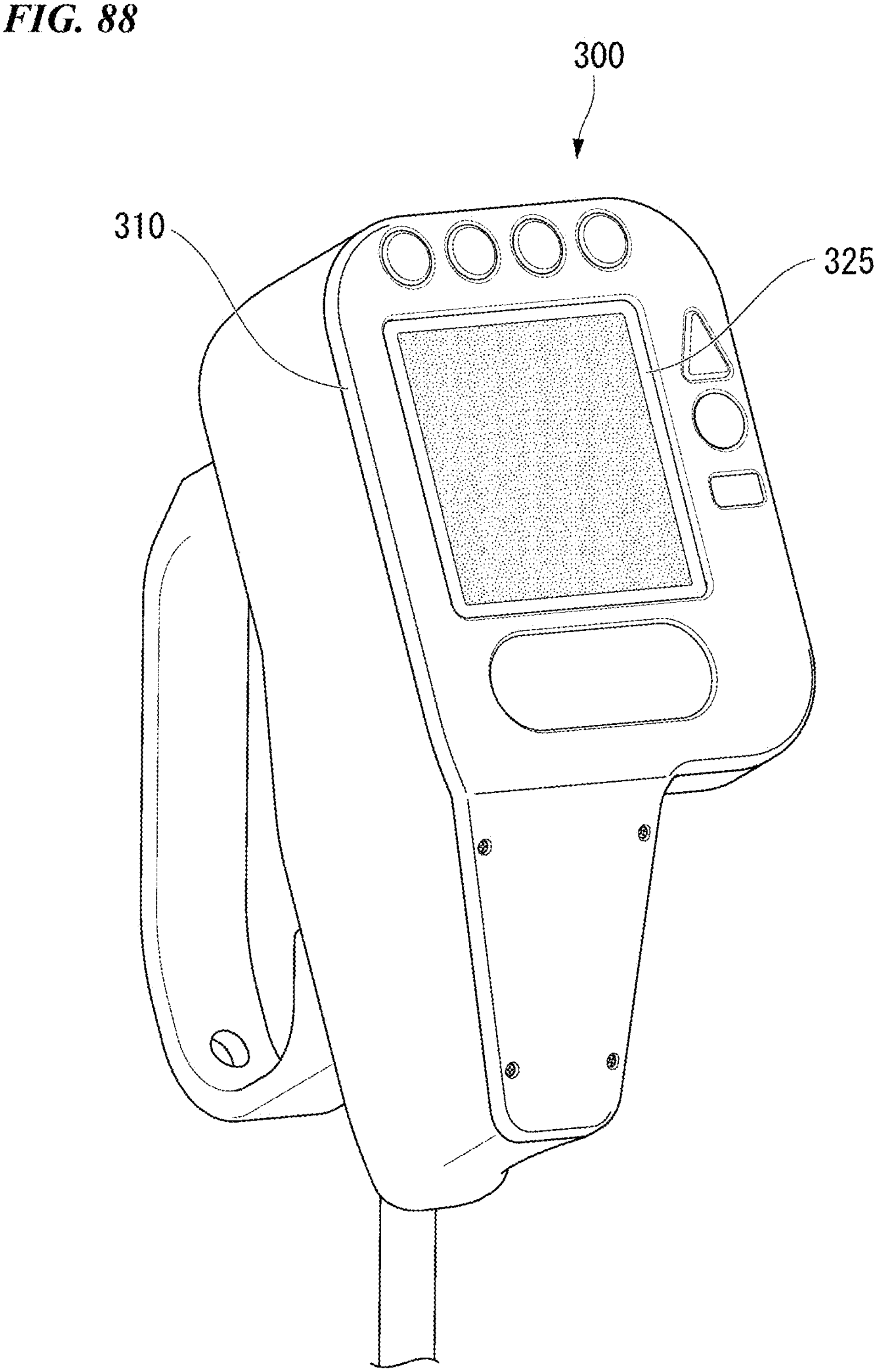
FIG. 88 illustrates an example of a view showing another aspect of the manipulation guide.

FIG. 88 is a view showing another aspect of the manipulation guide 325.

The manipulation guide 325 may be a portion provided at the end of the touchpad 380. The manipulation guide 325 shown in FIG. 88 is a portion different from other portions of the touchpad 380 in terms of tactile sensations such as material and surface roughness.

Figure 89:
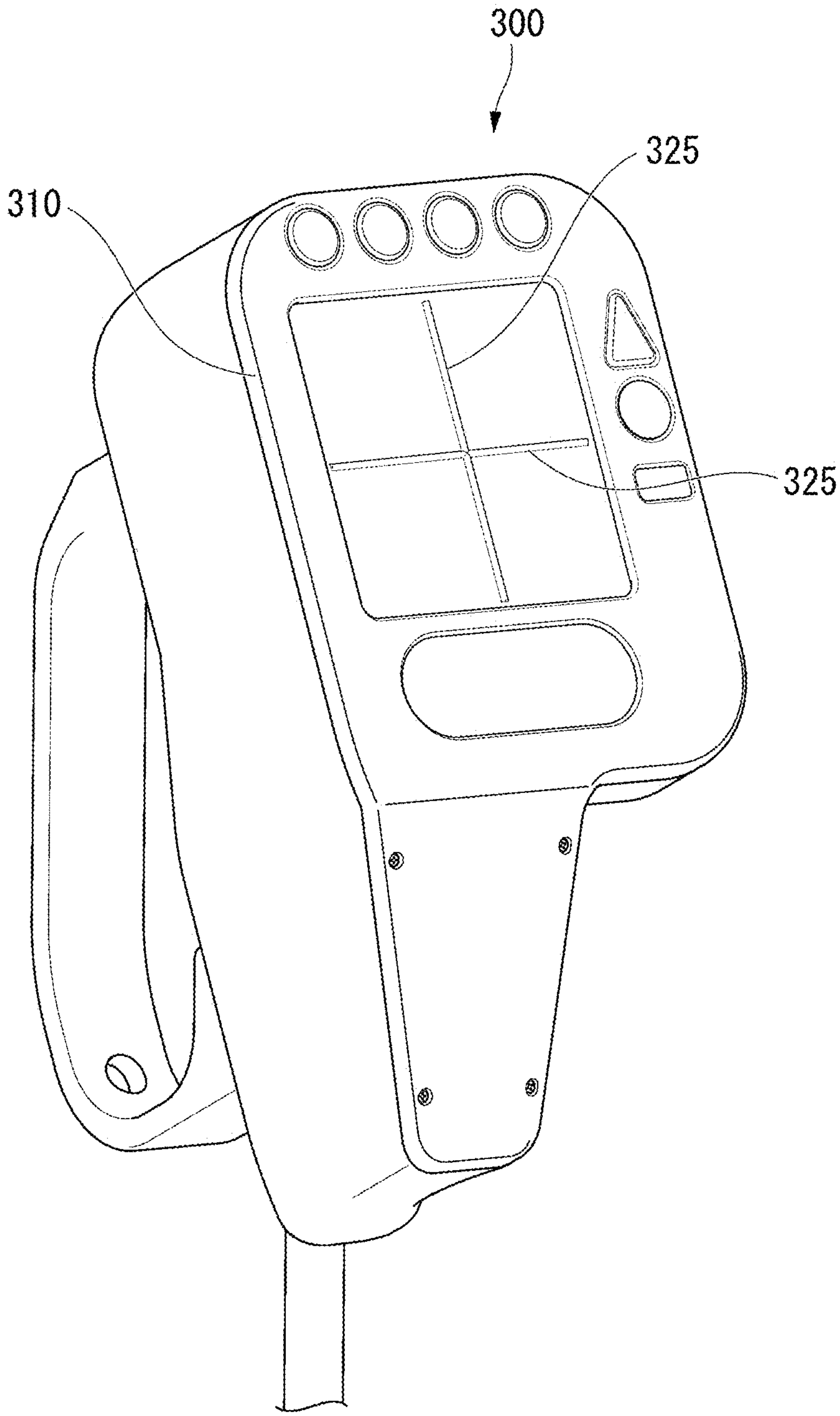
FIG. 89 illustrates an example of a view showing another aspect of the manipulation guide.

FIG. 89 is a view showing another aspect of the manipulation guide 325.

The manipulation guide 325 may be a convex portion provided on the touchpad 380 through embossing or the like. In this case, the manipulation guide 325 may be provided on a central portion of the touchpad 380 instead of the end of the touchpad 380.

The electric endoscope system 1000I according to the present embodiment can more efficiently perform observation and treatment using the endoscope 100. By using the first input mode and the second input mode separately, the scopist S can easily input the manipulation with the touchpad 380. Moreover, the scopist S can more appropriately manipulate the bending portion 112 or the like by observing the guide image IMG2.

Although the ninth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

In the above embodiment, the finger that manipulates the touchpad 380 may be a finger other than the thumb finger FT.

Tenth Embodiment

An electric endoscope system 1000J according to a tenth embodiment of the present disclosure will be described with reference to FIGS. 90 to 94. In the following description, constituent elements identical to those described above are denoted by the same reference signs and redundant description thereof will be omitted.

[Electric Endoscope System 1000J]

Figure 90:
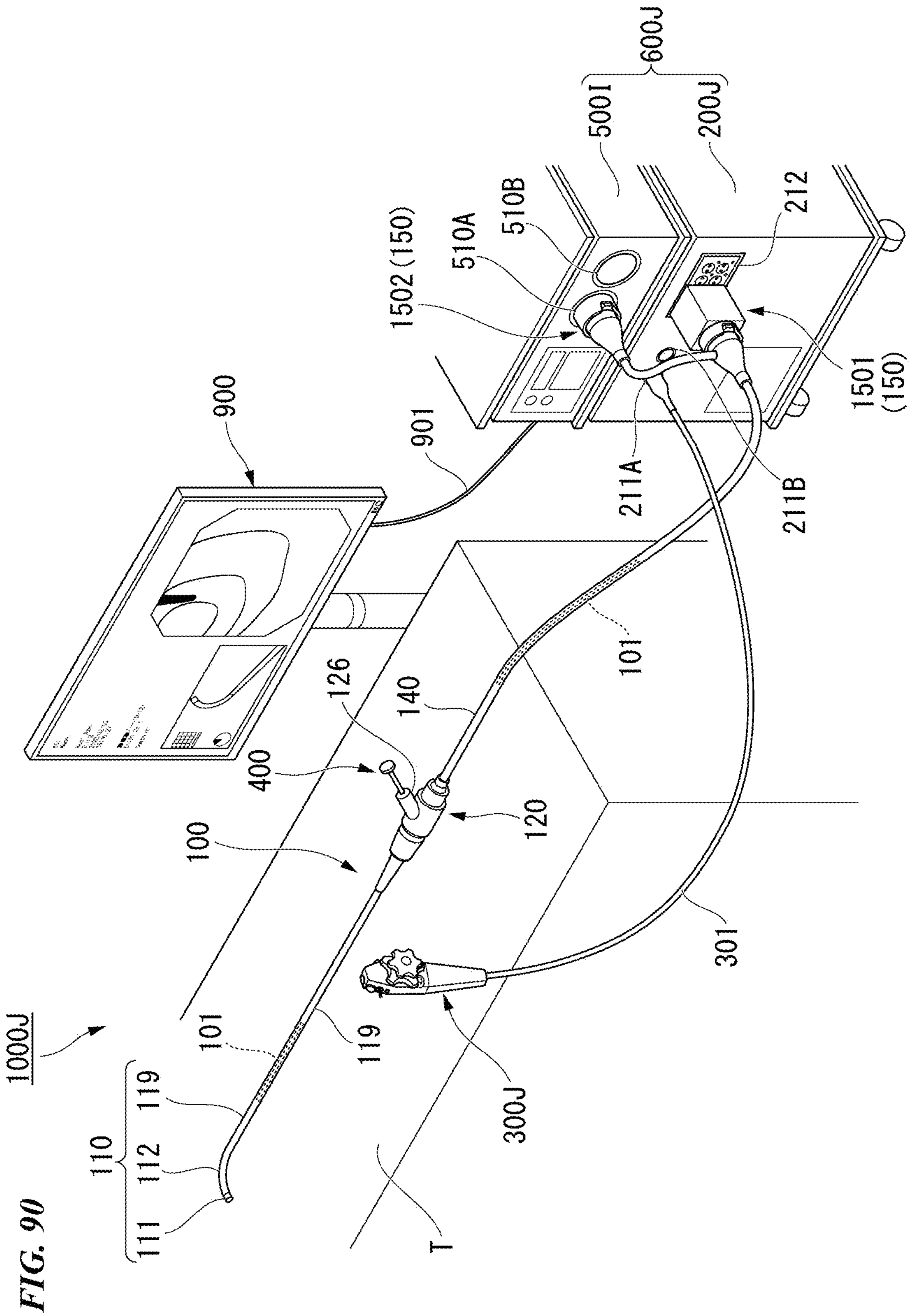
FIG. 90 illustrates an example of an overall view of an electric endoscope system according to a tenth embodiment.
Figure 91:
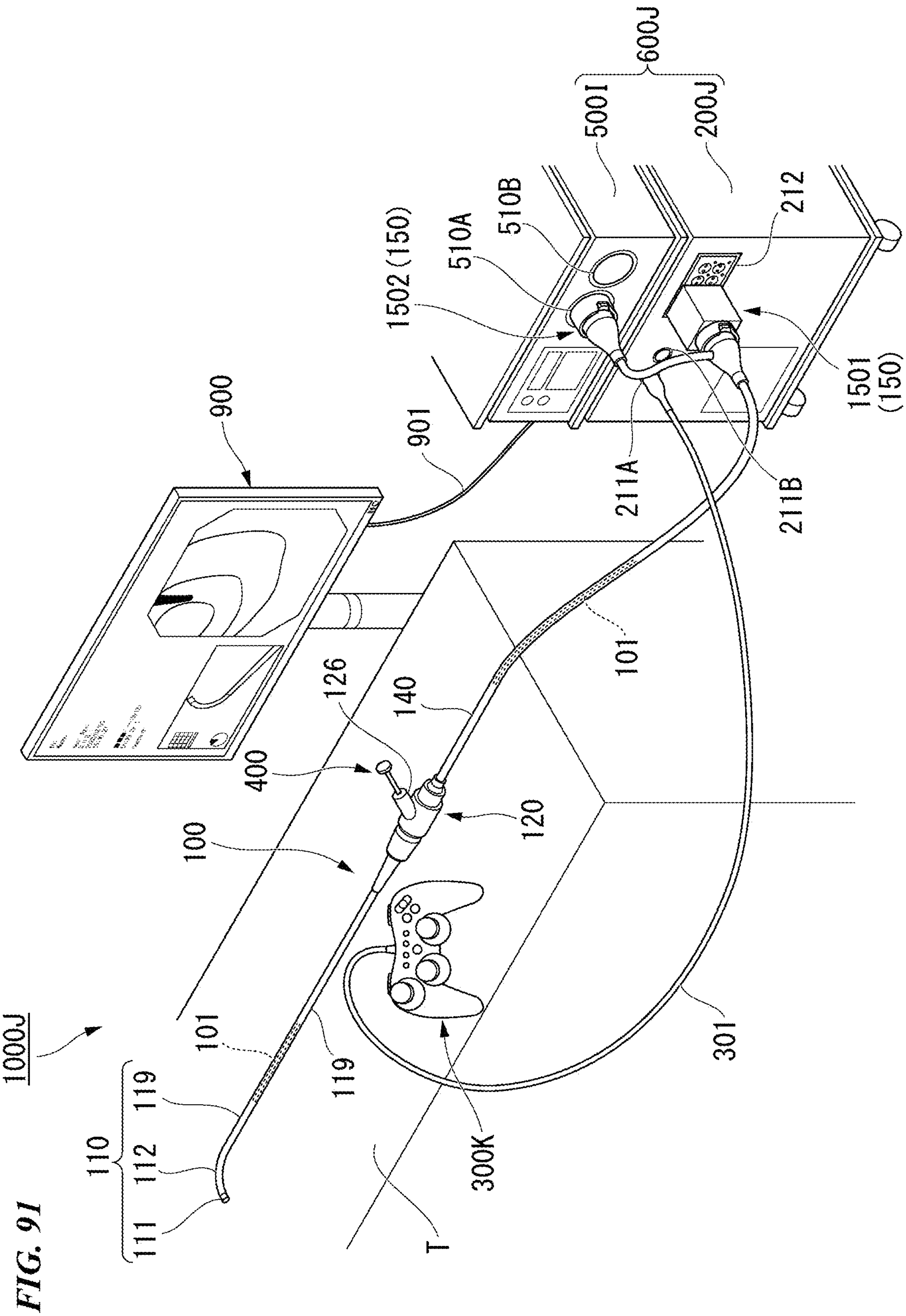
FIG. 91 illustrates an example of an overall view of another aspect of the electric endoscope system.

FIGS. 90 and 91 are overall views of the electric endoscope system 1000J according to the present embodiment. The electric endoscope system 1000J includes an endoscope 100, a drive device 200J, a manipulation device 300, a manipulation device 300J, or a manipulation device 300K, a treatment tool 400, a video control device 500I, and a display device 900. The drive device 200J and the video control device 500I constitute a control device 600J that controls the electric endoscope system 1000J.

The electric endoscope system 1000J is a system in which different types of manipulation devices such as the manipulation device 300J and the manipulation device 300K can be connected instead of the manipulation device 300. The manipulation device 300J is a manipulation device including an angle knob instead of the touchpad 380. The manipulation device 300K is a gamepad type manipulation device.

The drive device 200J is the same as the drive device 200 of the first embodiment, except that the drive device 200J has a function of connecting to an unregistered type of manipulation device that is not registered in the drive device 200J.

The manipulation device 300, the manipulation device 300J, and the manipulation device 300K have a non-volatile memory that stores manipulation device information. The manipulation device information is at least one of a manipulation device ID, manipulation parameters of the manipulation device, manipulation information of the manipulation device, and software for the manipulation device.

The manipulation device ID, for example, includes a plurality of alphanumeric characters and a model number indicating a type of the manipulation device 300 or the like is stored.

The manipulation parameters of the manipulation device are parameters necessary when the drive device 200J manipulates the endoscope 100 including the bending portion 112 on the basis of a manipulation input received from the manipulation device 300 or the like. The manipulation parameters are a part of the software for the manipulation device.

The manipulation information of the manipulation device is information for defining a display aspect of the manipulation information image IMG5 of the guide image IMG2 generated by the video control device 500I on the basis of a manipulation input received from the manipulation device 300 or the like.

The software for the manipulation device is software necessary for the drive device 200J to communicate with the manipulation device 300 and the like and receive manipulation inputs from the manipulation device 300 and the like. The software for the manipulation device is a part of a program that controls the drive controller 260.

[Operation of Electric Endoscope System 1000J]

Next, an operation of the electric endoscope system 1000J of the present embodiment will be described. Hereinafter, description will be given in accordance with the control flowchart of the drive controller 260 of the control device 600J shown in FIG. 92. When the manipulation device 300 is connected to the drive device 200J, the drive controller 260 starts the control flow shown in FIG. 92 (step S800). Subsequently, the drive controller 260 (mainly, the processor 261) executes step S810.

<Step S810>

In step S810, the drive controller 260 acquires manipulation device information from the connected manipulation device 300. The drive controller 260 subsequently executes step S820.

<Step S820>

In step S820, the drive controller 260 determines whether or not an update of a program or the like that controls the drive controller 260 is necessary from the acquired manipulation device information. For example, when a manipulation device ID of the acquired manipulation device information is not registered, the drive controller 260 determines that the update of the program or the like that controls the drive controller 260 is necessary. Even if the manipulation device ID of the acquired manipulation device information is registered or the manipulation device ID is not included in the manipulation device information, the drive controller 260 determines that the update of the program or the like that controls the drive controller 260 is necessary when the manipulation device information includes new information to be updated (manipulation parameters, manipulation information, and software for the manipulation device). When the update is necessary, the drive controller 260 subsequently executes step S830. When the update is not necessary, the drive controller 260 subsequently executes step S840.

<Step S830>

In step S830, when the manipulation device information includes software for the new manipulation device 300 to be updated, the drive controller 260 updates the program for controlling the drive controller 260 using the software for the manipulation device 300.

When the manipulation device information includes a new manipulation parameter to be updated, the drive controller 260 updates the program that controls the drive controller 260 using the manipulation parameter. For example, when a size of the touchpad 380 of the manipulation device 300 is changed, an amount of bending drive of the bending portion 112 for the manipulation input to the touchpad 380 is included as a new manipulation parameter in the manipulation device information. In this case, the drive controller 260 can correctly receive the manipulation input from the manipulation device 300 by updating some of the manipulation parameters using the new manipulation parameters without updating the software for the manipulation device 300.

Figure 93:
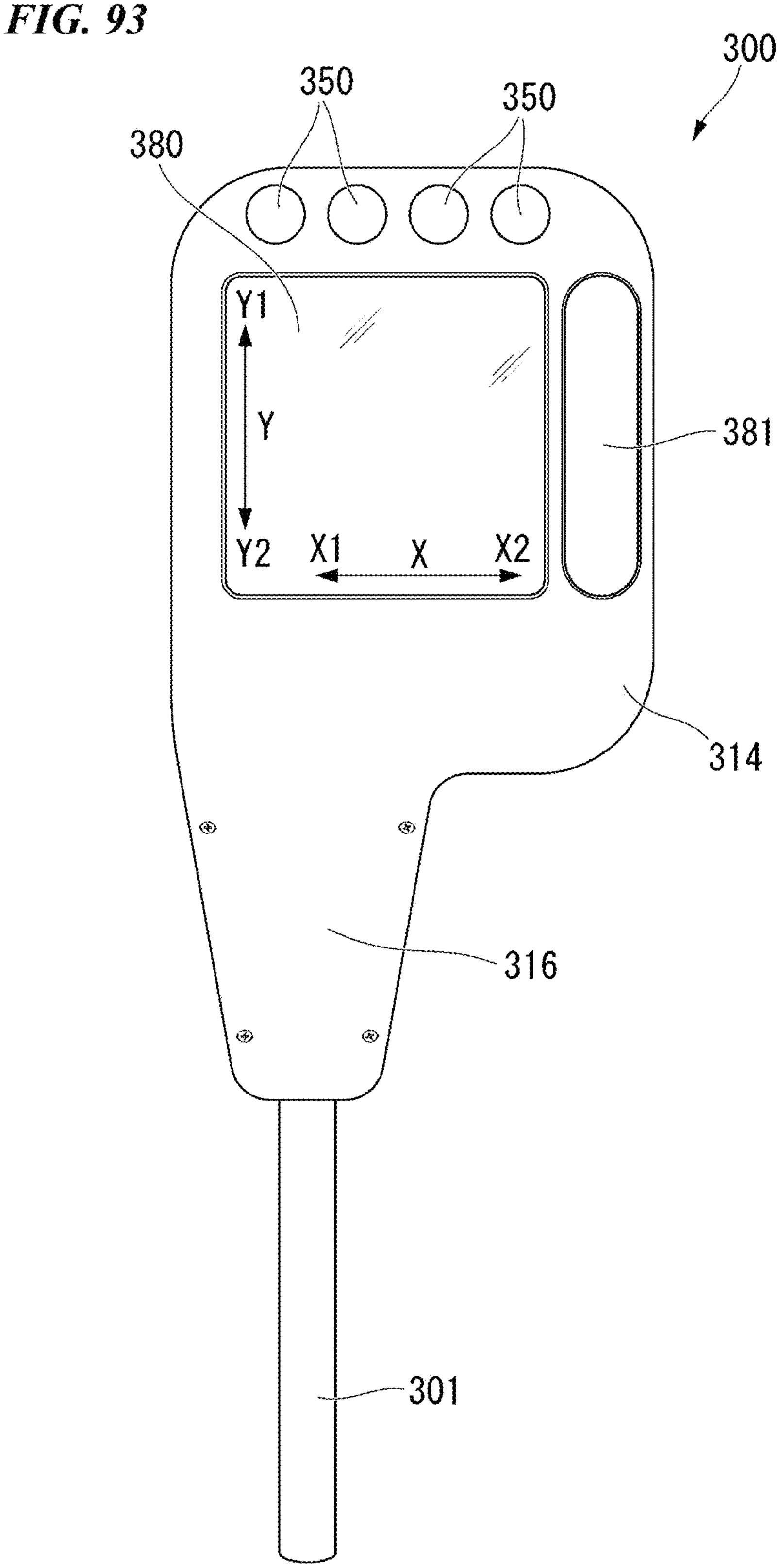
FIG. 93 illustrates an example of an explanatory view of an update of a manipulation information image using manipulation information.
Figure 94:
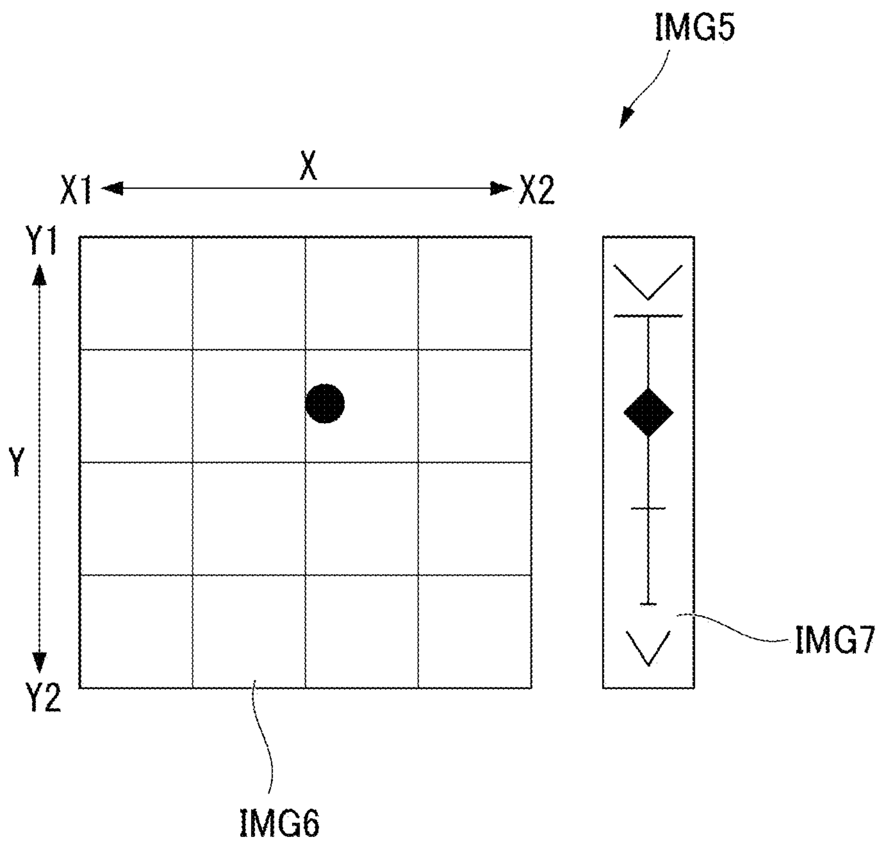
FIG. 94 illustrates an example of an explanatory view of an update of a manipulation information image using manipulation information.

FIGS. 93 and 94 are views showing an update of the manipulation information image IMG5 using the manipulation information. When the manipulation device information includes new manipulation information to be updated, the drive controller 260 causes the main controller 560 to update a display aspect of the manipulation information image IMG5 using the manipulation information. For example, as shown in FIG. 93, when the arrangement of the touch sensor 381 of the manipulation device 300 is changed to the right side of the touchpad 380, the arrangement information of the touch sensor 381 is included as new manipulation information in the manipulation device information. In this case, as shown in FIG. 94, the main controller 560 updates a display aspect of the manipulation information image IMG5 generated using the new manipulation information.

<Step S840>

Figure 92:
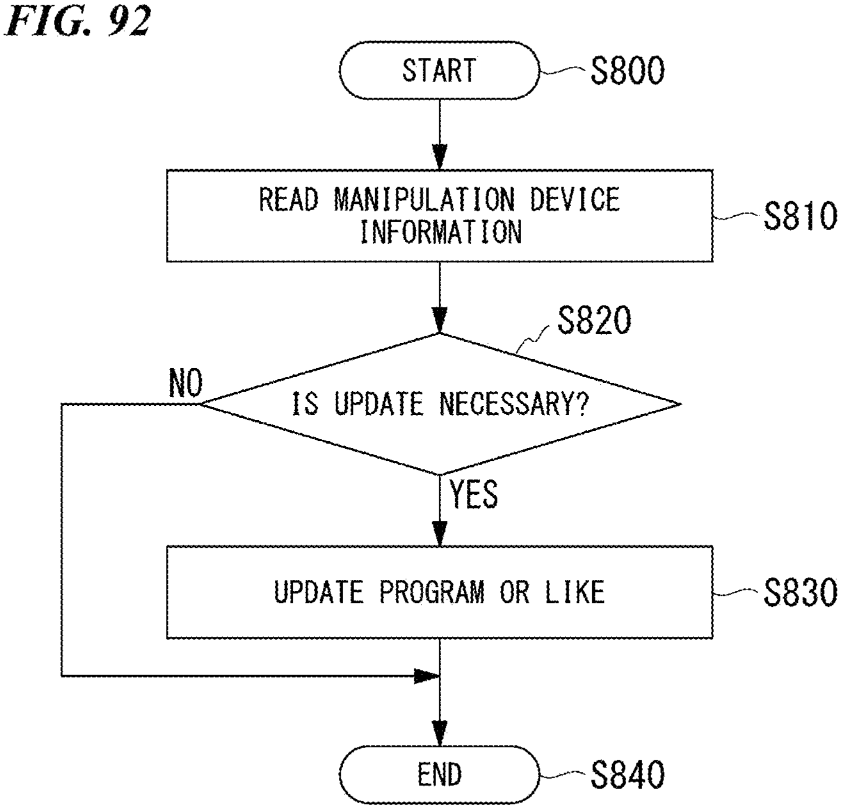
FIG. 92 illustrates an example of a control flowchart of a drive controller of a control device of the electric endoscope system.

The drive controller 260 ends a control flow shown in FIG. 92 in step S840. The drive controller 260 can receive a manipulation input from the manipulation device 300. Even when the manipulation device 300J and the manipulation device 300K are connected to the drive device 200J, the drive controller 260 can receive manipulation inputs from the manipulation device 300J and the manipulation device 300K by executing the control flow shown in FIG. 92.

The electric endoscope system 1000J according to the present embodiment can more efficiently perform observation and treatment using the endoscope 100. The scopist S can use a new manipulation device that is not registered by connecting it to the drive device 200J.

Although the tenth embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

Eleventh Embodiment

An electric endoscope system 1000L according to an eleventh embodiment of the present disclosure will be described with reference to FIGS. 95 to 99. In the following description, constituent elements identical to those described above are denoted by the same reference signs and redundant description thereof will be omitted.

The electric endoscope system 1000L includes an endoscope 100L, a drive device 200, a manipulation device 300L, a treatment tool 400, a video control device 500, and a display device 900.

Figure 95:
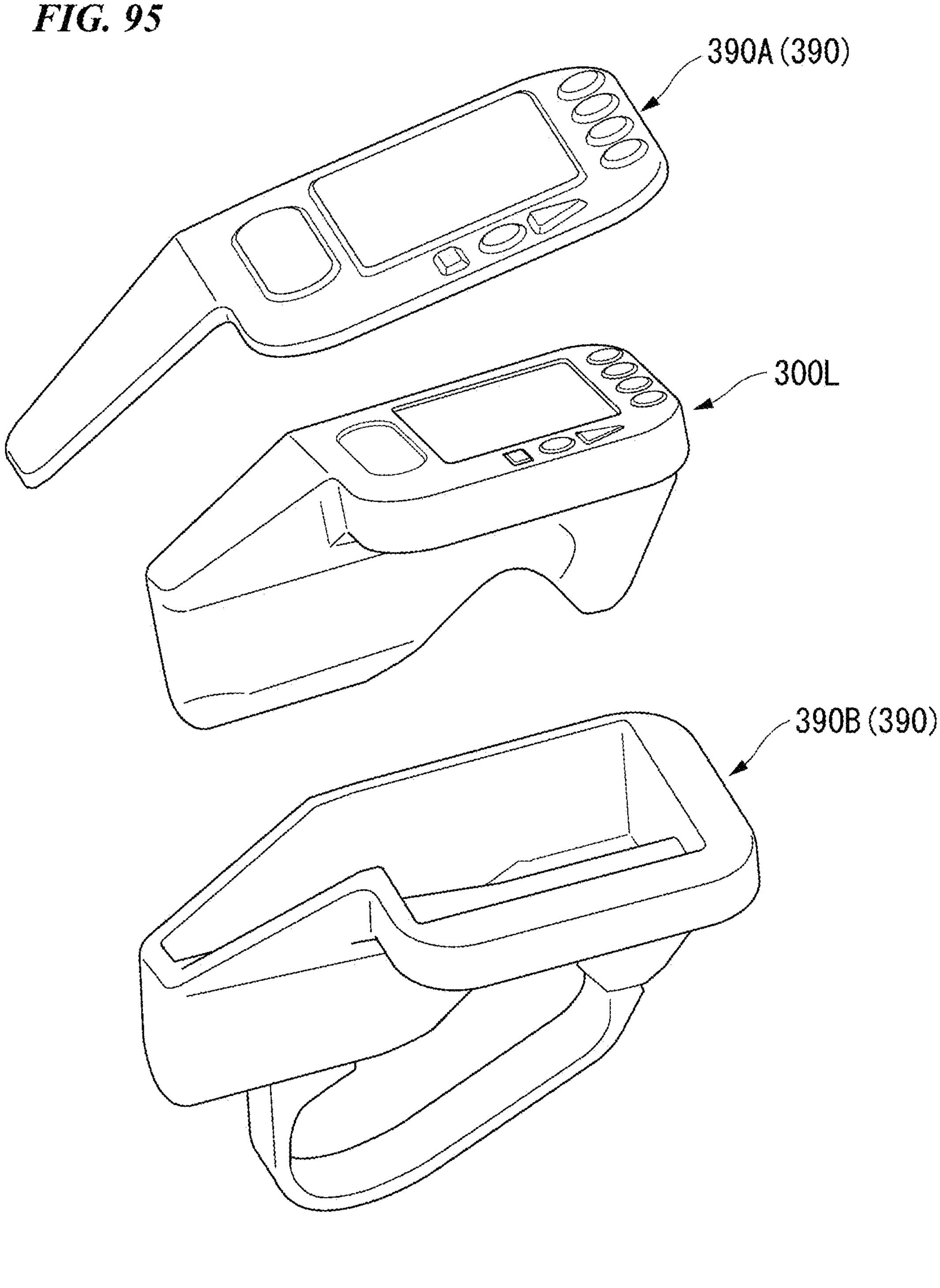
FIG. 95 illustrates an example of a view showing a manipulation device of an electric endoscope system according to an eleventh embodiment.

FIG. 95 is a view showing the manipulation device 300L.

The manipulation device 300L is obtained by removing a manipulation cable 301 from the manipulation device 300 of the first embodiment and communicates with the drive device 200 through wireless communication. A cover 390 can be attached to the manipulation device 300L. The cover 390 includes a top surface cover 390A formed of rubber or the like and a rigid back cover 390B. By sandwiching the manipulation device 300L between the top cover 390A and the back cover 390B, the entire manipulation device 300L can be covered. A scopist S can manipulate a touchpad 380 and the various buttons 350 by pressing the top cover 390A. It is only necessary for the scopist S or an assistant to mainly reprocess or discard the cover 390 after surgery, and the trouble of reprocessing the manipulation device 300L can be reduced.

The endoscope 100L includes an insertion portion 110L, a connection portion 120, an extracorporeal flexible portion 140L, a detachable portion 150L, a bending wire 160, and a built-in object 170.

Figure 96:
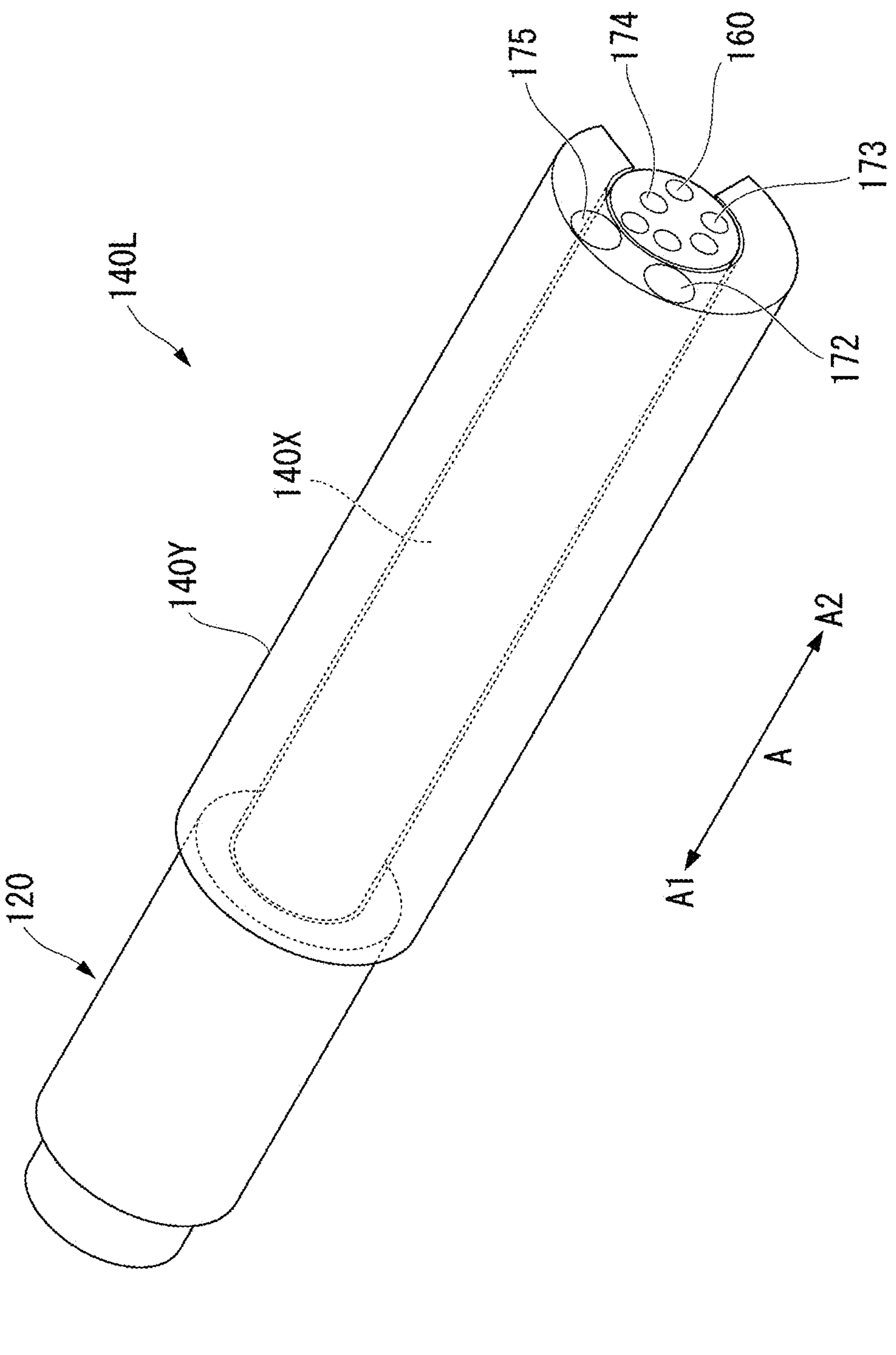
FIG. 96 illustrates an example of a view showing an extracorporeal flexible portion of the electric endoscope system.

FIG. 96 is a view showing the extracorporeal flexible portion 140L.

The extracorporeal flexible portion 140L has a double structure and includes an inner extracorporeal flexible portion 140X and an outer extracorporeal flexible portion 140Y. The outer extracorporeal flexible portion 140Y is detachably attached to the outer circumference of the inner extracorporeal flexible portion 140X.

A bending wire 160, an imaging cable 173, and a light guide 174 are inserted into the inner extracorporeal flexible portion 140X.

Figure 97:
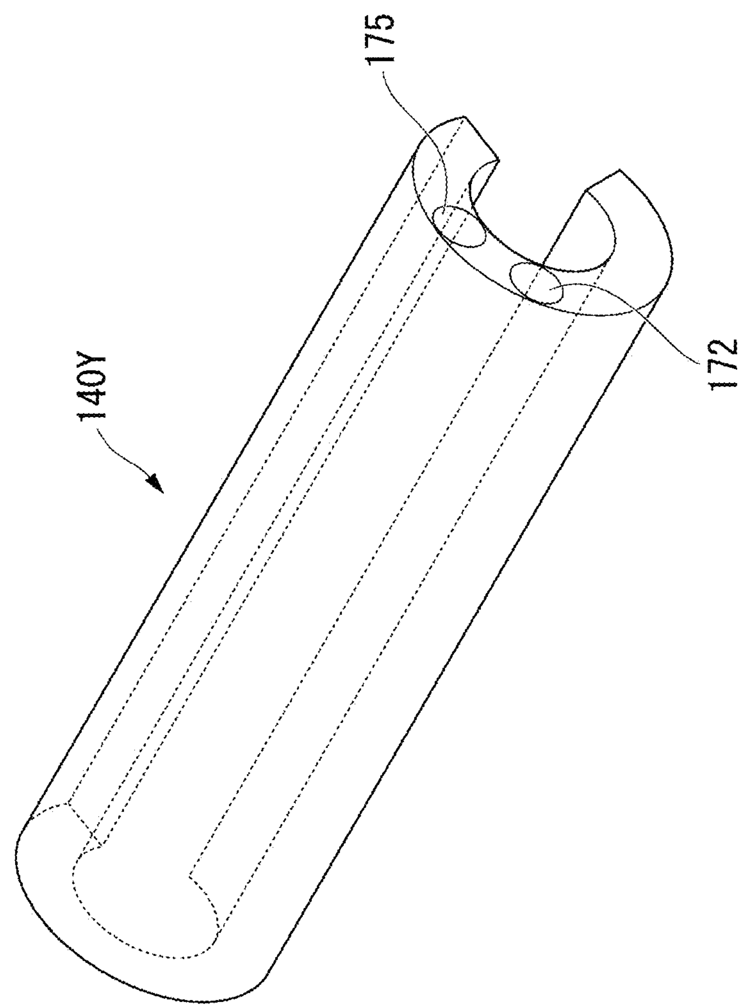
FIG. 97 illustrates an example of a view showing an outer extracorporeal flexible portion that has been removed.

FIG. 97 is a view showing the outer extracorporeal flexible portion 140Y that has been removed.

A suction tube 172 and an air/water supply tube 175 are inserted into the outer extracorporeal flexible portion 140Y. It is only necessary for the scopist S or the assistant to mainly reprocess or discard the outer extracorporeal flexible portion 140Y after surgery, and the trouble of reprocessing the extracorporeal flexible portion 140L can be reduced.

Figure 98:
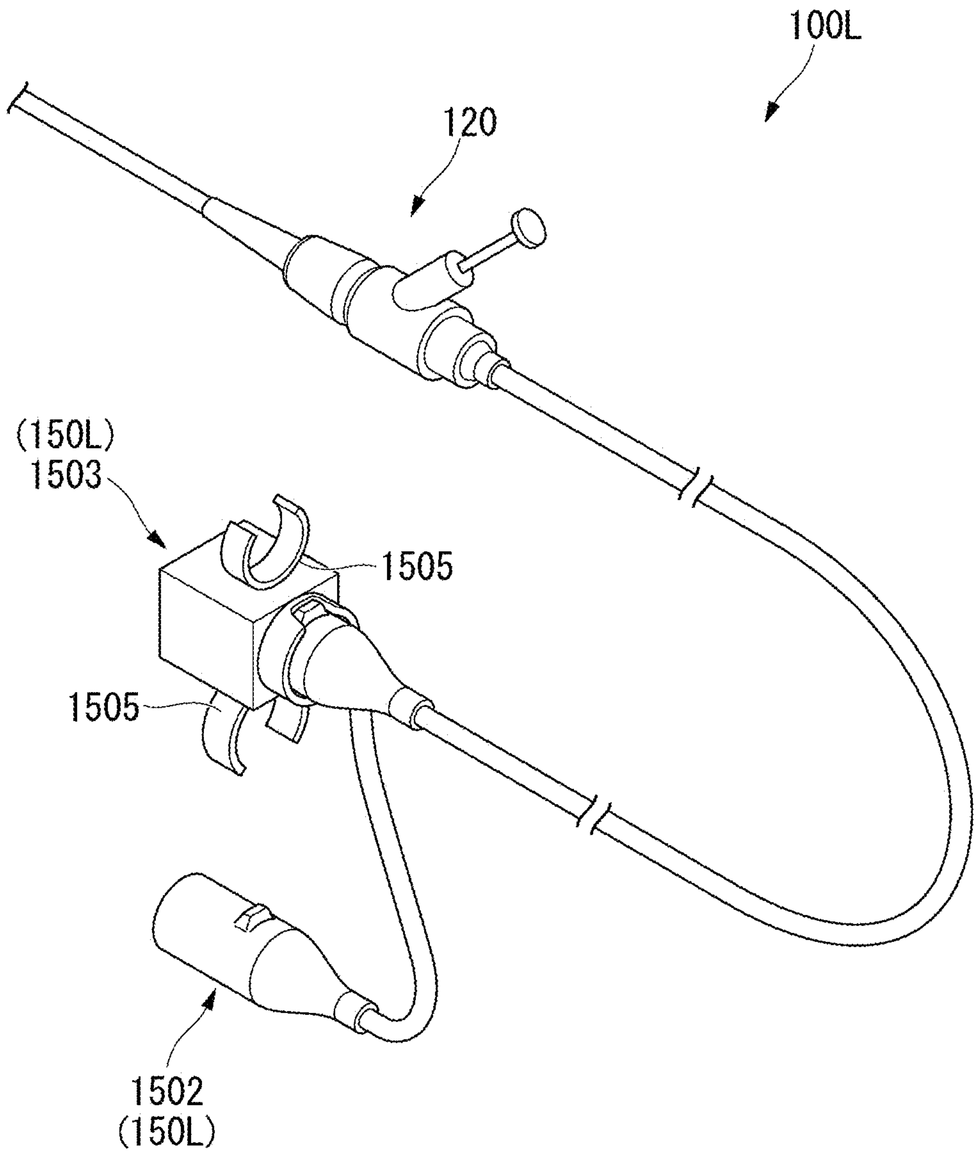
FIG. 98 illustrates an example of a view showing an endoscope of the electric endoscope system.

FIG. 98 is a view showing the endoscope 100L.

The detachable portion 150L includes a first detachable portion 1503 attached to the drive device 200 and a second detachable portion 1502 attached to the video control device 500.

Figure 99:
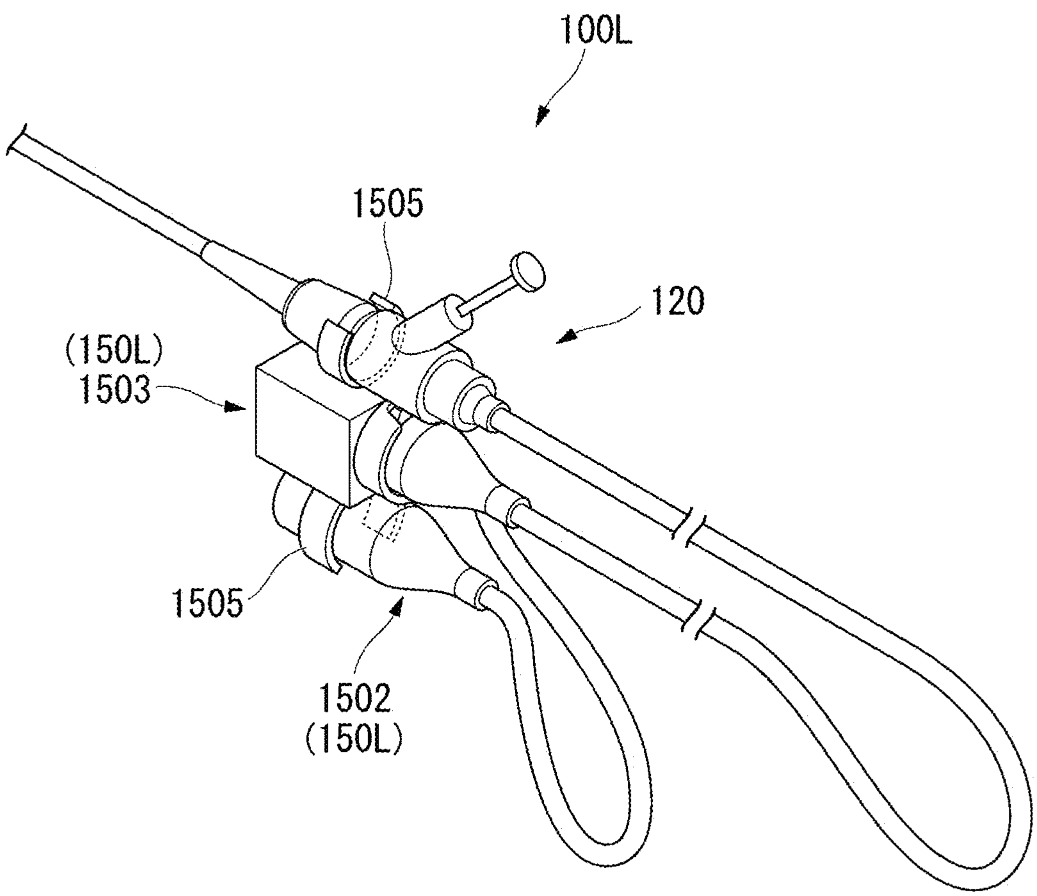
FIG. 99 illustrates an example of a view showing the endoscope at the time of transportation.

FIG. 99 is a view showing the endoscope 100L at the time of transportation.

The first detachable portion 1503 further includes an engagement portion 1505 as compared with the first detachable portion 1501 of the first embodiment. When the scopist S or the assistant removes and transports the endoscope 100L from the control device 600, the connection portion 120 and the second detachable portion 1502 are hooked to the engagement portion 1505 of the first detachable portion 1503. The scopist S or the assistant can hold the connection portion 120, the first detachable portion 1503, and the second detachable portion 1502 together.

The electric endoscope system 1000L according to the present embodiment can more efficiently carry and reprocess the endoscope 100.

Although the eleventh embodiment of the present disclosure has been described above in detail with reference to the drawings, a specific configuration is not limited to this embodiment and design changes and the like may be included without departing from the spirit and scope of the present disclosure. Moreover, constituent elements shown in the above-described embodiment and modified examples can be appropriately combined and configured.

A program in each embodiment may be recorded on a computer-readable recording medium and the program recorded on the recording medium may be read and executed by a computer system. The "computer system" used here is assumed to include an operating system (OS) or hardware such as peripheral devices. Moreover, the "computer-readable recording medium" refers to a flexible disk, a magneto-optical disc, a read-only memory (ROM), a portable medium such as a compact disc-ROM (CD-ROM), or a storage device such as a hard disk embedded in the computer system. Furthermore, the "computer-readable recording medium" may include a computer-readable recording medium for dynamically holding the program for a short time period as in a communication line when the program is transmitted via a network such as the Internet or a communication circuit such as a telephone circuit and a computer-readable recording medium for holding the program for a given time period as in a volatile memory inside the computer system serving as a server or a client when the program is transmitted. Moreover, the above-described program may be a program for implementing some of the above-described functions. Furthermore, the above-described program may be a program capable of implementing the above-described function in combination with a program already recorded on the computer system.

The present disclosure can be applied to a medical system for observing and treating the inside of a luminal organ or the like.

What is claimed is:

1. A medical manipulator system, comprising:
- a medical manipulator having a bending portion;
- an actuator connected to the medical manipulator and configured to bend the bending portion; and
- a controller into which a manipulation input for bending the bending portion is input, the controller including a touch pad,
- wherein the controller is configured to:
  - receive the manipulation input via the touch pad,
  - determine a bending direction in which the bending portion is bent based on a first part of the manipulation input received via the touch pad,
  - determine an amount of bending drive based on an entirety of the manipulation input received via the touch pad, the entirety of the manipulation input corresponding to a period from a start to an end of a manipulation operation detected by the controller, and
  - control the actuator to bend the bending portion by the determined amount of bending drive in the determined bending direction.

2. The medical manipulator system according to claim 1, wherein
- the controller is configured to determine the first part of the manipulation input, based on the manipulation input at a second position of the touch pad that is a predetermined distance away from a first position of the touch pad where the manipulation input has been started.

3. The medical manipulator system according to claim 2, wherein
- the controller is configured to determine the first part of the manipulation input based on the manipulation input at a second position of the touch pad that is an input position when a predetermined time has elapsed since the manipulation input was initiated at the first position of the touch pad.

4. The medical manipulator system according to claim 1, wherein the controller is configured to drive the bending portion by an amount of bending drive in a direction determined based on the first part of the manipulation input, and the controller is configured to determine the amount of bending drive based on an amount of movement of the manipulation input when it is assumed that the manipulation input continues to be input in the direction.

5. The medical manipulator system according to claim 1, wherein the controller is configured to drive the bending portion by an amount of bending drive in the bending direction determined based on the first part of the manipulation input, and the controller is configured to determine the amount of bending drive based on a length of a period during which the manipulation input is input.

6. The medical manipulator system according to claim 1, wherein the controller is configured to limit the bending direction in which the bending portion is bent, determined based on the first part of the manipulation input, to several direction types.

7. The medical manipulator system according to claim 1, wherein the controller is configured to switch between a first input mode in which the bending direction in which the bending portion is bent is determined based on a difference between a start of the manipulation input and an end of the manipulation input, and a second input mode in which the bending direction in which the bending portion is bent is determined based on the first part of the manipulation input.

8. The medical manipulator system according to claim 1, wherein the controller has a manipulation guide configured to guide the manipulation input to the touch pad in a straight line.

9. A control device that controls an actuator configured to bend a bending portion of a medical manipulator having the bending portion, wherein the control device is connected by wire or wirelessly to a controller having a touch pad into which a manipulation input for bending the bending portion is input, the control device being configured to:

receive the manipulation input via the touch pad, determine a bending direction in which the bending portion is bent based on a first part of the manipulation input received via the touch pad, determine an amount of bending drive based on an entirety of the manipulation input received via the touch pad, the entirety of the manipulation input corresponding to a period from a start to an end of a manipulation operation detected by the controller, and control the actuator to bend the bending portion by the determined amount of bending drive in the determined bending direction.

10. The control device according to claim 9, wherein the control device is connected by wire or wirelessly to the controller having the touch pad, and the control device is configured to determine the first part of the manipulation input, based on the manipulation input at a second position of the touch pad that is a predetermined distance away from a first position of the touch pad where the manipulation input has been started.

11. The control device according to claim 10, wherein the control device is configured to determine the first part of the manipulation input based on the manipulation input when a predetermined time has elapsed from the first position of the touch pad where the manipulation input has been started.

12. The control device according to claim 9, wherein the control device is configured to execute control to cause the actuator to drive the bending portion by an amount of bending drive in the bending direction determined based on the first part of the manipulation input, and determine the amount of bending drive based on an amount of movement of the manipulation input when it is assumed that the manipulation input continues to be input in the bending direction.

13. The control device according to claim 9, wherein the control device is configured to execute control to cause the actuator to drive the bending portion by an amount of bending drive in the bending direction determined based on the first part of the manipulation input, and determine the amount of bending drive based on a length of a period during which the manipulation input is input.

14. The control device according to claim 9, wherein the control device is configured to limit the bending direction in which the bending portion is bent, determined based on the first part of the manipulation input, to several direction types.

15. The control device according to claim 9, wherein the control device is configured to switch between a first input mode in which the bending direction in which the bending portion is bent is determined based on a difference between a start of the manipulation input and an end of the manipulation input, and a second input mode in which the bending direction in which the bending portion is bent is determined based on the first part of the manipulation input.

16. A controlling method of a medical manipulator, comprising:

receiving, by a controller via a touch pad, a manipulation input for bending a bending portion of the medical manipulator;

determining, by the controller, a bending direction in which the bending portion is bent based on a first part of the manipulation input received via the touch pad;

determining, by the controller, an amount of bending drive based on an entirety of the manipulation input received via the touch pad, the entirety of the manipulation input corresponding to a period from a start to an end of a manipulation operation detected by the controller; and causing an actuator, controlled by the controller, to bend the bending portion by the determined amount of bending drive in the determined bending direction.

17. The controlling method of the medical manipulator according to claim 16, further comprising:

inputting the manipulation input via the touch pad; and determining the first part of the manipulation input, based on the manipulation input at a second position of the touch pad that is a predetermined distance away from a first position of the touch pad where the manipulation input has been started.

18. The controlling method of the medical manipulator according to claim 17, further comprising:

determining the first part of the manipulation input based on the manipulation input at a second position of the touch pad that is an input position when a predetermined time has elapsed since the manipulation input was initiated at the first position of the touch pad.

19. The controlling method of the medical manipulator according to claim 16, further comprising:

driving the bending portion of the medical manipulator by an amount of bending drive in the bending direction determined based on the first part of the manipulation input; and determining the amount of bending drive based on an amount of movement of the manipulation input when it is assumed that the manipulation input continues to be input in the bending direction.

20. The controlling method of the medical manipulator according to claim 16, further comprising:

driving the bending portion of the medical manipulator by an amount of bending drive in the bending direction determined based on the first part of the manipulation input; and determining the amount of bending drive based on a length of a period during which the manipulation input is input.

* * * * *